United States Patent
Reddy et al.

(10) Patent No.: US 10,206,937 B2
(45) Date of Patent: *Feb. 19, 2019

(54) BORONIC ACID DERIVATIVES AND THERAPEUTIC USES THEREOF

(71) Applicant: Qpex Biopharma, Inc., San Diego, CA (US)

(72) Inventors: Raja K. Reddy, San Diego, CA (US); Tomasz Glinka, Cupertino, CA (US); Maxim Totrov, San Diego, CA (US); Scott Hecker, Del Mar, CA (US); Olga Rodny, Mill Valley, CA (US)

(73) Assignee: QPEX BIOPHARMA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/323,081

(22) PCT Filed: Jun. 29, 2015

(86) PCT No.: PCT/US2015/038364
§ 371 (c)(1),
(2) Date: Dec. 29, 2016

(87) PCT Pub. No.: WO2016/003929
PCT Pub. Date: Jan. 7, 2016

(65) Prior Publication Data
US 2017/0136047 A1 May 18, 2017

Related U.S. Application Data

(60) Provisional application No. 62/019,758, filed on Jul. 1, 2014.

(51) Int. Cl.
| | |
|---|---|
| *A61K 31/69* | (2006.01) |
| *A61K 45/06* | (2006.01) |
| *A61K 31/427* | (2006.01) |
| *C07F 5/02* | (2006.01) |
| *A61K 31/407* | (2006.01) |

(52) U.S. Cl.
CPC ............ *A61K 31/69* (2013.01); *A61K 31/407* (2013.01); *A61K 31/427* (2013.01); *A61K 45/06* (2013.01); *C07F 5/025* (2013.01); *Y02A 50/401* (2018.01); *Y02A 50/47* (2018.01); *Y02A 50/471* (2018.01); *Y02A 50/473* (2018.01); *Y02A 50/475* (2018.01); *Y02A 50/478* (2018.01); *Y02A 50/481* (2018.01); *Y02A 50/483* (2018.01)

(58) Field of Classification Search
None
See application file for complete search history.

(56) References Cited

U.S. PATENT DOCUMENTS

| | | |
|---|---|---|
| 3,686,398 A | 8/1972 | Kohn et al. |
| 4,194,047 A | 3/1980 | Christensen et al. |
| 4,260,543 A | 4/1981 | Miller |
| 4,353,807 A | 10/1982 | Braid |
| 4,409,214 A | 10/1983 | Takaya et al. |
| 4,822,786 A | 4/1989 | Zama et al. |
| 5,442,100 A | 8/1995 | Bjorkquiest et al. |
| 5,888,998 A | 3/1999 | Maiti et al. |
| 6,184,363 B1 | 2/2001 | Shoichet et al. |
| 6,586,615 B1 | 7/2003 | Kettner et al. |
| 7,271,186 B1 | 9/2007 | Shoichet et al. |
| 7,439,253 B2 | 10/2008 | Lampilas et al. |
| 7,582,621 B2 | 9/2009 | Baker et al. |
| 7,612,087 B2 | 11/2009 | Aszodi et al. |
| 7,674,913 B2 | 3/2010 | Campbell et al. |
| 7,825,139 B2 | 11/2010 | Campbell et al. |
| 8,680,136 B2 | 3/2014 | Hirst et al. |
| 9,012,491 B2 | 4/2015 | Reddy et al. |
| 9,101,638 B2 | 8/2015 | Reddy et al. |
| 9,132,140 B2 | 9/2015 | Reddy et al. |
| 9,156,858 B2 | 10/2015 | Reddy et al. |
| 9,296,763 B2 | 3/2016 | Hirst et al. |
| 9,511,142 B2 | 12/2016 | Burns et al. |
| 9,694,025 B2 | 7/2017 | Hirst et al. |
| 2004/0019203 A1 | 1/2004 | Micetich et al. |
| 2004/0157826 A1 | 8/2004 | Lampilas et al. |
| 2005/0020572 A1 | 1/2005 | Aszodi et al. |
| 2005/0070719 A1 | 3/2005 | Belyakov et al. |
| 2006/0019116 A1 | 1/2006 | Conley et al. |
| 2006/0178357 A1 | 8/2006 | Buynak et al. |
| 2006/0210883 A1 | 9/2006 | Chen et al. |
| 2010/0056478 A1 | 3/2010 | Desarbre et al. |
| 2010/0120715 A1 | 5/2010 | Burns et al. |

(Continued)

FOREIGN PATENT DOCUMENTS

| | | |
|---|---|---|
| EP | 1550657 A1 | 7/2005 |
| EP | 2508506 A1 | 10/2012 |

(Continued)

OTHER PUBLICATIONS

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

(Continued)

*Primary Examiner* — Karl J Puttlitz

(74) *Attorney, Agent, or Firm* — Knobbe Martens Olson & Bear LLP

(57) ABSTRACT

Disclosed herein are antimicrobial compounds compositions, pharmaceutical compositions, the use and preparation thereof. Some embodiments relate to boronic acid derivatives and their use as therapeutic agents.

43 Claims, No Drawings

(56) References Cited

U.S. PATENT DOCUMENTS

| | | |
|---|---|---|
| 2010/0256092 A1 | 10/2010 | Xia et al. |
| 2010/0292185 A1 | 11/2010 | Burns et al. |
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194284 A1 | 7/2014 | Reddy et al. |
| 2014/0194381 A1 | 7/2014 | Reddy et al. |
| 2014/0194382 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |

FOREIGN PATENT DOCUMENTS

| | | |
|---|---|---|
| FR | 2573070 A1 | 11/1984 |
| JP | 2003-229277 | 8/2003 |
| JP | 2004-291253 | 10/2004 |
| WO | WO 1987/05297 | 9/1987 |
| WO | WO 1989/10961 | 11/1989 |
| WO | WO 1998/56392 A1 | 12/1998 |
| WO | WO 2000/035904 A1 | 6/2000 |
| WO | WO 2000/035905 A1 | 6/2000 |
| WO | WO 2001/023374 A1 | 4/2001 |
| WO | WO 2001/030149 | 5/2001 |
| WO | WO 2002/022137 A1 | 3/2002 |
| WO | WO 2002/083884 | 10/2002 |
| WO | WO 2003/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2011/154953 | 12/2011 |
| WO | WO 2012/021455 A1 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/104897 A1 | 7/2013 |
| WO | WO 2013/122888 A2 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/151958 A1 | 9/2014 |
| WO | WO 2015/171398 A1 | 11/2015 |
| WO | WO 2015/171430 A1 | 11/2015 |
| WO | WO 2015/179308 A1 | 11/2015 |
| WO | WO 2016/065282 A1 | 4/2016 |

OTHER PUBLICATIONS

Adediran et al., "A 'cephalosporin-like' cyclic depsipeptide: Synthesis and reaction with beta-lactam-recognizing enzymes", Bioorg Med Chem Lett. (1999) 9(3):341-346.

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

Allen et al., "Ansel's Pharmaceutical Dosage Forms and Drug Delivery Systems", 8th Edition (2004) TOC only.

American Chemical Society. STN Chemical Database Registry RN: 1226917; Jun. 2010; 2 pages.

Arya et al., "Advances in asymmetric enolate methodology", Tetrahedron (2000) 56:917-947.

Babic et al., "What's new in antibiotic resistance? Focus on beta-lactamases", Drug Res Updates (2006) 9:142-156.

Bassetti et al., "New antibiotics for bad bugs: where are we?", Ann Clin Microbiol Antimicrob. (2013) 12:22-36.

Becker, Daniel E., "Antimicrobial Drugs", Anesth Prog (2013) 60:111-123.

Beenen et al., "Asymmetric copper-catalyzed synthesis of alpha-amino boronate esters from N-tert-butanesulfinyl aldimines", J Am Chem Soc. (2008) 130(22):6910-6911.

Biedrzycki et al., "Derivatives of tetrahedral boronic acids", J. Organomet. Chem. (1992) 431:255-270.

Bou et al., "Cloning, nucleotide sequencing, and analysis of the gene encoding an AmpC beta-lactamase in Acinetobacter baumannii", Antimicrob Agents Chemother (2000) 44(2):428-432.

Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.

Brabez et al., "Design, synthesis, and biological studies of efficient multivalent melanotropin ligands: tools toward melanoma diagnosis and treatment", J Med Chem. (2011) 54(20):7375-7384.

Brosz et al., "Resolution of alpha-aminoboronic esters by diastereoselective crystallization with pinanediols. Confirmation by x-ray analysis", Tetrahedron: Asymmetry (1997) 8(9):1435-1440.

Bush et al., "Minireview: Updated Functional Classification of beta-Lactamases," Antimicrob Agents Chemo. (2010) 54(3):969-976.

Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.

Chemicalland21.com. "Meglumine", Jun. 7, 2011. Downloaded from </www.chemicalland21.com/lifescience/phar/N-METHYL-D-GLUCAMINE.htm>; 2 pages.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.

Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", 6. Oct. 2014; retrieved online from URL:https://clinicaltrials.gov/archive/NCT02168946/20140_10_06.

(56) References Cited

OTHER PUBLICATIONS

Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamoylation of Heteroaromatic Bases", Heterocycles (1993) 36(12):2687-2696.
Coutts et al., "Two Efficient Methods for the Cleavage of Pinanediol Boronate Esters Yielding the Free Boronic Acids", Tetrahedron Lett. (1994) 35(29):5109-5112.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
Darses et al., "Potassium Organotrifluoroborates: New Perspectives in organic Synthesis", Chem Rev. (2008) 108:288-325.
Davoli et al., "Enantioselective total synthesis of (−)-microcarpalide", Tetrahedron (2005) 61:4427-4436.
Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.
Drawz et al., "Three Decades of beta-Lactamase Inhibitors", Clin Microbiol Reviews (Jan. 2010) 23(1):160-201.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure-Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/Monatshefte für Chemie (2009) 140(5):531-539.
Endo et al., "Chemoselective Suzuki coupling of diborylmethane for facile synthesis of benzylboronates", Org Lett. (2011) 13(13):3368-3371.
Fan, et al. (2009): STN International HCAPLUS database, Columbus (OH), accession No. 2009: 425839; 6 pages.
Farquhar et al., "Intensely potent doxorubicin analogues: structure—activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Giroux, A., "Synthesis of benzylic boronates via palladium-catalyzed cross-coupling reaction of bis(pinacolato)diboron with benzylic halides", Tetrahedron Lett. (2003) 44:233-235.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.
Greene, et al., "*Greene's Protective Groups in Organic Synthesis*", 4th Edition, (2007); pp. 774, 785 & 787.
Hama et al., "Palladium-Catalyzed alpha-Arylation of Zinc Enolates of Esters: Reaction Conditions and Substrate Scope", J Org Chem. (2013) 78(17):8250-8266.
Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol and Pinacol Boronate Esters via Fluorinated Intermediates", J Org Chem. (2010) 75(2):468-471.
Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.
Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]—boronates from (alpha-Haloalkyl)boronates", Org Chem. (1996) 61(22):7951-7954.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Kabalka et al., "Synthesis of a series of bornonated unnatural cyclic amino acids as potential boron neutron capture therapy agents", Appl Organomet Chem. (2008) 22(9):516-522.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Jul. 2009) 53(7):2799-2803.
Kint et al., "New-found fundamentals of bacterial persistence", Trends Microbiol. (2012) 20(12):577-585.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kumar et al., "Synthesis of intermediates for the lactone moiety of mevinic acids via tellurium chemistry", J. Org. Chem., (1994) 59(17):4760-4764.
Kumar et al., "Development of Practical Methodologies for the Synthesis of Functionalized Benzoboroxoles", Tetrahedron Lett. (Aug. 25, 2010) 51(34):4482-4485.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Kuti et al., "Use of Monte Carlo simulation to design an optimized pharmacodynamic dosing strategy for meropenem", J Clin Pharmacol. (Oct. 2003) 43(10:1116-1123.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Liu et al., "Selective Protein tyrosine phosphatase 1B inhibitors: Targeting the second phosphotyrosine binding site with non-carboxylic acid-containing ligands", J Med Chem. (2003) 46(16):3437-3440.

(56) References Cited

OTHER PUBLICATIONS

Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Livermore et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.
Lodise et al., "Penetration of meropenem into epithelial lining fluid of patients with ventilator-associated pneumonia", Antimicrob Agents Chemother. (Apr. 2011) 55(4):1606-1610.
Malfertheiner et al., "Current concepts in the management of Helicobacter pylori infection: the Maastricht III Consensus Report", Gut (2007) 56(6):772-781.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Synthesis of a (Beta-acetamido-alpha-acetoxyethyl) boronic ester via azido boronic esters", J Organomet Chem. (2008) 693:2258-2262.
Meanwell, "Synopsis of some recent tactical application of bioisosteres in drug design", J. Med. Chem. (2011) 54:2529-2591.
Micalizio et al., "A Boronic Ester Annulation Strategy for Diversity-Oriented Organic Synthesis", Angew Chem Int Ed Engl. (2002) 41(1):152-154.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nordmann et al., How to Detect NDM-1 Producers, J. Clin. Micro. (2011) 49:718-721.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Paterson et al., "Extended-Spectrum beta-Lactamases: a Clinical Update", Clin Microbiol Rev. (2005) 18(4):657-686.
Perez et al., "Why are we afraid of Acinetobacter baumannii?", Expert Rev Anti Infect Ther. (2008) 6(3):269-71.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34):11825-11827.
Powell et al., "Compendium of excipients for parenteral formulations", PDA J Pharm Sci Technol. (1998) 52(5):238-311.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Rodriguez-Martinez et al., "VIM-19, a Metallo-beta-lactamase with increased Carbapenemase Activity from *Escherichia coli* and Klebsiella pneumoniae", Antimicro Agents Chemother. (2010) 54(1):471-476.
Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.
Sawyer et al., "Physical properties and synthetic utility of a-alkoxyorganolithium species as studied through ligand selectivity in tin-lithium exchange", J. Am. Chem. Soc. (1988) 110:842-853.
Selander et al., "Palladium-catalyzed allylic C-OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3S,5R,7R,10R,11R)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C-H insertion", Tetrahedron (2002) 58:6545-6554.
Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
Vasil'Ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Waley, Stephen G., "A quick method for the determination of inhibition constants", Biochem J. (1982) 205(3):631-633.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Wohlrab et al., "Total synthesis of plusbacin A3: a depsipeptide antibiotic active against vancomycin-resistant bacteria", J. Am. Chem. Soc. (2007) 129:4175-4177.
Xia et al., "Synthesis and SAR of novel benzoxaboroles as a new class of beta-lactamase inhibitors", Bioorg Med Chem Lett. (2011) 21:2533-2536.
Yamamoto et al., "Iridium-catalyzed hydroboration of alkenes with pinacolborane", Tetrahedron (2004) 60:10695-10700.
Yanagisawa et al., "Nonpeptide angiotensin II receptor antagonists: synthesis, biological activities, and structure-activity relationships

(56) References Cited

OTHER PUBLICATIONS of imidazole-5-carboxylic acids bearing alkyl, alkenyl, and hydroxyalkyl substituents at the 4-position and their related compounds", J Med Chem. (1996) 39(1):323-338.
Yuen et al., "Deprotection of pinacolyl boronate esters via hydrolysis of intermediate potassium trifluoroborates", Tetrahed Lttr. (2005)46(46):7899-7903.
CAS Registry No. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015) see de Meijere below; 2 pages.
CAS Registry No. 105892-95-3 Boronic acid [1-(phenylsulfonyl)heptyl]-, dimethyl ester (2015) see FR2573070 above; 2 pages.
Gorovoy et al., "Boron-Containing Peptidomimetics—A Novel Class of Selective Anti-tubercular Drugs", Chem Biol Drug Des. (Jan. 2013) 81(3):408-413.
Jagannathan et al., "Synthesis of Boronic Acid Analogues of alpha-Amino Acids by Introducing Side Chains as Electrophiles", J Org Chem. (2001) 66(19):6375-6380.
Kawamorita et al., "Synthesis of Primary and Secondary Alkylboronates through Site-Selective C(sp3)-H Activation with Silica-supported Monophosphine-Ir Catalysts", J Am Chem Soc. (2013) 135(8):2947-2950.
Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131(51):18234-18235.
Lima et al., "Bioisosterism: A Useful Strategy for Molecular Modification and Drug Design", Curr Med Chem. (2005) 12:23-49.
de Meijere A. [Ed], Science of Synthesis—vol. 24; "Three Carbon-Heteroatom Bonds: Ketene Acetals and Yne-X Compounds", TOC 46 pages.
Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).
Matteson et al., "Cesium Alkyltrifluoroborates from Asymmetric Boronic Esters", Synlett (Jul. 2006) 20:3501-3503.
Mendoza et al., "Bis(phenylthio)methaneboronic Esters as Sources of Carbanions and Ketene Thioacetals", J Org Chem. (1979) 44(8):1352-1354.
Patani et al., "Bioisosterism: A Rational Approach in Drug Design", Chem Rev. (1996) 96:3147-3176.
Sun et al., "Programmed Synthesis of a Contiguous Stereotriad Motif by Triple Stereospecific Reagent-controlled Homologation", Org Lttr. (Jul. 2013) 15(17):4500-4503.

Webb et al., "Metal catalysed hydroboration of vinyl sulfides, sulfoxides, sulfones, and sulfonates", J Mol Cat A: Chem. (2007) 275:91-100.
Xie et al., "Group-assisted purification (GAP) chemistry for the synthesis of Velcade via asymmetric borylation of N-phosphinylimines", Beilstein J Org Chem (Mar. 2014) 10:746-751.
International Search Report and Written Opinion dated Aug. 25, 2015 for International Application No. PCT/US2015/038364, filed Jun. 29, 2015.
International Written Opinion (Rule 66) dated Jun. 7, 2016 for International Application No. PCT/US2015/038364, filed Jun. 29, 2015.
International Preliminary Report on Patentability (Chapter II) dated Aug. 20, 2016 for International Application No. PCT/US2015/038364, filed Jun. 29, 2015.
Valters et al., "Ring-Chain Tautomerism", Plenum press, New York and London, Softcover reprint of the hardcover $1^{st}$ edition 1985, V26, 1985.
Ambrose et al., Pharmacokinetics-pharmacodynamics of antimicrobial therapy: it's not just for mice anymore. Clin Infect Dis. (2007) 44: 79-86.
Bundgaard H. [Ed.], "Design of Prodrugs", Elsevier (1985); TOC, 2 pages.
CAS Registry No. 2005:329437 CAPLUS; "Product subclass 28: Vinylboranes", Vaultier et al., (2004); XP-002764965; 1 page.
CAS Registry No. 831209-98-4 6H-Dibenz[c,e][1,2]oxaborin, 6a, 10a-dihydro-6-hydroxy; Entered STN: Feb. 15, 2005; 1 page.
CAS Registry No. 831210-03-8 6H-Dibenz[c,e][1,2]oxaborin, 2,4-dibromo-6a, 10a-dihydro-6-hydroxy; Feb. 15, 2005; 1 page.
Dörwald F.Z., *Side Reactions in Organic Synthesis—A guide to Successful Synthesis Design*, Wiley-VCH Verlag GmbH & Co. KGaA, Weinheim, Germany (2005); Preface in 4 pages.
Higuchi et al., [Eds.] "Pro-drugs as Novel Drug Delivery Systems", ACS Sumposium Series 14 (1975); TOC, 3 pages.
Luithle et al., "Synthesis of enantiomerically pure cis-cyclopropylboronic esters", Eur J Org Chem. (2000) 14: 2557-2562.
Matteson, "Boronic Esters in Asymmetric Synthesis", J Org Chem. (Oct. 2013) 78(20): 10009-10023.
Pine et al., "Resonance vs. Tautomerism" in *Organic Chemistry*; McGraw-Hill, New York 4th Ed. (1980), pp. 218-219.
Rehm et al., "*Staphylococcus aureus*: Methicillin-susceptible *S. aureus* to Methicillin-resistant *S. aureus* and Vancomycin-resistant *S. aureus*" Clin Inf Diseases. (2010) 51(S2):S176-S182.
Singh et al., "Confronting the challenges of discovery of novel antibacterial agents", Bioorg Med Chem Lett. (2014) 24(16):3683-3689.
Sumida et al., "Boron-selective biaryl coupling approach to versatile dibenzoxaborins and application to concise synthesis of defucogilvocarcin M", Org Ltt. (Dec. 2014) 16(23):6240-6243.
Wilson D.N., "The A-Z of bacterial translation inhibitors", Crit Rev Biochem Mol Biolog. (2009) 44(6):393-433.

BORONIC ACID DERIVATIVES AND THERAPEUTIC USES THEREOF

CROSS-REFERENCE TO RELATED APPLICATIONS

This application is the U.S. National Phase of International Application No. PCT/US2015/038364 entitled BORONIC ACID DERIVATIVES AND THERAPEUTIC USES THEREOF, filed Jun. 29, 2015 and published on Jan. 7, 2016 as WO 2016/003929, which claims the benefit of U.S. Provisional Application No. 62/019,758, filed Jul. 1, 2014, all of which are incorporated herein by reference in their entirety.

BACKGROUND

Field of the Invention

The present invention relates to the fields of chemistry and medicine. More particularly, the present invention relates to boronic acid antimicrobial compounds, compositions, their preparation, and their use as therapeutic agents.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

The zinc-dependent class B metallo-β-lactamases are represented mainly by the VIM, IMP, and NDM types. IMP and VIM-producing *K. pneumonia* were first observed in 1990s in Japan and 2001 in Southern Europe, respectively. IMP-positive strains remain frequent in Japan and have also caused hospital outbreaks in China and Australia. However dissemination of IMP-producing Enterobacteriaceae in the rest of the word appears to be somewhat limited. VIM-producing enterobacteria can be frequently isolated in Mediterranean countries, reaching epidemic proportions in Greece. Isolation of VIM-producing strains remains low in Northern Europe and in the United States. In stark contrast, a characteristic of NDM-producing *K. pneumonia* isolates has been their rapid dissemination from their epicenter, the Indian subcontinent, to Western Europe, North America, Australia and Far East. Moreover, NDM genes have spread rapidly to various species other than *K. pneumonia*.

The plasmid-expressed class D carbapenemases belong to OXA-48 type. OXA-48 producing *K. pneumonia* was first detected in Turkey, in 2001. The Middle East and North Africa remain the main centers of infection. However, recent isolation of OXA-48-type producing organisms in India, Senegal and Argentina suggest the possibility of a global expansion. Isolation of OXA-48 in bacteria other than *K. pneumonia* underlines the spreading potential of OXA-48.

Treatment of strains producing any of these carbapenemases with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved β-lactamase inhibitors.

SUMMARY

Some embodiments disclosed herein include a compound having the structure of Formula (I):

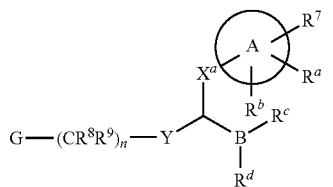

(I)

or pharmaceutically acceptable salts thereof, wherein:
A is selected from the group consisting of $C_{3-10}$ carbocyclyl, $C_{6-10}$ aryl, 5-10 membered heteroaryl, and 5-10 membered heterocyclyl;

$X^a$ is —C($R^e R^f$)—, —O—, —S—, —S(O)—, —S(O)$_2$—, or —NR$^1$—;

$R^a$ is selected from the group consisting of —H, halogen, optionally substituted —C$_{1-6}$ alkyl, —OH, —C(O)OR, optionally substituted —O—C$_{1-6}$ alkyl, —NR$^1$R$^2$, —N(OR$^3$)R$^2$, optionally substituted —S—C$_{1-6}$ alkyl, —C(O)NR$^1$R$^2$, —S(O)$_2$NR$^1$R$^2$, —CN, optionally substituted —S(O)—C$_{1-6}$ alkyl, optionally substituted —S(O)$_2$—C$_{1-6}$ alkyl, and a carboxylic acid isoster;

$R^b$ is selected from the group consisting of —H, halogen, optionally substituted —C$_{1-6}$ alkyl, —OH, —C(O)OR, optionally substituted —O—C$_{1-6}$ alkyl, —NR$^1$R$^2$, —N(OR$^3$)R$^2$, optionally substituted —S—C$_{1-6}$ alkyl, —C(O)NR$^1$R$^2$, —S(O)$_2$NR$^1$R$^2$, —CN, optionally substituted —S(O)—C$_{1-6}$ alkyl, optionally substituted —S(O)$_2$—C$_{1-6}$ alkyl, and a carboxylic acid isoster, and $R^c$ is selected from the group consisting of —OH, optionally substituted —O—C$_{1-6}$ alkyl, —NR' R$^2$, and —N(OR$^3$)R$^2$, or $R^b$ and $R^e$ together with intervening atoms form a 5-8 membered boron ester ring, optionally comprising additional 1-3 heteroatoms selected from Oxygen (O), Sulfur (S) or Nitrogen (N);

$R^d$ is selected from the group consisting of —OH, optionally substituted —O—C$_{1-6}$ alkyl, —NR$^1$R$^2$, and —N(OR$^3$)R$^2$, or when $R^b$ and $R^c$ do not together form a 5-8 membered boron ester ring, then optionally $R^c$ and $R^d$ together with intervening atoms form a 5-15 membered boron ester or amide ring, optionally comprising additional 1-3 heteroatoms selected from O, S, and N;

Y is selected from the group consisting of —S—, —S(O)—, —S(O)$_2$—, —O—, —CH$_2$— and —NR$^2$—;

G is selected from the group consisting of —NR$^1$R$^2$, —N$_3$, —C(O)NR$^1$R$^2$, —S(O)$_2$NR$^1$R$^2$, —SR$^3$, —OR$^3$, —CH$_2$NR$^1$C(O)R$^5$, —C(=NOR$^3$)—X, C(=NOR$^3$)—Z, —C(O)OR$^3$, —C(O)NR$^1$(OR$^3$), —NR$^1$(OR$^3$), —NR$^1$C(O)R$^5$, —NR$^1$C(O)NR$^2$R$^{1a}$, —NR$^1$C(O)OR$^3$, —NR$^1$S(O)$_2$R$^3$, —NR$^1$S(O)$_2$NR$^2$R$^{1a}$, —NR$^1$NR$^2$R$^{1a}$, —C(O)NR$^1$NR$^2$R$^{1a}$, —S(O)$_2$NR$^1$NR$^2$R$^{1a}$, —C(=NR$^1$)R$^5$, —C(=NR$^1$)NR$^2$R$^{1a}$, —NR$^1$CR$^5$(=NR$^2$), —NR$^1$CR$^5$(=NR$^2$), —NR$^1$C(=NR$^2$)NR$^{1a}$R$^{2a}$, —CN, C$_{1-10}$ alkyl optionally substituted by one or more R$^{10}$, C$_{2-10}$alkenyl optionally substituted by one or more R$^{10}$, C$_{2-10}$alkynyl optionally substituted by one or more R$^{10}$, C$_{3-7}$ carbocyclyl optionally substituted by one or more R$^{10}$, 3-10 membered heterocyclyl optionally substituted by one or more R$^{10}$, C$_{6-10}$aryl optionally substituted by one or more R$^{10}$, 5-10 membered heteroaryl optionally substituted by one or more R$^{10}$, C$_{1-6}$alkylene-C$_{3-7}$carbocyclyl optionally substituted by one or more R$^{10}$, C$_{1-6}$alkylene-3-10 membered heterocyclyl optionally substituted by one or more R$^{10}$, C$_{1-6}$alkylene-C$_{6-10}$aryl optionally substituted by one or more R$^{10}$, and C$_{1-6}$alkylene-5-10 membered heteroaryl optionally substituted by one or more R$^{10}$;

$R^e$ and $R^f$ are each independently selected from the group consisting of H, C$_{1-6}$ alkyl, —OH, —OC$_{1-6}$alkyl, —SC$_{1-6}$alkyl, C$_{3-10}$cycloalkyl, C$_{2-10}$alkenyl, C$_{2-10}$alkynyl, —NR$^1$C(O)R$^5$, —NR$^1$S(O)$_2$R$^3$, —C(O)R$^5$, —C(O)OR$^3$, alkylaryl, optionally substituted C$_{6-10}$ aryl, optionally substituted —O—C$_{6-10}$aryl, —CN, optionally substituted 5-10 membered heteroaryl, optionally substituted —O-heteroaryl, optionally substituted 3-10 membered heterocyclyl, —S(O)R$^3$, —S(O)$_2$R$^3$, —R$^1$—O—C(O)OR$^3$, or $R^e$ and $R^f$ together with the carbon to which they are attached form a C$_{3-8}$ cycloalkyl or a 4-8 membered heterocyclyl;

$R^7$ is present 1 to 5 times and each $R^7$ is independently selected from the group consisting of —H, —OH, halogen, —CH$_3$, —CF$_3$, C$_1$-C$_6$ alkenyl, C$_1$-C$_6$ alkynyl, C$_6$ heteroalkyl, C$_3$-C$_7$ carbocyclyl, 5-10 membered heterocyclyl, aryl, 3-10 membered heteroaryl, cyano, C$_1$-C$_6$ alkoxy(C$_1$-C$_6$)alkyl, aryloxy, sulfhydryl (mercapto), and —CH$_2$)$_m$—Y'—(CH$_2$)$_p$M', or two adjacent $R^7$ together with any intervening atoms form a 5-10 membered heteroaryl;

m and p are independently 0 to 3;

Y' is selected from the group consisting of —S—, —S(O)—, —S(O)$_2$—, —O—, —CR$^5$R$^6$—, and —NR$^1$—;

M' is selected from the group consisting of —C(O)NR$^1$R$^2$; —C(O)NR$^1$OR$^3$; —NR$^1$C(O)R$^5$; —NR$^1$C(O)NR$^2$R$^{1a}$; —NR$^1$C(O)OR$^3$; —NR$^1$S(O)$_2$R$^3$; —NR$^1$S(O)$_2$NR$^2$R$^{1a}$; —C(=NR$^1$)R$^5$; —C(=NR$^1$)NR$^2$R$^{1a}$; —NR$^1$CR$^5$(NR$^2$); —NR$^1$C(=NR$^2$)NR$^{1a}$R$^{2a}$; NR$^1$R$^2$; —SO$_3$R$^3$; —CN; C$_{1-4}$ alkyl optionally substituted with 0-2 substituents selected from the group consisting, —OR$^3$, —NR$^1$R$^2$, halogen, —C(O)NR$^1$R$^2$, and —NR$^1$C(O)R$^5$; C$_{3-10}$ cycloalkyl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; C$_{6-10}$ aryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; 5 to 10 membered heteroaryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; and 4 to 10 membered heterocyclyl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$;

X is hydrogen or optionally substituted C$_{1-9}$alkyl;

Z is selected from optionally substituted C$_{3-8}$ cycloalkyl, optionally substituted heterocyclyl, optionally substituted aryl, optionally substituted heteroaryl;

R is selected from the group consisting of —H, —C$_{1-9}$alkyl, —CR$^5$R$^6$OC(O)C$_{1-9}$alkyl, —CR$^5$R$^6$OC(O)OC$_{1-9}$alkyl, CR$^6$R$^7$OC(O)C$_{6-10}$aryl, CR$^6$R$^7$OC(O)OC$_{6-10}$aryl, and

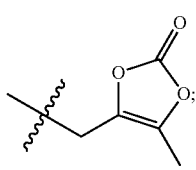 [SMILES: *Cc1oc(=O)oc1C]

- each $R^1$, $R^2$, $R^{1a}$ and $R^{2a}$ are independently selected from the group consisting of —H, optionally substituted —$C_{1-10}$alkyl, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;
- $R^3$ is hydrogen, optionally substituted $C_{1-10}$alkyl, -optionally substituted $C_{1-10}$alkyl-COOH, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;
- each $R^5$, $R^6$, $R^8$ and $R^9$ are independently selected from the group consisting of —H, —OH, —$NH_2$, -optionally substituted alkoxyl, optionally substituted —$C_{1-10}$alkyl, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;
- each n is independently 0-3;
- each $R^{10}$ is independently —$(CH_2)_{0-6}R^{11}$; and
- each $R^{11}$ is independently selected from $C_1$-$C_6$ alkyl; $C_2$-$C_6$ alkenyl; $C_2$-$C_6$ alkynyl; $C_1$-$C_6$ heteroalkyl; $C_3$-$C_7$ carbocyclyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; $C_3$-$C_7$-carbocyclyl-$C_1$-$C_6$-alkyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl-$C_1$-$C_6$-alkyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; aryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; aryl($C_1$-$C_6$)alkyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 5-10 membered heteroaryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 5-10 membered heteroaryl($C_1$-$C_6$)alkyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; $C_{1-6}$alkylene-$C_{3-7}$carbocyclyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; $C_{1-6}$alkylene-3-10 membered heterocyclyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; $C_{1-6}$alkylene-$C_{6-10}$aryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; $C_{1-6}$alkylene-5-10 membered heteroaryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; halo; cyano; hydroxy; $C_1$-$C_6$ alkoxy($C_1$-$C_6$)alkyl (ether); aryloxy; halo($C_1$-$C_6$)alkyl; halo($C_1$-$C_6$)alkoxy; amino; amino($C_1$-$C_6$)alkyl; nitro; 0-carbamyl; N-carbamyl; 0-thiocarbamyl; N-thiocarbamyl; C-amido; N-amido; S-sulfonamido; N-sulfonamido; C-carboxy; O-carboxy; acyl; cyanate; isocyanate; thiocyanato; isothiocyanato; sulfonyl; oxo; —$OR^3$; —$C_{1-6}$alkylene-$COOR^3$; —$SR^3$; $C(O)NR^1R^2$; —$NR^1R^2$; —$NR^1(CH_2)_{0-4}COR^5$; —$NR^1(CH_2)_{0-4}C(=NR^2)R^5$; —$NR^1$—CH—[$(CH_2)_{0-4}$—$NR^{1a}R^{2a}$]$_2$; —$NR^1$—$(CH_2)_{1-5}$—$R^3$; —$NR^1(CH_2)_{1-4}$—$NR^{1a}R^{2a}$; —N[$(CH_2)_{1-4}$—$NR^1R^2$]$_2$; —$S(CH_2)_{0-4}C(=NR^1)R^5$; —$S(CH_2)_{1-4}$—$R^3$; —$S(CH_2)_{0-4}$—$NR^1R^2$; —S—CH—[$(CH_2)_{0-4}$—$NR^1R^2$]$_2$; —S[$(CH_2)_{1-4}$—$NR^1R^2$]$_2$; —$S(CH_2)_{0-4}$-3-10 membered heterocyclyl; —S$(CH_2)_{0-4}$-3-10 membered heterocyclyl-$NR^1R^2$; —$S(CH_2)_{0-4}$-5-10 membered heteroaryl-$NR^1R^2$; —$S(O)_2NR^1R^2$; and —O—$C_{1-6}$alkylene-$NR^1R^2$.

Some embodiments disclosed herein include a compound having the structure of formula I-1 or formula I-2:

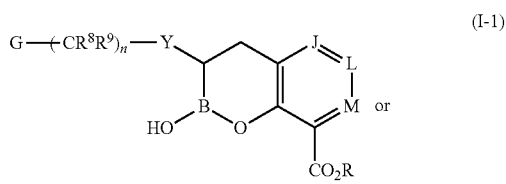

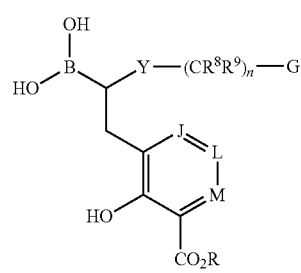

or pharmaceutically acceptable salt thereof,

Some embodiments disclosed herein include a compound having the structure of formula I-3 or formula I-4:

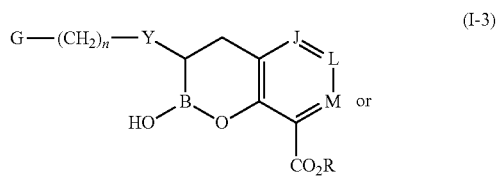

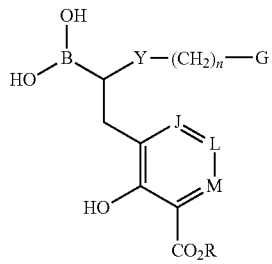

or pharmaceutically acceptable salt thereof, wherein:

Y is selected from the group consisting of —S—, —O—, —CH$_2$—, and —NH—;

n is 0-3;

G is selected from the group consisting of —C(O)NR$^1$R$^2$; —C(O)NR$^1$OR$^3$; —NR$^1$C(O)R$^5$; —NR$^1$C(O)NR$^2$R$^{2a}$; —NR$^1$C(O)OR$^3$; NR$^1$S(O)$_2$R$^3$; —NR$^1$S(O)$_2$NR$^2$R$^{1a}$; —C(=NR$^1$)R$^5$; —C(=NR$^1$)NR$^2$R$^{1a}$; —NR$^1$CR$^5$(=NR$^5$); —NR$^1$C(=NR$^2$)NR$^{1a}$R$^{2a}$; C$_{6-10}$aryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; 5-10 membered heteroaryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; and 5-10 membered heterocyclyl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$;

J, L, and M are each independently selected from the group consisting of CR$^7$ and N;

R is selected from a group consisting of —H, —C$_{1-9}$alkyl, —CR$^5$R$^6$OC(O)C$_{1-9}$alkyl, —CR$^5$R$^6$OC(O)OC$_{1-9}$alkyl, and

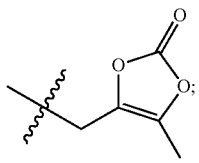 [SMILES: *Cc1oc(=O)oc1C]

R$^1$, R$^2$, R$^3$, R$^5$ and R$^6$ are each independently selected from —H and —C$_{1-4}$alkyl; and R$^7$ is selected from the group consisting of —H, —C$_{1-4}$alkyl, —OH, —OC$_{1-4}$alkyl, and halogen.

Some embodiments relate to a chemical complex, comprising a complex between a monosaccharide or monosaccharide derivative and a compound having the structure of formula (I) described herein.

Other embodiments disclosed herein include a pharmaceutical composition comprising a therapeutically effective amount of a compound disclosed herein and a pharmaceutically acceptable excipient.

Other embodiments disclosed herein include a method of treating or preventing a bacterial infection, comprising administering to a subject in need thereof a compound disclosed herein.

DETAILED DESCRIPTION

In some embodiments, compounds that contain a boronic acid moiety are provided that act as antimicrobial agents and/or as potentiators of antimicrobial agents Various embodiments of these compounds include compounds having the structures of Formula I as described above or pharmaceutically acceptable salts thereof.

In some embodiments of Formula (I), G is selected from the group consisting of —NR$^1$R$^2$, —N$_3$, —C(O)NR$^1$R$^2$, —S(O)$_2$NR$^1$R$^2$, —SR$^3$, —OR$^3$, —CH$_2$NR$^1$C(O)R$^5$, —C(=NOR$^3$)—X, C(=NOR$^3$)—Z, —C(O)NR$^1$(OR$^3$), —NR$^1$(OR$^3$), —NR$^1$C(O)R$^5$, —NR$^1$C(O)NR$^2$R$^{1a}$, —NR$^1$C(O)OR$^3$, —NR$^1$S(O)$_2$R$^3$, —NR$^1$S(O)$_2$NR$^2$R$^{1a}$, —NR$^1$NR$^2$R$^{1a}$, —C(O)NR$^1$NR$^2$R$^{1a}$, —S(O)$_2$NR$^1$NR$^2$R$^{1a}$, —C(=NR$^1$)R$^5$, —C(=NR$^1$)NR$^2$R$^{1a}$, —NR$^1$CR$^5$(=NR$^2$), —NR$^1$C(=NR$^2$)NR$^{1a}$R$^{2a}$, optionally substituted C$_{1-10}$ alkyl, optionally substituted C$_{2-10}$alkenyl, optionally substituted C$_{2-10}$alkynyl, optionally substituted C$_{3-7}$ carbocyclyl, optionally substituted 5-10 membered heterocyclyl, optionally substituted C$_{6-10}$aryl, optionally substituted 5-10 membered heteroaryl, optionally substituted C$_{1-6}$alkylene-C$_{3-7}$carbocyclyl, optionally substituted C$_{1-6}$alkylene-5-10 membered heterocyclyl, optionally substituted C$_{1-6}$alkylene-C$_{6-10}$aryl, and optionally substituted C$_{1-6}$alkylene-5-10 membered heteroaryl;

R$^7$ is present 1 to 5 times and each R$^7$ is independently selected from the group consisting of —H, —OH, halogen, —CF$_3$, C$_1$-C$_6$ alkenyl, C$_1$-C$_6$ alkynyl, C$_1$-C$_6$ heteroalkyl, C$_3$-C$_7$ carbocyclyl, 5-10 membered heterocyclyl, aryl, 5-10 membered heteroaryl, cyano, C$_1$-C$_6$ alkoxy(C$_1$-C$_6$)alkyl, aryloxy, sulfhydryl (mercapto), and —(CH$_2$)$_m$—Y'—(CH$_2$)$_p$M';

M' is selected from the group consisting of —C(O)NR$^1$R$^2$; —C(O)NR$^1$OR$^3$; —NR$^1$C(O)R$^5$; —NR$^1$C(O)NR$^2$R$^{1a}$; —NR$^1$C(O)OR$^3$; —NR$^1$S(O)$_2$R$^3$; —NR$^1$S(O)$_2$NR$^2$R$^{1a}$; —C(=NR$^1$)R$^5$; —C(=NR$^1$)NR$^2$R$^{1a}$; —NR$^1$CR$^5$(=NR$^2$); —NR$^1$C(=NR$^2$)NR$^{1a}$R$^{2a}$; C$_{1-4}$ alkyl optionally substituted with 0-2 substituents selected from the group consisting, —OR$^3$, —NR$^1$R$^2$, halogen, —C(O)NR$^1$R$^2$, and —NR$^1$C(O)R$^5$; C$_{3-10}$ cycloalkyl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; C$_{6-10}$ aryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; 5 to 10 membered heteroaryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; and 4 to 10 membered heterocyclyl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$;

R is selected from the group consisting of —H, —C$_{1-9}$alkyl, —CR$^5$R$^6$OC(O)C$_{1-9}$alkyl, —CR$^5$R$^6$OC(O)OC$_{1-9}$alkyl, and

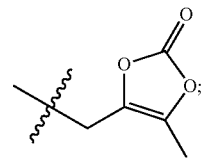

each R$^1$, R$^2$, R$^{1a}$ and R$^{2a}$ are independently selected from the group consisting of —H, optionally substituted —C$_{1-10}$alkyl, optionally substituted C$_{2-10}$alkenyl, optionally substituted C$_{2-10}$alkynyl, optionally substituted C$_{3-7}$ cycloalkyl, optionally substituted 3-8 membered heterocyclyl, optionally substituted C$_{6-10}$aryl, and optionally substituted 5-10 membered heteroaryl; and each R$^5$, R$^6$, R$^8$ and R$^9$ are independently selected from the group consisting of —H, —OH, -optionally substituted alkoxyl, optionally substituted —C$_{1-10}$alkyl, optionally substituted C$_{2-10}$alkenyl, optionally substituted C$_{2-10}$alkynyl, optionally substituted C$_{3-7}$cycloalkyl, optionally substituted 3-8 membered heterocyclyl, optionally substituted $C_{6-10}$aryl, and optionally substituted 5-10 membered heteroaryl.

In some embodiments of Formula (I), G can be selected from the group consisting of —$NR^1R^2$, —$N_3$, —C(O)$NR^1R^2$, —$S(O)_2NR^1R^2$, —$SR^3$, —$OR^3$, —$CH_2NR^1C(O)R^5$, —C(=$NOR^3$)—X, C(=$NOR^3$)—Z, —C(O)$OR^3$, —C(O)$NR^1(OR^3)$, —$NR^1(OR^3)$, —$NR^1C(O)R^5$, —$NR^1C(O)NR^2R^{1a}$, —$NR^1C(O)OR^3$, —$NR^1S(O)_2R^3$, —$NR^1S(O)_2NR^2R^{1a}$, —$NR^1NR^2R^{1a}$, —C(O)$NR^1NR^2R^{1a}$, —$S(O)_2NR^1NR^2R^{1a}$, —C(=$NR^1$)$R^5$, —C(=$NR^1$)$NR^2R^{1a}$, —$NR^1CR^5$(=$NR^2$), —$NR^1C$(=$NR^2$)$NR^{1a}R^{2a}$, optionally substituted $C_{1-10}$ alkyl, optionally substituted $C_{2-10}$alkenyl, optionally substituted $C_{2-10}$alkynyl, optionally substituted $C_{3-7}$ carbocyclyl, optionally substituted 5-10 membered heterocyclyl, optionally substituted $C_{6-10}$aryl, and optionally substituted 5-10 membered heteroaryl.

In some embodiments of Formula (I), each $R^{11}$ can be independently selected from $C_1$-$C_6$ alkyl; halo$C_{1-6}$alkyl; —$OR^3$; —$C_{1-6}$alkylene-$COOR^3$; —$SR^3$; halogen; —CO—$C_{1-4}$alkyl; C(O)$NR^1R^2$; —$NR^1R^2$; —$NR^1(CH_2)_{0-4}COR^5$; —$NR^1(CH_2)_{0-4}C$(=$NR^2$)$R^5$; [(CH$_2$)$_{0-4}$—$NR^{1a}R^{2a}$]$_2$; —$NR^1$—(CH$_2$)$_{1-5}$—$R^3$; —$NR^1$(CH$_2$)$_{1-4}$—$NR^{1a}R^{2a}$; —N[(CH$_2$)$_{1-4}$—$NR^1R^2$]$_2$; —S(CH$_2$)$_{0-4}$C(=$NR^1$)$R^5$; —S(CH$_2$)$_{1-4}$—$R^3$; —S(CH$_2$)$_{0-4}$—$NR^1R^2$; —S—CH—[(CH$_2$)$_{0-4}$—$NR^1R^2$]$_2$; —S[(CH$_2$)$_{1-4}$—$NR^1R^2$]$_2$; —S(CH$_2$)$_{0-4}$-3-10 membered heterocyclyl; —S(CH$_2$)$_{0-4}$-3-10 membered heterocyclyl-$NR^1R^2$; —S(CH$_2$)$_{0-4}$-5-10 membered heteroaryl-$NR^1R^2$; —$S(O)_2NR^1R^2$; and —O—$C_{1-6}$alkylene-$NR^1R^2$; $C_{3-7}$ carbocyclo optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 6 to 10 membered aryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; and 5-10 membered heteroaryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy.

In some embodiments of Formula (I), A can be selected from the group consisting of phenyl, biphenyl, naphthalenyl, phenanthrenyl, anthracenyl, tetralinyl, fluorenyl, indenyl, indanyl, pyridyl, pyrrolyl, oxazolyl, indolyl and thienyl. In some embodiments of Formula (I), A can be phenyl.

In some embodiments of Formula (I), $R^b$ is attached to ring A at a position that is vicinal to the point of attachment of $X^a$ to ring A.

In some embodiments, Y can be —$CH_2$—, —S(O)—, —$S(O)_2$—, —O— or —S—. In some embodiments, Y can be —$CH_2$—, —S(O)—, —$S(O)_2$—, —O—, —NH—, or —S—.

In some embodiments, Y can be —$CH_2$—, —O—, —S— or —NH—.

In some embodiments, Y can be —$CH_2$—, —O— or —S—.

In some embodiments, Y can be —O— or —S—.

In some embodiments, $R^d$ is —OH.

In some embodiments, $X^a$ is —$CH_2$—.

In some embodiments, $R^a$ is selected from the group consisting of —H, halogen, optionally substituted —$C_{1-6}$ alkyl, —OH, —C(O)OR, optionally substituted —O—$C_{1-6}$ alkyl, —$NR^1R^2$, —$N(OR^3)R^2$, optionally substituted —S—$C_{1-6}$ alkyl, —C(O)$NR^1R^2$, —$S(O)_2NR^1R^2$, CN, optionally substituted —S(O)—$C_{1-6}$ alkyl, and optionally substituted —$S(O)_2$—$C_{1-6}$ alkyl.

In some embodiments, $R^a$ is a carboxylic acid isoster.

In some embodiments, $R^b$ is selected from the group consisting of —H, halogen, optionally substituted —$C_{1-6}$ alkyl, —OH, —C(O)OR, optionally substituted —O—$C_{1-6}$ alkyl, —$NR^1R^2$, —$N(OR^3)R^2$, optionally substituted —S—$C_{1-6}$ alkyl, —C(O)$NR^1R^2$, —$S(O)_2NR^1R^2$, —CN, optionally substituted —S(O)—$C_{1-6}$ alkyl, and optionally substituted —$S(O)_2$—$C_{1-6}$ alkyl.

In some embodiments, $R^b$ is —OH.

In some embodiments, $R^b$ is a carboxylic acid isoster.

In some embodiments, $R^e$ is —OH.

Some embodiments of the compounds of Formula (I) or their pharmaceutically acceptable salts can have the structure of Formula (I'):

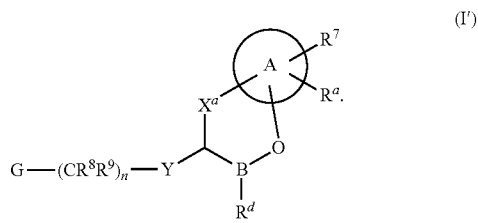

(I')

In some embodiments of Formula (I), (I'), (I-1) or (I-2), $R^8$ is H and $R^9$ is H.

Some embodiments of the compounds of Formula (I) or their pharmaceutically acceptable salts can have the structure of Formula (I-3) or Formula (I-4):

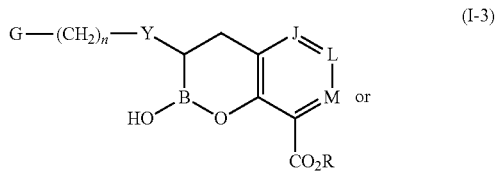

(I-3)

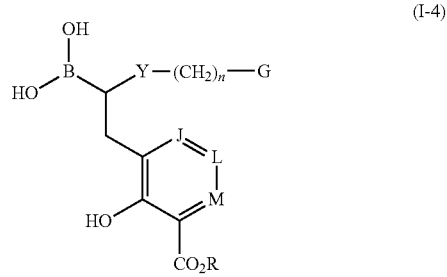

(I-4)

wherein J, L, and M are each independently selected from the group consisting of $CR^7$ and N.

In some embodiments of Formula (I-1), (I-2), (I-3), or (I-4), two adjacent $R^7$ together with any intervening atoms can form a 5-8 membered heteroaryl ring. In some embodiments, two adjacent $R^7$ together with any intervening atoms form an imidazole ring.

Some embodiments of compounds of Formula (I) or Formula (I-1) or their pharmaceutically acceptable salts have the following stereochemistry as shown in the structure of formula (Ia):

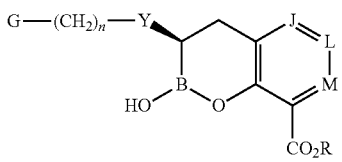

(Ia)

Some embodiments of compounds of Formula (I) or Formula (I-1) or their pharmaceutically acceptable salts have the following stereochemistry as shown in the structure of formula (Ib):

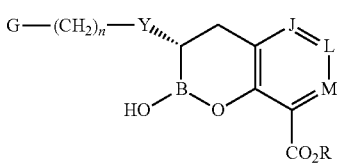

(Ib)

Some embodiments of compounds of Formula (I) or Formula (I-2) or their pharmaceutically acceptable salts have the following stereochemistry as shown in the structure of formula (Ic):

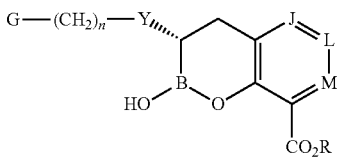

(Ic)

Some embodiments of compounds of Formula (I) or Formula (I-2) or their pharmaceutically acceptable salts have the following stereochemistry as shown in the structure of formula (Id):

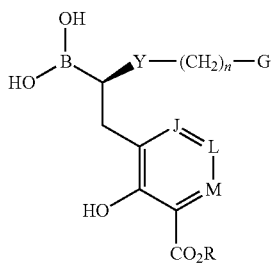

(Id)

In some embodiments, n is 0 or 1.

In some embodiments, Y is selected from the group consisting of —S—, —O—, —CH$_2$—, and —NH—; G is selected from the group consisting of —C(O)NR$^1$R$^2$; —C(O)NR$^1$OR$^3$; —NR$^1$C(O)R$^5$; —NR$^1$C(O)NR$^2$R$^{2a}$; —NR$^1$C(O)OR$^3$; —NR'S(O)$_2$R$^3$; —NR$^1$S(O)$_2$NR$^2$R$^{1a}$; —C(=NR$^1$)R$^5$; —C(=NR$^1$)NR$^2$R$^{1a}$; —NR$^1$CR$^5$(=NR$^5$); —NR$^1$C(=NR$^2$)NR$^{1a}$R$^{2a}$; C$_{6-10}$aryl optionally substituted with 0-2 substituents selected from the group consisting of C$_{1-4}$ alkyl, —OR$^3$, —C$_{1-6}$alkylene-COOR$^3$, —SR$^3$, —NR$^1$R$^2$, halogen, —C(O)NR$^1$R$^2$, and —NR$^1$C(O)R$^5$; 5-10 membered heteroaryl optionally substituted with 0-2 substituents selected from the group consisting of C$_{1-4}$ alkyl, —OR$^3$, —C$_{1-6}$alkylene-COOR$^3$, —SR$^3$, —NR$^1$R$^2$, halogen, —C(O)NR$^1$R$^2$, and —NR$^1$C(O)R$^5$; and 5-10 membered heterocyclyl optionally substituted with 0-2 substituents selected from the group consisting of C$_{1-4}$ alkyl, —OR$^3$, —C$_{1-6}$alkylene-COOR$^3$, —SR$^3$, —NR$^1$R$^2$, halogen, —C(O)NR$^1$R$^2$, and —NR$^1$C(O)R$^5$; R is selected from a group consisting of —H, —C$_{1-9}$alkyl, —CR$^5$R$^6$OC(O) C$_{1-9}$alkyl, and

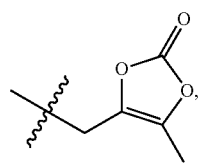 [SMILES: *Cc1oc(=O)oc1C]

each R$^1$, R$^2$, R$^{1a}$, R$^{2a}$, R$^3$, R$^5$ and R$^6$ are independently selected from —H and —C$_{1-4}$alkyl; and R$^7$ is selected from the group consisting of —H, —C$_{1-4}$alkyl, —OH, —OC$_{1-4}$alkyl, —SC$_{1-4}$alkyl and halogen.

In some embodiments, Y is O or S; G is selected from the group consisting of phenyl, imidazole, pyrazole, triazole, tetrazole, thiazole, thiadiazole, oxazole, oxadiazole, isoxazole, isothiazole, pyridine, azetidine, pyrazine, pyrimidine, pyridazine, and pyrazine, each optionally substituted by 0-2 substituents selected from the group consisting of C$_{1-4}$ alkyl, —OR$^3$, —NR$^1$R$^2$, halogen, —C(O)NR$^1$R$^2$, and —NR$^1$C(O) R$^5$; R$^1$, R$^2$ and R$^5$ in G are independently selected from —H and —C$_{1-4}$alkyl; and J, L and M are CR$^7$.

In some embodiments, Y is —O— or —S—; G is selected from the group consisting of phenyl, imidazole, pyrazole, triazole, tetrazole, thiazole, thiadiazole, oxazole, oxadiazole, isoxazole, isothiazole, pyridine, pyrazine, pyrimidine, pyridazine, azetidine, and pyrazine, each optionally substituted by 0-2 substituents selected from the group consisting of C$_{1-4}$ alkyl, —OR$^3$, —C$_{1-6}$alkylene-COOR$^3$, —SR$^3$, —NR$^1$R$^2$, halogen, —C(O)NR$^1$R$^2$, and —NR$^1$C(O)R$^5$, wherein R$^1$, R$^2$ and R$^5$ in G are independently selected from —H and —C$_{1-4}$alkyl; and J, L and M are CR$^7$.

In some embodiments, when Y is —NR$^1$, G cannot be —C(O)NR$^1$R$^2$ or —C(O)OR$^3$.

In some embodiments, n can be 0 or 1. In some such embodiments, n is 0. In some embodiments, n can be 1. In some embodiments, n can be 2. In some embodiments, n can be 3.

Some embodiments of Formula (I) can have the structure of Formula (Ie)

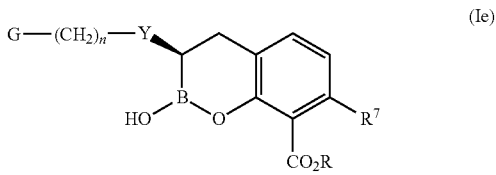

(Ie)

or pharmaceutically acceptable salts thereof, wherein n is 0; R$^7$ is selected from H, F, Cl, —CH$_3$, —CF$_3$, and —Y'—(CH$_2$)$_p$M'; and p is 0 or 1.

Some embodiments of Formula (I) can have the structure of Formula (If):

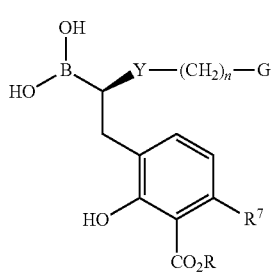

(If)

or pharmaceutically acceptable salts thereof,
wherein n is 0;
$R^7$ is selected from H, F, Cl, —$CH_3$, —$CF_3$, and —Y'—$(CH_2)_pM'$; and
p is 0 or 1.

In some embodiments, G can be a 5-10 membered heteroaryl optionally substituted with one or more $R^{10}$. In some embodiments, G can be a thiadiazole optionally substituted with one or more $R^{10}$. In some embodiments, G can be a thiazole optionally substituted with one or more $R^{10}$. In some embodiments, G can be an imidazole optionally substituted with one or more $R^{10}$. In some embodiments, G can be a triazole optionally substituted with one or more $R^{10}$ In some embodiments, G can be a 3-10 membered heterocyclyl optionally substituted with one or more $R^{10}$. In some embodiments, G can be an azetidine optionally substituted with one or more $R^{10}$. In some embodiments, G can be

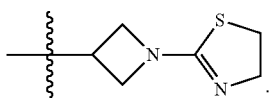 [SMILES: *C1CN(C2=NCCS2)C1]

In some embodiments, G can be a piperazine optionally substituted with one or more $R^{10}$. In some embodiments, G can be

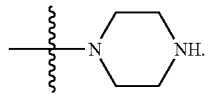

In some embodiments, G can be —$CONH_2$. In some embodiments, G can be —CN. In some embodiments, G can be —$C_{1-4}$ alkyl. In some embodiments, G can be —$CH_3$.

In some embodiments, $R^{10}$ is $R^{11}$. In some embodiments, $R^{10}$ is —$CH_2R^{11}$, —$(CH_2)_2R^{11}$, —$(CH_2)_3R^{11}$, or —$(CH_2)_4R^{11}$. In some embodiments, $R^{10}$ is —$CH_2R^{11}$. In some embodiments, $R^{10}$ is —$(CH_2)_2R^{11}$. In some embodiments, $R^{10}$ is —$(CH_2)_3R^{11}$. In some embodiments, $R^{10}$ is —$(CH_2)_4R^{11}$.

In some such embodiments, G is thiadiazole. In other embodiments, G is thiadiazole optionally substituted with —$NR^1R^2$ or —$NR^1C(O)R^5$, wherein $R^1$ and $R^5$ are independently H or —$C_{1-4}$alkyl. In other embodiments, G is triazole optionally substituted with $NR^1R^2$, wherein $R^1$, $R^2$ and $R^5$ are independently H or —$C_{1-4}$alkyl. In other embodiments, G is tetrazole optionally substituted with methyl. In still other embodiments, G is pyridine, thiazole, or phenyl.

In other embodiments, G is optionally substituted azetidine. In some embodiments, G is optionally substituted pyridine. In other embodiments, G is optionally substituted thiazole. In still other embodiments, G is optionally substituted phenyl. In some embodiments, G is triazole optionally substituted with —$C_{1-6}$alkylene-COOH. In some embodiments, G is triazole optionally substituted with —$(CH_2)_3$—COOH.

In some embodiments, Y is S; n is 1 or 2; G is —C(O)$NR^1R^2$ or C(=$NR^1$)$R^5$; and J, L, and M are $CR^7$. In some such embodiments, $R^7$ is H. In other embodiments, $R^1$ is H and $R^2$ is H. In some embodiments, $R^1$ is $C_{1-4}$ alkyl and $R^2$ is $C_{1-4}$ alkyl.

In some embodiments, Y is —$CH_2$—; n is 0 to 2; G is —C(O)$NR^1R^2$; and J, L and M are $CR^7$.

Some embodiments of Formula (I) can have the structure of Formula (Ig) or (Ih):

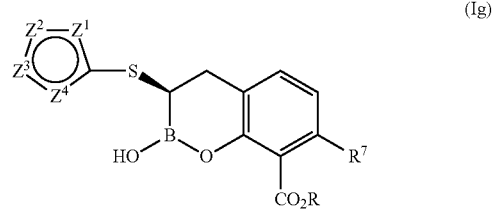

(Ig)

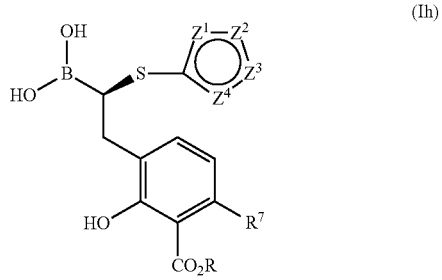

(Ih)

or pharmaceutically acceptable salts thereof, wherein n is 0;
each $Z^1$, $Z^2$, $Z^3$ and $Z^4$ are independently selected from N, $NR^{12}$, O, S, and $CR^{12}$ provided that $Z^1$ to $Z^4$ are selected such that a five membered aromatic ring is formed;
each $R^{12}$ is independently H or $(CH_2)_{0-5}R^{11}$; and
each $R^{11}$ is independently selected from $C_1$-$C_6$ alkyl; halo$C_{1-6}$alkyl; —$OR^3$; —$C_{1-6}$alkylene-$COOR^3$; —$SR^3$; halogen; —CO—$C_{1-4}$alkyl; C(O)$NR^1R^2$; —$NR^1R^2$; —$NR^1(CH_2)_{0-4}COR^5$; —$NR^1(CH_2)_{0-4}$C(=$NR^2$)$R^5$; —$NR^1$—CH—[$(CH_2)_{0-4}$—$NR^{1a}R^{2a}$]$_2$; —$NR^1$—$(CH_2)_{1-5}$—$R^3$; —$NR^1(CH_2)_{1-4}$—$NR^{1a}R^{2a}$; —N[$(CH_2)_{1-4}$—$NR^1R^2$]$_2$; —S$(CH_2)_{0-4}$C(=$NR^1$)$R^5$; —S$(CH_2)_{1-4}$—$R^3$; —S$(CH_2)_{0-4}$—$NR^1R^2$; —S—CH—[$(CH_2)_{0-4}$—$NR^1R^2$]$_2$; —S[$(CH_2)_{1-4}$—$NR^1R^2$]$_2$; —S$(CH_2)_{0-4}$-3-10 membered heterocyclyl; —S$(CH_2)_{0-4}$-3-10 membered heterocyclyl-$NR^1R^2$; —S$(CH_2)_{0-4}$-5-10 membered heteroaryl-$NR^1R^2$; —S(O)$_2NR^1R^2$; and —O—$C_{1-6}$alkylene-$NR^1R^2$; $C_{3-7}$ carbocyclyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 6 to 10 membered aryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; and 5-10 membered heteroaryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy. In some embodiments, $Z^1$ can be S. In some embodiments, $Z^2$ and $Z^3$ can be independently N, $NR^{12}$, or $CR^{12}$. In some embodiments, $Z^4$ can be N or $CR^{12}$. In some embodiments, $Z^1$ to $Z^4$ can be selected to form a five-membered aromatic ring selected from the group consisting of

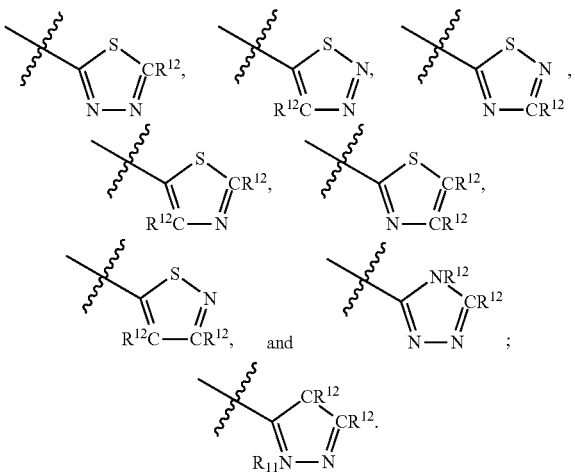

In some embodiments, $R^{12}$ can be H. In some embodiments, $R^{12}$ can be $R^{11}$. In some embodiments, $R^{12}$ can be —$CH_2$—$R^{11}$. In some embodiments, $R^{12}$ can be —$(CH_2)_2$—$R^{11}$. In some embodiments, $R^{12}$ can be —$(CH_2)_3$—$R^{11}$. In some embodiments, $R^{12}$ can be —$(CH_2)_4$—$R^{11}$.

In some embodiments, $R^{11}$ can be —$CF_3$, $CHF_2$, or $CH_2F$. In some embodiments, $R^{11}$ can be $CF_3$. In some embodiments, $R^{11}$ can be $C_1$-$C_6$ alkyl. In some embodiments, $R^{11}$ can be $CH_3$. In some embodiments, $R^{11}$ can be a $C_{1-4}$ alkyl optionally substituted with a 3-10 membered heterocyclyl. In some embodiments, $R^{11}$ can be —$CH_2$-piperazine. In some embodiments, $R^{11}$ can be an optionally substituted $C_{1-6}$alkylene-3-10 membered heterocyclyl. In some embodiments, $R^{11}$ can be azetidine optionally substituted with one or more $NH_2$. In some embodiments, $R^{11}$ can be

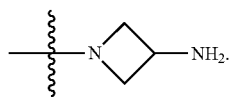

In some embodiments, $R^{11}$ can be —$(CH_2)_{0-4}NR^1R^2$. In some embodiments, $R^{11}$ can be $NH_2$, —$CH_2NH_2$, or —$(CH_2)_4NH_2$.

In some embodiments, $R^{11}$ can be $NR^1R^2$, $R^1$ is H, and $R^2$ is an optionally substituted —$C_{1-4}$alkyl or an optionally substituted 3-8 membered heterocyclyl. In some embodiments, $R^2$ can be azetidine. In some embodiments, $R^2$ can be

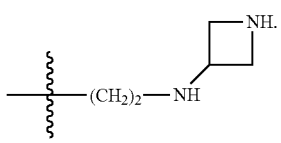

In some embodiments, $R^{11}$ can be

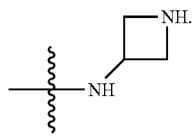 [SMILES: *NC1CNC1]

In some embodiments, $R^2$ can be —$(CH_2)_2$-piperazine. In some embodiments, $R^2$ can be pyrrolidine. In some embodiments, $R^2$ can be —$(CH_2)_2$—$NH_2$ or —$(CH_2)_3$—$NH_2$.

In some embodiments, $R^{11}$ can be —$C(O)NR^1R^2$. In some embodiments, $R^{11}$ can be —$CONH_2$. In some embodiments, $R^{11}$ can be —$NR^1C(O)R^5$. In some embodiments, $R^{11}$ can be —NHCOH or —$NHCOCH_3$. In some embodiments, $R^{11}$ can be —$N((CH_2)_{0-4}$—$NR^1R^2)_2$. In some embodiments, $R^{11}$ can be —$N((CH_2)_2$—$NH_2)_2$. In some embodiments, $R^{11}$ can be —$NR^1$—CH—$[(CH_2)_{0-4}$—$NR^{1a}R^{2a}]_2$. In some embodiments, $R^{11}$ can be —$NHCH(CH_2$—$NH_2)_2$. In some embodiments, $R^{11}$ can be —$NH(CH_2)_{1-4}$—$NR^1R^2$. In some embodiments, $R^{11}$ can be —$NH(CH_2)_2$—NH-azetidine. In some embodiments, $R^{11}$ can be —NR'$(CH_2)_{0-4}C(=NR^1)R^5$. In some embodiments, $R^{11}$ can be —$NHC(=NH)NH_2$. In some embodiments, $R^{11}$ can be —$S(CH_2)_{0-4}C(=NR^1)R^5$. In some embodiments, $R^{11}$ can be —$SCH_2C(=NH)NH_2$. In some embodiments, $R^{11}$ can be —$S(CH_2)_{0-4}$-3-10 membered heterocyclyl. In some embodiments, $R^{11}$ can be —$S(CH_2)_2$-piperazine. In some embodiments, $R^{11}$ can be —$S(O)_2NR^1R^2$. In some embodiments, $R^{11}$ can be —$S(O)_2NH_2$. In some embodiments, $R^{11}$ can be —$S(CH_2)_{0-4}$—$NR^1R^2$. In some embodiments, $R^{11}$ can be —$S(CH_2)_2NH_2$ or —$S(CH_2)_3NH_2$. In some embodiments, $R^{11}$ can be —$SR^3$. In some embodiments, $R^{11}$ can be azetidine or piperidine. In some embodiments, $R^{11}$ can be —$S(CH_2)_{1-4}$-3-10 membered heterocyclyl. In some embodiments, $R^{11}$ can be —$S(CH_2)_2$-morpholine. In some embodiments, $R^{11}$ can be —$S(CH_2)_{1-4}$—$R^3$. In some embodiments, $R^{11}$ can be —$S(CH_2)_{0-4}$-5-10 membered heteroaryl-$NH_2$. In some embodiments, $R^{11}$ can be

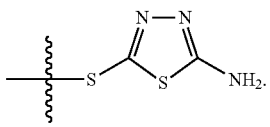 [SMILES: *Sc1nnc(N)s1]

In some embodiments, $R^{11}$ can be —$OR^3$. In some embodiments, $R^{11}$ can be —$O(CH_2)_{0-4}$—$NR^1R^2$. In some embodiments, $R^{11}$ can be —$O(CH_2)_2NH_2$.

In some embodiments, $R^7$ is selected from the group consisting of —H, —OH, —$C_{1-4}$alkyl, —O—$C_{1-4}$alkyl, —S—$C_{1-4}$alkyl, halogen, —$CF_3$, and cyano. In other embodiments, $R^7$ is selected from the group consisting of F, Cl, Me, —$CF_3$, —SMe, and —OMe. In some embodiments, $R^7$ is H. In other embodiments, $R^7$ is F. In some embodiments, $R^7$ is —OMe. In some embodiments, $R^7$ is —SMe. In some embodiments, $R^7$ is —S(O)Me. In some embodiments, $R^7$ is independently selected from —OH, —$C_{1-4}$alkyl, —O—$C_{1-4}$alkyl, —S—$C_{1-4}$alkyl, —S(O)—$C_{1-4}$alkyl, and halogen. In some embodiments, $R^7$ is present 1 to 3 times and each $R^7$ is triazole.

In some embodiments, $R^7$ is present 1 to 3 times and each $R^7$ is independently —$(CH_2)_m$—Y'—$(CH_2)_p$M'; m and p are independently 0 to 3; Y' is selected from the group consisting of —S—, —O— and —NR'—; M' is selected from the group consisting of NR¹R², —SO₃R³, —CN, —C(O)NR¹R²; —C₁₋₄ alkyl optionally substituted with 1-2 substituents selected from the group consisting, —OR³, —NR¹R², halogen, —C(O)NR¹R², and —NR¹C(O)R⁵; C₃₋₁₀ cycloalkyl optionally substituted with 1-2 substituents selected from the group consisting of C₁₋₄ alkyl, —OR³, —NR¹R², halogen, —C(O)NR¹R², and —NR¹C(O)R⁵; C₆₋₁₀ aryl optionally substituted with 1-2 substituents selected from the group consisting of C₁₋₄ alkyl, —OR³, —NR¹ R², halogen, —C(O)NR¹R², and —NR¹ C(O)R⁵; 5 to 10 membered heteroaryl optionally substituted with 1-2 substituents selected from the group consisting of C₁₋₄ alkyl, —OR³, —NR¹R², halogen, —C(O)NR¹R², and —NR¹C(O)R⁵; and 4 to 10 membered heterocyclyl optionally substituted with 1-2 substituents selected from the group consisting of C₁₋₄ alkyl, —OR³, —NR¹R², halogen, —C(O)NR¹R², and —NR¹C(O)R⁵.

In some embodiments, R⁷ is present once. In some embodiments, R⁷ is present twice. In some embodiments, R⁷ is present three times.

In some embodiments, Y' is O. In some embodiments, Y' is NH. In some embodiments, p is 0, 1, or 2.

In some embodiments, M' is cyclopropyl, —SO₃CH₃, SCH₃, —NH₂, or —CN. In some embodiments, M' is C₁₋₄ alkyl optionally substituted with 0-2 substituents selected from the group consisting, —OR³, —NR¹R², halogen, —C(O)NR¹R², and —NR¹C(O)R⁵. In some embodiments, M' is CHF₂, CF₃, (CH₂)₂F, or (CH₂)₂OCH₃, In some embodiments, M' is CH₃, CH₂CH₃, or CH(CH₃)₂CH₂CH(CH₃)₂. In some embodiments, M' is C(O)NR¹R². In some embodiments, R¹ is H and R¹ is azetidine. In some embodiments, R⁷ is

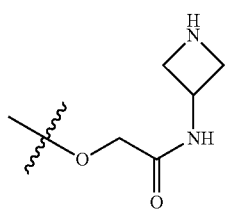

In some embodiments, R⁷ is —O(CH₂)CONH₂. In some embodiments, M' is a 5 to 10 membered heteroaryl. In some embodiments, M' is thiadiazole.

In some embodiments, R⁷ is present 1 to 3 times and each R⁷ is independently selected from the group consisting of —OH, halogen, —CF₃, C₁-C₆ alkenyl, C₁-C₆ alkynyl, C₁-C₆ heteroalkyl, C₃-C₇ carbocyclyl, 5-10 membered heterocyclyl, aryl, 5-10 membered heteroaryl, cyano, C₁-C₆ alkoxy(C₁-C₆)alkyl, aryloxy, sulfhydryl (mercapto), and —(CH₂)ₘ—Y'—(CH₂)ₚM'; m and p are independently 0 to 3; Y' is selected from the group consisting of —S—, —S(O)—, —S(O)₂—, —O—, —CR⁵R⁶—, and —NR¹—; M' is selected from the group consisting of —C(O)NR¹R²; —C(O)NR¹OR³; —NR¹C(O)R⁵; —NR¹C(O)NR²R¹ᵃ; —NR¹C(O)OR³; —NR¹S(O)₂R³; —NR¹S(O)₂NR²R¹ᵃ; —C(=NR¹)R⁵; —C(=NR¹)NR²R¹ᵃ; —NR¹CR⁵(=NR²); —NR¹C(=NR²)NR¹ᵃR²ᵃ; C₁₋₄ alkyl optionally substituted with 0-2 substituents selected from the group consisting, —OR³, —NR¹R², halogen, —C(O)NR¹R², and —NR¹C(O)R⁵; C₃₋₁₀ cycloalkyl optionally substituted with 0-2 substituents selected from the group consisting of C₁₋₄ alkyl, —OR³, —NR¹R², halogen, —C(O)NR¹R², and —NR¹C(O)R⁵; C₆₋₁₀ aryl optionally substituted with 0-2 substituents selected from the group consisting of C₁₋₄ alkyl, —OR³, —NR¹R², halogen, —C(O)NR¹R², and —NR¹C(O)R⁵; 5 to 10 membered heteroaryl optionally substituted with 0-2 substituents selected from the group consisting of C₁₋₄ alkyl, —OR³, —NR¹R², halogen, —C(O)NR¹R², and —NR¹C(O)R⁵; and 4 to 10 membered heterocyclyl optionally substituted with 0-2 substituents selected from the group consisting of C₁₋₄ alkyl, —OR³, —NR¹R², halogen, —C(O)NR¹R², and —NR¹C(O)R⁵; and with the proviso that the compound does not have the structure selected from the group consisting of

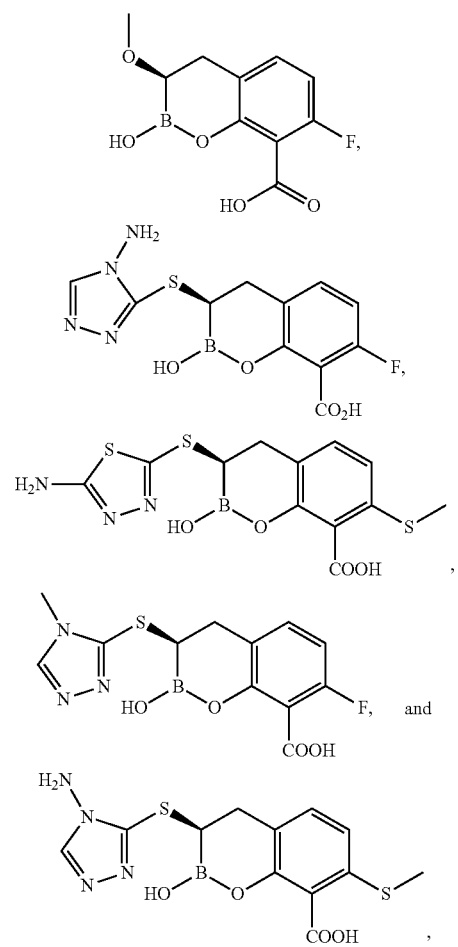

or pharmaceutically acceptable salts thereof.

In some embodiments, R⁷ is independently selected from —OH, —C₁₋₄alkyl, —O—C₁₋₄alkyl, —S(O)—C₁₋₄alkyl, and halogen; and with the proviso that the compound does not have the structure selected from the group consisting of

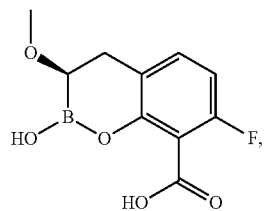

-continued

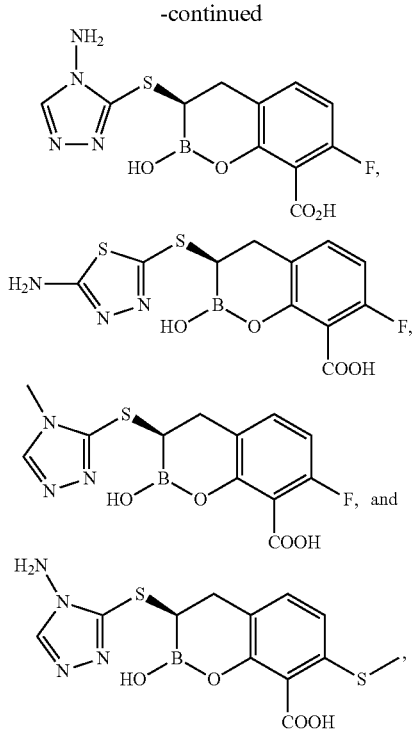

or pharmaceutically acceptable salts thereof.

In some embodiments, $R^a$ can be C(O)OH. In some embodiments, $R^a$ can be C(O)OR, and R can be —$CR^5R^6$OC(O)$C_{1-9}$alkyl or —$CR^5R^6$OC(O)O$C_{1-9}$alkyl. In some embodiments, R can be —$CH_2$OC(O)OCH$(CH_3)_2$. In some embodiments, R can be —$CH_2$OC(O)OC$(CH_3)_3$. In some embodiments, R can be —$CH_2$OC(O)OC$(CH_2)_2CH_3$. In some embodiments, R can be —$CH_2$OC(O)OCH $(CH_2CH_3)_2$. In some embodiments, R can be —$CH_2$C(O) OCH$_2$CH$_3$. In some embodiments, R can be

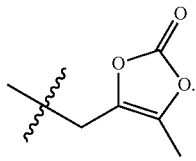 [SMILES: *Cc1oc(=O)oc1C]

For some embodiments of Formula (I), M' is selected from the group consisting of —C(O)NR$^1$R$^2$; —C(O) NR$^1$OR$^3$; —NR$^1$C(O)R$^5$; —NR$^1$C(O)NR$^2$R$^{1a}$; —NR$^1$C(O) OR$^3$; —NR$^1$S(O)$_2$R$^3$; —NR$^1$S(O)$_2$NR$^2$R$^{1a}$; —C(=NR$^1$) NR$^2$R$^{1a}$; —NR$^1$CR$^5$(=NR$^2$); —NR$^1$C(=NR$^2$)NR$^{1a}$R$^{2a}$; aryl optionally substituted with 0-2 substituents selected from the group consisting of —OR$^3$, —NR$^1$R$^2$, halogen, —C(O)NR$^1$R$^2$, and —NR$^1$C(O)R$^5$; heteroaryl optionally substituted with 0-2 substituents selected from the group consisting of —OR$^3$, —NR$^1$R$^2$, halogen, —C(O)NR$^1$R$^2$, and —NR$^1$C(O)R$^5$; and heterocyclyl optionally substituted with 0-2 substituents selected from the group consisting of —OR$^3$, —NR$^1$R$^2$, halogen, —C(O)NR$^1$R$^2$, and —NR$^1$C(O) R$^5$.

Some specific embodiments of the compounds described herein have the following structures:

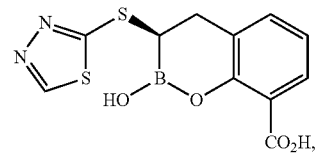

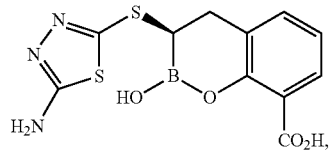

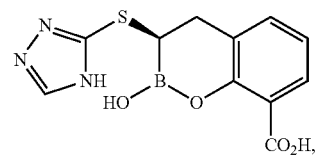

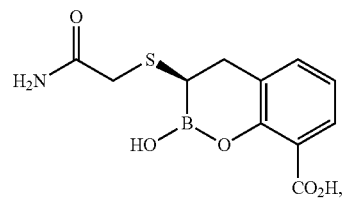

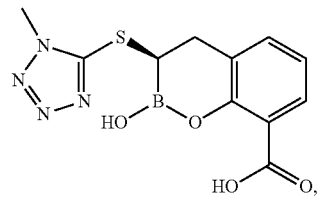

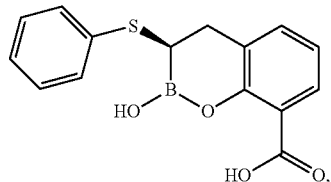

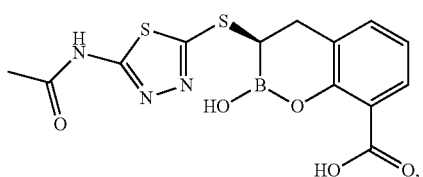

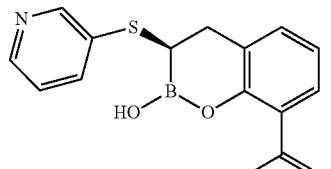

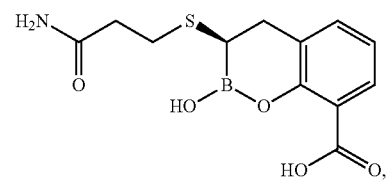

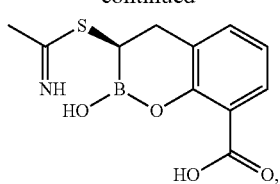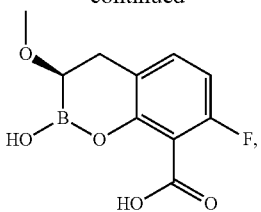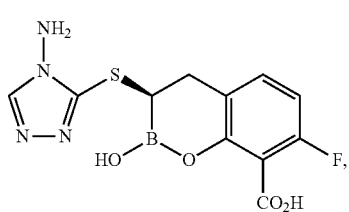
Some specific embodiments of the compounds described herein have the following structures:
or pharmaceutically acceptable salts thereof.
Some specific embodiments of the compounds described herein have the following structures:

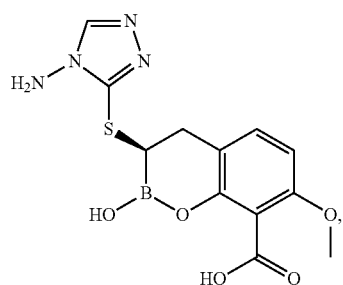
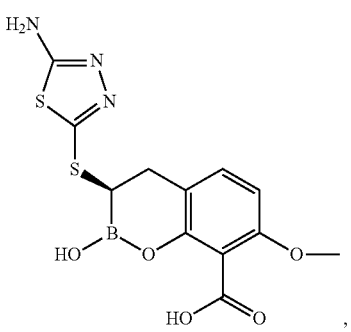
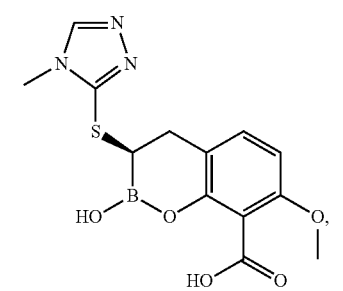
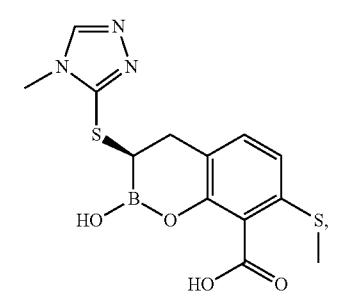
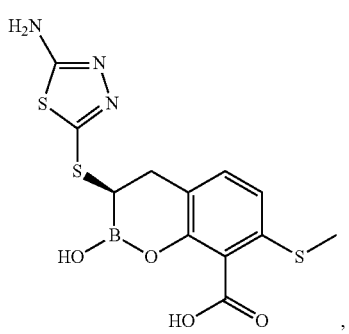
-continued
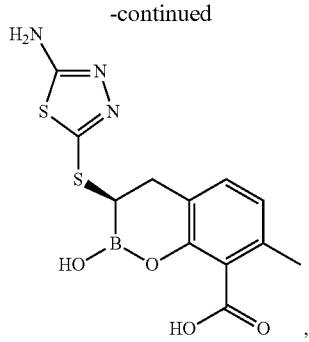
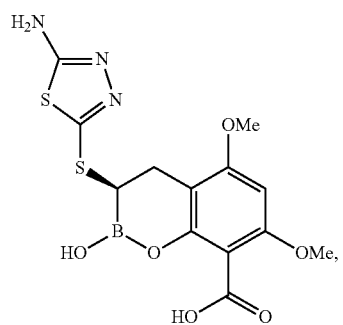
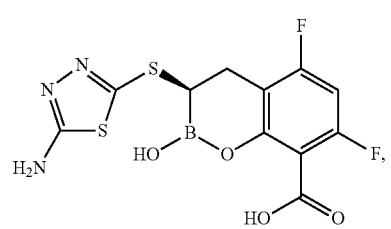
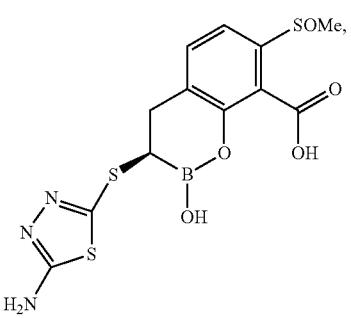
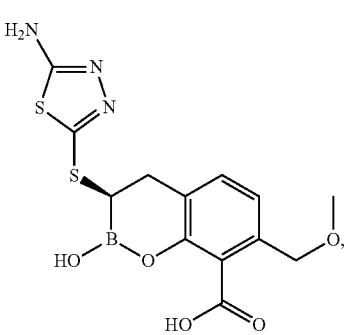

-continued
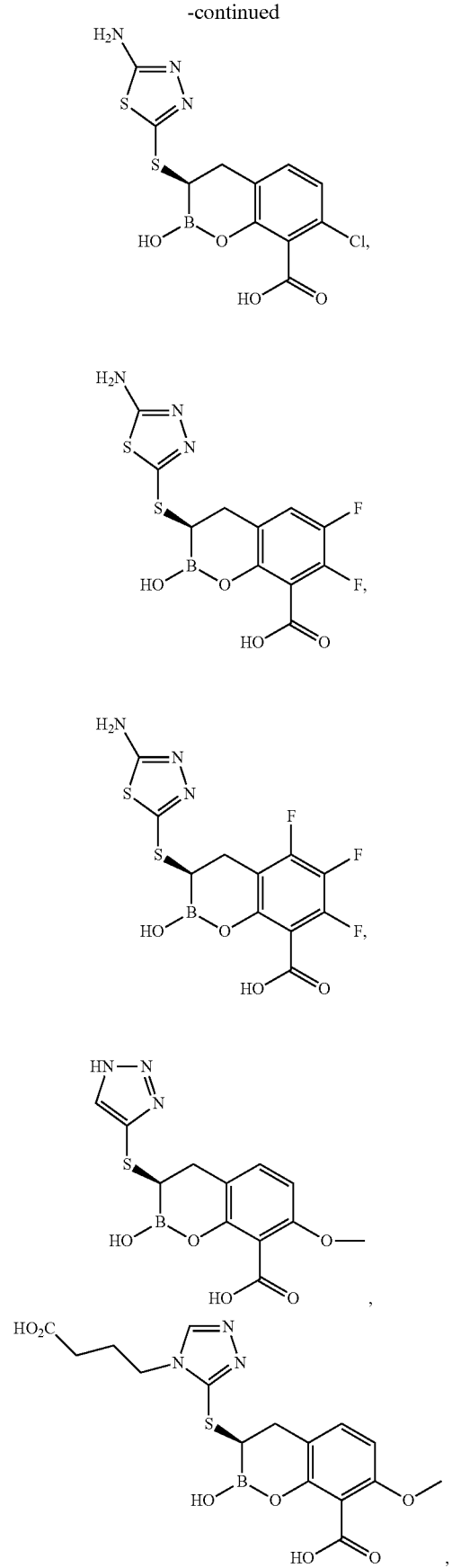
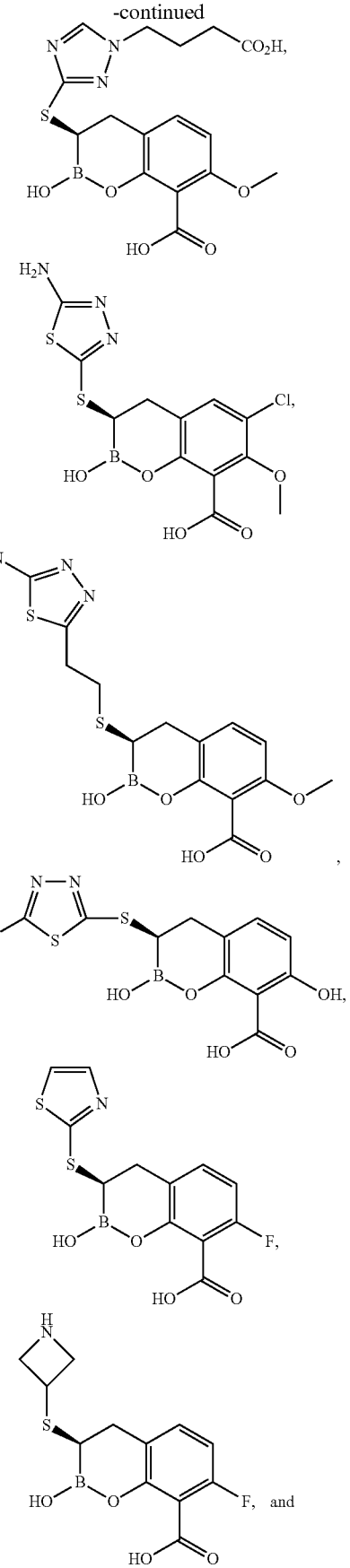

-continued
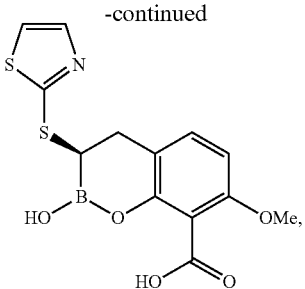
or pharmaceutically acceptable salts thereof.
Some specific embodiments of the compounds described herein have the following structures:
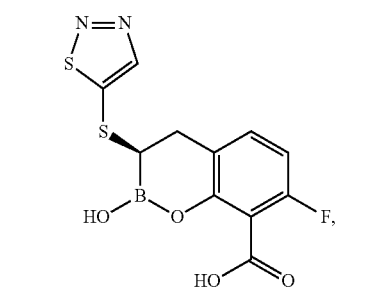
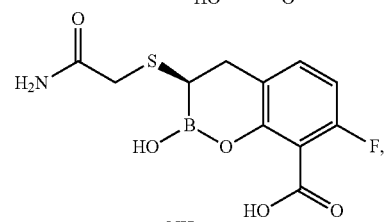
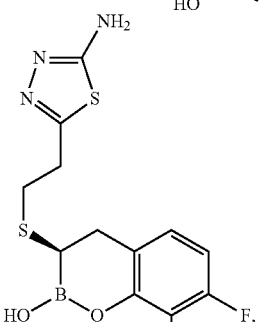
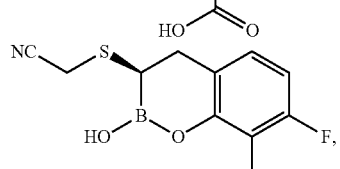
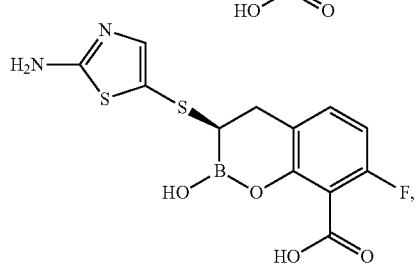
-continued
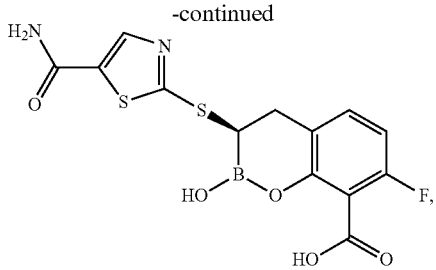
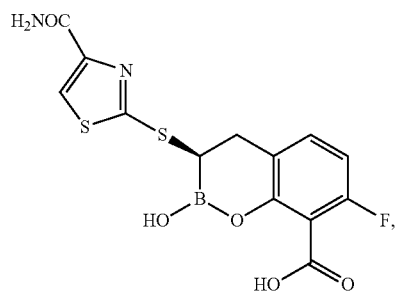
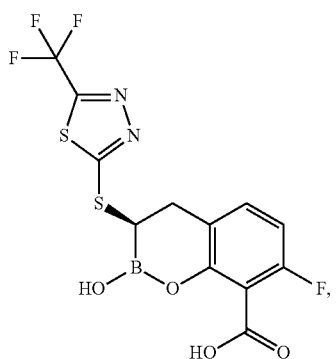
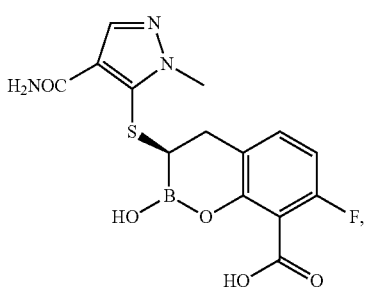
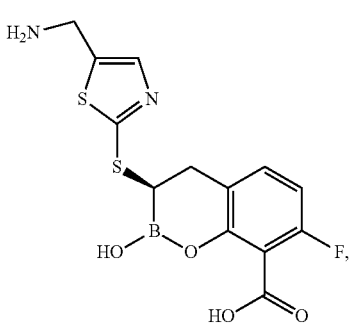

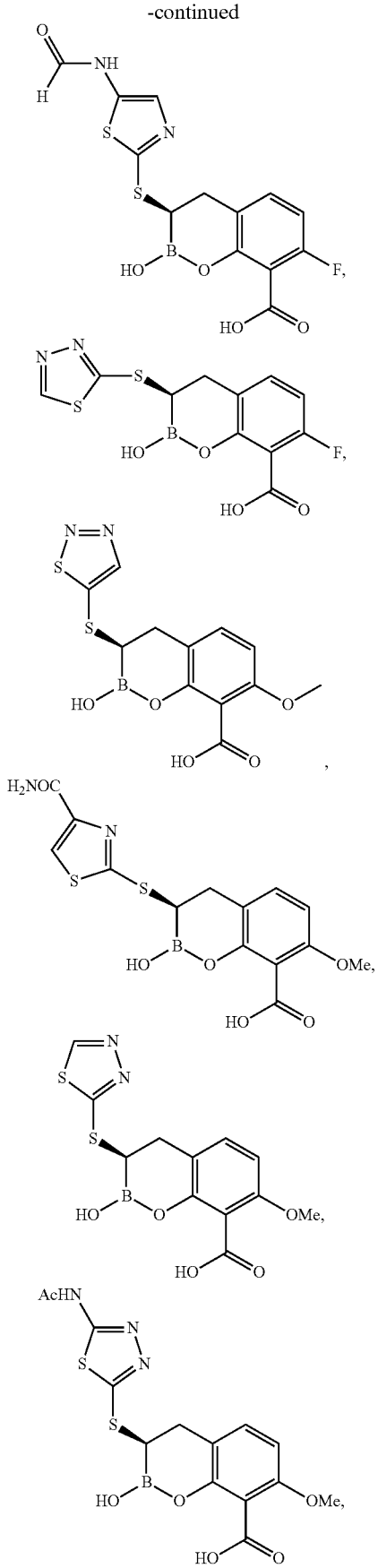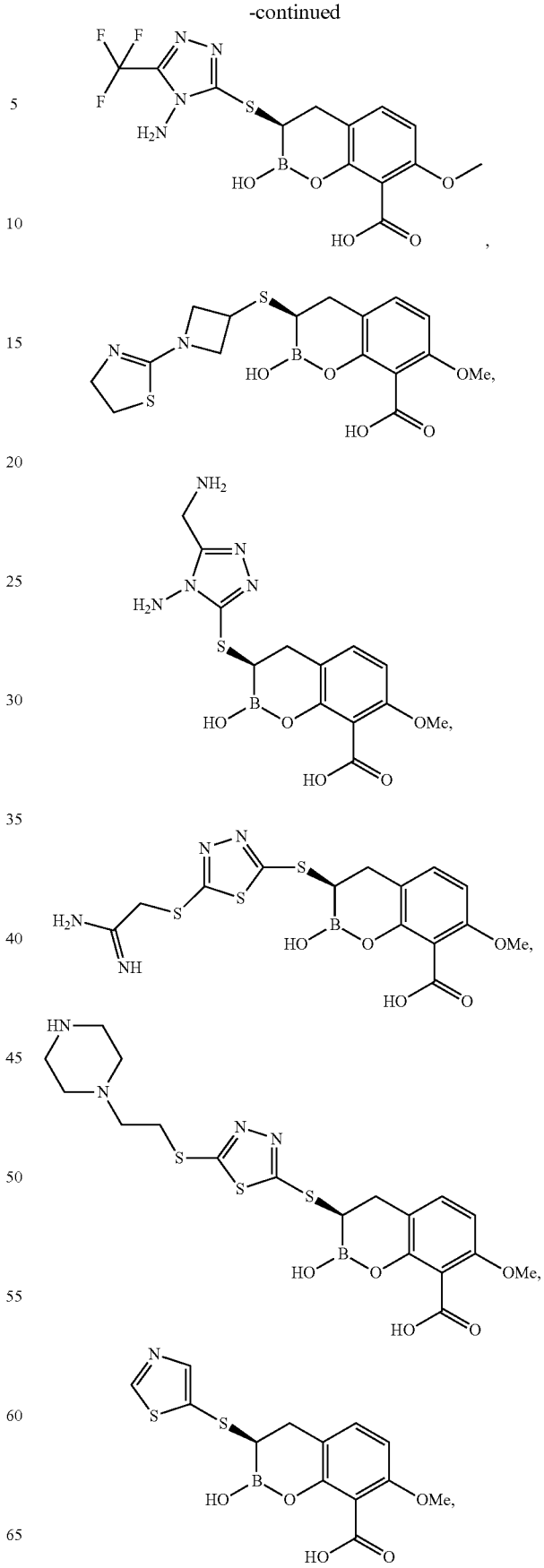

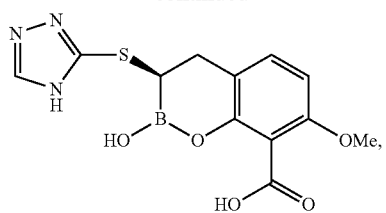
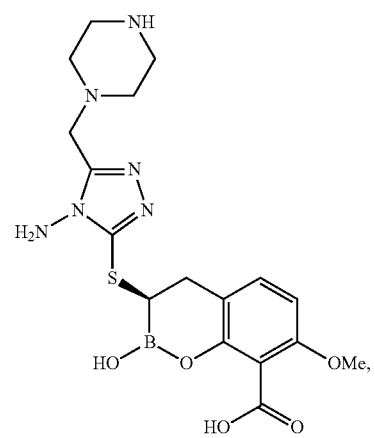
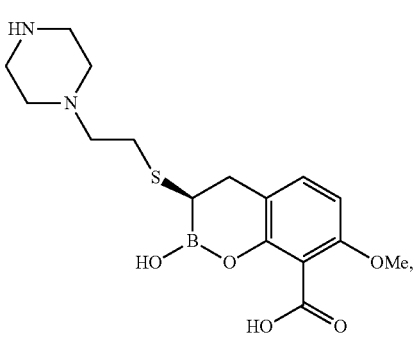
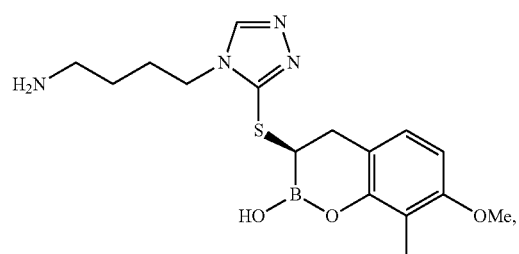
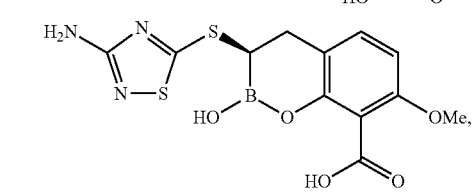
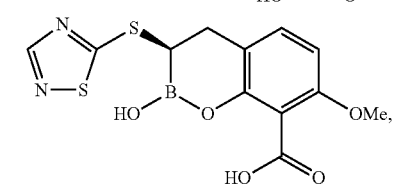
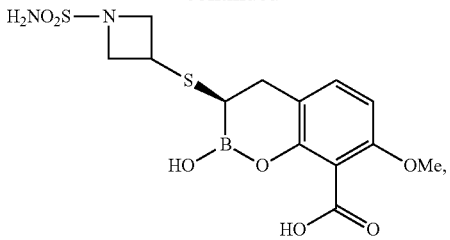
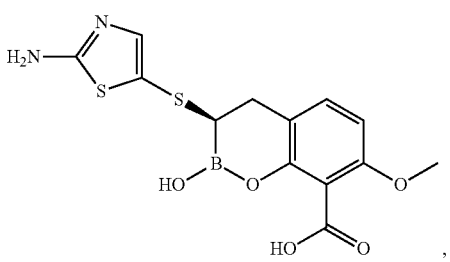
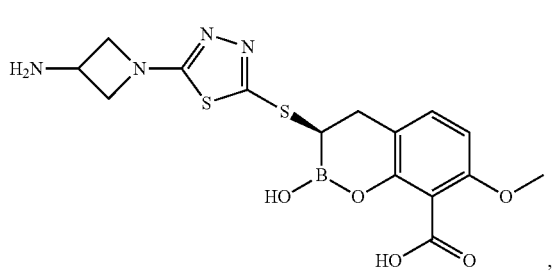
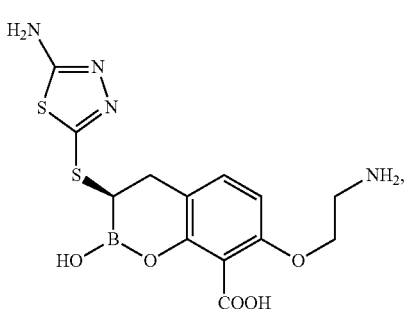
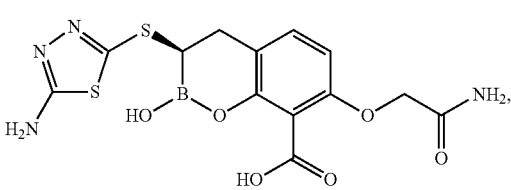
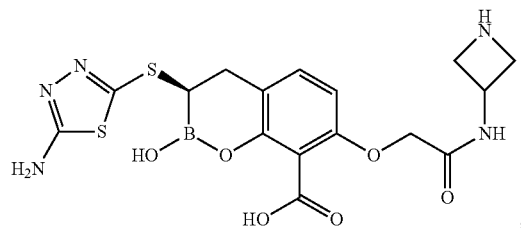

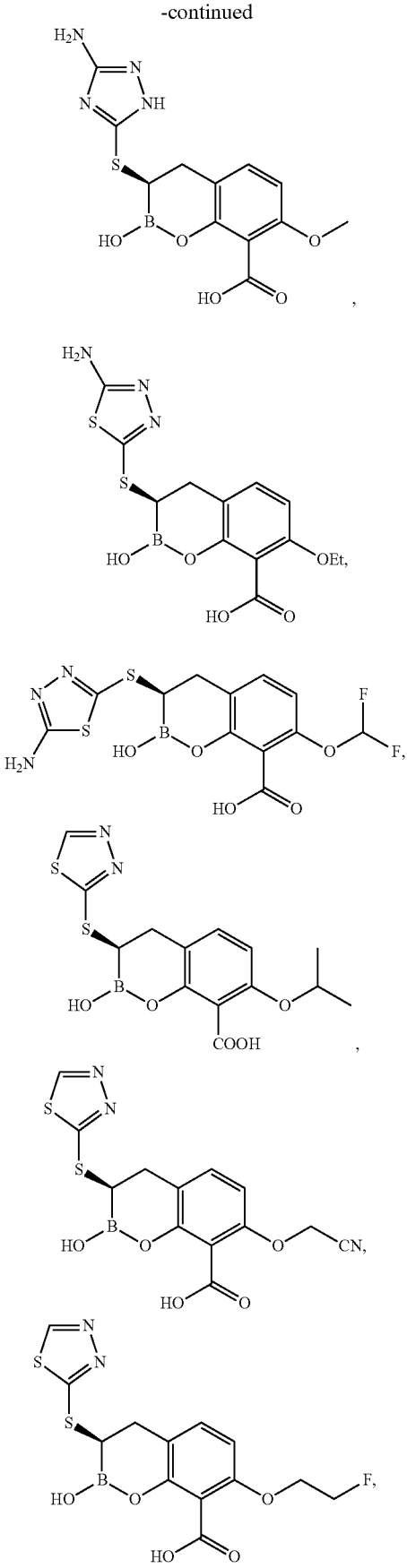
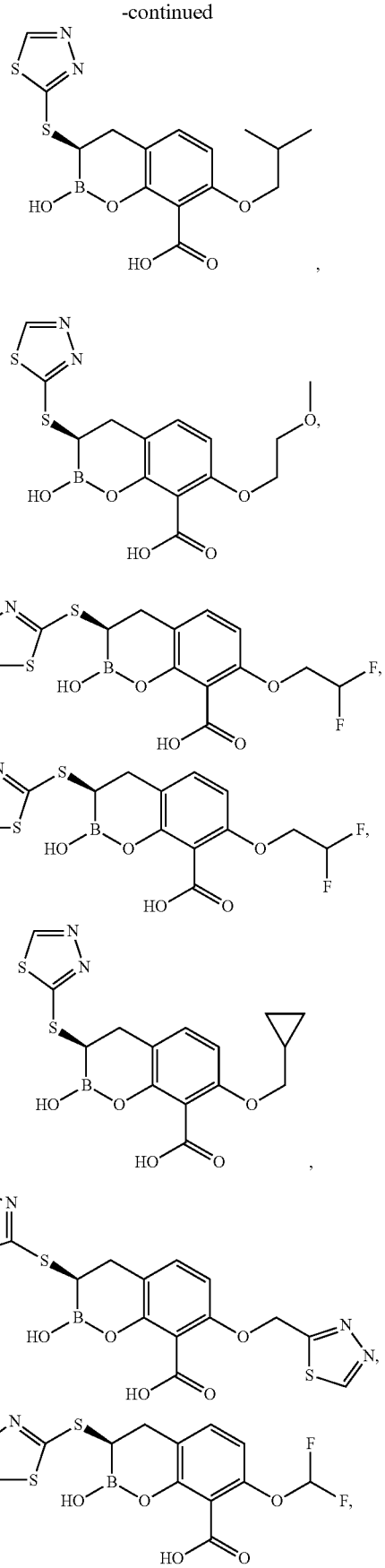

35
-continued
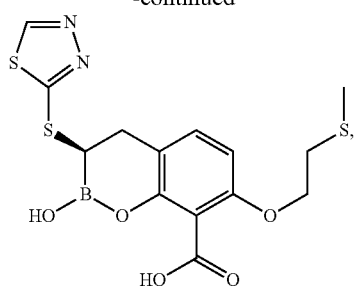
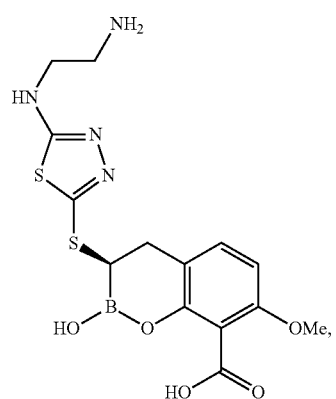
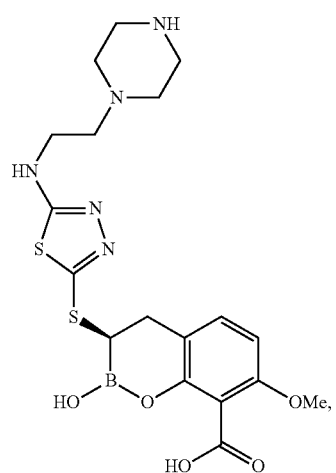
36
-continued
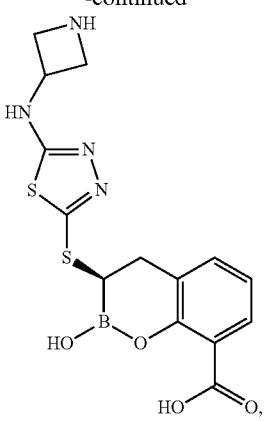
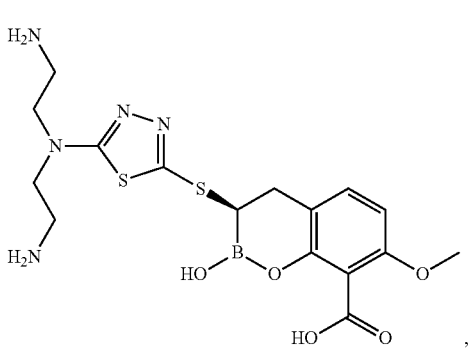

37
-continued
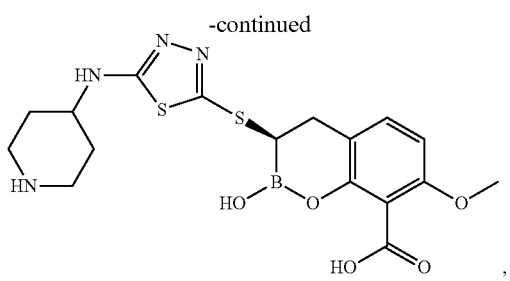
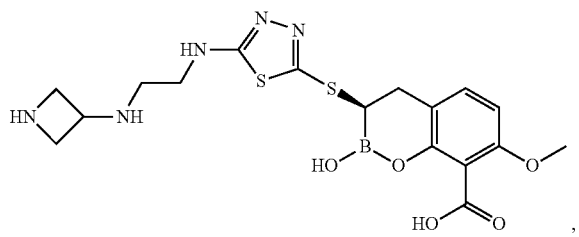
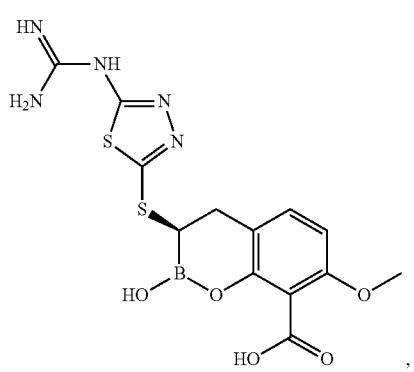
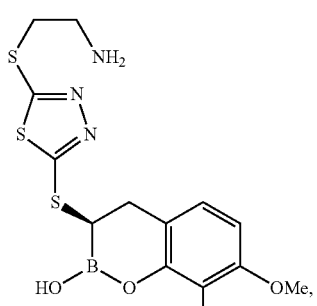
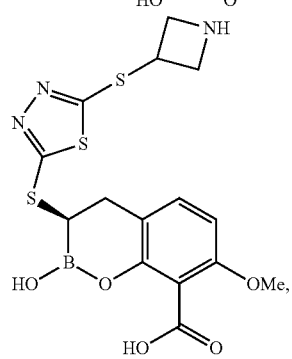
38
-continued
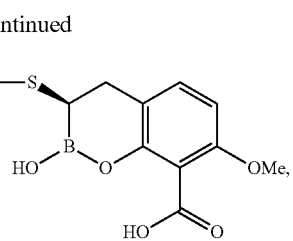
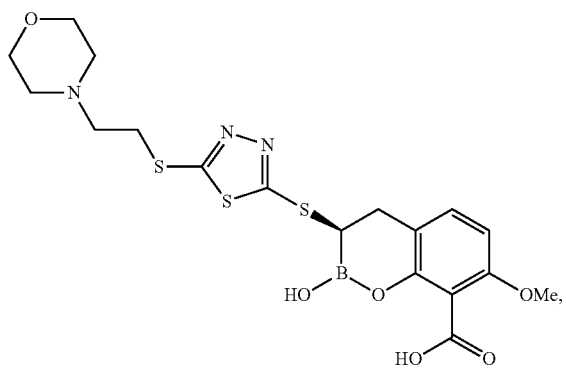
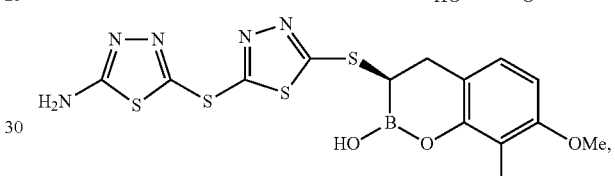
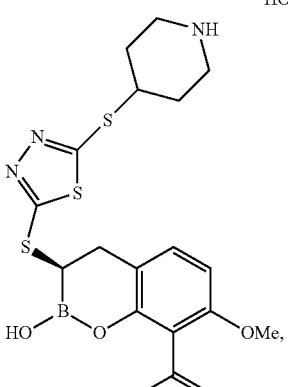
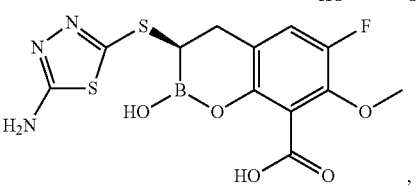

39
-continued
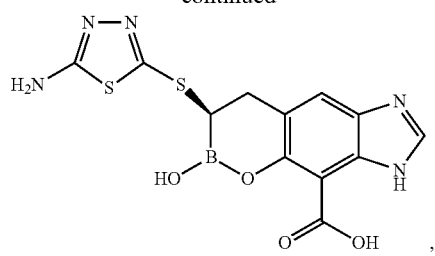
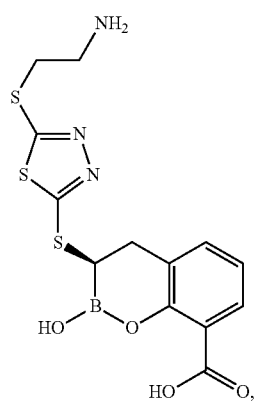
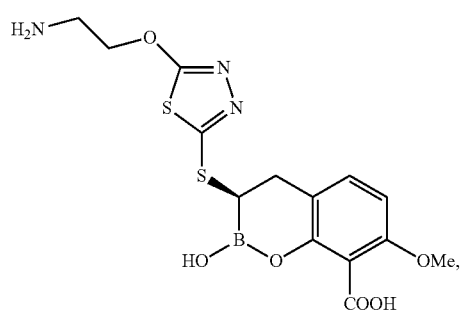
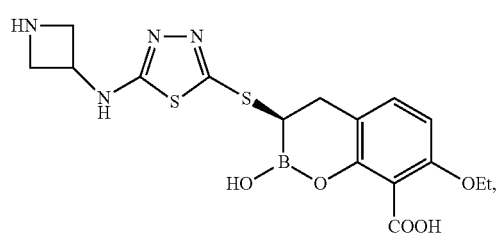
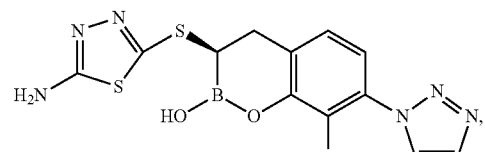
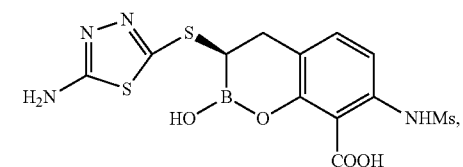
40
-continued
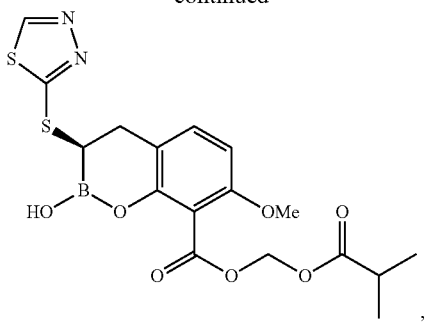
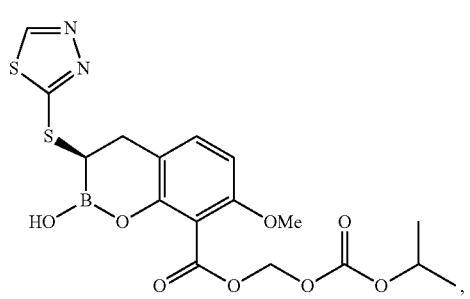
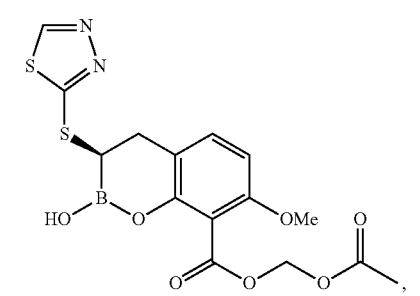
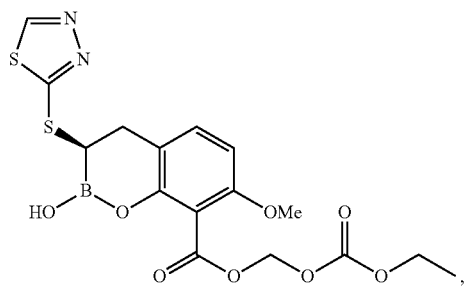
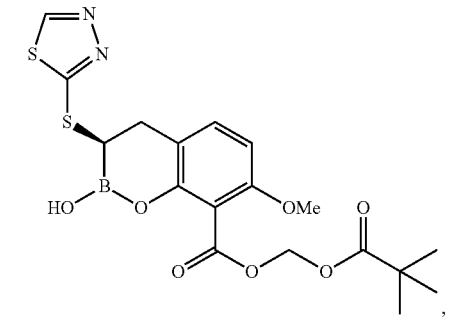

-continued
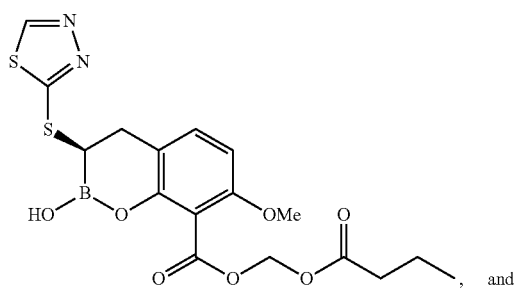, and
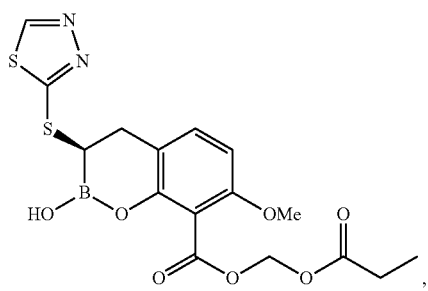,
or pharmaceutically acceptable salts thereof.
In some embodiments, the compound described herein does not have the structure selected from the group consisting of:
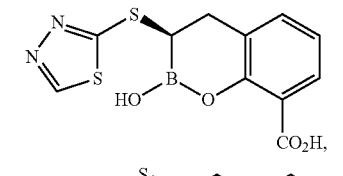,
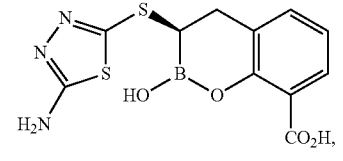,
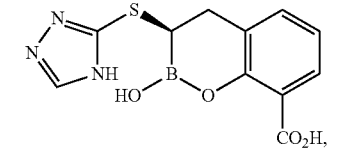,
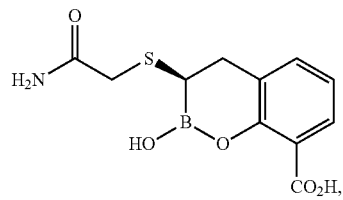,
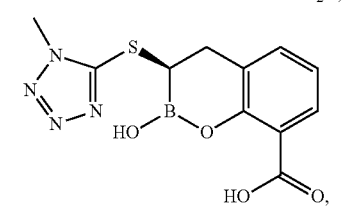,
-continued
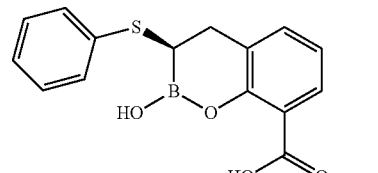,
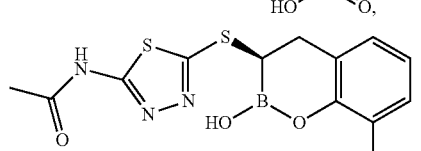,
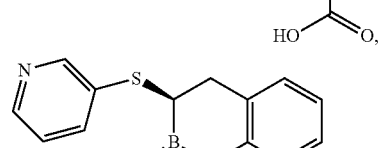,
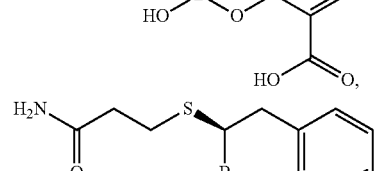,
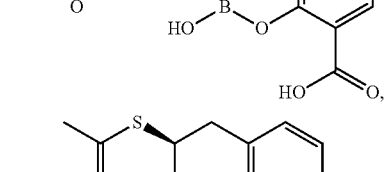,
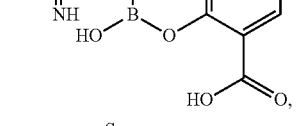,
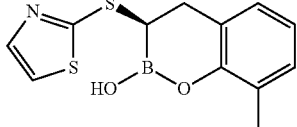,
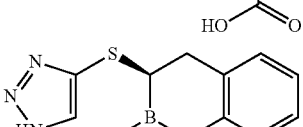,
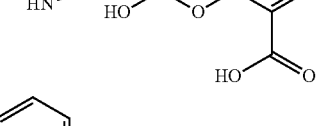,
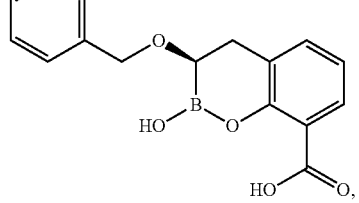,
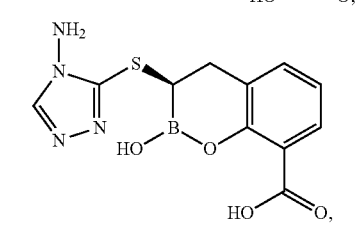, -continued

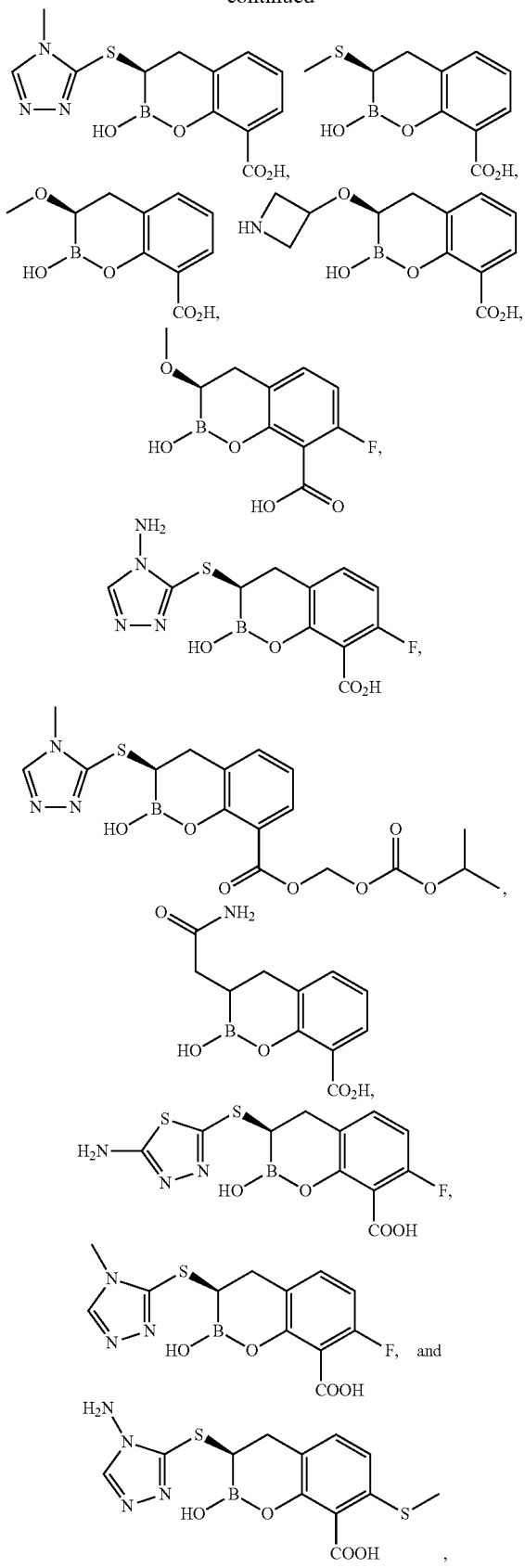

or pharmaceutically acceptable salts thereof.

Some embodiments of any of the compounds described above include prodrugs (e.g., prodrug esters), metabolites, stereoisomers, hydrates, solvates, polymorphs, and pharmaceutically acceptable salts of those compounds.

In some embodiments, the monosaccharide or monosaccharide derivative is meglumine.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

In some embodiments, due to the facile exchange of boron esters, the compounds described herein may convert to or exist in equilibrium with alternate forms. Accordingly, in some embodiments, the compounds described herein may exist in combination with one or more of these forms. For example, as shown below, the compounds disclosed herein may exist in cyclic form as cyclic boronate monoesters as formula I or in acyclic form as boronic acids as formula I.1 (*Biochemistry*, 2000, 39, 5312-21), or may exist as a mixture of the two forms depending on the medium.

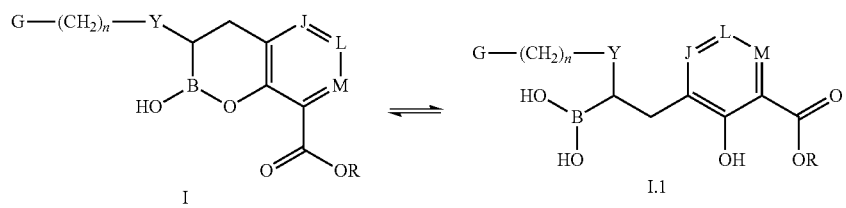

In some embodiments, the compounds described herein may exist in cyclic dimeric form as Formula (C) or trimeric form as Formula (D), tetrameric form as Formula (E) as shown below, or acrylic dimeric, trimeric or tetrameric forms and the like. In some embodiments, X' is —Y—(CR⁸R⁹)n-G in Formula C, D and E. In some embodiments, X' can be —Y—CH₂-G in Formula C, D and E.

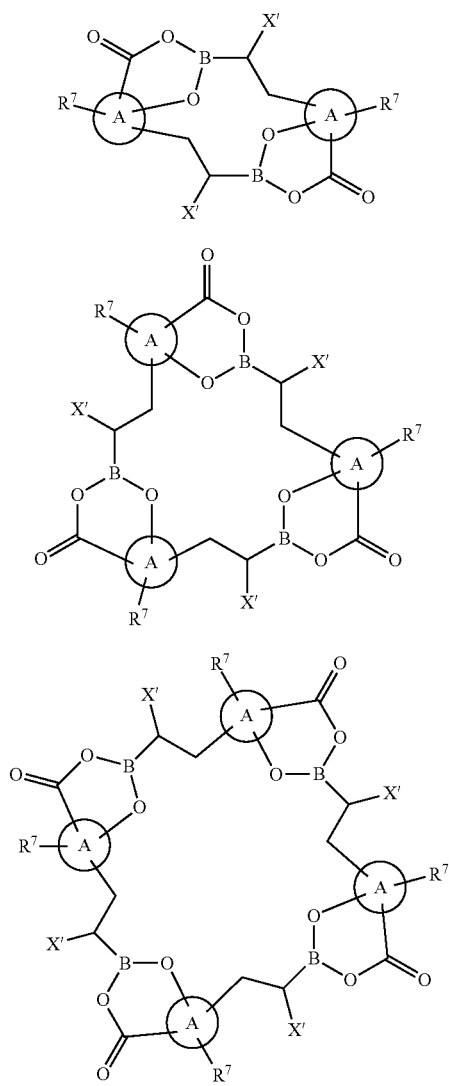

Definitions

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Prodrugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group of the compounds may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group of the compounds may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO- and RS-, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O) OH).

A "cyano" group refers to a "—CN" group.
A "cyanato" group refers to an "—OCN" group.
An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, a$C_{6-10}$ ryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

In some embodiments, substituted group(s) is (are) substituted with one or more substituent(s) individually and independently selected from $C_1$-$C_1$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

"Monosaccharide" as used herein refers to a chemical compound of general formula $C_x(H_2O)_x$, where x is 3 to 10. Examples of monosaccharide include but are not limited to glucose (dextrose), arabinose, mannitol, fructose (levulose) and galactose. "Monosaccharide derivative" as used herein refers to a monosaccharide wherein one or more —OH groups can be replaced by the substituents described above in the definition of "substituted." In some monosaccharide derivatives, one ore more —OH groups on the monosaccharide can be replaced by one or more —$NH_2$ or —NH—$CH_3$ groups. One example of a monosaccharide derivative includes meglumine. Other examples of a monosaccharide derivative can include an amino alcohol.

As used herein, "isosteres" are different compounds that have different molecular formulas but exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —COOH, —$SO_3H$, —$SO_2HNR^9$, —$PO_2(R^9)_2$, —$PO_3(R^9)_2$, —$CONHNSO_2R^9$, —$COHNSO_2R^9$, and —$CONR^9CN$. In addition, carboxylic acid isosteres can include 5-7 membered carbocycles or heterocycles containing any combination of $CH_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with $R^9$.

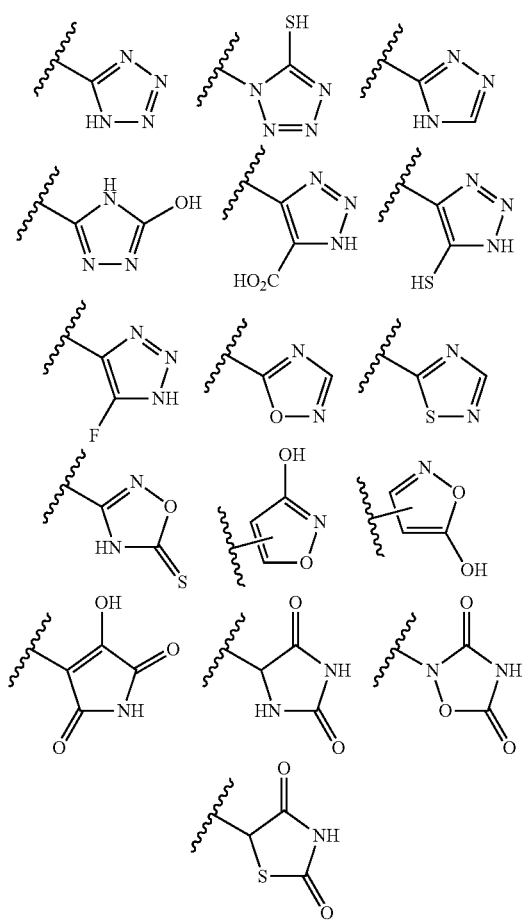

It is also contemplated that when chemical substituents are added to a carboxylic isostere, the compound retains the properties of a carboxylic isostere. It is contemplated that when a carboxylic isostere is optionally substituted with one or more moieties selected from $R^9$, then the substitution cannot eliminate the carboxylic acid isosteric properties of the compound. It is also contemplated that the placement of one or more $R^9$ substituents upon a carbocyclic or heterocyclic carboxylic acid isostere shall not be permitted at one or more atom(s) which maintain(s) or is/are integral to the carboxylic acid isosteric properties of the compound, if such substituent(s) would destroy the carboxylic acid isosteric properties of the compound. Other carboxylic acid isosteres not specifically exemplified or described in this specification are also contemplated.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups for oxygen atoms are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)). Handling of protecting and/or sterodirecting groups specific to boronic acid derivatives is described in a recent review of chemistry of boronic acids: D. G. Hall (Ed.), Boronic Acids. Preparation and Application in Organic Synthesis and Medicine, Wiley VCH (2005) and in earlier reviews: Matteson, D. S. (1988). Asymmetric synthesis with boronic esters. Accounts of Chemical Research, 21(8), 294-300, and Matteson, D. S. (1989). Tetrahedron, 45(7), 1859-1885), all of which are incorporated herein by reference in their entirety. The latter review articles also describe methodology for stereoselective insertion of halomethine functionality next to the boronate which is employed in the synthetic schemes below.

In addition to standard acid catalyzed deprotection, special methods for removal of boronic acid protecting and/or sterodirecting groups methods using fluorides (Yuen, A. K. L., & Hutton, C. A. (2005). Tetrahedron Letters, 46(46), 7899-7903—incorporated herein by reference in its entirety) or periodate oxidation (Coutts, S. J., et al. (1994). Tetrahedron Letters, 35(29), 5109-5112—incorporated herein by reference in its entirety) can also be employed in preparations of the compounds disclosed herein.

In strategies employing pinanediol or other diol-based chiral auxiliaries for stereospecific introduction of new chiral centers, the early stages of chemistry on boronic intermediates can be performed on chiral boronate esters or alternatively nonchiral borate/boronate intermediates can be used in early stages followed by transesterification with chiral diols prior to the step where stereoselection is required.

Synthesis of Compounds of Formula I

The following example schemes are provided for the guidance of the reader, and collectively represent an example method for making the compounds encompassed herein. Furthermore, other methods for preparing compounds described herein will be readily apparent to the person of ordinary skill in the art in light of the following reaction schemes and examples. Unless otherwise indicated, all variables are as defined above.

Compounds of formula Ia where R is H can be prepared as depicted in scheme 1 from key intermediates of formula III, which may be assembled by known reactions (Boronic Acids: Preparations and Applications in Organic Synthesis, Medicine and Materials, D. G. Hall, ed., Wiley-VCH, Weinheim, 2011).

Scheme 1

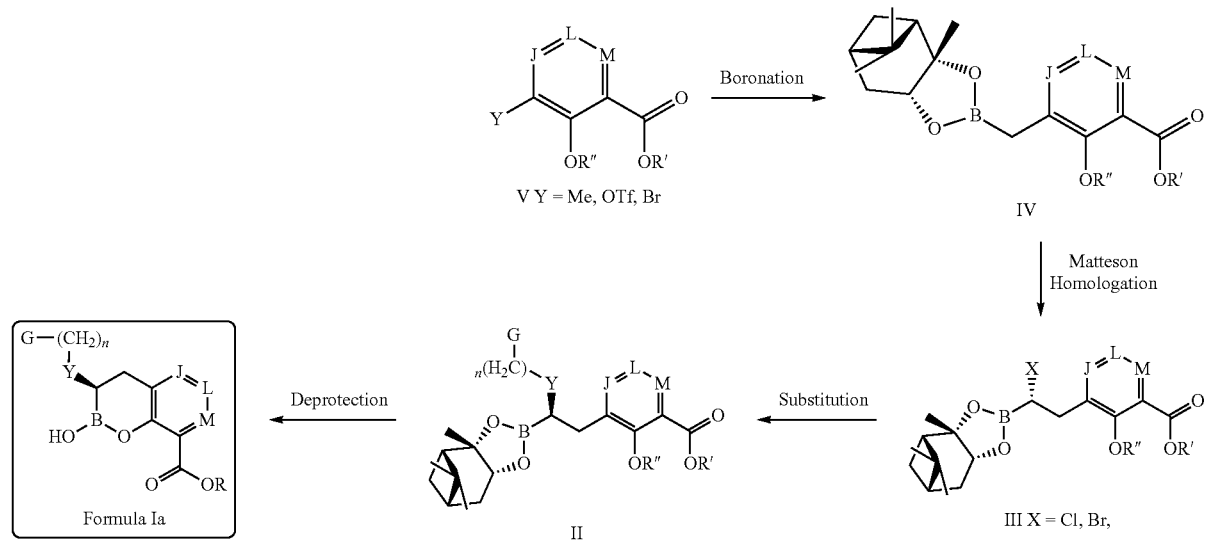

Such key intermediates of formula III where X═Cl and R' and R" are alkyl groups may be prepared by earlier described methods (WO09064414, WO10130708). In an alternate sequence, compounds of formula III where X═Cl and R' is Boc and R" is t-Butyl or R' and R" are protected together as isopropylidine or any other groups protected separately or together in cyclic form may be made from compounds of formula IV via homologation to give chloromethylene addition product with good stereocontrol by Matteson reaction conditions (WO0946098). Compounds of formula III where X is bromo may be made analogously to the chloro compounds of Scheme 1, utilizing dibromomethane (1. Am. Chem. Soc. 1990, 112, 3964-969). The halo derivatives of formula III where X is Cl or Br undergo stereospecific substitution to form thioethers (WO 04064755), ethers (WO 12067664), amines (J. Organomet. Chem. 1979, 170, 259-64) or acetates (Tetrahedron 2005, 61, 4427-4536), to give compounds of formula II. In an alternate approach, compounds of formula II where Y is S can be made via a thiol intermediate by alkylation or arylation to introduce various G groups. Such compounds may also be made via alkyl or thiomethylene boronate esters by reaction with substituted benzyl halides (U.S. Pat. No. 6,586,615).

Matteson reaction precursors of formula IV may be made by palladium mediated coupling of pinanediol diboronate from corresponding appropriately protected benzyl alcohols (J. Am. Chem. Soc. 2011, 133, 409-411) or benzyl bromides of V (Tetrahedron Letters 2003, 44, 233-235; J. Am. Chem. Soc., 2010, 132, 11825-11827). The compounds of formula V may be achieved by means of several earlier known methods (WO0458679) with conventional protecting groups, such as those described in Protective Groups in Organic Chemistry (ed. J. F. W. McOmie, Plenum, 1973); and Protecting Groups in Organic Synthesis P. G. M. Wutts, T. W. Green, Wiley, New York, 1999) from commercially available salicylic acid derivatives. Compounds of formula V where X is methyl can be readily transformed to corresponding benzyl bromides (Bioorg. Med. Chem. Lett. 1999, 9, 34-346) for boronation reaction to give IV.

Simultaneous deprotection of pinane ester and salicylic acid protective groups of compounds of formula II can be achieved by heating with dilute HCl, affording the desired compounds of structure I. This transformation may also be achieved by treatment with $BCl_3$ or $BBr_3$ (WO09064414). Alternatively, the deprotection may be attained via transesterification with isobutyl boronic acid in presence of dilute acid (WO09064413) or via other known methods (J. Org. Chem. (2010), 75, 468-471).

Compounds of formula Ib may be made following the sequence described above via (−)-pinanediol substituted intermediate of IV.

One exemplary but non-limiting general synthetic scheme for preparing a compound of Formula Ia is shown below in Scheme 1a. The starting compound of Ia-1 can be a salicyclic acid derivative, wherein Y' can be —OH, halogen, —$CH_3$, halogen substituted —$CH_3$, or a protected hydroxyl group; and J, L, M can be $CR^7$ or N. The compound of Formula Ia-1 can be treated first with protection groups and then undergo halogenation to form a benzyl halide compound of Formula Ia-3. The halogen of Formula Ia-3 (e.g., bromide) can then react with Bis(pinacolato)diboron to yield a boronic ester compound of Formula Ia-4. The compound of Formula Ia-4 undergoes homologation to yield a compound of Formula Ia-5 (wherein X' is a halogen). Various types of thiol, amine, alcohol and other precursors can then react with the compound of Formula Ia-5 to substitute the halogen X' and form a compound of Formula Ia-6. The compound of Formula Ia-6 can then undergo the deprotection of the pinane ester and salicylic acid protective groups to afford the compound of Formula Ia where R is H.

Scheme 1a

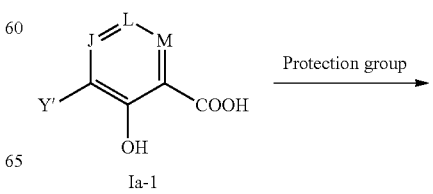

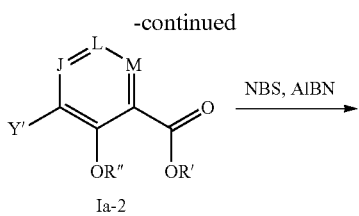

Ia-2

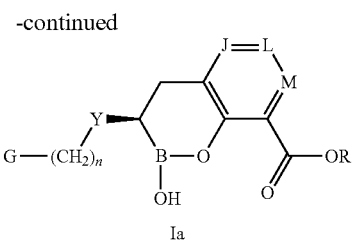

Ia

X' = Cl, Br

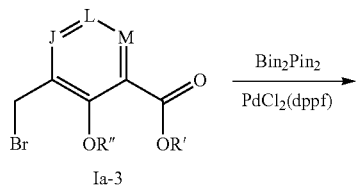

Ia-3

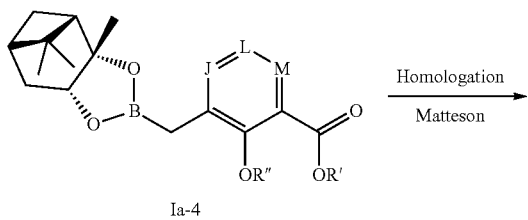

Ia-4

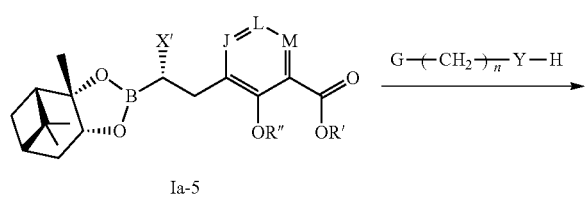

Ia-5

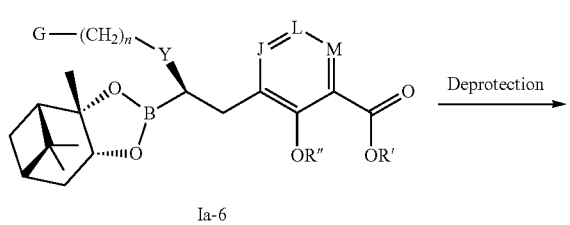

Ia-6

A compound of Formula (I-1) wherein Y is —CH$_2$— can be prepared by using the general synthetic Scheme 1b illustrated below. The starting compound of Formula I-1a can be a salicyclic acid derivative. The compound of Formula I-1b can be treated with a protection group and then undergo a cross coupling reaction to form a vinyl compound of Formula I-1c. The double bond of Formula I-1c can be converted into an aldehyde of Formula I-1d. The aldehyde compound of Formula I-1d then undergoes a Wittig reaction to yield a compound of Formula I-1e, which then reacts with boronation agent to form a pinacol boronic ester of Formula I-1f. The G' group in Formula I-1e, added by a Wittig reagent, can be any group that is suitable to couple to the negatively charged carbon of the Wittig reagent. Examples of the G's groups can include, but are not limited to, —COOR$^1$, —C(O)R', amide, and C$_{1-9}$alkyl. In some embodiments, G' can be —C(O)OC(CH$_3$)$_3$. The boronic ester compound of Formula I-1f can react with pinanediol to yield a Pinanediol Methylboronic Ester compound of Formula I-1g. In some embodiments, the compound of Formula I-1g can undergo deprotection of the pinane ester and salicylic acid protective groups to afford the compound of Formula I-1, and G' can be the final G group in the compound of Formula I-1 (i.e., G' and G are the same).

In some alternative embodiments, after removing the protection group on the G' group, the compound of Formula I-1g can react with different types of thiol, amine, and alcohol precursors to replace the G' group with a G group (as defined herein) to form a compound of Formula I-1h. The compound of Formula I-1h can then undergo the deprotection of the pinane ester and salicylic acid protective groups to afford the compound of Formula I-1.

Scheme 1b

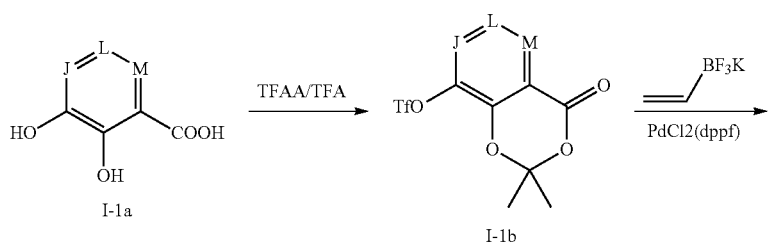

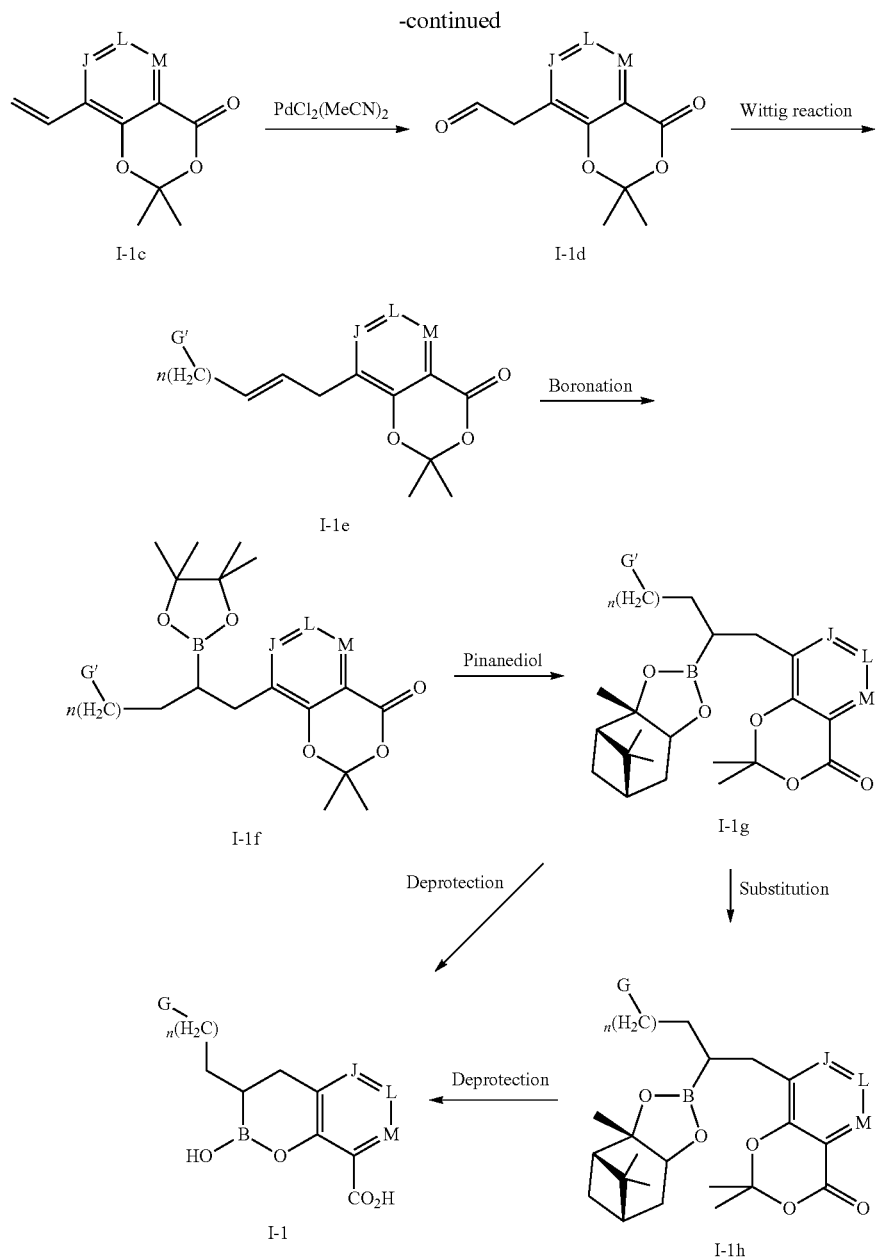

Synthesis of Prodrugs

Compounds of formula I where the R is a prodrug moiety may be synthesized by a variety of known methods of different carboxylic acid prodrugs (*Prodrugs: Challenges and Rewards*, V. J. Stella, et al., ed., Springer, New York, 2007). These prodrugs include but are not limited to substituted or non-substituted alkyl esters, (acyloxy)alkyl (*Synthesis* 2012, 44, 207), [(alkoxycarbonyl)oxy]methyl esters (WO10097675), or (oxodioxolyl)methyl esters (*J. Med. Chem.* 1996, 39, 323-338). Such prodrugs can be made from compounds of formula I where R=H by treatment with acid or in neutral conditions (e.g., carbodiimide coupling) in the presence of alcohols (ROH) or via base promoted esterification with RX where X is a leaving group in the presence of an appropriate base.

One exemplary but non-limiting general synthetic scheme for preparing the prodrug is shown in Scheme 2a below. The boronic acid of Formula Ia where R is hydrogen can react with a chloro/bromo-substituted prodrug moiety to form a prodrug of Formula If. Examples of the prodrug moiety $R^{1'}$ can be —$C_{1-9}$alkyl, —$CR^1R^2OC(O)C_{1-9}$alkyl, —$CR^1R^2OC(O)OC_{1-9}$alkyl, —$CR^1R^2OC(O)C_{1-9}$aryl, —$CR^1R^2OC(O)OC_{1-9}$aryl, and

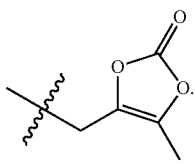 [SMILES: *Cc1oc(=O)oc1C]

Scheme 2a

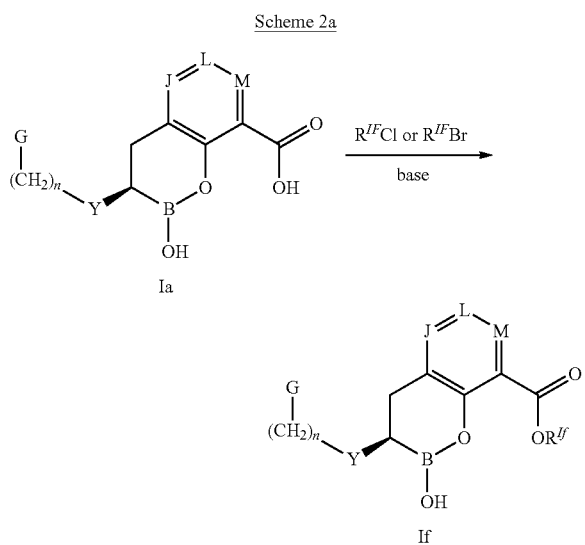

Alternatively, boronate esters of formula VI or corresponding tetrafluoroborates (*Chem. Rev.* 2008, 108, 288-325) may be also utilized for introduction of prodrugs and convert them to final prodrugs (Scheme 2b). Such carboxylic acids (VI) can be made from compounds of formula II by selective deprotection of OR'. The prodrug group may also be introduced earlier in the sequence in compounds of formula V where R' is R. Such sequence where prodrug is introduced in earlier intermediates is only feasible when the ester is stable under the final deprotection conditions to remove the phenol protective group and boronate ester group.

Scheme 2b

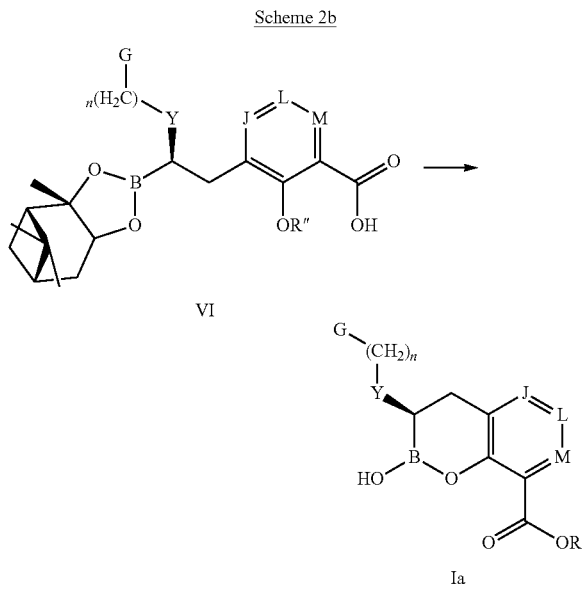

Synthesis of Ortho-Carboxylate Substituted Compounds

Compounds of formula VII to attain compounds of formula Ia where M is $CR_7$ may be prepared as shown in scheme 3. Such intermediates of formula VII can be synthesized from VIII where X' is substituted as bromomethylene or triflate or bromo or iodo fuctionalities. Compounds of formula VIII where X' is substituted as —$CH_2Br$ may be transformed to VII under palladium catalysed reaction conditions utilizing diboronate ester of desired enantiomerically pure pinanediol ester (*Tetrahedron Lett.*, 2003, 44, 233-235). Intermediates of formula VIII where X=Br, I, OTf can be transformed to VII by utilizing Reformatsky reagent of bromomethylene boronate ester (*J. Org. Chem.*, 2013, 78, 8250-8266; *Chem Lett.*, 1993, 845-848.), or by reaction of methylenediboronate ester (Org. Lett. 2011, 13, 3368-3371). Derivatives of VIII where X'=—CHO and Z'=F may be utilized to introduce diverse groups of R7 containing OR or SR' by displacement of corresponding F group (*Journal of Medicinal Chemistry*, 2008, 51, 1925-1944). Such benzaldehyde derivatives of VIII can be converted to bromomethyl intermediates via one (*Tetrahedron Lett.*, 1984, 25, 1103-1104) or two step transformations via reduction and halide formation. Compounds where X' is substituted with bromo or iodo groups can be attained from appropriately protected commercial 2,5-hydroxy-benzoic acid derivatives (*J. Med. Chem.*, 2003, 46, 3437-3440). Intermediates of VIII can also be prepared via carboxylation of derivatives of formula IX where Z' is a fluoro, OR''', or SR''' by earlier described methods (WO12106995).

Scheme 3

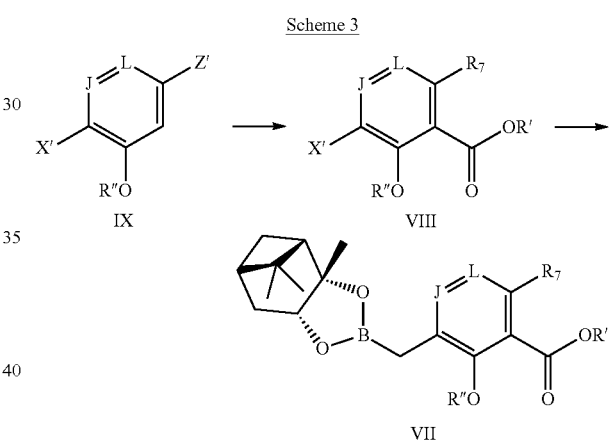

X' = Me, OR, Br, I Z' = Cl, F, OR''', SR'''

One exemplary but non-limiting general synthetic scheme for preparing ortho-Carboxylate Substituted compound of formula VII is shown below in scheme 3a. The starting compound of Formula VII-1 can be prepared from a protected phenol derivative, wherein $X^{3a}$ can be $C_{1-4}$ alkyl, —$OR^1$, or halogen; and $R^{3a}$ can be a suitable hydroxyl protection group and $R^{3b}$ can be a suitable carboxyl protecting group. The compound of Formula VII-2 can be prepared via carboxylation of the phenol derivative of Formula VII-1. The carboxylic group on the Formula VII-2 is protected. The compound of Formula VII-2 can then react with a boronation agent at $X^{3a}$ to form a Pinanediol Methylboronic Ester compound of Formula VII-3. The boron ester of Formula VII-3 can then undergo a homologation reaction to yield a compound of Formula VII-4. Various types of thiol, amine, alcohol, and other precursors can then react with the compound of Formula VII-4 to substitute the halogen and form a compound of Formula VII-5. The compound of Formula VII-5 then undergoes the deprotection of the pinane ester and salicylic acid protective groups to afford the compound of Formula VII.

Scheme 3a

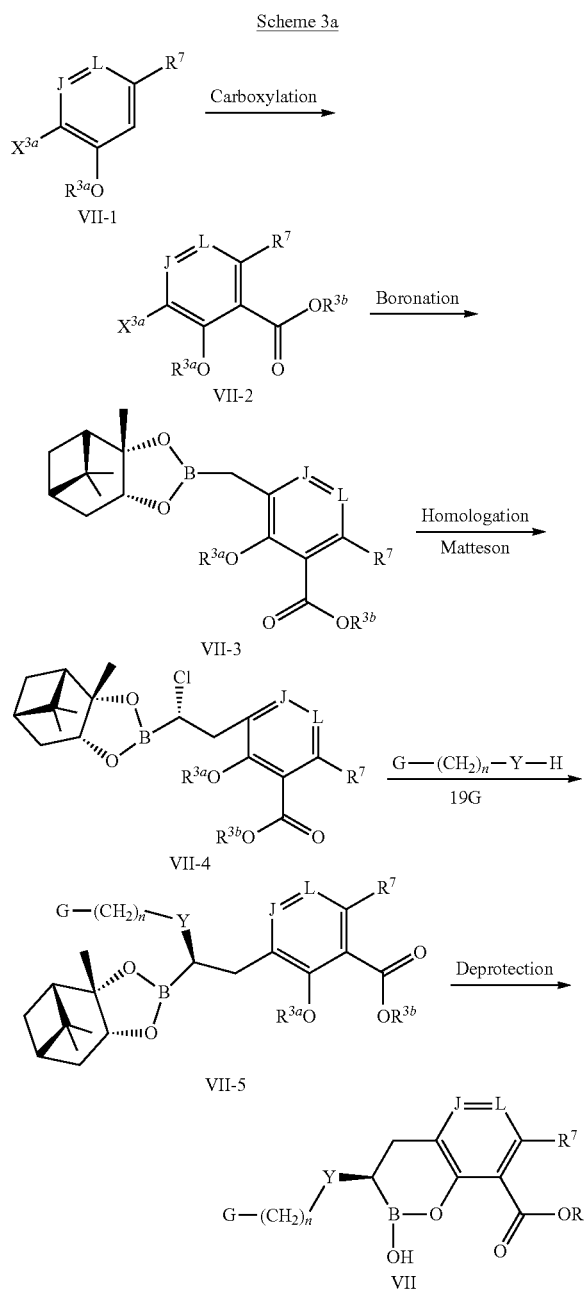

In another exemplary synthetic scheme 3b, the compound of formula VII-2 where $X^{3a}$ is a —CH$_2$OH group can be prepared from a salicylic acid derivative of Formula VII-6. The compound of Formula VII-6 upon diallylation under basic conditions followed by thermal Claisen rearrangement (*Org. React.* 1975, 22, 1-252) and ester hydrolysis gives compound of Formula VII-7. Such compounds undergo isomerization of double bond to give a styryl derivative, The styryl double bond can be oxidized to form an aldehyde of Formula VII-8. The halogen group $X^{3b}$ in the compound of Formula VII-8 can be replaced by various R$^7$ groups to form a compound of Formula VII-9, which then undergoes reduction to convert the aldehyde group into the hydroxyl group of Formula VII-2. The compound of Formula VII-2 can further undergo the steps listed above in Scheme 3a to form an ortho-carboxylate-substituted compound of formula VII.

Scheme 3b.

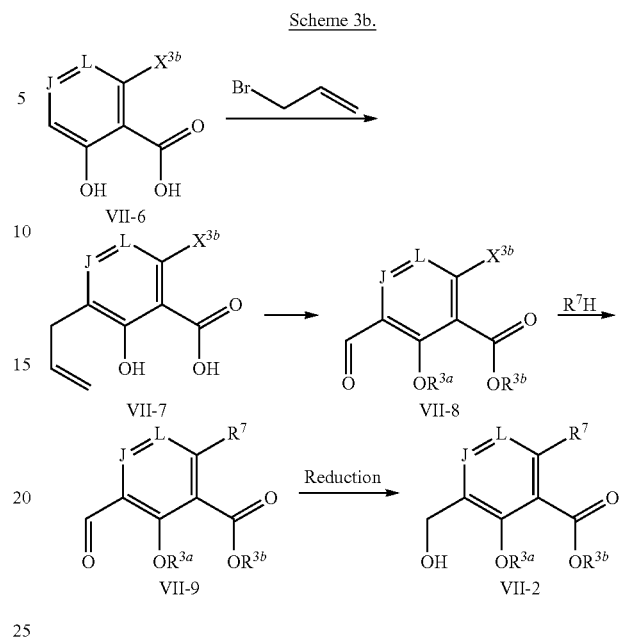

One exemplary but non-limiting general synthetic scheme for preparing the compound of Formula VII is shown in scheme 3c. The compound of Formula VII-2, $X^{3a}$ can be —C$_{1-4}$ alkyl, —C$_{1-4}$alkyl-OH, —OR$^1$, or halogen; R$^{1a}$ can be a suitable hydroxyl protection group; and R$^{3b}$ can be a suitable carboxyl protecting group. The compound of Formula VII-2 can be prepared from the compound of Formula VII-1a through either a carboxylation step followed by a halogenation step or a halogenation step followed by a carboxylation step. The compound of Formula VII-2 can then undergo boronation to form the compound of Formula VII-3 as shown in scheme 3a above.

Scheme 3c

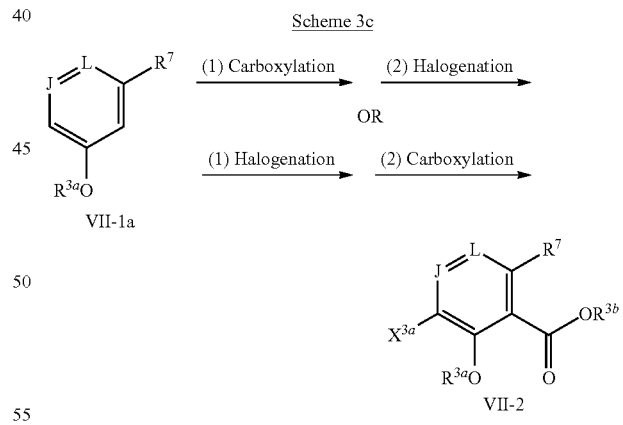

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Some boronic acid derivatives described herein can form an oligomer such as a dimer, trimer or tetramer. To prevent the boronic acid derivatives from forming such oligomers, some embodiments include pharmaceutical compositions in which an excipient is included that prevents or limits the formation of oligomers. In some embodiments, the excipient can be a monosaccharide or monosaccharide derivative. In one embodiment, the excipient is meglumine. Other excipients include but are not limited to ethanolamine, diethanolamine, tris(hydroxymethyl)aminomethane (Tris), L-lysine, and Pyridine-2-methanol.

Some embodiments described herein relate to a chemical complex formed between the monosaccharide or monosaccharide derivative and the compound of Formula (I) described herein. In some embodiments, the interaction between the two components helps increase the stability and/or solubility of the compound of Formula (I).

More generally, in some embodiments the monosaccharide or monosaccharide derivative can form a chemical complex with any compound containing a boronate moiety. In some embodiments, the compound containing a boronate moiety can be a boronic acid derivative described herein such as a compound of Formula (I) described herein. In other embodiments, the compound containing a boronate moiety can be any other boronate containing compounds, for example, known boronate-containing pharmaceutical agents. In some other embodiments, the monosaccharide or monosaccharide derivative used in forming the stable complex can be meglumine.

In some embodiments, of the inclusion of meglumine in a pharmaceutical composition prevents or reduces the formation of oligomers at a pH range desirable for pharmaceutical administration. In some embodiments, the pH of the composition can be in the range of about 5 to about 9, about 6 to about 8, about 6 to about 7.5, about 7.1 to about 7.3, or about 7.1 to about 7.2. In some embodiments, the pH of the composition can be in the range of about 7.0-7.3. In some embodiments, the pH of the composition can be about 6.5, 6.6, 6.7, 6.8, 6.9, 7.0, 7.1, 7.2, 7.3, 7.4, 7.5, 7.6, 7.7, and 7.8. In some embodiments, the pH of the composition can be about 7.1. In some embodiments, the pH of the composition can be about 7.2.

The amount of the boronic acid derivatives that are present in a monomer form can vary depending on the pH of the solution, the oligomer-preventing excipient included, and the amount of the excipient in the composition. In some embodiments, the percentage of the monomer form can be more than 85%, more than 88%, more than 90%, more than 92%, more than 95%, more than 97% by weight, based on the total amount of the boronic acid derivative in the composition. In some embodiments, the percentage of the monomer form can be more than 96% by weight based on the total amount of the boronic acid derivative in the composition. In some embodiments, the percentage of the monomer form can be more than 97% by weight based on the total amount of the boronic acid derivative in the composition.

Methods of Treatment

Some embodiments of the present invention include methods of treating bacterial infections with the compounds and compositions comprising the compounds described herein. Some methods include administering a compound, composition, pharmaceutical composition described herein to a subject in need thereof. In some embodiments, a subject can be an animal, e.g., a mammal (including a human). In some embodiments, the bacterial infection comprises a bacteria described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Examples of additional medicaments include an antibacterial agent, antifungal agent, an antiviral agent, an anti-inflammatory agent and an anti-allergic agent.

Preferred embodiments include combinations of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Ceftazidime, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam and Carumonam.

Preferred embodiments include β-lactams such as Ceftazidime, Biapenem, Doripenem, Ertapenem, Imipenem, Meropenem, Tebipenem, Apapenem, and Panipenem. In some embodiments, the β-lactam can be Tebipenem or Apapenem. In some embodiments, the β-lactam can be Tebipenem.

Additional preferred embodiments include β-lactams such as Aztreonam, Tigemonam, and Carumonam.

Some embodiments include a combination of the compounds, compositions and/or pharmaceutical compositions described herein with an additional agent, wherein the additional agent comprises a monobactam. Examples of monobactams include aztreonam, tigemonam, nocardicin A, carumonam, and tabtoxin. In some such embodiments, the compound, composition and/or pharmaceutical composition comprises a class A, C, or D beta-lactamase inhibitor. Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises a class B beta lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises one or more agents that include a class A, B, C, or D beta lactamase inhibitor. Some embodiments include co-administering the compound, composition or pharmaceutical composition described herein with the one or more additional agents.

Indications

The compounds and compositions comprising the compounds described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Bacillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

The following examples will further describe the present invention, and are used for the purposes of illustration only, and should not be considered as limiting.

EXAMPLES

Example 1: (R)-3-(1,3,4-thiadiazol-2-ylthio)-2-hydroxy-3,4-dihydro-2H-benzo[e][1,2]oxaborinine-8-carboxylic acid (1)

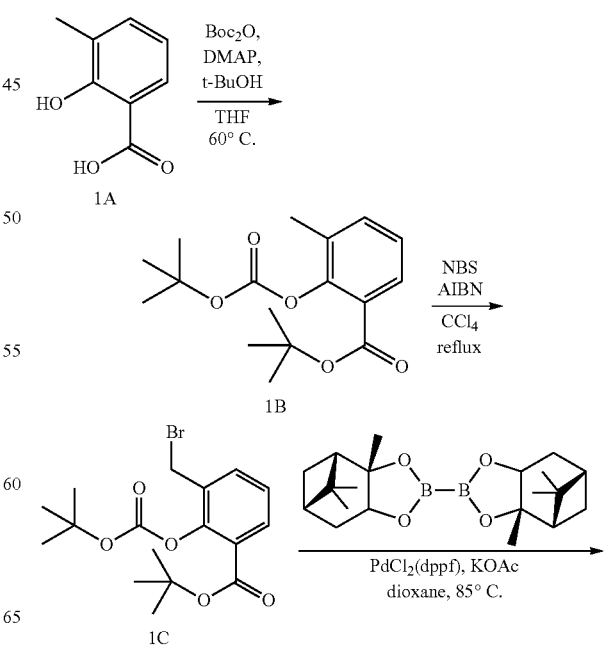

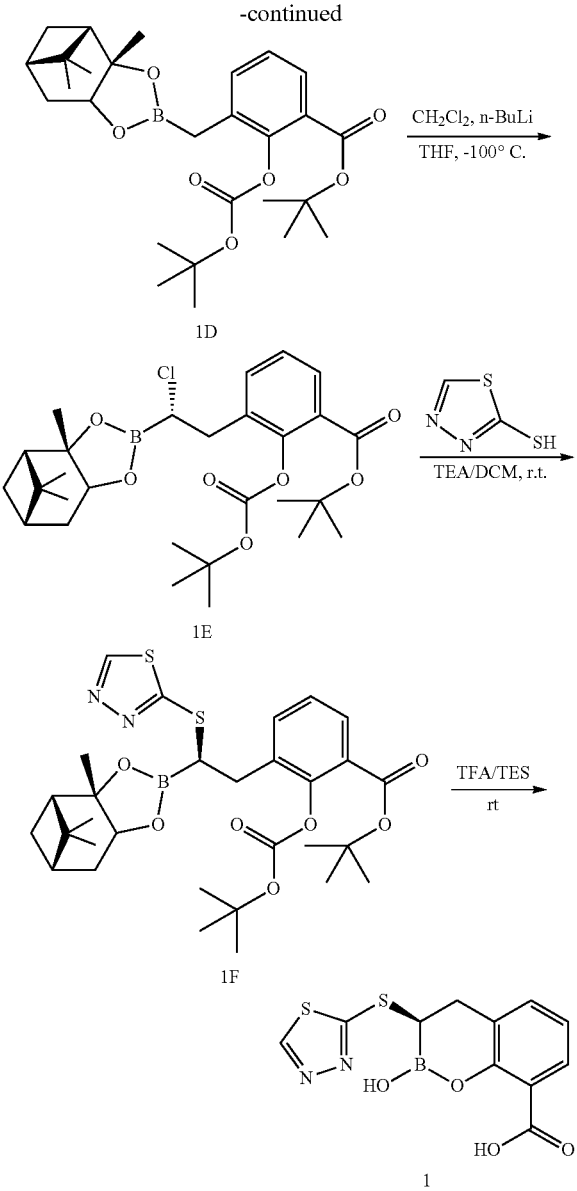

Step 1: Synthesis of Compound 1B

To the solution of compound 1A (100 g, 0.657 mol) in THF (400 mL) was added Boc₂O (573 g, 2.63 mol), DMAP (24 g, 0.197 mol) and ᵗBuOH (800 mL). The resulting solution was stirred at 60° C. for 6 hours before it was concentrated in vacuo. The residue was purified by flash column chromatography (ethyl acetate/hexanes, v/v, 1/200~1/100) to give the titled compound 1B (85.9 g, 42.5% yield) as colorless oil.

Step 2: Synthesis of Compound 1C

To the solution of compound 1B (44.3 g, 144 mmol) and NBS (28.1 g, 158 mmol) in CCl₄ (400 mL) was added BPO (3.5 g, 14.4 mmol). The resulting mixture was refluxed at 80° C. for 15 hours. The solid was filtered off and the filtrate was concentrated in vacuo. The residue was recrystallized with hexanes to afford the titled compound 1C (32.0 g, 57.6% yield) as white solid.

Step 3: Synthesis of Compound 1D

The mixture of compound 1C (47.5 g, 123 mmol), bis (pinanediolato)diboron (39.9 g, 112 mmol), KOAc (32.9 g, 336 mmol) and PdCl₂(dppf) (4.5 g, 5.6 mmol) in dioxane (500 mL) was degassed for three times and flushed with nitrogen. The mixture was stirred at 95° C. for 8 hours. After concentrated to dryness, the residue was purified by column chromatography (ethyl acetate/hexanes, v/v, 1/200~1/100) to give the titled compound 1D (40 g, 59% yield) as slightly yellow oil.

Step 4: Synthesis of Compound 1E

To a solution of CH₂Cl₂ (4.2 mL, 65.8 mmol) in THF (160 mL) at −100° C. was added 2.5 M n-butyl lithium in hexane (18.4 mL, 46.0 mmol) slowly under nitrogen and down the inside wall of the flask, maintaining the temperature below −90° C. The reaction mixture was stirred at −100° C. for another 30 minutes before the addition of Compound 1D from step 3 (16.0 g, 32.9 mmol) in THF (30 mL) at −90° C. and then the reaction was allowed to warm to room temperature where it was stirred for 16 h. The reaction was concentrated in vacuo directly to dryness and then chromatographed (100% hexane-20% EtOAc-hexane) to obtain the titled compound 1E (15.0 g, 85% yield) as slightly yellow oil.

Step 5: Synthesis of 1F

To the solution of compound 1E (113 mg, 0.21 mmol) and 2-mercapto-1,3,4-thiadiazole (32 mg, 0.27 mmol) in DCM (1.5 mL) was added triethylamine (42 mg, 0.42 mmol) at room temperature. After stirring for 2 hours, the reaction diluted with DCM and washed with dilute aqueous HCl and water. After concentration, the titled compound 1F (132 mg) was obtained as slightly yellow oil, which was used for next step without further purification.

Step 6: Synthesis of (R)-3-(1,3,4-thiadiazol-2-yl-thio)-2-hydroxy-3,4-dihydro-2H-benzo[e][1,2]oxa-borinine-8-carboxylic acid (1)

To the mixture of TFA (6 mL) and triethylsilane (1 mL) was added compound 1F (127 mg, crude). The resulting solution was stirred at room temperature for 1 hour before it was concentrated to dryness. The residue purified by reverse-phase prep-HPLC to afford 1 (43.2 mg) as white solid.

¹H NMR (400 MHz, CD₃OD) δ 9.28 (s, 1H), 7.76 (d, 1H, J=8.0 Hz), 7.35 (d, 1H, J=7.6 Hz), 6.94 (dd, 1H, J=8.0, 8.0 Hz), 3.80-3.90 (m, 1H), 3.25-3.30 (m, 1H), 3.08 (dd, 1H, J=2.8, 16 Hz).

MS calcd for (C₁₁H₉BN₂O₄S₂): 308.

MS (ESI, positive) found: (M+1): 309.

MS (ESI, negative) found: (M+H2O−1): 325.

Example 2: (R)-3-(4H-1,2,4-triazol-3-ylthio)-2-hydroxy-3,4-dihydro-2H-benzo[e][1,2]oxaborinine-8-carboxylic acid (2)

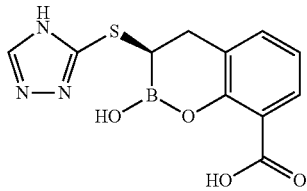

(R)-3-(4H-1,2,4-triazol-3-ylthio)-2-hydroxy-3,4-dihydro-2H-benzo[e][1,2]oxaborinine-8-carboxylic acid (2) was prepared following similar procedure described in example 1 (steps 1-6) replacing 2-mercapto-1,3,4-thiadiazole in step 5 with 4H-1,2,4-triazole-3-thiol $^1$H NMR (400 MHz, CD$_3$OD) δ 8.61 (bs, 1H), 7.73 (d, 1H, J=7.6 Hz), 7.31 (d, 1H, J=7.6 Hz), 6.91 (dd, 1H, J=7.6, 7.6 Hz), 3.82 (s, 1H), 3.22 (dd, 1H, J=5.2, 15.6 Hz), 2.98 (dd, 1H, J=2.8, 15.6 Hz).

MS calcd for (C$_{11}$H$_{10}$BN$_3$O$_4$S): 291.
MS (ESI, positive) found: (M+1): 292.
MS (ESI, negative) found: (M−1): 290.

Example 3: (R)-3-(2-amino-2-oxoethylthio)-2-hydroxy-3,4-dihydro-2H-benzo[e][1,2]oxaborinine-8-carboxylic acid (3)

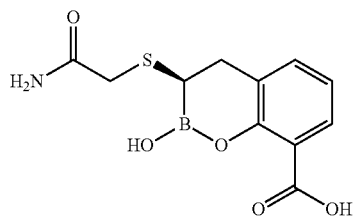

(R)-3-(2-amino-2-oxoethylthio)-2-hydroxy-3,4-dihydro-2H-benzo[e][1,2]oxaborinine-8-carboxylic acid (3) was prepared following similar procedure described in example 1 (steps 1-6) replacing 2-mercapto-1,3,4-thiadiazole in step 5 with 2-mercaptoacetamide.

$^1$H NMR (400 MHz, CD$_3$OD) δ 7.82 (dd, 1H, J=1.6, 8.0 Hz), 7.30 (m, 1H), 6.90 (dd, 1H, J=7.6, 8.0 Hz), 3.35 (d, 1H, J=13.6 Hz), 3.35 (d, 1H, J=14.0 Hz), 3.07 (dd, 1H, J=5.2, 15.6 Hz), 2.75 (dd, 1H, J=7.6, 15.6 Hz), 2.53 (dd, 1H, J=5.2, 7.6 Hz).

MS calcd for (C$_{11}$H$_{12}$BNO$_5$S): 281.
MS (ESI, positive) found: (M+1): 282.
MS (ESI, negative) found: (M−1): 280.

Example 4: (R)-3-(5-amino-1,3,4-thiadiazol-2-ylthio)-2-hydroxy-3,4-dihydro-2H-benzo[e][1,2]oxaborinine-8-carboxylic acid (4)

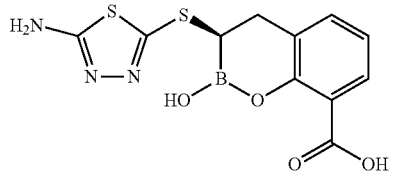

(R)-3-(5-amino-1,3,4-thiadiazol-2-ylthio)-2-hydroxy-3,4-dihydro-2H-benzo[e][1,2]oxaborinine-8-carboxylic acid (4) was prepared following similar procedure described in example 1 (steps 1-6) replacing 2-mercapto-1,3,4-thiadiazole in step 5 with 5-amino-1,3,4-thiadiazole-2-thiol.

$^1$H NMR (400 MHz, CD$_3$OD) δ 7.80 (d, 1H, J=8.0 Hz), 7.34 (d, 1H, J=7.6 Hz), 6.96 (dd, 1H, J=7.6, 7.6 Hz), 3.69 (S, 1H), 3.23 (dd, 1H, J=5.6, 16 Hz), 3.02 (d, 1H, J=16 Hz).

MS calcd for (C$_{11}$H$_{10}$BN$_3$O$_4$S$_2$): 323.
MS (ESI, positive) found: (M+1): 324.
MS (ESI, negative) found: (M−1): 322.

Example 5: (R)-2-hydroxy-3-(1-methyl-1H-tetrazol-5-ylthio)-3,4-dihydro-2H-benzo[e][1,2]oxaborinine-8-carboxylic acid (5)

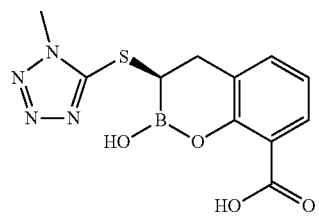

Compound 5 was prepared following similar procedure described in example 1 (steps 1-6) replacing 2-mercapto-1,3,4-thiadiazole in step 5 with 1-methyl-1H-tetrazole-5-thiol.

$^1$H NMR (400 MHz, CD$_3$OD) δ 7.70-7.78 (m, 1H), 7.22-7.33 (m, 1H), 6.78-6.90 (m, 1H), 3.82-3.88 (m, 4H), 3.08-3.20 (m, 2H).

MS calcd for (C$_{11}$H$_{11}$BN$_4$O$_4$S): 306.
MS (ESI, positive) found: (M+1): 307.
MS (ESI, negative) found: (M+H2O−1): 323.

Example 6: (R)-2-hydroxy-3-(phenylthio)-3,4-dihydro-2H-benzo[e][1,2]oxaborinine-8-carboxylic acid (6)

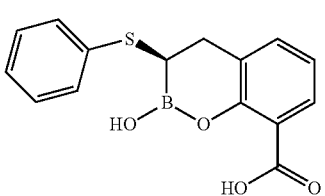

Compound 6 was prepared following similar procedure described in example 1 (steps 1-6) replacing 2-mercapto-1,3,4-thiadiazole in step 5 with benzenethiol.

$^1$H NMR (400 MHz, CD$_3$OD) δ 7.70-7.81 (m, 1H), 7.07-7.42 (m, 4H), 6.75-6.95 (m, 2H), 2.72-3.24 (m, 3H).
MS calcd for (C$_{15}$H$_{13}$BO$_4$S): 300.
MS (ESI, positive) found: (M+1): 301.
MS (ESI, negative) found: (M+H2O−1): 317.

Example 7: (R)-3-(5-acetamido-1,3,4-thiadiazol-2-ylthio)-2-hydroxy-3,4-dihydro-2H-benzo[e][1,2]oxaborinine-8-carboxylic acid (7)

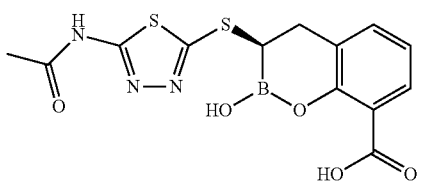

Compound 7 was prepared following similar procedure described in example 1 (steps 1-6) replacing 2-mercapto-1,3,4-thiadiazole in step 5 with N-(5-mercapto-1,3,4-thiadiazol-2-yl)acetamide.

$^1$H NMR (400 MHz, CD$_3$OD) δ 7.77 (d, 1H, J=7.6 Hz), 7.34 (d, 1H, J=7.6 Hz), 6.94 (dd, 1H, J=7.6, 7.6 Hz), 3.76 (s, 1H), 3.03-3.30 (m, 2H), 2.20 (s, 3H).
MS calcd for (C$_{13}$H$_{12}$BN$_3$O$_5$S$_2$): 365.
MS (ESI, positive) found: (M+1): 366.
MS (ESI, negative) found: (M−1): 364.

Example 8: (R)-2-hydroxy-3-(pyridin-3-ylthio)-3,4-dihydro-2H-benzo[e][1,2]oxaborinine-8-carboxylic acid (8)

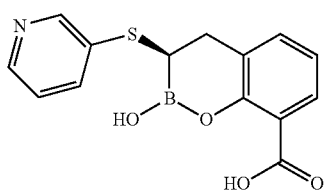

Compound 8 was prepared following similar procedure described in example 1 (steps 1-6) replacing 2-mercapto-1,3,4-thiadiazole in step 5 with pyridine-3-thiol.

$^1$H NMR (400 MHz, DMSO-d$_6$) δ 7.80-8.80 (m, 3H), 7.55-7.70 (m, 2H), 7.19-7.32 (m, 1H), 6.74-6.85 (m, 1H), 2.48-3.16 (m, 3H).
MS calcd for (C$_{14}$H$_{12}$BNO$_4$S): 301.
MS (ESI, positive) found: (M+1): 302.
MS (ESI, negative) found: (M+H2O−1): 318.

Example 9: (R)-3-(3-amino-3-oxopropylthio)-2-hydroxy-3,4-dihydro-2H-benzo[e][1,2]oxaborinine-8-carboxylic acid (9)

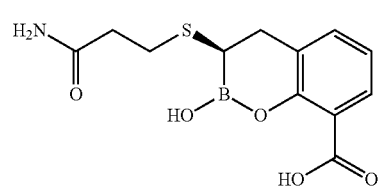

Compound 9 was prepared following similar procedure described in example 1 (steps 1-6) replacing 2-mercapto-1,3,4-thiadiazole in step 5 with 3-mercaptopropanamide.

$^1$H NMR (400 MHz, CD$_3$OD) δ 7.69-7.74 (m, 1H), 7.30-7.35 (m, 1H), 6.77-6.83 (m, 1H), 2.40-3.10 (m, 7H).
MS calcd for (C$_{12}$H$_{14}$BNO$_5$S): 295.
MS (ESI, positive) found: (M+1): 296.
MS (ESI, negative) found: (M−1): 294.

Example 10: (R)-2-hydroxy-3-(1-iminoethylthio)-3,4-dihydro-2H-benzo[e][1,2]oxaborinine-8-carboxylic acid (10)

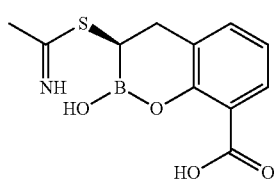

Compound 10 was prepared following similar procedure described in example 1 (steps 1-6) replacing 2-mercapto-1,3,4-thiadiazole in step 5 with thioacetamide.

$^1$H NMR (400 MHz, CD$_3$OD) δ 11.0 (bs, 1H), 7.81 (d, 1H, J=8.0 Hz), 7.31 (d, 1H, J=7.6 Hz), 6.94 (dd, 1H, J=8.0, 8.0 Hz), 3.30 (s, 1H), 2.90-3.12 (m, 2H), 2.30 (s, 3H).
MS calcd for (C$_{11}$H$_{12}$BNO$_4$S): 265.
MS (ESI, positive) found: (M+1): 266.
MS (ESI, negative) found: (M−1): 264.

Example 11: (R)-2-hydroxy-3-(thiazol-2-ylthio)-3,4-dihydro-2H-benzo[e][1,2]oxaborinine-8-carboxylic acid (11)

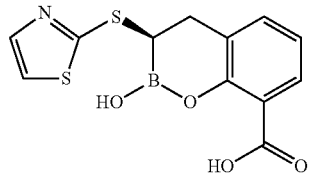

Compound 11 was prepared following similar procedure described in example 1 (steps 1-6) replacing 2-mercapto-1,3,4-thiadiazole in step 5 with thiazole-2-thiol.

¹H NMR (400 MHz, CD₃OD) δ 7.78 (d, 0.5H, J=4.0 Hz), 7.60-7.65 (m, 1.5H), 4.78-7.50 (m, 1H), 7.23 (d, 1H, J=7.6 Hz), 6.84 (dd, 1H, J=8.0, 16.0 Hz), 3.79-3.90 (m, 1H), 3.15-3.36 (m, 1H), 2.89-2.95 (m, 1H).

MS calcd for (C₁₂H₁₀BNO₄S₂): 307.
MS (ESI, positive) found: (M+1): 308.
MS (ESI, negative) found: (M−H2O−1): 290.

Example 12: (R)-3-(1H-1,2,3-triazol-4-ylthio)-2-hydroxy-3,4-dihydro-2H-benzo[e][1,2]oxaborinine-8-carboxylic acid (12)

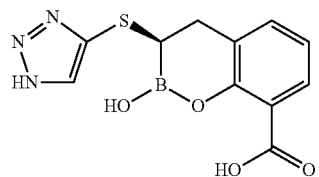

12

Compound 12 was prepared following similar procedure described in example 1 (steps 1-6) replacing 2-mercapto-1,3,4-thiadiazole in step 5 with 1H-1,2,3-triazole-4-thiol.

¹H NMR (400 MHz, CD₃OD) δ 7.79 (s, 1H), 7.78 (dd, 1H, J=0.8, 8.0 Hz), 7.33 (d, 1H, J=7.6 Hz), 6.92 (dd, 1H, J=8.0, 8.0 Hz), 3.67 (t, 1H, J=4.4 Hz), 3.23 (dd, 1H, J=5.2, 15.2 Hz), 2.95 (dd, 1H, J=3.6, 15.2 Hz).

MS calcd for (C₁₁H₁₀BN₃O₄S): 291.
MS (ESI, positive) found: (M+1): 292.
MS (ESI, negative) found: (M−1): 290.

Example 13: (R)-3-(benzyloxy)-2-hydroxy-3,4-dihydro-2H-benzo[e][1,2]oxaborinine-8-carboxylic acid (13)

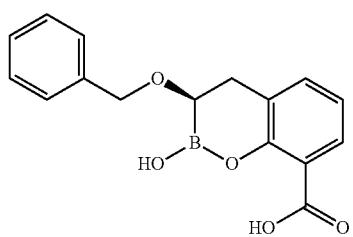

13

(R)-3-(benzyloxy)-2-hydroxy-3,4-dihydro-2H-benzo[e][1,2]oxaborinine-8-carboxylic acid (13) was prepared following similar procedure described in example 1 (steps 1-5) replacing 2-mercapto-1,3,4-thiadiazole in step 5 with benzyl alcohol to attain benzylated product with a procedure as described in EP1550657.

Final deprotection (step 6) was done by isobutyl boronic acid following procedure described in step 7 of example 19.

¹H NMR (400 MHz, CD₃OD) δ 7.74 (d, 1H, J=8.0 Hz), 7.05-7.37 (m, 6H), 6.84 (dd, 1H, J=4.0, 4.0 Hz), 4.26-4.60 (m, 2H), 3.55 (t, 1H, J=6.4 Hz), 2.94-3.05 (m, 2H).

MS calcd for (C₁₆H₁₅BO₅): 298.
MS (ESI, positive) found: (M+1): 299.

Example 14: (R)-3-(4-amino-4H-1,2,4-triazol-3-ylthio)-2-hydroxy-3,4-dihydro-2H-benzo[e][1,2]oxaborinine-8-carboxylic acid (14)

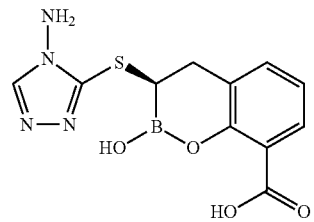

14

Compound 14 was prepared following similar procedure described in example 1 (steps 1-6) replacing 2-mercapto-1,3,4-thiadiazole in step 5 with 4-amino-4H-1,2,4-triazole-3-thiol.

¹H NMR (400 MHz, CD₃OD) δ 8.45 (s, 1H), 7.78 (dd, 1H, J=0.8, 8.0 Hz), 7.33 (d, 1H, J=7.6 Hz), 6.92 (dd, 1H, J=8.0, 8.0 Hz), 3.77 (t, 1H, J=4.4 Hz), 3.23 (dd, 1H, J=5.2, 15.2 Hz).

MS calcd for (C₁₁H₁₁BN₄O₄S): 306.
MS (ESI, positive) found: (M+1): 307.
MS (ESI, negative) found: (M−1): 305.

Example 15: (R)-2-hydroxy-3-(4-methyl-4H-1,2,4-triazol-3-ylthio)-3,4-dihydro-2H-benzo[e][1,2]oxaborinine-8-carboxylic acid (15)

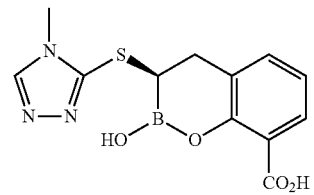

15

Compound 15 was prepared following similar procedure described in example 1 (steps 1-6) replacing 2-mercapto-1,3,4-thiadiazole in step 5 with 4-methyl-4H-1,2,4-triazole-3-thiol.

¹H-NMR (400 MHz, CD₃OD) δ 8.41 (s, 1H), 7.76 (d, 1H), 7.33 (d, 1H), 6.92 (t, 1H), 3.92 (dd, 1H), 3.52 (s, 3H), 3.25 (dd, 1H), 3.05 (dd, 1H).

MS calcd for (C₁₂H₁₂BN₃O₄S) 305.
MS (ESI, positive) found: (M+1): 306.

Example 16: (R)-2-hydroxy-3-(methylthio)-3,4-dihydro-2H-benzo[e][1,2]oxaborinine-8-carboxylic acid (16)

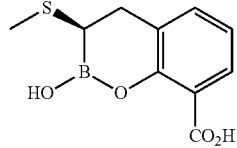

16

Compound 16 was prepared following similar procedure described in example 1 (steps 1-6) replacing 2-mercapto-1,3,4-thiadiazole in step 5 with methyl thiol. ¹H-NMR (400 MHz, CD₃OD) δ 7.73 (d, 1H), 7.33 (d, 1H), 6.82 (t, 1H), 2.85-3.00 (m, 2H), 2.49 (m, 1H), 2.06 (s, 3H).

MS calcd for (C₁₀H₁₁BO₄S) 238.
MS (ESI, negative) found: (2M−1): 475.

Example 17: (R)-2-hydroxy-3-methoxy-3,4-dihydro-2H-benzo[e][1,2]oxaborinine-8-carboxylic acid (17)

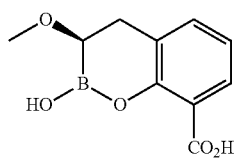

Compound 17 was prepared following similar procedure described in example 1 replacing 2-mercapto-1,3,4-thiadiazole in step 5 with methanol as in step 6 of example 19. Deprotection was done by isobutyl boronic acid following procedure described in step 7 of example 19.

¹H-NMR (400 MHz, CD₃OD) δ 7.74 (d, 1H), 7.34 (d, 1H), 6.82 (t, 1H), 3.38 (s, 1H), 3.33 (s, 3H), 2.95-3.20 (m, 2H).

MS calcd for (C₁₀H₁₁BO₅) 222.
MS (ESI, negative) found: (2M−1): 443.

Example 18: (R)-3-(azetidin-3-yloxy)-2-hydroxy-3,4-dihydro-2H-benzo[e][1,2]oxaborinine-8-carboxylic acid (18)

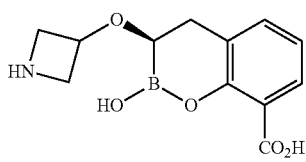

Compound 18 was prepared following similar procedure described in example 1 replacing 2-mercapto-1,3,4-thiadiazole in step 5 with N-Boc-3-hydroxy-azetidine as in step 6 of example 19. Deprotection was done by isobutyl boronic acid following procedure described in step 7 of example 19.

¹H-NMR (400 MHz, CD₃OD) δ 7.73-7.78 (m, 1H), 7.32-7.34 (m, 1H), 6.77-6.89 (m, 1H), 3.70-4.70 (m, 6H), 2.90-3.20 (m, 2H).

MS calcd for (C₁₂H₁₄BNO₅) 263.
MS (ESI, negative) found: (2M−1): 525.

Example 19: (R)-7-fluoro-2-hydroxy-3-methoxy-3,4-dihydro-2H-benzo[e][1,2]oxaborinine-8-carboxylic acid (19)

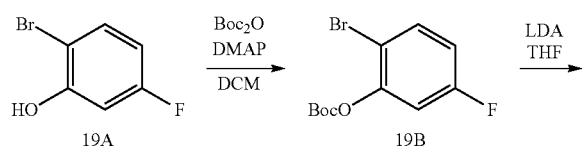

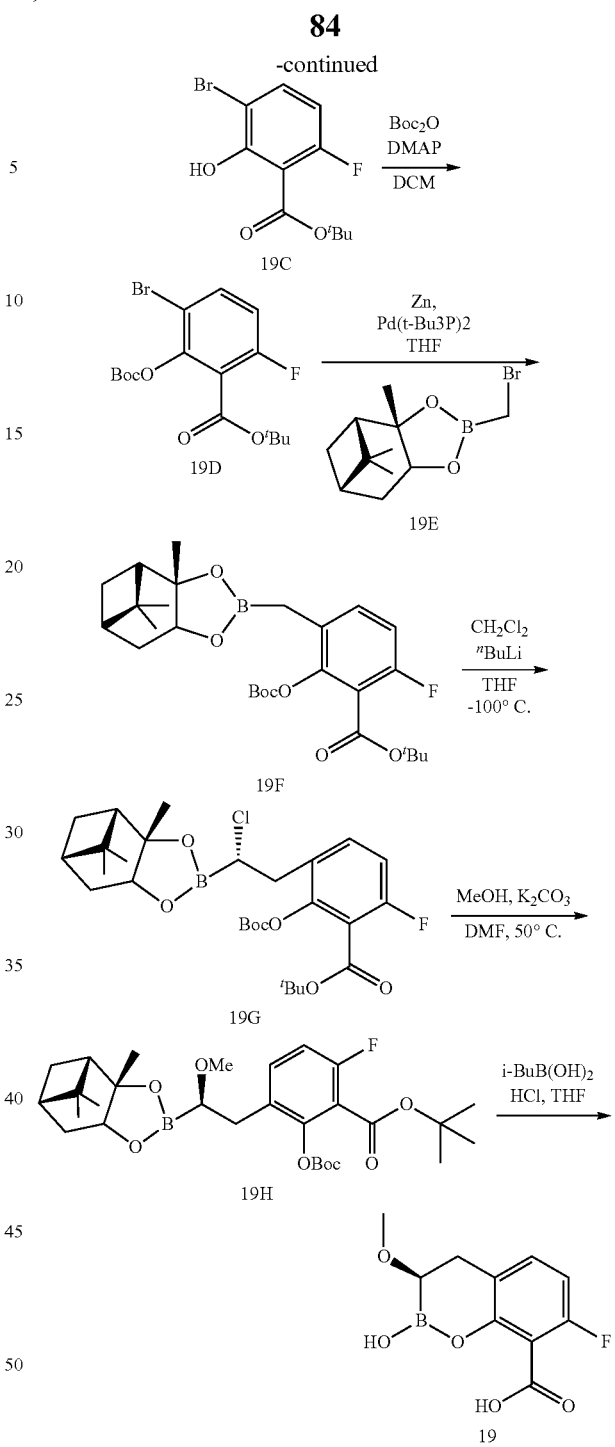

Step 1: Synthesis of 19B

To a solution of 2-bromo-5-fluorophenol (19A) (13.5 g, 71 mmol) and Boc₂O (18.5 g, 85 mmol) in DCM (300 mL) at r.t. was added DMAP (439 mg, 3.6 mmol), the mixture was stirred at r.t. for 0.5 h, concentrated to dryness, and purified by silica gel chromatography to afford compound 19B (20.1 g, 97%).

¹H NMR (400 MHz, CDCl₃) δ 7.54 (m, 1H), 6.98 (m, 1H), 6.89 (m, 1H), 1.56 (s, 9H).

Step 2: Synthesis of 19C

To a solution of compound 19B (21.7 g, 74.6 mmol) in THF (150 mL) at −78° C. was added freshly prepared LDA solution (140 mL, 82.1 mmol), the mixture was stirred at −78° C. for 1 h, then warmed up slowly to r.t., quenched with 1 N HCl (aq., 200 mL), extracted with EtOAc, washed with water and brine, dried over $Na_2SO_4$, filtered and the filtrate was evaporated to dryness to afford compound 19C (17.9 g, 83%) which was used directly to the next step without further purification.

$^1$H NMR (400 MHz, $CDCl_3$) δ 12.23 (s, 1H), 7.59 (m, 1H), 6.53 (m, 1H), 1.61 (s, 9H).

Step 3: Synthesis of 19D

To a solution of compound 19C (17.99 g, 62 mmol) and $Boc_2O$ (20.2 g, 92.7 mmol) in DCM (200 mL) at r.t. was added DMAP (400 mg, 3.1 mmol), the mixture was stirred at r.t. overnight, evaporated to dryness, purified by silica gel chromatography to afford compound 19D (19.1 g, 79%).

$^1$H NMR (400 MHz, $CDCl_3$) δ 7.59 (m, 1H), 6.93 (m, 1H), 1.56 (s, 9H), 9, 1.52 (s, 9H).

Step 4: Synthesis of 19F

To a mixture of Zn powder (10.8 g, 166 mmol) and compound 19E (WO2013/56163) (362 mg, 1.3 mmol) in anhydrous THF (60 mL) was added DIBAL-H (2 mL, 3 mmol, 1.5 M in toluene) at r.t., the mixture was stirred at room temperature for 5 min, then more compound 19E (17.7 g, 65 mmol) in anhydrous THF (60 mL) was added drop-wise into the mixture over 20 min, the reaction mixture was warmed up to 50° C. and stirred at this temperature for 1 h, then the clear solution on the up-layer was transferred into a mixture of compound 19D (17.3 g, 44 mmol) and Pd(t-$Bu_3P)_2$ (558 mg, 1.1 mmol) in THF (60 mL), the mixture was stirred at r.t. under $N_2$ for 1 h, concentrated, and purified by silica gel chromatography directly to afford the titled compound 19F (18.5 g, 83%).

$^1$H NMR (400 MHz, CDCl3) δ 7.27-7.39 (m, 1H), 6.88-6.92 (m, 1H), 4.25-4.27 (m, 1H), 2.26-2.32 (m, 1H), 2.20 (m, 3H), 2.00-2.03 (m, 1H), 1.81-1.88 (m, 2H), 1.56 (s, 9H), 1.54 (s, 9H), 1.38 (s, 3H), 1.27 (s, 3H), 1.16-1.19 (d, 1H), 0.82 (s, 3H).

Step 5: Synthesis of 19G

To a solution of DCM (4.73 mL, 73.4 mmol) in anhydrous THF (400 mL) at −100° C. was added drop-wise n-BuLi (2.5 M in hexane, 21 mL, 51.2 mmol) over 1 h, the mixture was stirred at this temperature for 30 min, then a solution of compound 19F (18.5 g, 36.7 mmol) in anhydrous THF (100 mL) was added drop-wise into this mixture at −100° C. over 30 min, the mixture was slowly warmed up to r.t. and stirred at r.t. overnight, evaporated to dryness, and purified by silica gel chromatography to afford the titled compound 19G (16.3 g, 80%).

$^1$H NMR (400 MHz, $CDCl_3$) δ 7.35-7.39 (m, 1H), 6.92-6.96 (m, 1H), 4.35-4.37 (m, 1H), 3.61-3.65 (m, 1H), 3.13-3.19 (m, 1H), 2.94-3.00 (m, 1H), 2.33-2.36 (m, 1H), 2.30-2.31 (m, 1H), 2.18-2.20 (m, 1H), 1.89-1.93 (m, 2H), 1.56 (s, 9H), 1.54 (s, 9H), 1.38 (s, 3H), 1.28 (s, 3H), 1.08 (d, 1H), 0.82 (s, 3H).

Step 6: Synthesis of 19H

To the solution of compound 19G (490 mg, 0.89 mmol) in DMF (6 mL) was added MeOH (43 mg, 1.33 mmol), followed by $K_2CO_3$ (490 mg, 3.55 mmol). The resulting mixture was stirred at 50° C. for one hour before it was diluted with EtOAc/hexanes and washed with saturated $NH_4Cl$ and water. The organic layer was concentrated to dryness and purified by column chromatography (100% hexane~20% EtOAc-hexane) to obtain the titled compound 19H (250 mg, 51% yield) as slightly yellow oil.

MS calcd for ($C_{29}H_{42}BFO_8$): 548.
MS (ESI, positive) found: (M+1): 549.
MS (ESI, negative) found: (M−1): 547.

Step 7: Synthesis of 19

To the solution of compound 19H (240 mg, 0.44 mmol) in THF (2 mL) was added isobutylboronic acid (89 mg, 0.88 mmol), followed by concentrate HCl (2 mL). The resulting solution was stirred at room temperature for 2 hour before it was concentrated to dryness. The residue was purified by purified by prep-HPLC (C18, acetonitrile and water as mobile phases, 0.1% formic acid) to obtain the titled compound 19 (50 mg) as white solid.

$^1$H-NMR (400 MHz, $CD_3OD$) δ 7.24 (dd, 1H), 6.56 (dd, 1H), 3.36 (s, 3H), 3.05 (m, 1H), 2.92 (m, 2H).
MS calcd for ($C_{10}H_{10}BFO_5$): 240.
MS (ESI, positive) found: (M+1): 24.

Example 20: (R)-3-(4-amino-4H-1,2,4-triazol-3-ylthio)-7-fluoro-2-hydroxy-3,4-dihydro-2H-benzo[e][1,2]oxaborinine-8-carboxylic acid (20)

Compound (20) was prepared from 19G (example 19) following methods described in steps 5 and 6 of example 1 utilizing 4-amino-4H-1,2,4-triazole-3-thiol.

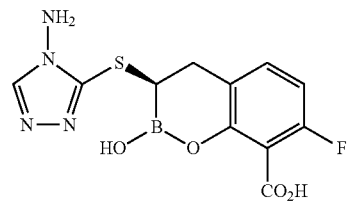

$^1$H-NMR (400 MHz, $CD_3OD$) δ 8.34 (s, 1H), 7.14 (dd, 1H), 6.57 (dd, 1H), 3.70 (s, 1H), 3.17 (dd, 1H), 2.94 (dd, 1H).
MS calcd for ($C_{11}H_{10}BFN_4O_4S$) 324.
MS (ESI, negative) found: (M−1): 323.

Example 21: (R)-(isopropoxycarbonyloxy)methyl 2-hydroxy-3-(4-methyl-4H-1,2,4-triazol-3-ylthio)-3,4-dihydro-2H-benzo[e][1,2]oxaborinine-8-carboxylate (21)

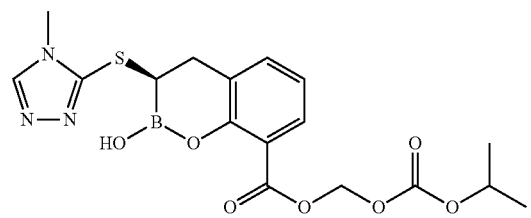

To the solution of acid 15 (0.5 mmol) in DMF (5 mL) was added chloromethyl isopropyl carbonate (1 mmol), followed by K$_2$CO$_3$ (0.75 mmol). The resulting mixture was stirred at 50° C. for 18 hours and brought to room temperature and concentrated. The residue was purified by purified by prep-HPLC (C18, acetonitrile and water as mobile phases, 0.1% formic acid) to obtain the titled compound.

$^1$H-NMR (400 MHz, CD$_3$OD) δ 8.33 (s, 1H), 7.47 (d, 1H), 7.22 (d, 1H), 6.78 (t, 1H), 5.89 (dd, 2H), 3.70 (m, 1H), 3.52 (s, 3H), 3.17 (dd, 1H), 2.93 (dd, 1H), 1.28 (d, 6H).

MS calcd for (C$_{17}$H$_{20}$BN$_3$O$_7$S) 421.

MS (ESI, positive) found: (M+Na): 444.

Example 22: 3-(2-amino-2-oxoethyl)-2-hydroxy-3, 4-dihydro-2H-benzo[e][1,2]oxaborinine-8-carboxylic acid (22)

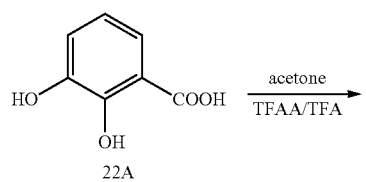

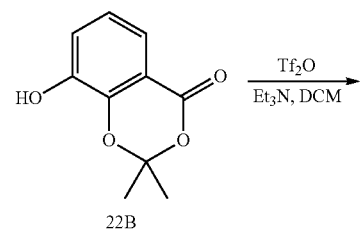

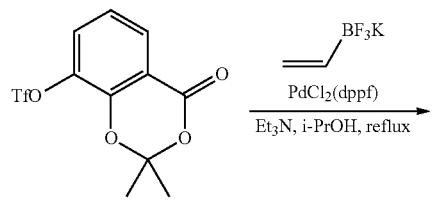

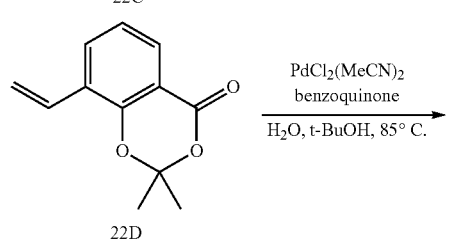

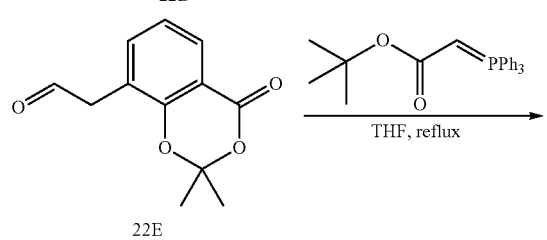

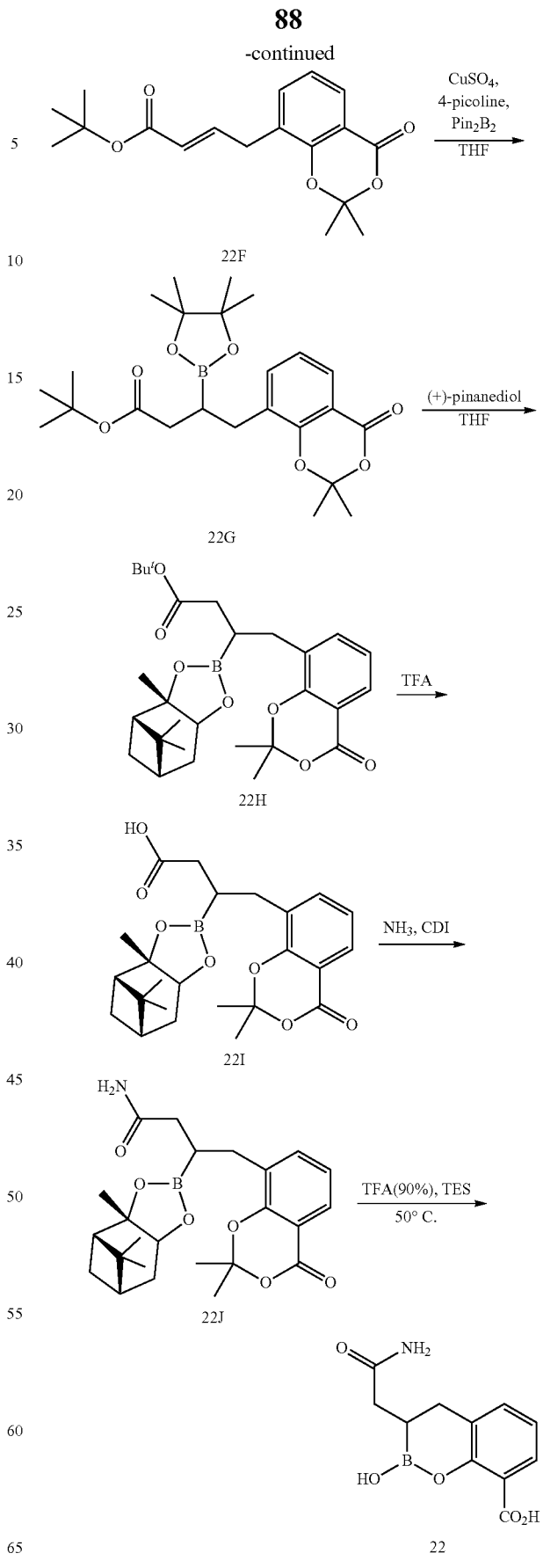

Step 1: Synthesis of Compound 22B

To the mixture of TFAA (225 mL) and TFA (370 mL) was added compound 22A (45 g, 292 mmol) slowly at −10° C., followed by the addition of acetone (60 g, 1.03 mmol) in TFA (77 mL) over 1 h. After being stirred at −4° C. for 3 h, the solution was warmed up to room temperature and stirred for 2 days before it was concentrated in vacuo to dryness. The residue was dissolved in EtOAc, washed with NaHCO$_3$ solution, dried over Na$_2$SO$_4$. Column chromatography (hexanes/ethyl acetate/DCM, v/v/v, 20/1/20) gave the titled compound 22B (28 g, 49% yield) as slightly yellow oil.

Step 2: Synthesis of Compound 22C

To the solution of compound 22B (28 g, 144.2 mmol) and triethylamine (73 g, 721 mmol) in dichloromethane (300 mL) at −78° C. was added Tf$_2$O (81.3 g, 288.4 mmol, 2 eq). The resulting mixture was warmed up to 0° C. slowly and stirred at 0° C. for 1 hour before it was quenched with water. The mixture was extracted with DCM and dried over Na$_2$SO$_4$. After concentrated to dryness, the residue was purified by column chromatography (ethyl acetate/hexanes, v/v, 1/40) to give the titled compound 22C (44 g, 94%) as a slightly yellow oil.

$^1$H-NMR (400 MHz, CDCl$_3$) δ 7.99 (d, 1H), 7.50 (d, 1H), 7.17 (t, 1H), 1.78 (s, 6H).

Step 3: Synthesis of Compound 22D

The mixture of compound 22C (6.55 g, 20 mmol), potassium vinyltrifluoroborate (3.22 g, 24 mmol), triethylamine (5.6 mL, 40 mmol) and PdCl$_2$(dppf) (820 mg, 1 mmol) in 2-propanol (150 mL) was degassed and filled with nitrogen (3 times) and refluxed for 15 hours. The reaction mixture was cooled down and concentrated to dryness. The residue was purified by column chromatography (ethyl acetate/hexanes, v/v, 1/6 to 1/3) to give the titled compound 22D (4.1 g, 75%) as a slightly yellow solid.

$^1$H-NMR (400 MHz, CDCl$_3$) δ 7.86 (d, 1H), 7.72 (d, 1H), 7.18 (t, 1H), 6.86 (dd, 1H), 5.82 (d, 1H), 5.39 (d, 1H), 1.77 (s, 6H).

Step 4: Synthesis of Compound 22E

To t-BuOH (160 mL) was added PdCl$_2$(MeCN)$_2$ (130 mg, 0.5 mmol) and 1,4-benzoquinone (2.5 g, 23 mmol) at 85° C., followed by water (0.36 mL, 20 mmol) and compound 22D (4.1 g, 20 mmol). The reaction mixture was stirred at 85° C. for about 30 minutes until TLC showed the disappearance of 22D. The reaction mixture was cooled down and concentrated to dryness. The residue was purified by column chromatography (ethyl acetate/hexanes, v/v, 1/3 to 1/2) to give the titled compound 22E (3.15 g, 70%) as yellow solid.

$^1$H-NMR (400 MHz, CDCl$_3$) δ 9.75 (s, 1H), 7.92 (d, 1H), 7.42 (d, 1H), 7.11 (t, 1H), 3.73 (s, 2H), 1.72 (s, 6H).

Step 5: Synthesis of Compound 22F

To the solution of compound 22E (2.51 g, 11.4 mmol) in THF (40 mL) was added (tert-Butoxycarbonylmethylene)triphenylphosphorane (5.15 g, 13.7 mmol). The reaction mixture was refluxed for 1.5 hours before it was cooled down and concentrated to dryness. The residue was purified by column chromatography (ethyl acetate/hexanes, v/v, 1/40 to 1/20) to give the titled compound 22F (2.73 g, 75%) as yellow solid.

$^1$H-NMR (400 MHz, CDCl$_3$) δ 7.88 (d, 1H), 7.39 (d, 1H), 7.08 (t, 1H), 6.92 (m, 1H), 5.70 (d, 1H), 3.47 (dd, 2H), 1.73 (s, 6H), 1.45 (s, 9H).

Step 6: Synthesis of Compound 22G

To the solution of compound 22F (2.0 g, 6.3 mmol) in THF (10 mL) was added bis(pinacolato)diboron (2.4 g, 9.4 mmol), 4-picoline (58.7 mg, 0.63 mmol), followed by CuSO$_4$ (16 mg, 0.063 mmol) in water (19 mL). The reaction mixture was stirred at room temperature for overnight before it was concentrated to dryness. The residue was purified by column chromatography (ethyl acetate/hexanes, v/v, 1/40 to 1/20) to give the titled compound 22G (0.94 g, 33%) as yellow solid.

MS calcd for (C$_{24}$H$_{35}$BO$_7$): 446.
MS (ESI, positive) found: (M+1): 447.

Step 7: Synthesis of Compound 22H

The solution of compound 22G (720 mg, 1.6 mmol) and (+)-pinanediol (412 mg, 2.4 mmol) in THF (15 mL) was stirred at room temperature for overnight before it was concentrated to dryness. The residue was purified by column chromatography (ethyl acetate/hexanes, v/v, 1/40 to 1/20) to give the titled compound 22H (756 mg, 95%) as yellow solid.

MS calcd for (C$_{28}$H$_{39}$BO$_7$): 498.
MS (ESI, positive) found: (M+1): 499.

Step 8: Synthesis of Compound 22I

To the solution of compound 22H (756 mg, 1.5 mmol) in DCM (10 mL) was added TFA (10 mL, 90% aqueous). The solution was stirred at room temperature for 1 hour before it was concentrated to dryness. The residue is the crude titled compound 22I (749 mg) as yellow oil, which was used for next step without further purification.

MS calcd for (C$_{24}$H$_{31}$BO$_7$): 442.
MS (ESI, positive) found: (M+1): 443.

Step 9: Synthesis of Compound 22J

To the solution of compound 22I (100 mg, 0.23 mmol) in DMF (4.5 mL) was added CDI (48 mg, 0.30 mmol). The solution was stirred at 36° C. for 1 hour and then cooled to room temperature. Ammonia gas was bubbled in. After 2 hour at room temperature, the reaction mixture was concentrated and purified by column chromatography (ethyl acetate/hexanes, v/v, 1/10 to 1/1) to give the titled compound 22J (81 mg, 81%) as yellow solid.

MS calcd for (C$_{24}$H$_{32}$BNO$_6$): 441.
MS (ESI, positive) found: (M+1): 442.

Step 10: Synthesis of Compound 22

To the mixture of compound 22J (81 mg, 0.18 mmol) and triethylsilane (0.7 mL) was added TFA (6.5 mL, 90% aqueous). The solution was stirred at 50° C. for 1.5 hour and then cooled to room temperature. The reaction mixture was concentrated to dryness and purified by prep-HPLC (C18, acetonitrile and water as mobile phases, 0.1% formic acid) to obtain the titled compound 22 (8.8 mg) as white solid.

$^1$H-NMR (400 MHz, CD$_3$OD) δ 7.82 (d, 1H), 7.33 (d, 1H), 6.93 (t, 1H), 2.86-2.99 (m, 2H), 2.53-2.58 (m, 1H), 2.22-2.28 (m, 1H), 1.61-1.65 (m, 1H).
MS calcd for (C$_{11}$H$_{12}$BNO$_5$): 249.
MS (ESI, positive) found: (M+1): 250.
MS (ESI, negative) found: (M−1): 248.

Example 23: (R)-3-(5-amino-1,3,4-thiadiazol-2-ylthio)-7-fluoro-2-hydroxy-3,4-dihydro-2H-benzo[e][1,2]oxaborinine-8-carboxylic acid (23)

Compound 23 was prepared from Compound 19G (example 19) following methods described in steps 5 and 6 of Example 1 utilizing 2-amino-5-mercapto-1,3,4-thiadiazole.

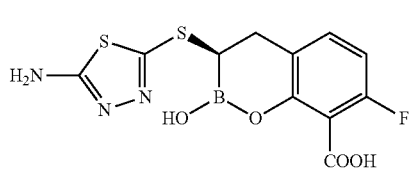
23

¹H NMR (400 MHz, CD₃OD) δ 7.15 (dd, 1H), 6.61 (dd, 1H), 3.56, (s, 1H), 3.16 (dd, 1H), 2.94 (dd, 1H).
MS calcd for (C₁₁H₉BFN₃O₄S₂): 341.
MS (ESI, positive) found: (M+1): 342.
MS (ESI, negative) found: (M−1): 340.

Example 24: (R)-7-fluoro-2-hydroxy-3-(4-methyl-4H-1,2,4-triazol-3-ylthio)-3,4-dihydro-2H-benzo[e][1,2]oxaborinine-8-carboxylic acid (24)

Compound 24 was prepared from Compound 19G (example 19) following methods described in steps 5 and 6 of Example 1 utilizing 4-methyl-3-mercapto-1,2,4-triazole.

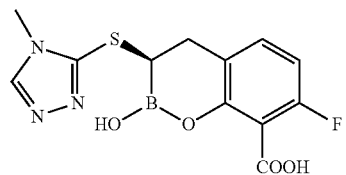
24

¹H NMR (400 MHz, CD₃OD) δ 8.38 (s, 1H), 7.13 (dd, 1H), 6.57 (dd, 1H), 3.78, (s, 1H), 3.57 (s, 3H), 3.16 (dd, 1H), 2.94 (dd, 1H).
MS calcd for (C₁₂H₁₁BFN₃O₄S): 323.
MS (ESI, positive) found: (M+1): 324.
MS (ESI, negative) found: (M−1): 322.

Example 25. (R)-3-(4-amino-4H-1,2,4-triazol-3-ylthio)-2-hydroxy-7-(methylthio)-3,4-dihydro-2H-benzo[e][1,2]oxaborinine-8-carboxylic acid (25)

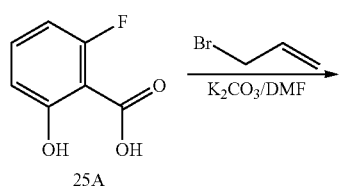

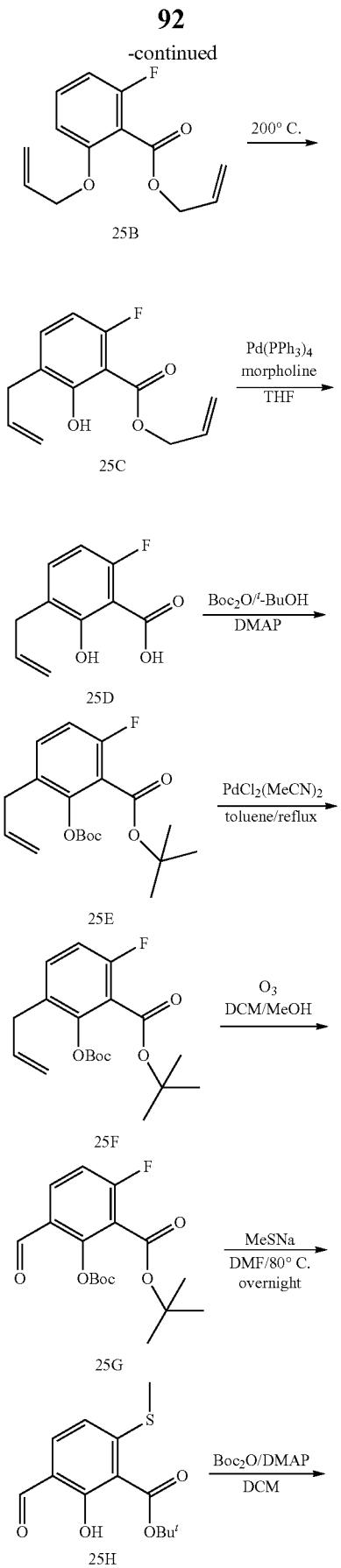

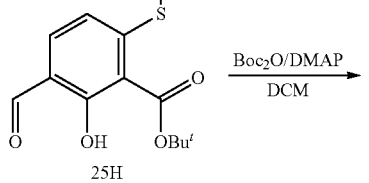

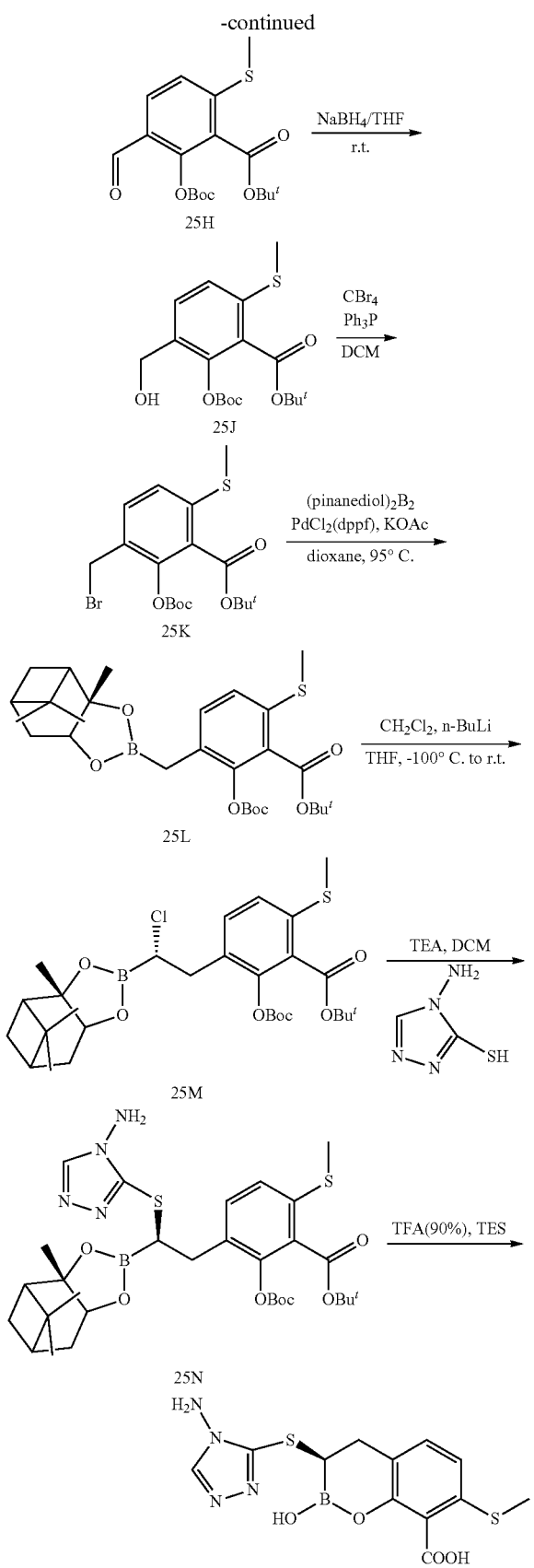

Step 1: Synthesis of Compound 25B

To the mixture of compound 25A (100 g, 0.64 mol) and allylbromide (232 g, 1.92 mol) in DMF (500 mL) was added $K_2CO_3$ (265 g, 1.92 mol). The resulting mixture was stirred at room temperature for 16 hours before it was concentrated in vacuo. The residue was purified by flash column chromatography (ethyl acetate/hexanes, v/v, 1/200~1/100) to give the titled compound 25B (162 g) as a yellow oil.

Step 2: Synthesis of Compound 25C

Compound 25B (162 g, 0.64 mol) was heated up to 200° C. for 8 hours under nitrogen. Column chromatography (ethyl acetate/hexanes, v/v, 1/200~1/100) gave the titled compound 25C (153 g) as yellow oil.

Step 3: Synthesis of Compound 25D

To the solution of 25C (153 g, 0.64 mol) in THF (1.2 L) was added $Pd(PPh_3)_4$ (22 g, 19.2 mmol) and morpholine (557 g, 6.4 mmol). The resulting solution was stirred at room temperature for two days. The reaction mixture was concentrated to dryness and purified by column chromatography (ethyl acetate/hexanes, v/v, 1/20~1/8) to obtain the titled compound 25D as slightly yellow oil.
$^1$H-NMR (400 MHz, $CDCl_3$) δ 11.50 (bs, 1H), 7.45-7.70 (m, 1H), 7.25-7.31 (m, 1H), 6.55-6.62 (m, 1H), 5.93-6.01 (m, 1H), 5.08 (d, 1H), 3.38 (s, 2H).

Step 4: Synthesis of Compound 25E

To the solution of compound 25D (95 g, 0.48 mol) in THF (1.0 L) was added $Boc_2O$ (418 g, 1.92 mol), DMAP (2.9 g, 24 mmol) and $^t$BuOH (1.0 L). The resulting solution was stirred at 60° C. overnight before it was concentrated in vacuo. The residue was purified by flash column chromatography (ethyl acetate/hexanes, v/v, 1/200~1/100) to give the titled compound 25E as slightly yellow oil.
$^1$H-NMR (400 MHz, $CDCl_3$) δ 7.20-7.26 (m, 1H), 6.92-6.97 (m, 1H), 5.85-5.90 (m, 1H), 5.05-5.11 (m, 2H), 3.30 (d, 2H), 1.57 (s, 9H), 1.53 (s, 9H).

Step 5: Synthesis of Compound 25F

The solution of 25E (109 g, 0.31 mol) and $PdCl_2(MeCN)_2$ (4.0 g, 15.5 mmol) in toluene (500 mL) was heated at 100° C. for 3 hours. After concentration, the residue was purified by flash column chromatography (ethyl acetate/hexanes, v/v, 1/200~1/100) to give the titled compound 25F as colorless oil, which contains some Boc-depleted side-product.
$^1$H-NMR (400 MHz, $CDCl_3$) δ 7.44-7.49 (m, 1H), 6.92-6.97 (m, 1H), 6.34-6.39 (m, 1H), 6.16-6.20 (m, 1H), 1.87 (d, 3H), 3.30 (d, 2H), 1.57 (s, 9H), 1.53 (s, 9H).

Step 6: Synthesis of Compound 25G

To the solution of 25F (27 g, 77 mmol, contains some Boc-depleted side product) in MeOH (100 mL) and DCM (500 mL) was bubbled ozone gas (generated is situ from oxygen) at −78° C. until light blue color appeared. Nitrogen gas was bubbled in to remove the blue color and then $Me_2S$ (50 mL) was added in. The resulting solution was slowly warmed up to room temperature overnight. After concentration, the residue was purified by column chromatography (ethyl acetate/hexanes, v/v, 1/50~1/20) to obtain the titled compound 25G (containing some Boc-depleted side product) as slightly yellow oil.

$^1$H-NMR (400 MHz, CDCl$_3$) δ 10.10 (s, 1H), 7.95 (dd, 1H), 7.14 (dd, 1H), 1.59 (s, 9H), 1.57 (s, 9H).

Step 7: Synthesis of Compound 25H

To the solution of 25G (19 g, 56 mmol, contains some Boc-depleted side product) in DMF (150 mL) was added NaSMe (11.8 g, 168 mmol). The resulting solution was stirred at 80° C. overnight, cooled to r.t., concentrated to small volume, and the pH was adjust to 5 with 1 N HCl solution, extracted with EtOAc, washed with water and brine, evaporated to dryness, the residue was purified by column chromatography (ethyl acetate/hexanes, v/v, 1/20~1/10) to obtain the titled compound 25H as slightly yellow oil.

$^1$H-NMR (400 MHz, CDCl$_3$) δ 12.03 (s, 1H), 10.14 (s, 1H), 7.67 (d, 1H), 6.79 (d, 1H), 2.48 (s, 3H), 1.65 (s, 9H).

Step 8: Synthesis of Compound 25I

To the solution of compound 25H (9.0 g, 34 mmol) in THF (50 mL) was added Boc$_2$O (7.4 g, 34 mol), DMAP (210 mg, 1.7 mmol) and $^t$BuOH (50 mL). The resulting solution was stirred at 60° C. overnight before it was concentrated in vacuo. The residue was purified by flash column chromatography (ethyl acetate/hexanes, v/v, 1/200~1/100) to give the titled compound 25I as slightly yellow oil.

$^1$H-NMR (400 MHz, CDCl$_3$) δ 10.00 (s, 1H), 7.82 (d, 1H), 7.21 (d, 1H), 2.52 (s, 3H), 1.65 (s, 9H), 1.61 (s, 9H).

Step 9: Synthesis of Compound 25J

To the solution of compound 25I (2.95 g, 8.0 mmol) in anhydrous THF (30 mL) was added NaBH$_4$ (240 mg, 6.4 mmol). The resulting solution was stirred at room temperature for 40 minutes before it was quenched with saturated NH$_4$Cl solution. The reaction mixture was extracted with EtOAc three times, after concentration in vacuo, the residue was purified by flash column chromatography (ethyl acetate/hexanes, v/v, 1/20~1/5) to give the titled compound 25J (1.5 g, 51% yield) as colorless oil.

$^1$H-NMR (400 MHz, CDCl$_3$) δ 7.47 (d, 1H), 7.20 (d, 1H), 4.55 (s, 2H), 2.47 (s, 3H), 1.65 (s, 9H), 1.61 (s, 9H).

Step 10: Synthesis of Compound 25K

To the solution of compound 25J (1.5 g, 4.0 mmol) in DCM (15 mL) was added CBr$_4$ (1.99 g, 6.0 mmol), followed by PPh$_3$ (1.57 g, 6.0 mmol). The resulting reaction mixture was stirred at room temperature for one hour before it was concentration in vacuo to dryness. The residue was purified by flash column chromatography (ethyl acetate/hexanes, v/v, 1/200~1/100) to give the titled compound 25K as yellow solid.

$^1$H-NMR (400 MHz, CDCl$_3$) δ 7.40 (d, 1H), 7.13 (d, 1H), 4.41 (s, 2H), 2.46 (s, 3H), 1.60 (s, 9H), 1.55 (s, 9H).

Step 11: Synthesis of Compound 25L

The mixture of compound 25K (1.4 g, 3.2 mmol), bis(pinanediolato)diboron (1.03 g, 2.88 mmol), PdCl$_2$(dppf) (130 mg, 0.16 mmol) and KOAc (940 mg, 9.6 mmol) in dioxane (10 mL) was flushed with nitrogen (3 times) and then stirred at 100° C. for 10 hours before it was concentration in vacuo to dryness. The residue was purified by flash column chromatography (ethyl acetate/hexanes, v/v, 1/200~1/100) to give the titled compound 25L as slightly yellow oil.

MS calcd for (C$_{28}$H$_{41}$BO$_7$S): 532.
MS (ESI, positive) found: (M+1): 533.

Step 12: Synthesis of Compound 25M

To a solution of CH$_2$Cl$_2$ (0.18 mL, 2.9 mmol) in THF (20 mL) at −100° C. was added 2.5 M n-butyl lithium in hexane (0.8 mL, 2.03 mmol) slowly under nitrogen and down the inside wall of the flask, maintaining the temperature below −90° C. The reaction mixture was stirred at −100° C. for another 30 minutes before the addition of compound 25L (0.77 g, 1.45 mmol) in THF (10 mL) at −90° C. and then the reaction was allowed to warm to room temperature where it was stirred for 16 h. The reaction was concentrated in vacuo directly to dryness and purified by column chromatography (100% hexane-20% EtOAc-hexane) to obtain the titled compound 25M as slightly yellow oil.

MS calcd for (C$_{29}$H$_{42}$BClO$_7$S): 580.
MS (ESI, positive) found: (M+1): 581.

Compound (25) was prepared from compound 25M following methods described in steps 5 and 6 of example 1 utilizing 4-amino-4H-1,2,4-triazole-3-thiol.

$^1$H NMR (400 MHz, CD$_3$OD) δ 8.33 (s, 1H), 7.15 (d, 1H), 6.81 (d, 1H), 3.74, (s, 1H), 3.18 (dd, 1H), 2.94 (dd, 1H), 2.35 (s, 3H).

MS calcd for (C$_{12}$H$_{13}$BN$_4$O$_4$S$_2$): 352.
MS (ESI, positive) found: (M+1): 353.
MS (ESI, negative) found: (M−1): 351.

Example 26: (R)-3-(4-amino-4H-1,2,4-triazol-3-ylthio)-2-hydroxy-7-methoxy-3,4-dihydro-2H-benzo[e][1,2]oxaborinine-8-carboxylic acid (26)

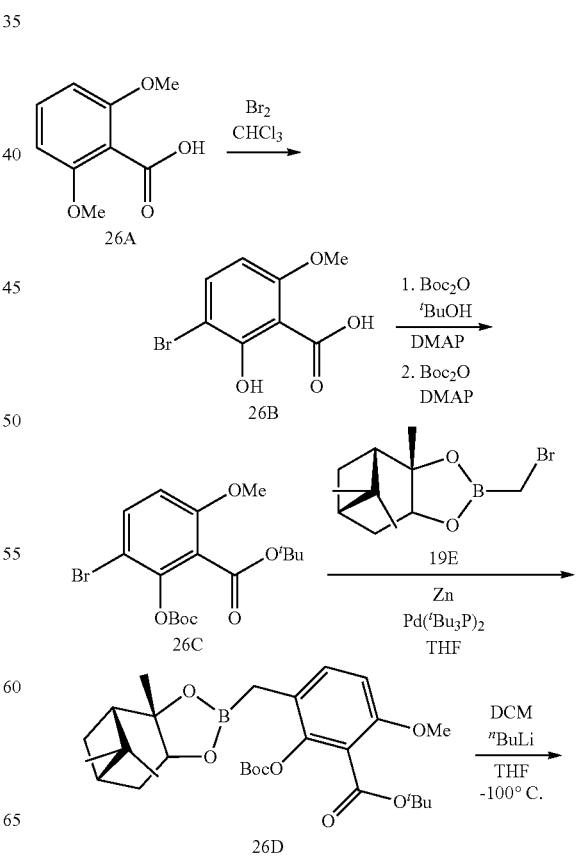

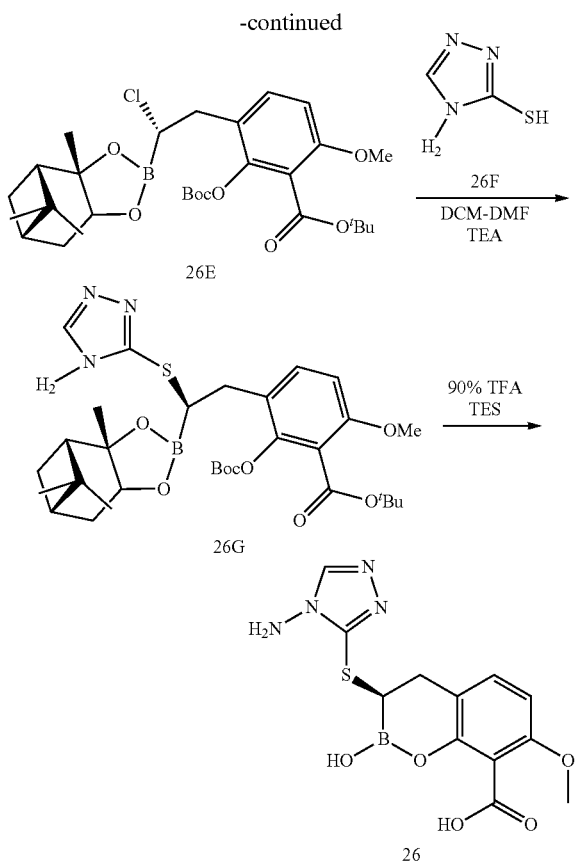

Step 1: Synthesis of 26B

To a solution of 2, 6-dimethoxybenzoic acid (26A) (50 g, 0.275 mol) in CHCl3 (1 L) at 0° C. was added dropwise bromine (14.4 mL, 0.263 mol). The reaction mixture was stirred at 25° C. for 30 hours, before it was concentrated to dryness. The residue was purified by column chromatography (ethyl acetate/hexanes) to afford compound 26B (32.5 g, 48%) as white solid.

Step 2: Synthesis of 26C

To the solution of compound 26B (32.5 g, 0.132 mol) in THF (200 mL) was added Boc2O (114.7 g, 0.526 mol), DMAP (4.8 g, 0.04 mol) and tBuOH (400 mL). The resulting solution was stirred at 60° C. for 6 hours before it was concentrated in vacuo. The residue was quickly passed through a silica gel column (ethyl acetate/hexanes) to give the corresponding t-butyl ester. To the solution of this ester and Boc$_2$O (17 g, 0.078 mol) in DCM (300 mL) was added DMAP (475 mg, 3.89 mmol). The resulting reaction mixture was stirred at room temperature for 1 hour before it was concentrated to dryness. The residue was purified by column chromatography (ethyl acetate/hexanes) to afford compound 26C (52.1 g, 98%) as white solid.

Step 3: Synthesis of 26D

To a mixture of Zn powder (20 g, 0.302 mol) and compound 19E (100 mg, 0.37 mmol) in anhydrous THF (100 mL) was added DIBAL-H (2.45 mL, 6.05 mmol, 1.5 M in toluene) at room temperature. The mixture was stirred at room temperature for 5 min, then more compound 19E (33 g, 0.121 mol) in anhydrous THF (100 mL) was added dropwise into the mixture over 20 min. The reaction mixture was warmed up to 50° C. and stirred at this temperature for 1 hour before it was settled down at room temperature. The top layer of clear solution was transferred into a mixture of compound 26C (20 g, 50 mmol) and Pd(t-Bu3P)2 (917 mg, 1.79 mmol) in THF (300 mL) at room temperature under N$_2$. After stirring at room temperature for 1 hour, the reaction mixture was concentrated, and purified by column chromatography (ethyl acetate/hexanes) to afford compound 26D (21 g, 81%) as light yellow solid.

Step 4: Synthesis of 26E

To a solution of dichloromethane (4.2 mL, 0.066 mol) in anhydrous THF (200 mL), was added dropwise n-butyllithium (2.5 M in hexane, 18.5 mL, 0.046 mol) along the wall of the flask over 1 h at −100° C. (cooled with liquid nitrogen and methanol), while keeping the internal temperature below −90° C. After the addition, the mixture was stirred at −100° C. for 30 min before slow addition of the solution of compound 26D (17 g, 0.033 mol) in anhydrous THF (60 mL) over 1 h at −100° C. The reaction mixture was slowly warmed up to room temperature over a period of 6 hours and stirred overnight. The solvent was evaporated and the residue was purified by column chromatography (ethyl acetate/hexanes) to afford compound 26E (16.5 g, 88%) as light yellow solid.

Step 5: Synthesis of 26G

Compound 26G was prepared following similar procedure described in step 5 of example 1 replacing 2-mercapto-1,3,4-thiadiazole in step 5 with 4-amino-4H-1,2,4-triazole-3-thiol (26F).

Step 6: Synthesis of 26

Compound 26 was prepared starting from 26G following similar procedure described in step 6 of example 1.
$^1$H NMR (300 MHz, CD$_3$OD) δ 8.42 (s, 1H), 6.65 (d, 1H), 6.32 (d, 1H), 3.84 (s, 3H), 3.02 (dd, 2H), 2.63 (dd, 1H).
MS calcd for (C$_{12}$H$_{13}$BN$_4$O$_5$S): 336.
MS (ESI, positive) found: (M+1): 337.
MS (ESI, negative) found: (M−1): 335.

Example 27: (R)-3-(5-amino-1,3,4-thiadiazol-2-ylthio)-2-hydroxy-7-methoxy-3,4-dihydro-2H-benzo[e][1,2]oxaborinine-8-carboxylic acid (27)

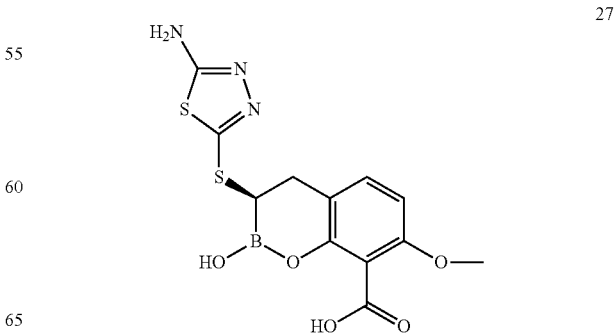

Compound 27 was prepared following the procedure described in Example 26 except replacing 4-amino-4H-1,2,4-triazole-3-thiol in step 5 with 5-amino-1,3,4-thiadiazole-2-thiol.

$^1$H NMR (300 MHz, CD$_3$OD) δ 6.85 (d, 1H), 6.25 (d, 1H), 3.74 (s, 3H), 3.05 (dd, 1H), 2.85 (dd, 2H).

MS calcd for (C$_{12}$H$_{12}$BN$_3$O$_5$S$_2$): 353.

MS (ESI, positive) found: (M+1): 354.

MS (ESI, negative) found: (M−1): 352.

Example 28: (R)-2-hydroxy-7-methoxy-3-(4-methyl-4H-1,2,4-triazol-3-ylthio)-3,4-dihydro-2H-benzo[e][1,2]oxaborinine-8-carboxylic acid (28)

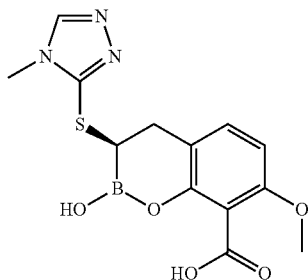

58] Compound 28 was prepared following the procedure described in Example 26 except replacing 4-amino-4H-1,2,4-triazole-3-thiol in step 5 with 4-methyl-4H-1,2,4-triazole-3-thiol.

$^1$H NMR (400 MHz, CD$_3$OD) δ 8.45 (s, 1H), 7.05 (d, 1H), 6.48 (d, 1H), 3.85 (m, 1H), 3.75 (s, 3H), 3.74 (s, 3H), 3.15 (dd, 1H), 2.85 (dd, 1H). 7.23 (d, 1H), 6.78 (d, 1H), 3.53 (t, 1H), 3.21 (dd, 1H), 2.95 (dd, 1H), 2.45 (s, 3H).

MS calcd for (C$_{13}$H$_{14}$BN$_3$O$_5$S): 335.

MS (ESI, positive) found: (M+1): 336.

MS (ESI, negative) found: (M−1): N/A.

Example 29: (R)-2-hydroxy-3-(4-methyl-4H-1,2,4-triazol-3-ylthio)-7-(methylthio)-3,4-dihydro-2H-benzo[e][1,2]oxaborinine-8-carboxylic acid (29)

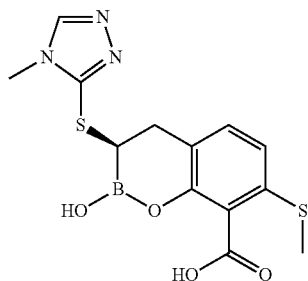

Compound 29 was prepared following the procedure described in Example 25 except replacing 4-amino-4H-1,2,4-triazole-3-thiol with 4-methyl-4H-1,2,4-triazole-3-thiol.

$^1$H NMR (400 MHz, CD$_3$OD) δ 8.37 (s, 1H), 7.15 (d, 1H), 6.82 (d, 1H), 3.83 (s, 1H), 3.53 (s, 3H), 3.17 (d, 1H), 2.96 (d, 1H), 2.36 (d, 3H).

MS calcd for (C$_{13}$H$_{14}$BN$_3$O$_4$S$_2$): 351.

MS (ESI, positive) found: (M+1): 352.

MS (ESI, negative) found: (M−1): N/A.

Example 30: (R)-3-(5-amino-1,3,4-thiadiazol-2-ylthio)-2-hydroxy-7-(methylthio)-3,4-dihydro-2H-benzo[e][1,2]oxaborinine-8-carboxylic acid (30)

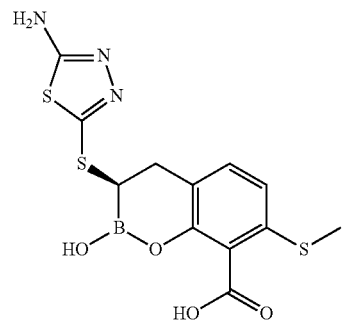

Compound 30 was prepared following the procedure described in Example 25 except replacing 4-amino-4H-1,2,4-triazole-3-thiol with 5-amino-1,3,4-thiadiazole-2-thiol.

$^1$H NMR (400 MHz, CD$_3$OD) δ 7.23 (d, 1H), 6.85 (d, 1H), 3.65 (s, 1H), 3.30 (m, 1H), 2.95 (d, 1H), 2.45 (s, 3H).

MS calcd for (C$_{12}$H$_{12}$BN$_3$O$_4$S$_3$): 369.

MS (ESI, positive) found: (M+1): 370.

MS (ESI, negative) found: (M−1): 368.

Example 31: (R)-3-(5-amino-1,3,4-thiadiazol-2-ylthio)-2-hydroxy-7-methyl-3,4-dihydro-2H-benzo[e][1,2]oxaborinine-8-carboxylic acid (31)

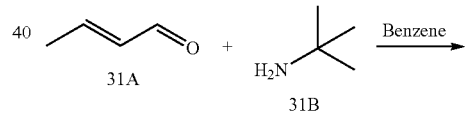

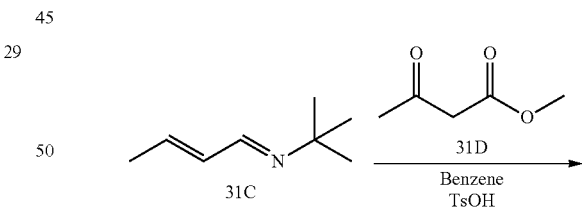

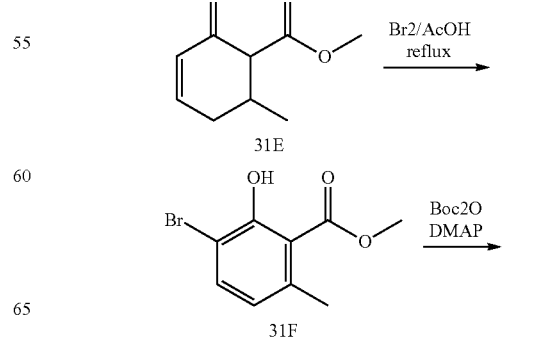

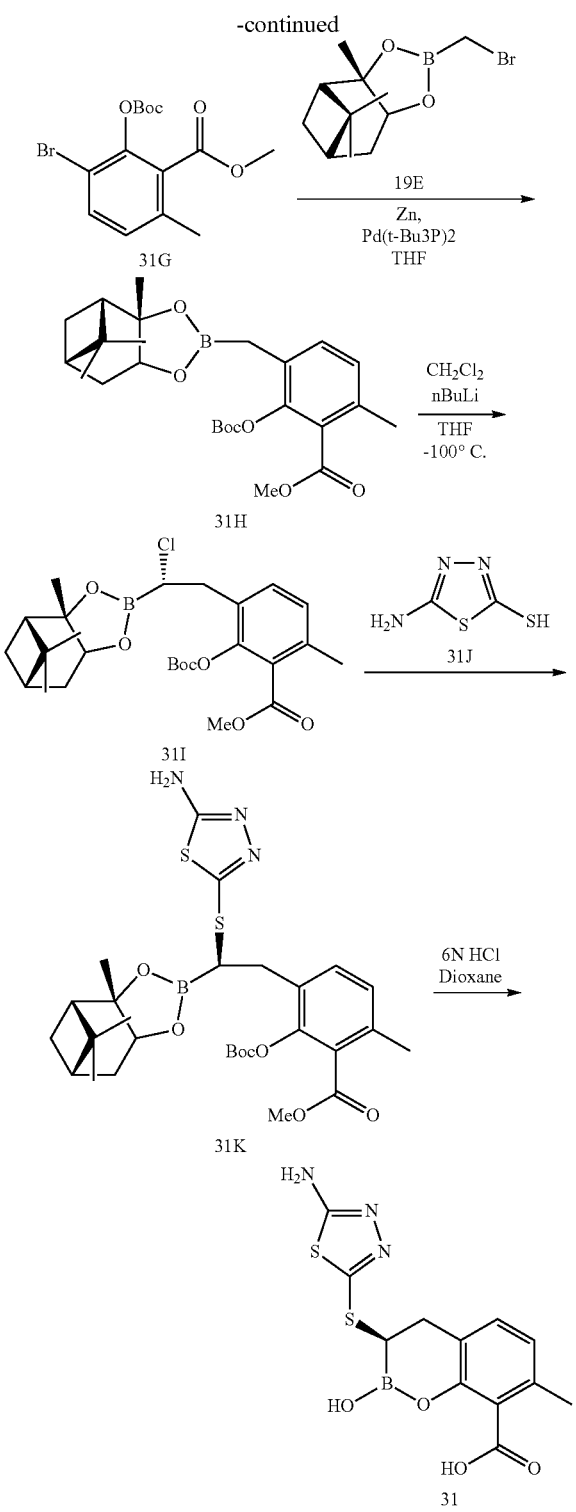

Step 1: Synthesis of 31C

To a solution of compound 31A (84 g, 1.198 mol) and compound 31B (87.5 g, 1.198 mol) in benzene (500 mL) was stirred at r.t. for 2 h under N2, Then heated in a Dean-Stark apparatus until H₂O formation ceases (ca. 2 h). The mixture was cooled to r.t. The mixture was washed with water (500 mL) and dried over MgSO4, filtered and concentrated and the residue was distilled to afford compound 31C (45.76 g, 30%).

Step 2: Synthesis of 31E

To a solution of compound 31C (45.76 g, 0.366 mol) and compound 31D (42.47 g, 0.366 mol) in benzene (800 mL) was added TsOH (1.39 g, 7.322 mmol) at room temperature, and stirred at room temperature for 72 h under $N_2$. The mixture was washed with water (500 mL) and dried over $MgSO_4$. The organic extract was filtered and concentrated, purified by silica gel chromatography to afford compound 31E (20 g, 32.5%).

Step 3: Synthesis of 31F

To a solution of compound 31E (20 g, 119.048 mmol) in AcOH (100 ml) was added dropwise $Br_2$ at 0° C. The mixture was stirred at 100° C. for 24 h under $N_2$, cooled to r.t. and concentrated. The residue was purified by distillation to afford compound 31F (20.3 g, 70%).

Step 4: Synthesis of 31G

To a solution of compound 31F (20 g, 81.6 mmol) and Boc₂O (17.8 g, 81.6 mmol) in DCM (200 mL) was added DMAP (500 mg, 4.1 mmol) at room temperature. The mixture was stirred at room temperature for 3 h, then evaporated to dryness. The residue was purified by silica gel chromatography to afford compound 31G (22 g, 78%).

Step 5: Synthesis of 31H

To a solution of 31G (1.5 g, 4.35 mmol) and Pd(P^tBu₃)₂ (66.7 mg, 0.13 mmol) in THF (20 mL) was added zinc reagent of 19E (freshly prepared as step 4 of Example 19) (5.65 mmol) at room temperature. The mixture was stirred at room temperature overnight, then evaporated to dryness. The crude product was purified by silica gel chromatography to afford compound 31H (0.82 g, 40.2%).

Step 6: Synthesis of 31I

To a solution of dichloromethane (0.304 g, 3.58 mmol) in anhydrous THF (20 mL) in a three-neck flask at −100° C., cooled with liquid nitrogen and methanol was added dropwise n-butyllithium (1 mL, 2.5 mmol), through the wall of the flask over 0.5 h while keeping the internal temperature of the flask below −90° C. After the addition, the mixture was stirred at this temperature for 30 min, To the mixture at −100° C. was added dropwise a solution of compound 31H (0.82 g, 1.79 mmol) in anhydrous THF (10 mL) over 0.5 h. After the addition, the mixture was slowly warmed up to room temperature, and stirred overnight. The solvent was evaporated to dryness to give a residue, which was purified by silica gel chromatography (PE: EA, 5:1) to afford compound 31I (0.74 g, 81.6%).

Step 7: Synthesis of 31K

To a solution of compound 31I (0.3 g, 0.59 mmol) and compound 31J (0.12 mg, 0.889 mmol) in DCM/DMF (5 mL/2 mL) was added TEA (0.12 mg, 1.19 mmol) at room temperature. The mixture was stirred at room temperature overnight, then evaporated to 3 mL, extracted with EA, washed with brine, dried over NaSO₄, filtered. The filtrate was evaporated to dryness, purified by silica gel chromatography to afford compound 31K (0.35 g, 97.8%).

Step 8: Synthesis of 31

A solution of compound 31K (200 mg) in 6 N HCl/dioxane (3 mL/2 mL) was stirred at 100° C. for 2 h. The mixture was then evaporated to dryness and purified by prep-HPLC to afford 31 (5.6 mg).

1H NMR (400 MHz, CD3OD) δ 7.04 (d, 1H), 6.71 (d, 1H), 3.57 (t, 1H), 3.20 (dd, 1H), 2.92 (d, 1H), 2.37 (m, 3H).
MS calcd for ($C_{12}H_{12}BN_3O_4S_2$): 337.
MS (ESI, positive) found: (M+1): 338.
MS (ESI, negative) found: (M−1): 336.

Example 32: (R)-3-(5-amino-1,3,4-thiadiazol-2-ylthio)-2-hydroxy-5,7-dimethoxy-3,4-dihydro-2H-benzo[e][1,2]oxaborinine-8-carboxylic acid (32)

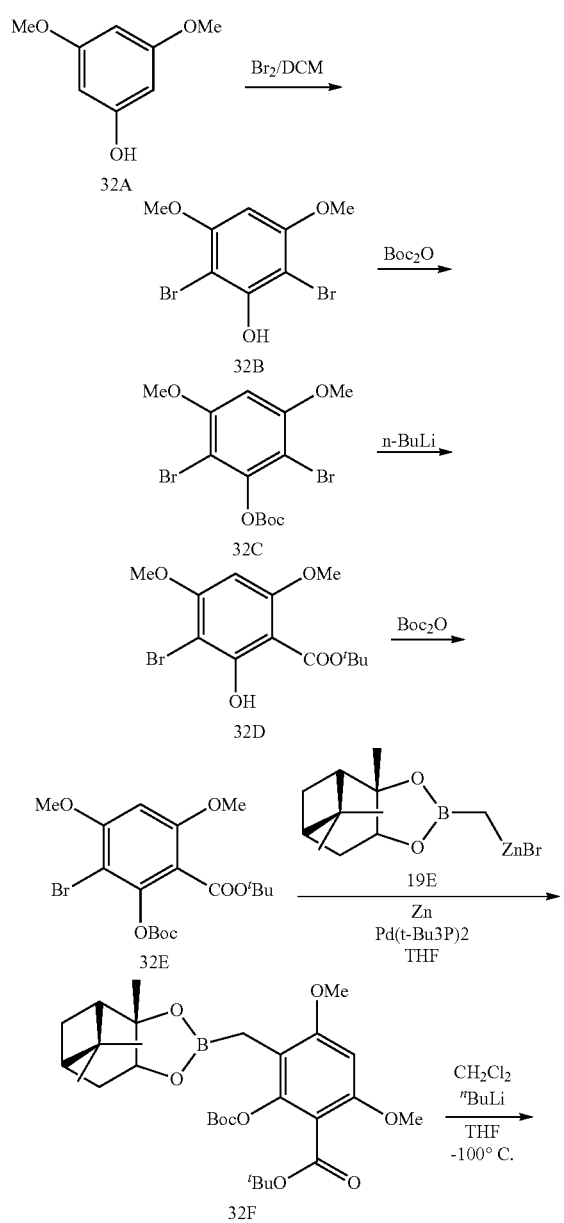

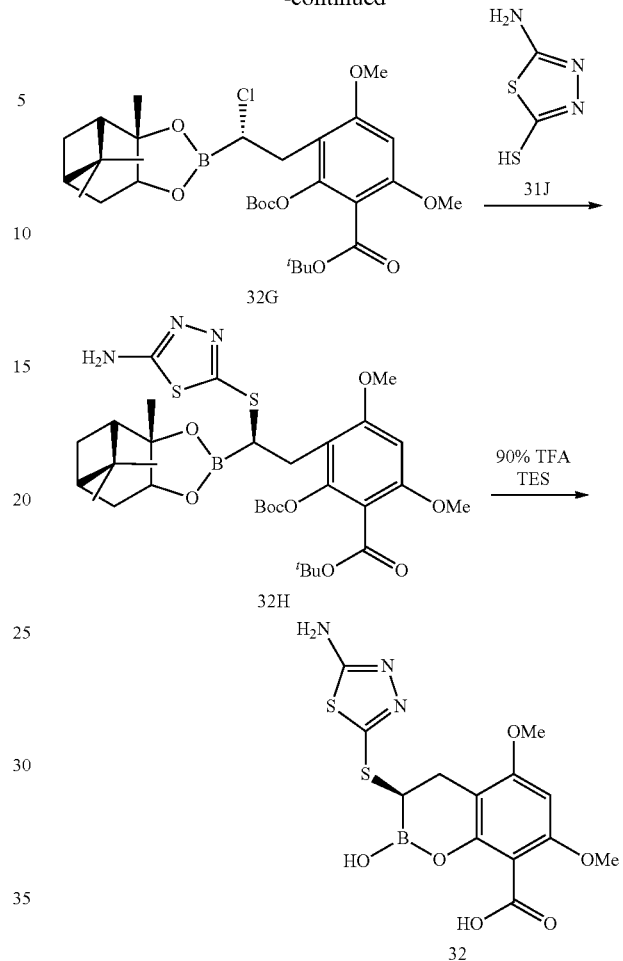

Step 1: Synthesis of 32B (*Can. J. Chem.*, 1989, 67, 335-344)

To a solution of compound 32A (5 g, 32.4 mmol) in DCM (50 mL) was added dropwise a solution of $Br_2$ (10.4 g, 64.8 mmol) in DCM (20 mL) at 0° C. and the mixture was stirred at 0° C. for 1 h. To the mixture was then added a solution of $Na_2S_2O_3$ (5.1 g, 32.4 mmol) in water (20 mL), and extracted with EtOAc, washed with saturated $NaHCO_3$ and brine. The extract was dried over $Na_2SO_4$, filtered and concentrated to afford compound 32B (10 g, 99%).

Step 2: Synthesis of 32C

To a solution of compound 32B (10 g, 32.15 mmol) and $Boc_2O$ (7 g, 32.15 mmol) in DCM (100 mL) was added DMAP (196 mg, 1.61 mmol) at room temperature. The mixture was stirred at room temperature for 3 h, then evaporated to dryness. The crude product was purified by silica gel chromatography to afford compound 32C (7.1 g, 65.3%).

Step 3: Synthesis of 32D

To a solution of compound 32C (6.85 g, 16.63 mmol) in anhydrous THF (100 mL) was added dropwise n-BuLi (6.65 mL, 16.63 mmol) at −78° C. under $N_2$. The mixture was stirred at −78° C. for 15 min, then warmed up to room temperature. Reaction mixture was diluted with EtOAc (100 mL), washed with 0.5 N HCl (50 mL) and brine, dried over $NaSO_4$. The organic extract was filtered and concentrated to afford compound 32D (5.5 g, 99%).

Step 4: Synthesis of 32E

To a solution of compound 32D (5.5 g, 16.6 mmol) and $Boc_2O$ (5.4 g, 24.8 mmol) in DCM (100 mL) was added DMAP (202 mg, 1.66 mmol) at room temperature. The mixture was stirred at room temperature for 3 h, then evaporated to dryness. The crude product was purified by silica gel chromatography to afford compound 32E (6.2 g, 85.6%).

Step 5: Synthesis of 32F

To a solution of compound 32E and $Pd(P^tBu_3)_2$ (40 mg, 0.45 mmol) in THF (50 mL) was added zinc reagent of 19E (prepared as step 4 of Example 19) (25.5 mmol) at room temperature. The mixture was stirred at room temperature overnight, then evaporated to dryness. The crude product purified by silica gel chromatography to afford compound 32F (7.2 g, 78.3%).

Step 6: Synthesis of 32G

To a solution of dichloromethane (1.1 g, 12.7 mmol) in anhydrous THF (50 mL) in a three-neck flask at −100° C., cooled with liquid nitrogen and methanol, was added dropwise n-butyllithium (3.6 mL, 8.88 mmol) through the wall of the flask over 0.5 h while keeping the internal temperature of the flask below −90° C. After the addition, the mixture was stirred at this temperature for 30 min, To the mixture at −100° C. was added dropwise a solution of compound 32F (3 g, 6.34 mmol) in anhydrous THF (10 mL) over 0.5 h. After the addition, the mixture was slowly warmed up to room temperature and stirred overnight. The reaction solvent was evaporated to dryness to give a residue, which was purified by silica gel chromatography (PE: EA, 5:1) to afford the compound 32G (2.4 g, 72.7%).

Step 7: Synthesis of 32H

To a solution of compound 32G (1.2 g, 2.3 mmol) and compound 31J (367 mg, 2.8 mmol) in DCM/DMF (10 mL/3 mL) was added TEA (349 mg, 3.5 mmol) at room temperature. The mixture was stirred at room temperature overnight, then concentrated. The mixture was extracted with EA, washed with brine, dried over $NaSO_4$, filtered and evaporated to dryness. The crude product was purified by silica gel chromatography to afford compound 32H (210 mg, 16.5%).

Step 8: Synthesis of 32

A solution of compound 32H (210 mg) in TFA (90%)/TES (5 mL/1 mL) was stirred at room temperature for 2 h. The reaction was then evaporated to dryness and purified by pre-HPLC to afford 32 (32 mg, 25.4%).
$^1$H NMR (400 MHz, CD3OD) 6.6.26 (s, 1H), 3.88 (s, 3H), 3.83 (s, 3H), 3.54 (s, 1H), 3.23 (s, 1H), 2.75 (dd, 1H).
MS calcd for ($C_{13}H_{14}BN_3O_6S_2$): 383.
MS (ESI, positive) found: (M+1): 384.
MS (ESI, negative) found: (M−1): 382.

Example 33: (R)-3-(5-amino-1,3,4-thiadiazol-2-ylthio)-5,7-difluoro-2-hydroxy-3,4-dihydro-2H-benzo[e][1,2]oxaborinine-8-carboxylic acid (33)

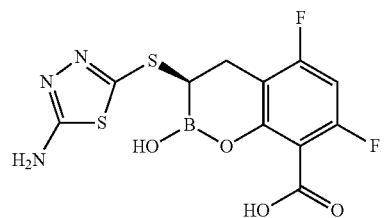

33

Compound 33 was prepared from 2,4-Difluoro-6-hydroxybenzoic acid (WO 2009129938) following the procedure described in Example 26 except replacing 4-amino-4H-1,2,4-triazole-3-thiol in step 5 with 5-amino-1,3,4-thiadiazole-2-thiol.
$^1$H NMR (400 MHz, $CD_3OD$) δ 6.55 (t, 1H), 3.60 (t, 1H), 3.21 (dd, 1H), 2.95 (dd, 1H).
MS calcd for ($C_{11}H_8BF_2N_3O_4S_2$): 359.
MS (ESI, positive) found: (M+1): 360.
MS (ESI, negative) found: (M−1): 358.

Example 34: (3R)-3-(5-amino-1,3,4-thiadiazol-2-ylthio)-2-hydroxy-7-(methylsulfinyl)-3,4-dihydro-2H-benzo[e][1,2]oxaborinine-8-carboxylic acid (34)

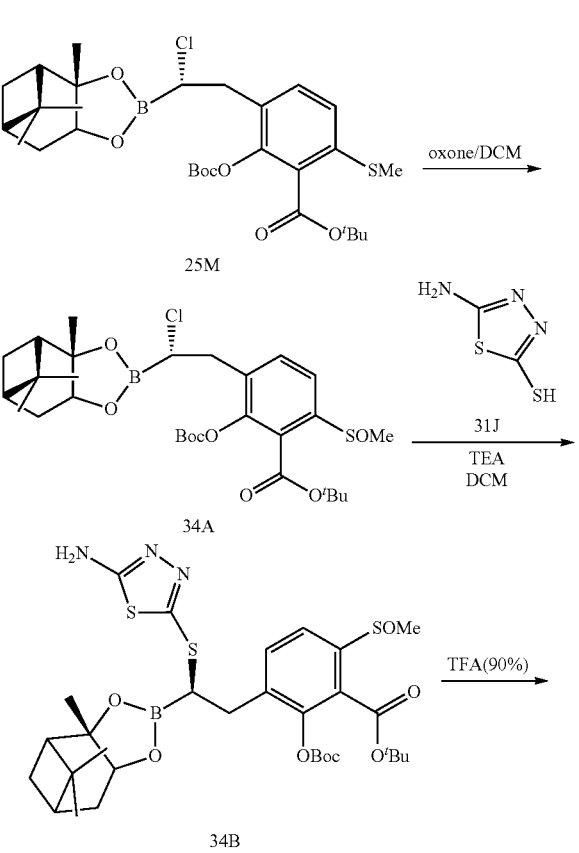

-continued

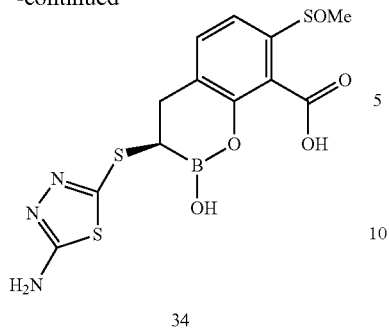

34

Step 1: Synthesis of 34A

To a solution of compound 25M (from Example 25) (2.5 g, 4.69 mmol) in DCM (100 mL) at room temperature was added oxone (14.4 g, 46.94 mmol). The mixture was stirred at 35° C. for 48 h, then filtrated and concentrated to dryness. The residue was purified by silica gel chromatography to afford compound 34A (1 g, 38.9%).

Step 2: Synthesis of 34B

To a solution of compound 34A (210 mg, 0.35 mmol) and compound 31J (71 mg, 0.53 mmol) in DCM/DMF (2 mL/1 mL) at room temperature was added TEA (70 mg, 0.7 mmol) and the mixture was stirred at room temperature overnight. The mixture was then evaporated to 1 mL, extracted with EA, washed with brine and dried over $Na_2SO_4$. The organic extract was filtered and evaporated to dryness and purified by silica gel chromatography to afford compound 34B (150 mg, 61.5%).

Step 3: Synthesis of 34B

A solution of compound 34B (150 mg) in 90% aq.TFA (3 mL) was stirred at room temperature for 2 h. The reaction mixture was then evaporated to dryness and purified by pre-HPLC to afford 34 (18 mg, 21.7%).

$^1$H NMR (400 MHz, $CD_3OD$) δ 7.65 (d, 1H), 7.60 (d, 1H), 5.23 (d, 1H), 3.72 (s, 1H), 3.30 (m, 1H), 3.15 (d, 1H), 2.82 (dd, 3H).

MS calcd for ($C_{12}H_{12}BN_3O_5S_3$): 385.
MS (ESI, positive) found: (M+1): 386.
MS (ESI, negative) found: (M−1): 384.

Example 35: (R)-3-(5-amino-1,3,4-thiadiazol-2-ylthio)-2-hydroxy-7-(methoxymethyl)-3,4-dihydro-2H-benzo[e][1,2]oxaborinine-8-carboxylic acid (35)

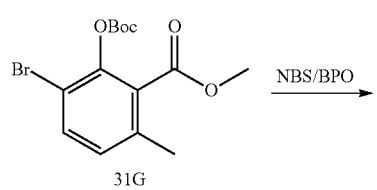

31G

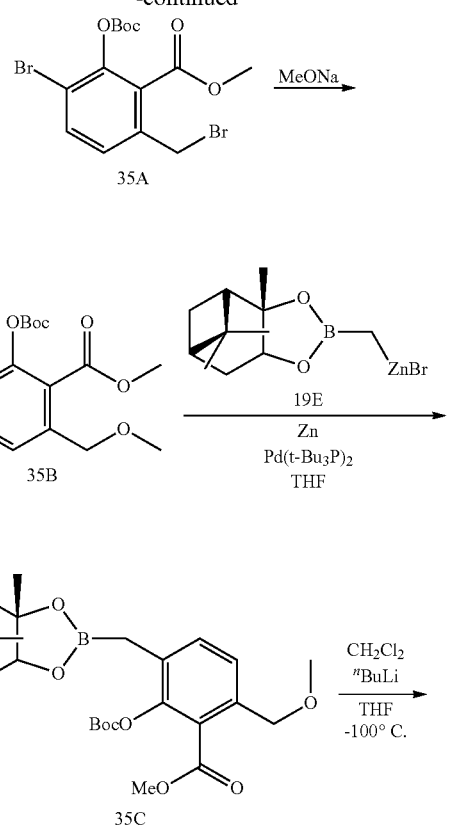

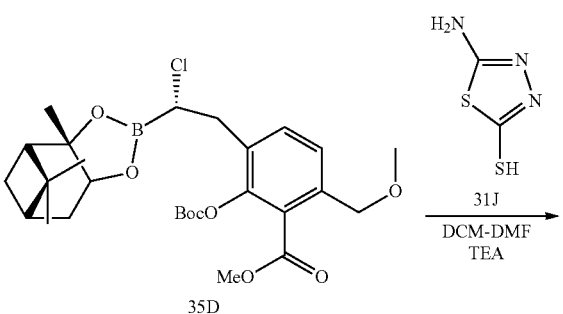

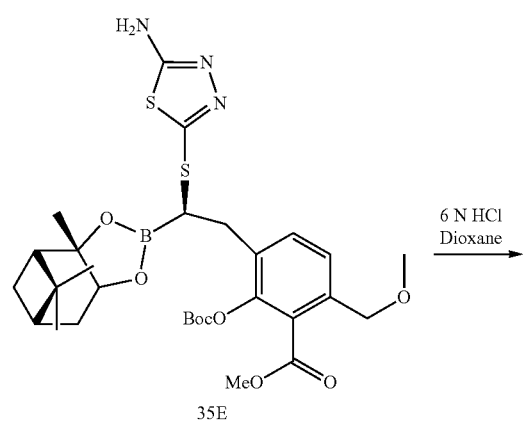

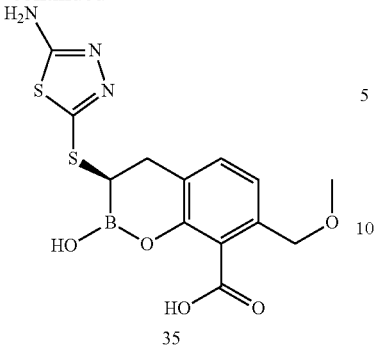

35

Step 1: Synthesis of 35A

To a solution of compound 31G (1.1 g, 3.19 mmol) and BPO (0.077 g, 0.319 mmol) in CCl₄ (100 mL) at room temperature was added NBS (0.851 g, 4.78 mmol). The mixture was stirred at 100° C. overnight, then concentrated to dryness. The residue was purified by silica gel chromatography to afford compound 35A (1.3 g, 97%).

Step 2: Synthesis of 35B

To a solution of compound 35A (1.3 g, 3.081 mmol) and MeONa (199 mg, 3.697 mmol) in MeOH (10 mL) was stirred at 80° C. for 4 h. The reaction mixture was then evaporated to dryness and purified by silica gel chromatography to afford compound 35B (700 mg, 60.9%).

Step 3: Synthesis of 35C

To a solution of compound 35B (0.7 g, 2.01 mmol) and Pd(P$^t$Bu₃)₂ (61.5 mg, 0.12 mmol) in THF (20 mL) was added zinc reagent of 19E (freshly prepared as in step 4 of Example 19) (3.01 mmol) at room temperature. The mixture was stirred at room temperature overnight, then evaporated to dryness. The crude product was purified by silica gel chromatography to afford compound 35C (600 mg, 61.2%).

Step 4: Synthesis of 35D

To a solution of dichloromethane (0.209 g, 2.46 mmol) in anhydrous THF (10 mL) in a three-neck flask at −100° C., cooled with liquid nitrogen and methanol, was added dropwise n-butyllithium (0.74 mL, 1.84 mmol) through the wall of the flask over 0.5 h while keeping the internal temperature of the flask below −90° C. After the addition, the mixture was stirred at this temperature for 30 min, To the mixture at −100° C. was added dropwise a solution of compound 35C (0.6 g, 1.23 mmol) in anhydrous THF (10 mL) over 0.5 h. After the addition, the mixture was slowly warmed up to room temperature, and stirred overnight. The reaction solvent was evaporated to dryness to give a residue, which was purified by silica gel chromatography (PE: EA, 5:1) to afford the compound 35D (530 mg, 80.3%).

Step 5: Synthesis of 35E

To a solution of compound 35D (520 mg, 0.97 mmol) and compound 31J (193.5 mg, 1.45 mmol) in DCM/DMF (10 mL/5 mL) was added TEA (0.3 ml, 1.94 mmol) at room temperature. The mixture was stirred at room temperature overnight, then evaporated to 3 mL. The reaction was diluted with EtOAc, washed with brine and dried over NaSO₄. The organic extract was filtered, evaporated to dryness, and purified by silica gel chromatography to afford compound 35E (600 mg, 97.7%).

Step 6: Synthesis of 35

A solution of compound 35E (200 mg) in 6 N HCl/dioxane (4 mL/2 mL) was stirred at 100° C. for 2 h. The reaction mixture was then evaporated to dryness and purified by pre-HPLC to afford 35 (17.1 mg).

1H NMR (400 MHz, CD3OD) δ 7.17 (d, 1H), 6.99 (d, 1H), 4.59 (s, 2H), 3.59 (t, 1H), 3.39 (s, 3H), 3.22 (dd, 2H), 2.93 (dd, 2H).

MS calcd for ($C_{13}H_{14}BN_3O_5S_2$): 367.

MS (ESI, positive) found: (M+1): 368.

MS (ESI, negative) found: (M−1): 366.

Example 36: (R)-3-(5-amino-1,3,4-thiadiazol-2-ylthio)-7-chloro-2-hydroxy-3,4-dihydro-2H-benzo[e][1,2]oxaborinine-8-carboxylic acid (36)

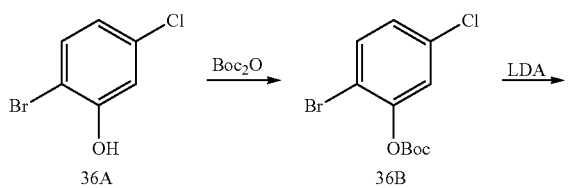

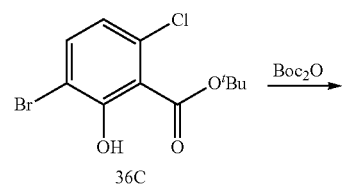

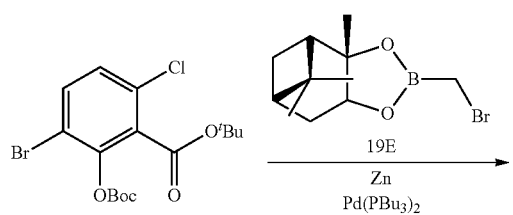

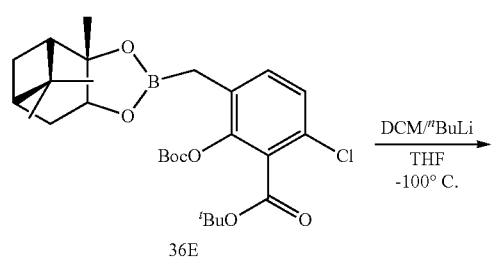

-continued

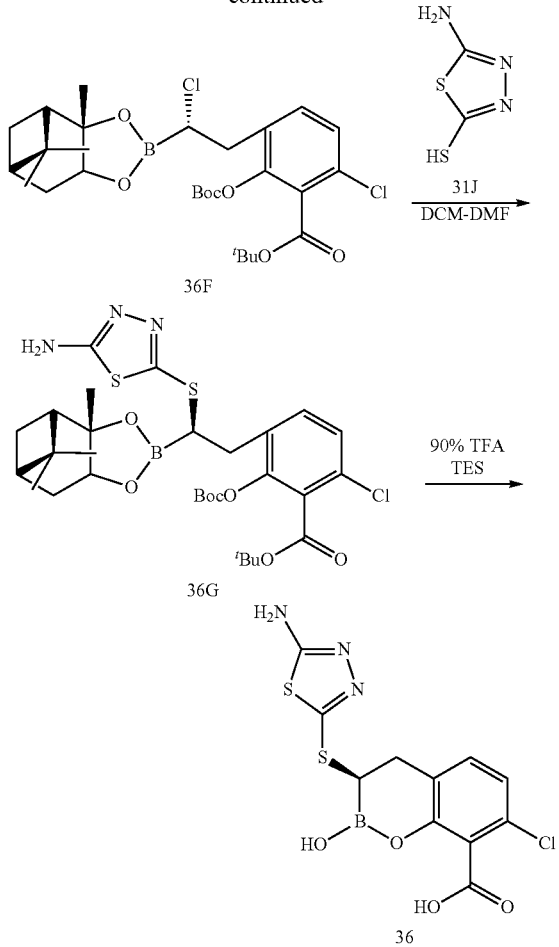

Step 1: Synthesis of 36B

To a solution of compound 36A (5 g, 24.1 mol) and Boc₂O (6.61 g, 31.33 mol) in DCM (50 mL) at rt was added DMAP (0.147 g, 1.205 mol). The mixture was stirred at rt for 24 h and concentrated to dryness. The crude product was purified by silica gel chromatography to afford compound 36B (7 g, 94.6%).

Step 2: Synthesis of 36C

To a solution of compound 36B (500 mg, 1.634 mmol) in THF (5 mL) at −78° C. was added freshly prepared LDA solution (0.72 mL, 1.797 mmol). The mixture was stirred at −78° C. for 1 h, then warmed up slowly to rt. The reaction was then quenched with 1 N HCl (aq., 5 mL), extracted with EtOAc, washed with water and brine and dried over Na₂SO₄. The extract was filtered and the filtrate was evaporated to dryness to afford compound 36C (484 mg, 80.1%). The crude product was used directly to the next step without further purification.

Step 3: Synthesis of 36D

To a solution of compound 36C (484 mg, 1.57 mol) and Boc₂O (445.6 mg, 2.044 mol) in DCM (4 mL) at rt was added DMAP (9.6 mg, 0.0786 mmol). The mixture was stirred at r.t. overnight and evaporated to dryness. The residue was purified by silica gel chromatography to afford compound 36D (598.6 mg, 93.6%).

Step 4: Synthesis of 36E

To a mixture of Zn powder (1.06 g, 16.3 mol) and compound 19E (0.5 g, 0.00183 mol) in anhydrous THF (2 mL) was added DIBAL-H (0.217 mL, 0.325 mmol, 1.5 M in toluene) at rt, the mixture was stirred for 5 min, then more compound 19E (1.274 g, 0.0047 mol) in anhydrous THF (18 mL) was added dropwise into the mixture over 20 min. The reaction mixture was warmed up to 50° C. and stirred at this temperature for 1 h. The resulting clear solution of the top layer was transferred into a solution of compound 36D (596 mg, 1.47 mol) and Pd(t-Bu₃P)₂ (74.98 mg, 0.15 mmol) in THF (5 mL). The mixture was then stirred at rt under N₂ for 1 h and concentrated. The crude product was purified by silica gel chromatography directly to afford the compound 36E (460 mg, 62.2%).

Step 5: Synthesis of 36F

To a solution of dichloromethane (0.12 mL, 153 mg, 0.624 mmol, 2.0 eq) in anhydrous THF (4 mL) in a three-neck flask at −100° C., cooled with liquid nitrogen and methanol, was added dropwise n-butyllithium (2.5 M in hexane, 0.54 mL, 1.35 mmol, 1.5 eq) through the wall of the flask over 1 h while keeping the internal temperature of the flask below −90° C. After the addition, the mixture was stirred at this temperature for 30 min. To the mixture at −100° C. was added dropwise a solution of compound 36E (468 mg, 0.899 mmol, 1.0 eq) in anhydrous THF (8 mL) over 1 h. After the addition, the mixture was slowly warmed up to room temperature, and stirred overnight. The reaction solvent was evaporated to dryness to get crude compound 36F (440 mg, 85.9%).

Step 6: Synthesis of 36g

To a solution of compound 36F (440 mg, 0.7732 mmol) in DCM (5 mL)/DMF (5 mL) was added 5-amino-1,3,4-thiadiazole-2-thiol (113.12 mg, 0.85 mol), TEA (156.2 mg, 0.1.54 mmol), the mixture was stirred at room temperature for 16 h before it was concentrated in vacuo. The residue was purified by column chromatography (PE/EA, v/v, 1/10~1/2) to afford the compound of 36G (369.6 mg, 71.7%).

Step 7: Synthesis of 36

A solution of compound 36G (369 mg, 0.554 mmol) in TFA (90%)/TES (6 mL/0.5 mL) was stirred at room temperature overnight. The mixture was evaporated to dryness under reduced pressure. The residual oil was purified by pre-HPLC to afford the compound of 36 (17.1 mg).

$^1$H NMR (400 MHz, CD₃OD) δ 7.02 (d, 1H), 6.81 (d, 1H), 3.54 (d, 1H), 3.30 (dd, 1H), 2.93 (dd, 1H).

MS calcd for ($C_{11}H_9BClN_3O_4S_2$): 357.

MS (ESI, positive) found: (M+1): 358.

MS (ESI, negative) found: (M−1): 356.

Example 37: (R)-3-(5-amino-1,3,4-thiadiazol-2-ylthio)-6,7-difluoro-2-hydroxy-3,4-dihydro-2H-benzo[e][1,2]oxaborinine-8-carboxylic acid (37)

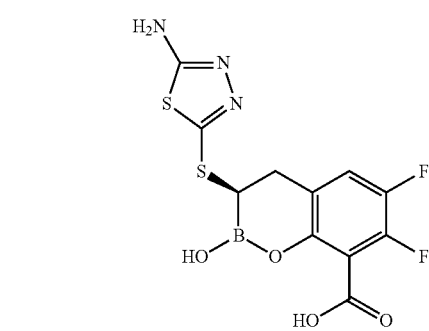

Compound 37 was made starting from 3,4-difluorophenol following procedures described in Example 38.

$^1$H NMR (400 MHz, CD$_3$OD) δ 7.15 (t, 1H), 3.52 (t, 1H), 3.25 (dd, 1H), 2.85 (dd, 1H).

MS calcd for (C$_{11}$H$_8$BF$_2$N$_3$O$_4$S$_2$): 359.

MS (ESI, positive) found: (M+1): 360.

MS (ESI, negative) found: (M−1): 358.

Example 38: (R)-3-(5-amino-1,3,4-thiadiazol-2-ylthio)-5,6,7-trifluoro-2-hydroxy-3,4-dihydro-2H-benzo[e][1,2]oxaborinine-8-carboxylic acid (38)

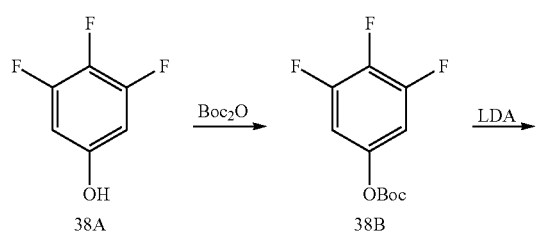

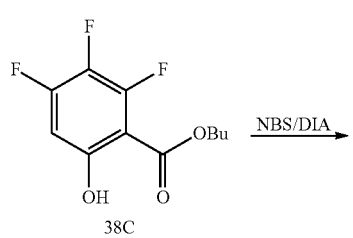

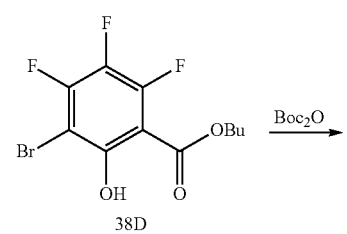

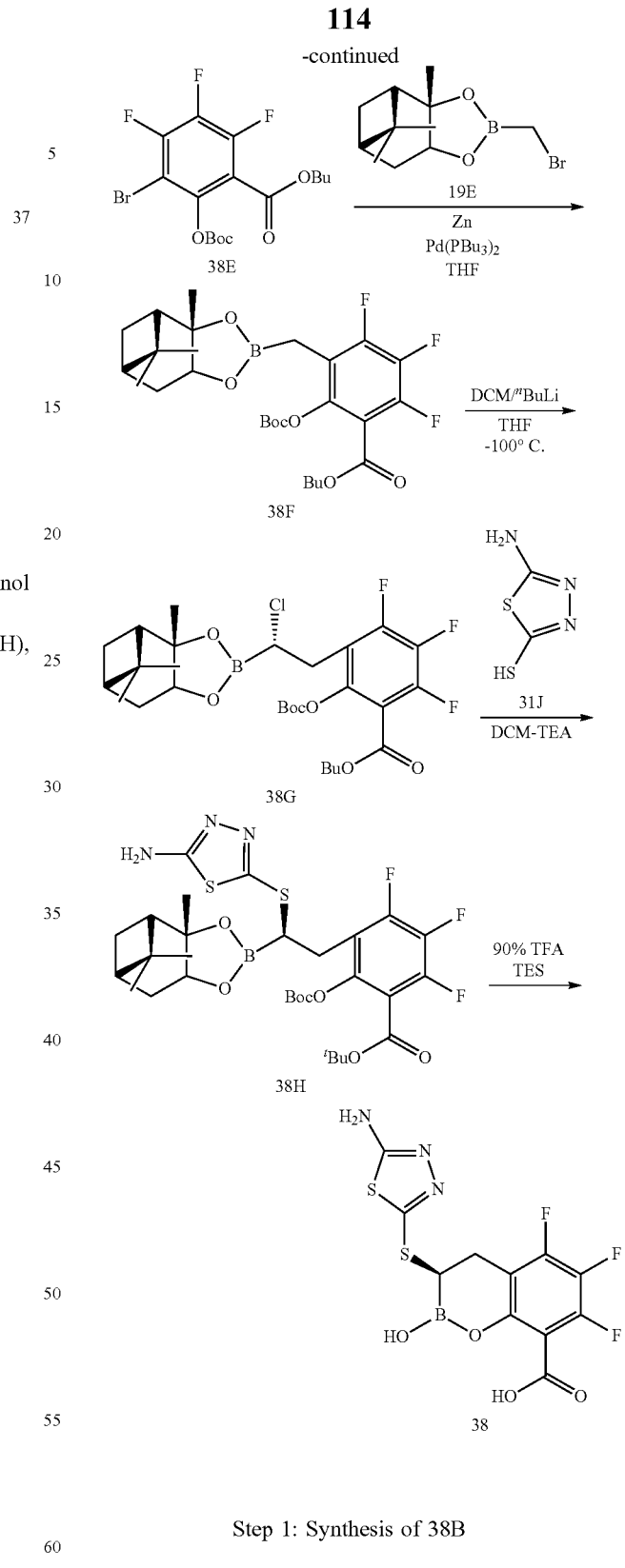

Step 1: Synthesis of 38B

To a solution of compound 38A (6.5 g, 60.19 mmol) in DCM (24 mL) was added Boc$_2$O (6.5 g, 71.41 mmol) and DMAP (6.5 g, 71.41 mmol) at room temperature. The mixture was stirred at rt overnight. The reaction was then concentrated and purified by silica gel chromatography to afford the compound 38B (3.3 g, 33.6%).

Step 2: Synthesis of 38C

To a solution of compound 38B (3.3 g, 13.3 mmol) in THF (25 mL) at −78° C. was added freshly prepared LDA solution (5.85 mL, 14.6 mmol). The mixture was stirred at −78° C. for 1 h, then warmed up slowly to rt. The reaction was quenched with 1 N HCl (aq., 5 mL), extracted with EtOAc, washed with water and dried. The extract was filtered and the filtrate was evaporated to dryness to afford compound 38C (3.05 g, 92%). The crude product was used directly in the next step without further purification.

Step 3: Synthesis of 38D

To a solution of compound 38C (3 g, 12.1 mmol) and NBS (2.26 g, 12.70 mmol) in DCM (50 mL) was added DIA (0.34 mL, 2.42 mmol) at 0° C. under $N_2$. The mixture was stirred at room temperature for 2 h, then washed with water, brine and dried over $Na_2SO_4$. The extract was filtered and evaporated to dryness and crude was purified by silica gel chromatography to afford the compound 38D (4 g, 100%).

Step 4: Synthesis of 38E

To a solution of compound 38D (4 g, 12.23 mmol) in DCM (50 mL) was added $Boc_2O$ (3.47 g, 15.9 mmol) and DMAP (75 mg, 0.61 mmol) at room temperature. The reaction was stirred at room temperature for overnight. The mixture was concentrated and purified by silica gel chromatography to afford the compound 38E (3.7 g, 71.0%).

Step 5: Synthesis of 38F

To a solution of compound 38E (303 mg, 0.71 mmol) and $Pd(P^tBu_3)_2$ (18.1 mg, 0.04 mmol) in anhydrous THF (10 mL) was added zinc reagent of 19E (freshly prepared as in step 4 of Example 19) (1.06 mmol) at room temperature. The mixture was stirred at room temperature overnight, then evaporated to dryness. The crude product was purified by silica gel chromatography to afford the compound 38F (330 mg, 86.1%).

Step 6 Synthesis of 38G

To a solution of dichloromethane (104 mg, 1.22 mmol) in anhydrous THF (3 mL) in a three-neck flask at −100° C., cooled with liquid nitrogen and methanol, was added dropwise n-butyllithium (0.37 mL, 0.92 mmol), through the wall of the flask over 0.5 h while keeping the internal temperature of the flask below −90° C. After the addition, the mixture was stirred at this temperature for 30 min, To the mixture at −100° C. was added dropwise a solution of compound 38F (330 mg, 0.61 mmol) in anhydrous THF (3 mL) over 0.5 h. After the addition, the mixture was slowly warmed up to room temperature, and stirred overnight. The reaction solvent was evaporated to dryness, the residue was dissolved in DCM and washed with water and brine, dried over $Na_2SO_4$, filtered and concentrated to afford the compound 38G (290 mg, 80.7%).

Step 7: Synthesis of 38H

To a solution of compound 38G (290 mg, 0.49 mmol) in DCM (5 mL) was added compound 31J (66 mg, 0.49 mmol) and TEA (0.1 mL, 0.74 mmol) at room temperature. The reaction was stirred at room temperature overnight. The mixture was then diluted with DCM, washed with water, brine and dried over $Na_2SO_4$. The extract was filtered and evaporated to dryness, purified by silica gel chromatography to afford the compound 38H (114 mg, 33.7%).

Step 8: Synthesis of 38

To a solution of compound 38H (109 mg, 0.16 mmol) in 90% TFA (5 mL) was added TES (0.2 mL) at room temperature. The reaction was stirred at room temperature for 2 h. The mixture was then evaporated to dryness and purified by pre-HPLC to afford the compound 38 (6.3 mg).
$^1$H NMR (400 MHz, $CD_3OD$) δ 3.56 (t, 1H), 3.30 (s, 1H), 2.93 (dd, 1H).
MS calcd for ($C_{11}H_7BF_3N_3O_4S_2$): 377.
MS (ESI, positive) found: (M+1): 378.
MS (ESI, negative) found: (M−1): 376.

Example 39: (R)-3-(1H-1,2,3-triazol-4-ylthio)-2-hydroxy-7-methoxy-3,4-dihydro-2H-benzo[e][1,2]oxaborinine-8-carboxylic acid (39)

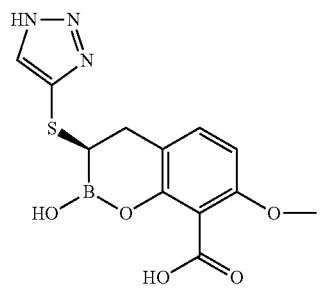

Compound 39 was prepared following the procedure described in Example 26 except replacing 4-amino-4H-1,2,4-triazole-3-thiol in step 5 with 1H-1,2,3-triazole-4-thiol.
$^1$H NMR (400 MHz, $CD_3OD$) δ 7.75 (s, 1H), 7.02 (d, 1H), 6.48 (d, 1H), 3.85 (s, 3H), 3.75 (t, 1H), 3.15 (dd, 1H), 2.70 (dd, 2H).
MS calcd for ($C_{12}H_{12}BN_3O_5S$): 321.
MS (ESI, positive) found: (M+1): 322.
MS (ESI, negative) found: (M−1): 320.

Examples 40 and 41: (R)-3-(1-(3-carboxypropyl)-1H-1,2,4-triazol-3-ylthio)-2-hydroxy-7-methoxy-3,4-dihydro-2H-benzo[e][1,2]oxaborinine-8-carboxylic acid (40) and (R)-3-(4-(3-carboxypropyl)-4H-1,2,4-triazol-3-ylthio)-2-hydroxy-7-methoxy-3,4-dihydro-2H-benzo[e][1,2]oxaborinine-8-carboxylic acid (41)
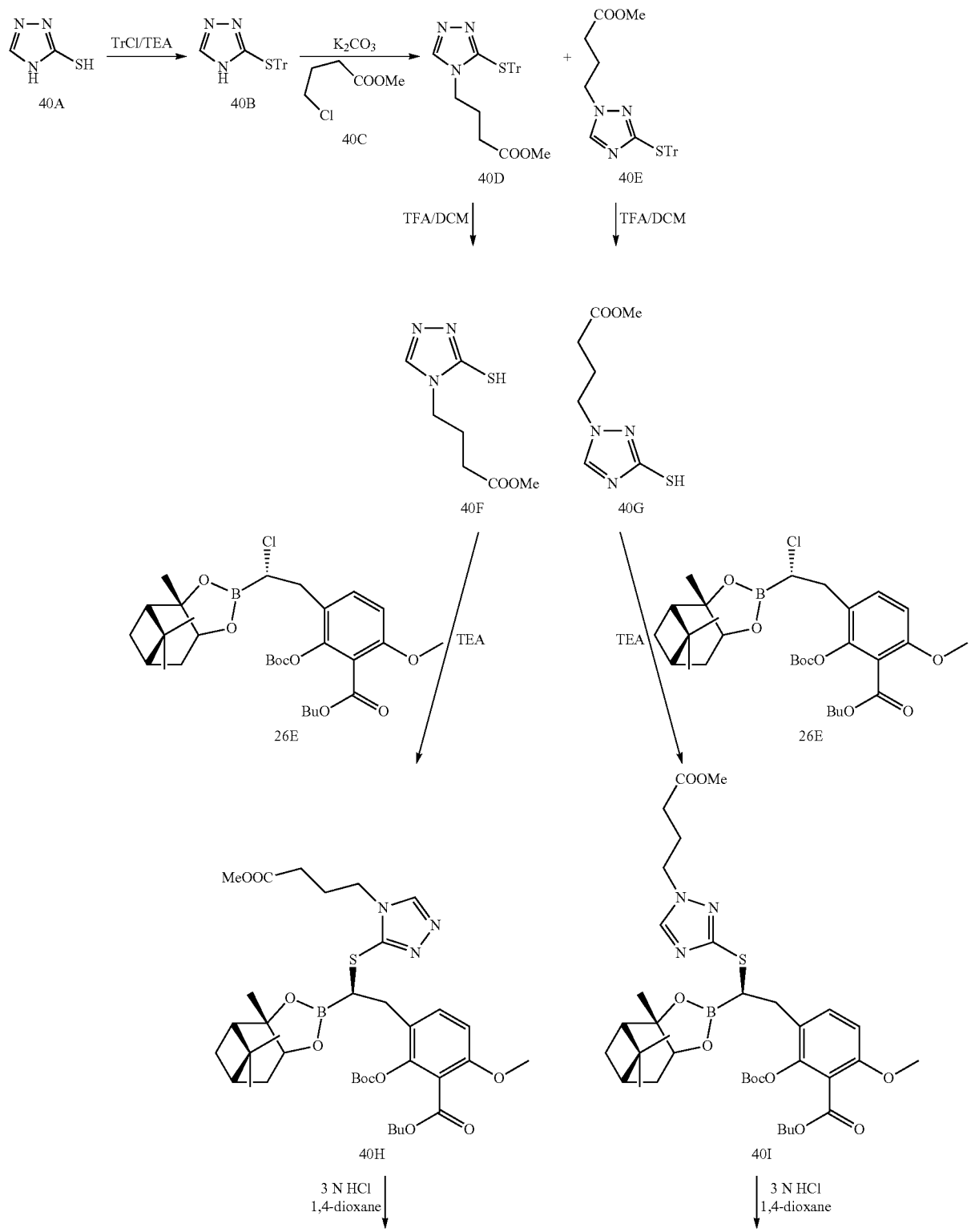

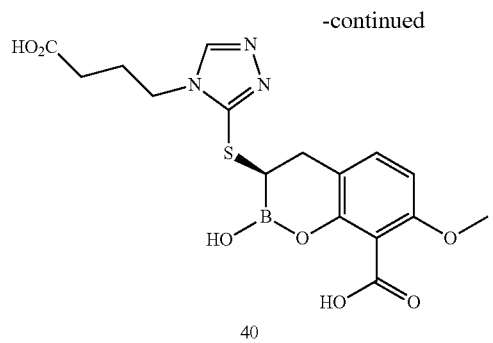
40

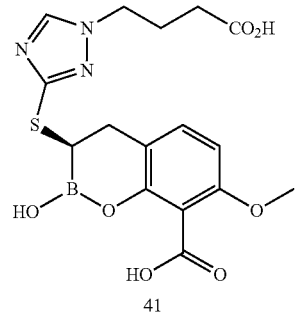
41

Step 1: Synthesis of 40B

To a solution of compound 40A (2 g, 19.78 mmol) and TrCl (6.05 g, 22.76 mmol) in DCM (20 ml) was added TEA (6.0 g, 59.34 mmol). The mixture was stirred at 30° C. for 24 h. The reaction was quenched with water (20 mL) and then extracted with DCM. The extract was washed with water, brine and dried over $Na_2SO_4$. The organic layer was filtered, evaporated to dryness, and the crude product was purified by silica gel chromatography to afford compound 40B (2.6 g, 38.8%).

Step 2: Synthesis of 40D and 40E

To a solution of compound 40B (2.48 g, 7.23 mmol) and compound 40C (2.62 g, 9.4 mmol) in DMF (20 mL) was added $K_2CO_3$ (1.99 g, 14.46 mmol) under $N_2$. The reaction mixture was stirred at 25° C. for 24 h. The reaction was diluted with and then extracted with hexane:EtOAc (1:1) mixture. The mixture was washed with water, brine and dried over $Na_2SO_4$. The extract was filtered and evaporated to dryness, purified by silica gel chromatography to afford compound 40D (1.165 g, 36.4%), and compound 40E (0.98 g, 30.6%).

Step 3: Synthesis of 40F and 40G

A solution of compound 40D (1.165 g, 2.6 mmol) in 90% TFA/TES (10 mL/1 mL) was stirred at 25° C. for 2 h, evaporated to dryness, purified by silica gel chromatography to afford compound 40F (550 mg, 98%).

A solution of compound 40E (0.98 g, 2.2 mmol) in 90% TFA/TES (10 mL/1 mL) was stirred at 25° C. for 2 h, evaporated to dryness, purified by silica gel chromatography to afford compound 40G (420 mg, 95.5%).

Step 4: Synthesis of 40H and 40I

To a solution of compound 40F (181 mg, 0.90 mmol) and compound 26E (463 mg, 0.82 mmol) in DCM (5 mL) was added TEA (273 mg, 2.7 mmol). The mixture was stirred at 25° C. for 24 h and evaporated to dryness. The crude was purified by silica gel chromatography to afford compound 40H (330 mg, 55%), To a solution of compound 40G (168.5 mg, 0.84 mmol) and compound 26E (430 mg, 0.76 mmol) in DCM (5 mL) was added TEA (254 mg, 2.5 mmol). The mixture was stirred at 25° C. for 24 h, evaporated to dryness. The crude was purified by silica gel chromatography to afford compound 40I (201 mg, 39.8%).

Step 5: Synthesis of 40 and 41

A solution of compound 40H (325 mg, 0.45 mmol) in 3 N HCl (3 mL) and 1,4-dioxane (3 mL) was stirred at 100° C. for 1 h. The mixture was then evaporated to dryness and purified by pre-HPLC to afford 40 (19.4 mg).

$^1$H NMR (400 MHz, $CD_3OD$) δ 8.19 (s, 1H), 7.01 (d, 1H), 6.43 (d, 1H), 4.02 (t, 2H), 3.81 (d, 1H), 3.79 (s, 3H), 3.11 (dd, 1H), 2.85 (dd, 1H), 2.17 (t, 2H), 2.02 (t, 2H).

MS calcd for ($C_{16}H_{18}BN_3O_7S$): 407.

MS (ESI, positive) found: (M+1): 408.

MS (ESI, negative) found: (M−1): 406.

A solution of compound 40I (200 mg, 0.27 mmol) in 3 N HCl (3 mL) and 1,4-dioxane (3 mL) was stirred at 100° C. for 1 h. The mixture was then evaporated to dryness and purified by pre-HPLC to afford 41 (39.4 mg).

$^1$H NMR (400 MHz, $CD_3OD$) δ 9.07 (s, 1H), 7.01 (d, 1H), 6.43 (d, 1H), 4.26 (t, 2H), 3.74 (s, 3H), 3.52 (t, 1H), 3.05 (dd, 1H), 2.80 (dd, 2H), 2.30-2.09 (m, 4H).

MS calcd for ($C_{16}H_{18}BN_3O_7S$): 407.

MS (ESI, positive) found: (M+1): 408.

MS (ESI, negative) found: (M−1): 406.

Example 42: (R)-3-(5-amino-1,3,4-thiadiazol-2-ylthio)-6-chloro-2-hydroxy-7-methoxy-3,4-dihydro-2H-benzo[e][1,2]oxaborinine-8-carboxylic acid (42)

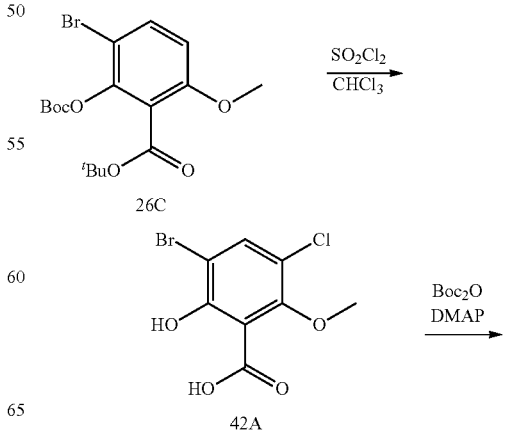

-continued

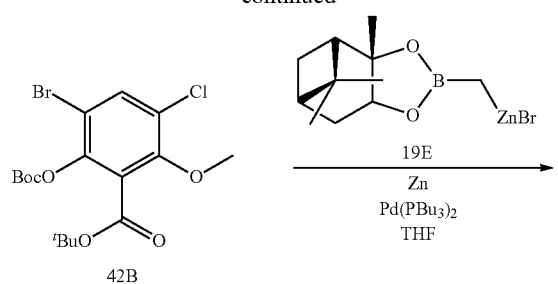

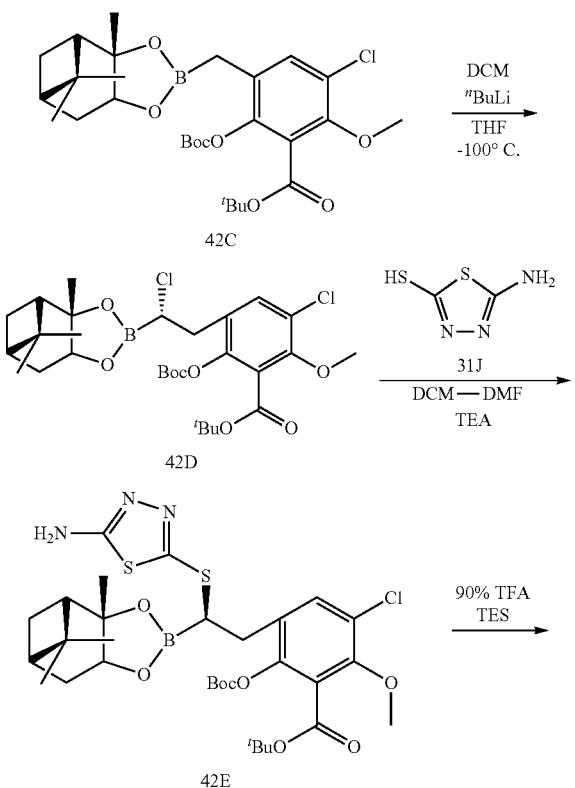

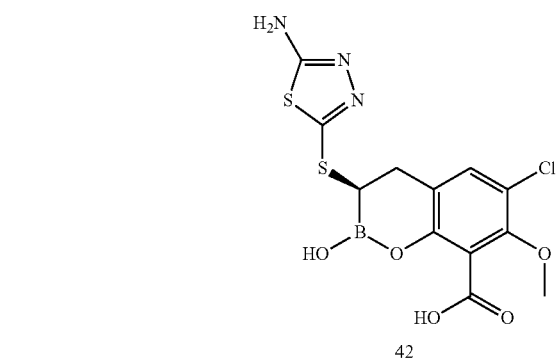

Step 1: Synthesis of 42A

To a solution of compound 26C (from Example 26) (6 g, 14.93 mmol) in CHCl$_3$ (100 mL) at room temperature was added SO$_2$Cl$_2$ (10 g, 74.63 mmol). The mixture was stirred at 40° C. in the glass tube reactor for 12 h and then cooled to room temperature. The precipitated product was filtered to afford pure compound 42A (2.4 g, 57.4%).

Step 2: Synthesis of 42B

To a solution of compound 42A (2.4 g, 8.54 mmol) and Boc$_2$O (7.45 g, 34.16 mmol) in tert-BuOH/THF (30 mL/30 mL) at room temperature was added DMAP (104 mg, 0.85 mmol). The reaction was stirred at 65° C. overnight. The mixture was then cooled to room temperature and evaporated to dryness. The residue was purified by silica gel chromatography to afford compound 42B (3.4 g, 94.1%).

Step 3: Synthesis of 42C

To a solution of compound 42B (3.4 g, 7.78 mmol) and Pd(P$^t$Bu$_3$)$_2$ (400 mg, 0.78 mmol) in THF (100 mL) at room temperature was added zinc reagent of 19E (freshly prepared as in step 4 of Example 19) (10.11 mmol). The mixture was stirred at room temperature overnight, then evaporated to dryness. The crude product was purified by silica gel chromatography to afford compound 42C (3.1 g, 72.3%).

Step 4: Synthesis of 42D

To a solution of dichloromethane (0.96 g, 11.25 mmol) in anhydrous THF (40 mL) in a three-neck flask at −100° C., cooled with liquid nitrogen and methanol, was added dropwise n-butyllithium (3.2 mL, 7.88 mmol), through the wall of the flask over 0.5 h while keeping the internal temperature of the flask below −90° C. After the addition, the mixture was stirred at this temperature for 30 min, To the mixture at −100° C. was added dropwise a solution of compound 42C (3.1 g, 5.63 mmol) in anhydrous THF (20 mL) over 0.5 h. After the addition, the mixture was slowly warmed up to room temperature and stirred overnight. The reaction solvent was evaporated to dryness to give a residue, which was purified by silica gel chromatography (PE: EA, 25:1) to afford the compound 42D (2.5 g, 74.2%).

Step 5: Synthesis of 42E

To a solution of compound 42D (400 mg, 0.67 mmol) and compound 31J (133 mg, 1.0 mmol) in DCM/DMF (3 mL/1 mL) was added TEA (70 mg, 0.7 mmol) at room temperature. The reaction was stirred at room temperature overnight and then evaporated to 1 mL. The mixture was then extracted with EtOAc, washed with brine and dried over Na$_2$SO$_4$. The organic extract was filtered and evaporated to dryness. The resulting crude product was purified by silica gel chromatography to afford compound 42E (330 mg, 70.8%).

Step 6: Synthesis of 42

A solution of compound 42E (200 mg, 0.287 mmol) in TFA (90% aq.)/TES (4 mL/1 mL) was stirred at room temperature for 2 h. The reaction was then evaporated to dryness. The crude product was purified by pre-HPLC to afford 42 (32 mg).

$^1$H NMR (400 MHz, CD$_3$OD) δ 7.11 (s, 1H), 3.82 (s, 3H), 3.53 (t, 1H), 3.14 (dd, 1H), 2.88 (dd, 1H).

MS calcd for (C$_{12}$H$_{11}$BClN$_3$O$_5$S$_2$): 387.

MS (ESI, positive) found: (M+1): 388.

MS (ESI, negative) found: (M−1): 386.

Example 43: (R)-3-(2-(5-amino-1,3,4-thiadiazol-2-yl)ethylthio)-2-hydroxy-7-methoxy-3,4-dihydro-2H-benzo[e][1,2]oxaborinine-8-carboxylic acid (43)

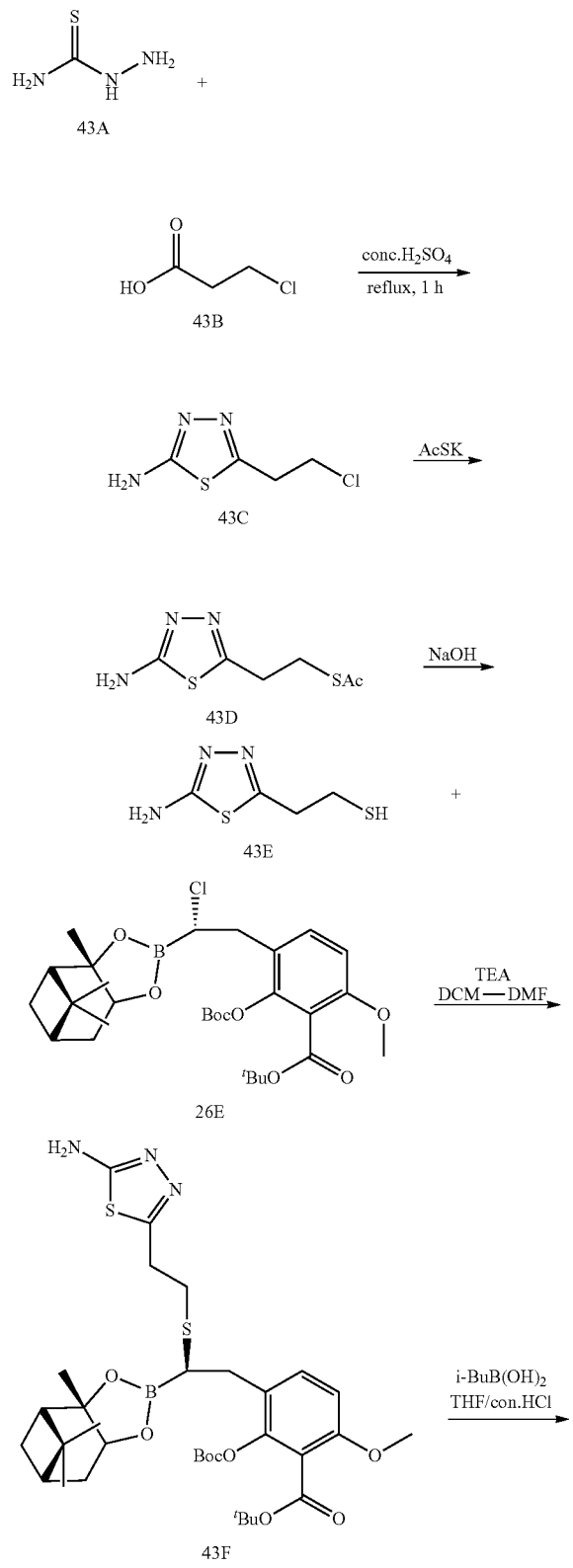

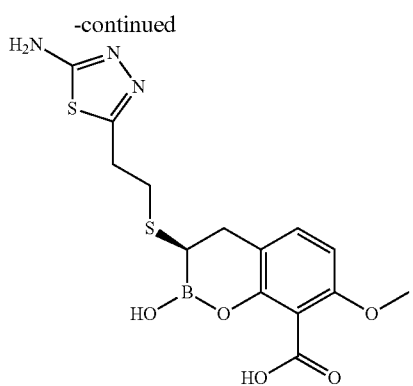

Step 1: Synthesis of 43C

To a solution of compound 43A (6.5 g, 60.19 mmol) in sulfuric acid (24 mL) was added compound 43B (6.5 g, 71.41 mmol) at rt. The reaction was stirred at 110° C. for 1 h. The mixture was then cooled to rt and poured into ice-water and neutralized with ammonia. The resulting precipitate was filtered, rinsed with water and dried under reduced pressure to afford the compound 43C (3.3 g, 33.6%).

Step 2: Synthesis of 43D

To a solution of compound 43C (1 g, 6.11 mmol) in DMF (10 mL) was added AcSK (2.1 g, 18.33 mmol) at room temperature. The reaction was stirred at room temperature overnight. The mixture was then concentrated and crude product was purified by silica gel chromatography to afford compound 43D (720 mg, 58.0%).

Step 3: Synthesis of 43E

To a solution of compound 43D (110 mg, 0.54 mmol) in MeOH/water (2.5 mL/5 mL) was added NaOH (43 mg, 1.08 mmol) at rt. The mixture was stirred at rt for 1 h and MeOH was removed under vacuum. The water layer was lyophilized to afford compound 43E. The crude 43E was directly used in next step without further purification.

Step 4: Synthesis of 43F

To a solution of compound 43E and compound 26E (306 mg, 0.54 mmol) in DCM/DMF (5 mL/0.5 mL) was added TEA (0.11 mL, 0.81 mmol) at room temperature. The reaction was stirred at room temperature overnight. The mixture was then washed with water, brine and dried over $Na_2SO_4$. The extract was filtered and evaporated to dryness. The crude product was purified by silica gel chromatography to afford compound 43F (245 mg, 65.6% overall two steps).

Step 5: Synthesis of 43

To a solution of compound 43F (214 mg, 0.31 mmol) and i-BuB(OH)$_2$ (63.3 mg, 0.62 mmol) in THF (3 mL) was added conc.HCl (3 mL) at room temperature. The reaction was stirred at room temperature for 1 h and concentrated to dryness. The crude product was purified by pre-HPLC to afford 43 (10 mg).

¹H NMR (400 MHz, CD₃OD) δ 7.20-7.00 (m, 1H), 6.50-6.45 (m, 1H), 3.75 (s, 3H), 3.15-2.50 (m, 6H), 2.11 (m, 1H).

MS calcd for (C₁₄H₁₆BN₃O₅S₂): 381.
MS (ESI, positive) found: (M+1): 382.
MS (ESI, negative) found: (M−1): N/A.

Example 44: (R)-3-(5-amino-1,3,4-thiadiazol-2-ylthio)-2,7-dihydroxy-3,4-dihydro-2H-benzo[e][1,2]oxaborinine-8-carboxylic acid (44)

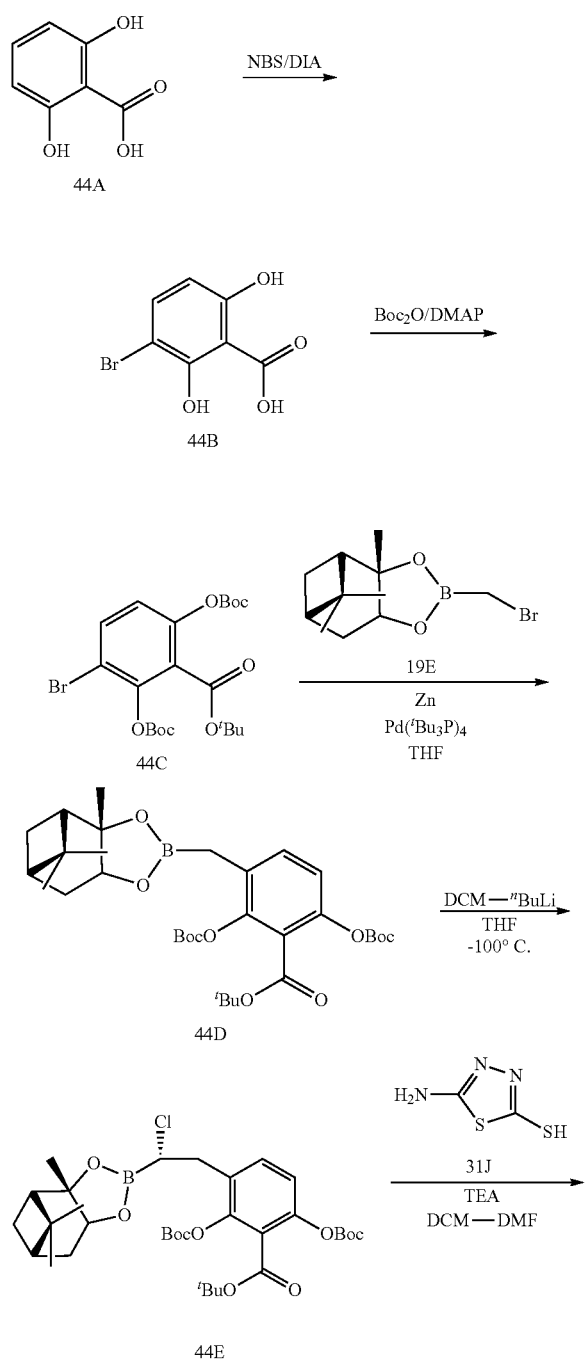

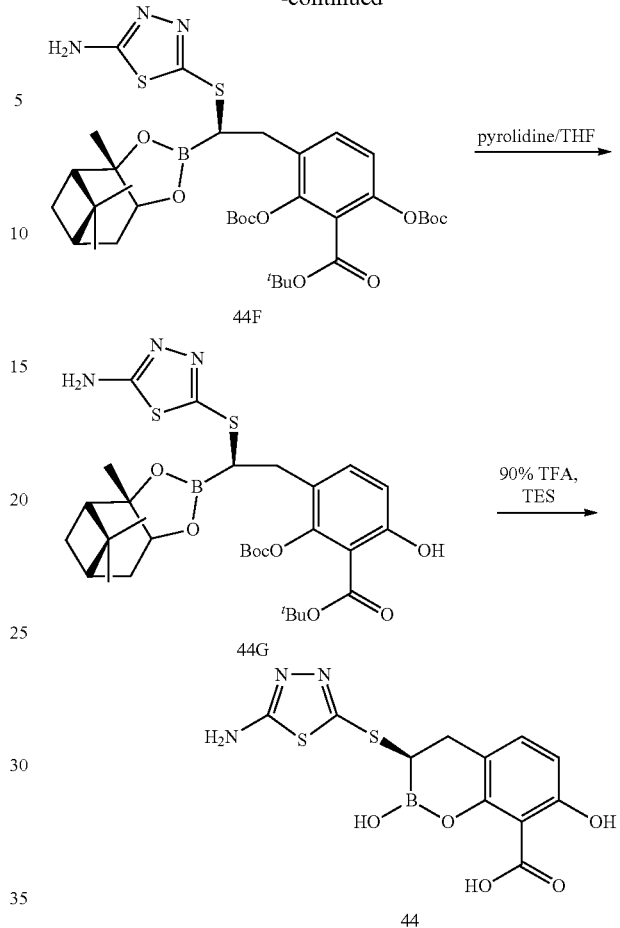

Step 1: Synthesis of 44B

To a solution of 44A (10 g, 0.065 mol) in DCM (300 mL) at −78° C. was added DIA (3.28 g, 0.033 mol), and NBS (12.7 g, 0.071 mol). The reaction mixture was stirred at room temperature for 16 hours before it was concentrated to dryness. The residue was diluted with 1 N HCl (500 mL) at 0° C. The precipitate was filtered to afford compound 44B (10.5 g, 69.4%) as white solid.

Step 2: Synthesis of 44C

To a solution of compound 44B (10.5 g, 0.047 mol) in THF (50 mL) was added Boc₂O (61.8 g, 0.283 mol), DMAP (0.576 g, 0.005 mol) and ᵗBuOH (25 mL). The resulting solution was stirred at 60° C. for 16 hours before it was concentrated in vacuo. The residue was then passed through a silica gel column (ethyl acetate/hexanes, v/v, 1/200~1/50) to afford compound 44C (17.1 g, 74%) as colorless oil.

Step 3: Synthesis of 44D

To a mixture of Zn powder (7.02 g, 0.107 mol) and compound 19E (100 mg, 0.37 mmol) in anhydrous THF (60 mL) was added DIBAL-H (1.5 mL, 2.15 mmol, 1.5 M in toluene) at room temperature. The mixture was stirred at room temperature for 5 min, then more compound 19E (12 g, 0.043 mmol) in anhydrous THF (60 mL) was added dropwise into the mixture over 20 min. The reaction mixture was warmed to 50° C. and stirred at this temperature for 1 hour before cooling to room temperature. The top layer of clear solution was transferred into a mixture of compound 44C (8.9 g, 18.2 mmol) and Pd(tBu3P)2 (279 mg, 5.46 mmol) in THF (120 mL) at room temperature under N2. After stirring at room temperature for 1 hour, the reaction mixture was concentrated, and purified by column chromatography (ethyl acetate/hexanes, v/v, 1/200~1/50) to afford compound 44D (9.5 g, 86%) as colorless oil.

Step 4: Synthesis of 44E

To a solution of dichloromethane (2.68 g, 0.032 mol) in anhydrous THF (100 mL) was added dropwise n-butyl-lithium (2.5 M in hexane, 7.6 mL, 0.019 mol) along the wall of the flask over 1 h at −100° C. (cooled with liquid nitrogen and methanol), while keeping the internal temperature below −90° C. After the addition, the mixture was stirred at −100° C. for 30 min before slow addition of the solution of compound 44D (9.5 g, 0.016 mol) in anhydrous THF (60 mL) over 1 h at −100° C. The reaction mixture was slowly warmed up to room temperature over a period of 6 hours and stirred overnight. The solvent was evaporated and the residue was purified by column chromatography (ethyl acetate/hexanes, v/v, 1/200~1/50) to afford compound 44E (9.1 g, 88%) as yellow oil.

Step 5: Synthesis of 44F

To a solution of compound 44E (9.1 g, 0.014 mol) in DCM (100 mL) was added 5-amino-1,3,4-thiadiazole-2-thiol (31J) (2.1 g, 0.016 mol) and TEA (2.06 g, 0.020 mol). The mixture was stirred at room temperature for 16 h before it was concentrated in vacuo. The residue was purified by column chromatography (ethyl acetate/DCM, v/v, 1/10~1/2) to afford compound 44F (9.1 g, 87%) as white solid.

Step 6: Synthesis of 44G

To a solution of compound 44F (3 g, 4 mmol) in anhydrous THF (30 mL) was added pyrrolidine (285 mg, 4 mmol). The mixture was stirred at r.t. for 3 h before it was concentrated in vacuo. The residue was purified by column chromatography (ethyl acetate/DCM, v/v, 1/10~1/2) to afford compound 44G (2.25 g, 87%) as white solid.

Step 7: Synthesis of 44

A solution of compound 44G (170 mg, 0.263 mmol) in TFA (90%)/TES (6 mL/0.5 mL) was stirred at room temperature overnight before it was evaporated to dryness. The residue oil was purified by pre-HPLC to afford 44 (11 mg).

$^1$H NMR (400 MHz, CD$_3$OD) δ 7.17 (t, 1H), 6.45 (d, 1H), 3.65 (m, 1H), 3.16 (dd, 1H), 2.90 (dd, 1H).

MS calcd for (C$_{11}$H$_{10}$BN$_3$O$_5$S$_2$): 339.

MS (ESI, positive) found: (M+1): 340.

MS (ESI, negative) found: (M−1): 338.

Example 45: (R)-7-fluoro-2-hydroxy-3-(thiazol-2-ylthio)-3,4-dihydro-2H-benzo[e][1,2]oxaborinine-8-carboxylic acid (45)

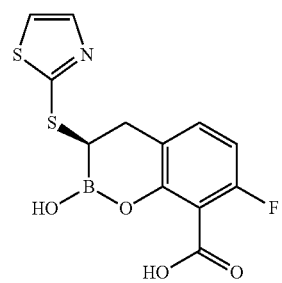

45

Compound (45) was prepared from 19G (example 19) following methods described in steps 5 and 6 of example 1 utilizing 2-mercaptothiol in step 5 $^1$H NMR (400 MHz, CD$_3$OD) δ 7.78 (d, 1H), 7.52 (d, 1H), 7.23 (t, 1H), 6.53 (t, 1H), 3.74 (t, 1H), 3.43-3.23 (m, 1H), 2.85-2.80 (m, 1H).

MS calcd for (C$_{12}$H$_9$BFNO$_4$S$_2$): 325.

MS (ESI, positive) found: (M+1): 326.

MS (ESI, negative) found: (M−1): 324.

Example 46: (R)-3-(azetidin-3-ylthio)-7-fluoro-2-hydroxy-3,4-dihydro-2H-benzo[e][1,2]oxaborinine-8-carboxylic acid (46)

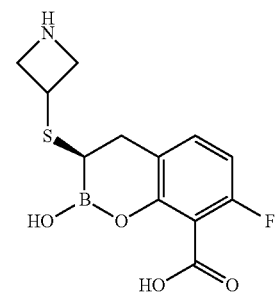

46

Compound (46) was prepared from 19G (example 19) following methods described in steps 5 and 6 of example 1 utilizing N-Boc-3-mercapto-azetidine in step 5.

$^1$H NMR (400 MHz, CD$_3$OD) δ 7.18-7.05 (m, 1H), 6.52 (q, 1H), 4.38-4.05 (m, 2H), 4.03-3.92 (m, 1H), 3.78-3.65 (m, 2H), 3.15-2.63 (m, 2H), 2.53-2.42 (m, 1H).

MS calcd for (C$_{12}$H$_{13}$BFNO$_4$S): 297.

MS (ESI, positive) found: (M+1): 298.

MS (ESI, negative) found: (M−1): 296.

Example 47: (R)-2-hydroxy-7-methoxy-3-(thiazol-2-ylthio)-3,4-dihydro-2H-benzo[e][1,2]oxaborinine-8-carboxylic acid (47)

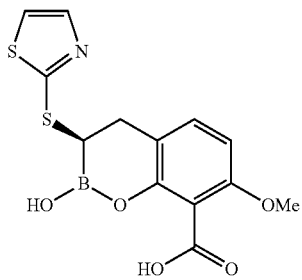

Compound 47 was prepared following the procedure described in Example 26 except replacing 4-amino-4H-1,2,4-triazole-3-thiol in step 5 with 2-mercaptothiazole.

$^1$H NMR (400 MHz, CD$_3$OD) δ 7.62 (d, 1H), 7.52 (d, 1H), 7.0 (d, 1H), 6.42 (d, 1H), 3.72 (s, 3H), 3.2-3.0 (m, 2H), 2.8 (m, 2H).

MS calcd for (C$_{13}$H$_{12}$BNO$_5$S$_2$): 337.

MS (ESI, positive) found: (M+1): 338.

MS (ESI, negative) found: (M−1): N/A.

Example 48: (3R)-7-fluoro-2-hydroxy-3-(thiadiazol-5-ylsulfanyl)-3,4-dihydro-1,2-benzoxaborinine-8-carboxylic acid (48)

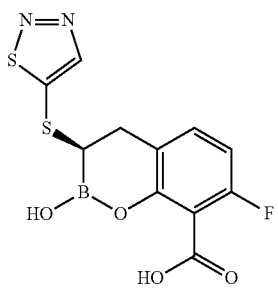

Compound 48 was prepared from 19G (Example 19) following methods described in steps 5 and 6 of Example 1 except replacing 2-mercapto-1,3,4-thiadiazole with 5-mercapto-1,2,3-thiadiazole (U.S. Pat. No. 4,758,557).

$^1$H NMR (400 MHz, CD$_3$OD): δ 8.65 (s, 1H), 7.22-7.15 (m, 1H), 6.58-6.54 (m, 1H), 3.30-3.05 (m, 3H).

MS calcd for (C$_{11}$H$_8$BFN$_2$O$_4$S$_2$): 326.

MS (ESI, positive) found: (2M+1): 653.

MS (ESI, negative) found: (2M−1): 651.

Example 49: (3R)-3-(2-amino-2-oxo-ethyl)sulfanyl-7-fluoro-2-hydroxy-3,4-dihydro-1,2-benzoxaborinine-8-carboxylic acid (49)

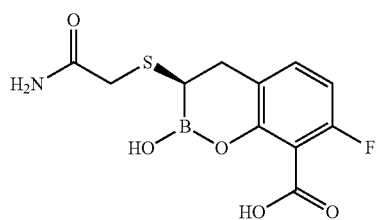

Compound 49 was prepared from 19G (Example 19) following methods described in steps 5 and 6 of Example 1 except replacing 2-mercapto-1,3,4-thiadiazole with 2-mercaptoacetamide (U.S. Pat. No. 4,758,557).

$^1$H NMR (400 MHz, CD$_3$OD): δ 7.07 (m, 1H), 6.52 (m, 1H), 3.58 (m, 1H), 3.22-3.13 (m, 2H), 2.99 (m, 1H), 2.64 (m, 1H).

MS calcd for (C$_{11}$H$_{11}$BFNO$_5$S): 299.

MS (ESI, positive) found: (M+1): 300.

MS (ESI, negative) found: (M−1): 298.

Example 50: (3R)-3-[2-(5-amino-1,3,4-thiadiazol-2-yl)ethylsulfanyl]-7-fluoro-2-hydroxy-3,4-dihydro-1,2-benzoxaborinine-8-carboxylic acid (50)

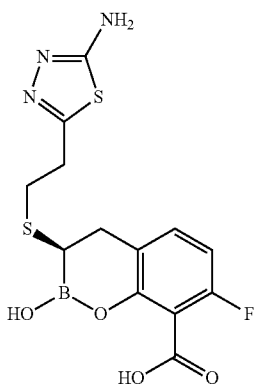

Compound 50 was prepared following methods described in Example 43 except replacing 26E in step 4 with 19G of Example 19.

$^1$H NMR (400 MHz, CD$_3$OD): δ 7.28-7.20 (m, 1H), 6.55-3.45 (m, 1H), 3.60-1.77 (m, 7H).

MS calcd for (C$_{13}$H$_{13}$BFN$_3$O$_4$S$_2$): 369.

MS (ESI, positive) found: (M+1): 370.

Example 51: (3R)-3-(cyanomethylsulfanyl)-7-fluoro-2-hydroxy-3,4-dihydro-1,2-benzoxaborinine-8-carboxylic acid (51)

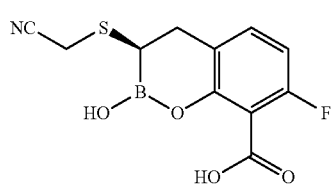

Compound 51 was prepared following methods described Example 19 replacing MeOH-potassium carbonate in step 6 with mercaptoacetonitrile sodium salt (WO10135504).

$^1$H NMR (400 MHz, CD$_3$OD): δ 7.30-7.22 (m, 1H), 6.50-6.35 (m, 1H), 3.75-3.60 (m, 1H), 3.22-3.13 (m, 2H), 2.90 (m, 1H), 2.64 (m, 1H).

MS calcd for (C$_{11}$H$_9$BFNO$_4$S): 281.
MS (ESI, positive) found: (M+1): 282.
MS (ESI, negative) found: (M−1): 280.

Example 52: (3R)-3-(2-aminothiazol-5-yl)sulfanyl-7-fluoro-2-hydroxy-3,4-dihydro-1,2-benzoxaborinine-8-carboxylic acid (52)

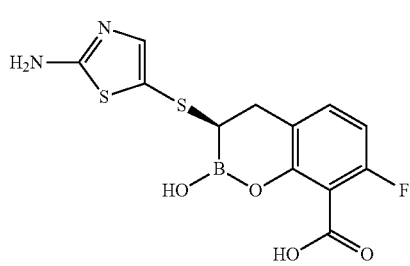

Compound 49 was prepared from 19G (Example 19) following methods described in step 5 of Example 1 except replacing 2-mercapto-1,3,4-thiadiazole with 2-aminothiazole-5-thiol.

Final deprotection was done by isobutyl boronic acid following procedure described in step 7 of example 19.

$^1$H NMR (400 MHz, CD$_3$OD): δ 7.31-6.96 (m, 2H), 6.57-6.51 (m, 1H), 3.13-2.77 (m, 3H).

MS calcd for (C$_{12}$H$_{10}$BFN$_2$O$_4$S$_2$): 340.
MS (ESI, positive) found: (M+1): 341.
MS (ESI, negative) found: (M−1): 339.

Example 53: (3R)-3-(5-carbamoylthiazol-2-yl)sulfanyl-7-fluoro-2-hydroxy-3,4-dihydro-1,2-benzoxaborinine-8-carboxylic acid (53)

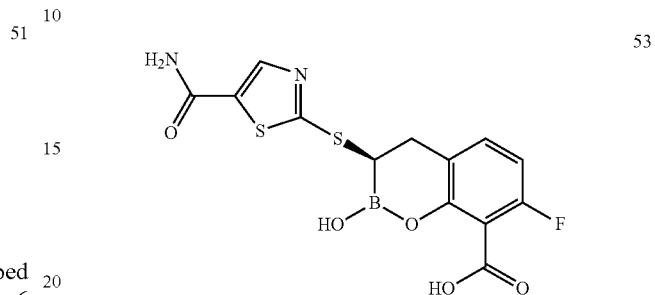

Compound 53 was prepared from 19G (Example 19) following methods described in steps 5 and 6 of Example 1 and replacing 2-mercapto-1,3,4-thiadiazole with 2-sulfanylthiazole-5-carboxamide.

$^1$H NMR (400 MHz, CD$_3$OD): δ 8.25 (s, 1H), 7.11 (t, J=7.2 Hz, 1H), 6.59 (t, J=8.4 Hz, 1H), 3.77-3.74 (m, 1H), 3.21-3.16 (m, 1H), 2.98-2.94 (m, 1H).

MS calcd for (C$_{13}$H$_{10}$BFN$_2$O$_5$S$_2$): 368.
MS (ESI, positive) found: (M+1): 369.

Example 54: (3R)-3-(4-carbamoylthiazol-2-yl)sulfanyl-7-fluoro-2-hydroxy-3,4-dihydro-1,2-benzoxaborinine-8-carboxylic acid (54)

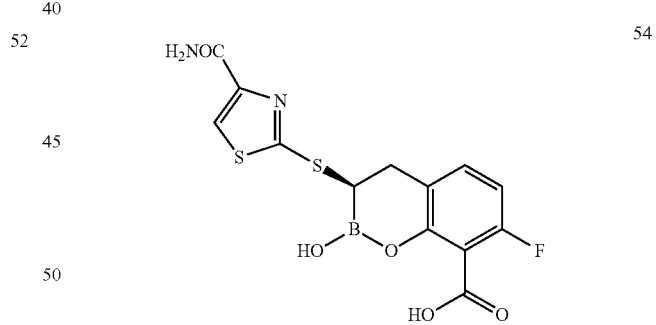

Compound 54 was prepared from 19G (Example 19) following methods described in steps 5 and 6 of Example 1 except replacing 2-mercapto-1,3,4-thiadiazole with 2-sulfanylthiazole-4-carboxamide as described in Sanghvi et. al., *J. Heterocyclic Chem.*, 1988, 25, (623-633), which is incorporated herein by reference in its entirety.

$^1$H NMR (400 MHz, CD$_3$OD): δ 8.13 (s, 1H), 7.11 (t, J=7.2 Hz, 1H), 6.59 (t, J=8.8 Hz, 1H), 3.81-3.80 (m, 1H), 3.31-3.18 (m, 1H), 2.98-2.94 (m, 1H).

MS calcd for (C$_{13}$H$_{10}$BFN$_2$O$_5$S$_2$): 368.
MS (ESI, positive) found: (M+1): 369.
MS (ESI, negative) found: (M−1): 367.

Example 55: (3R)-7-fluoro-2-hydroxy-3-[[5-(trifluoromethyl)-1,3,4-thiadiazol-2-yl]sulfanyl]-3,4-dihydro-1,2-benzoxaborinine-8-carboxylic acid (55)

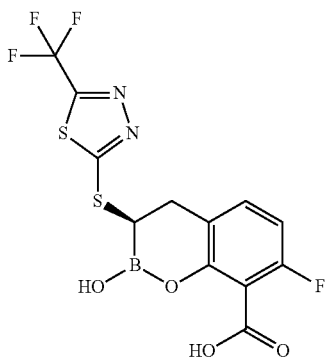

Compound 55 was prepared from 19G (Example 19) following methods described in step 5 of Example 1 except replacing 2-mercapto-1,3,4-thiadiazole with 5-(trifluoromethyl)-1,3,4-thiadiazole-2-thiol as described in PCT publication WO 2010/030811, Wagman et al., which is incorporated herein by reference in its entirety.

Final deprotection was done by isobutyl boronic acid following procedure described in step 7 of example 19.

$^1$H NMR (400 MHz, CD$_3$OD): δ 7.11 (t, J=7.2 Hz, 1H), 6.58 (t, J=8.8 Hz, 1H), 3.74-3.72 (m, 1H), 3.23-3.18 (m, 1H), 3.04-2.99 (m, 1H).

MS calcd for (C$_{12}$H$_7$BF$_4$N$_2$O$_4$S$_2$): 394.

MS (ESI, positive) found: (M+1): 395.

Example 56: (3R)-3-(4-carbamoyl-2-methyl-pyrazol-3-yl)sulfanyl-7-fluoro-2-hydroxy-3,4-dihydro-1,2-benzoxaborinine-8-carboxylic acid (56)

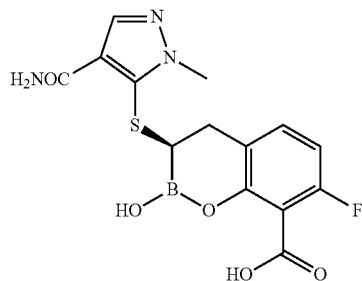

Compound 56 was prepared from 19G (Example 19) following methods described in steps 5 and 6 of Example 1 except replacing 2-mercapto-1,3,4-thiadiazole with 1-methyl-5-sulfanyl-pyrazole-4-carboxamide.

$^1$H NMR (400 MHz, CD$_3$OD): δ 7.87 (s, 1H), 7.11-7.09 (m, 1H), 6.52-6.47 (m, 1H), 3.96-3.78 (m, 1H), 3.39 (s, 3H), 3.29-2.81 (m, 1H), 0.84-0.81 (m, 1H).

MS calcd for (C$_{14}$H$_{13}$BFN$_3$O$_5$S): 365.

MS (ESI, positive) found: (M+1): 366.

MS (ESI, negative) found: (M−1): 364.

Example 57: (3R)-3-[5-(aminomethyl)thiazol-2-yl]sulfanyl-7-fluoro-2-hydroxy-3,4-dihydro-1,2-benzoxaborinine-8-carboxylic acid (57)

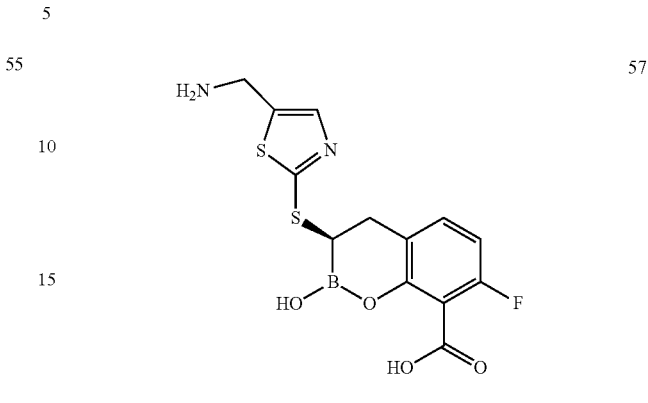

Compound 57 was prepared from 19G (Example 19) following methods described in steps 5 and 6 of Example 1 and replacing 2-mercapto-1,3,4-thiadiazole with 5-(aminomethyl)thiazole-2-thiol in step 5.

$^1$H NMR (400 MHz, CD$_3$OD): δ 7.77 (s, 1H), 7.08 (t, J=8.4 Hz, 1H), 6.55 (t, J=8.8 Hz, 1H), 4.36-4.31 (m, 2H), 3.76-3.74 (m, 1H), 3.18-3.13 (m, 1H), 2.96-2.91 (m, 1H).

MS calcd for (C$_{13}$H$_{12}$BFN$_2$O$_4$S$_2$): 354.

MS (ESI, positive) found: (M+1): 355.

MS (ESI, negative) found: (M−1): 353.

Example 58: (3R)-7-fluoro-3-(5-formamidothiazol-2-yl)sulfanyl-2-hydroxy-3,4-dihydro-1,2-benzoxaborinine-8-carboxylic acid (58)

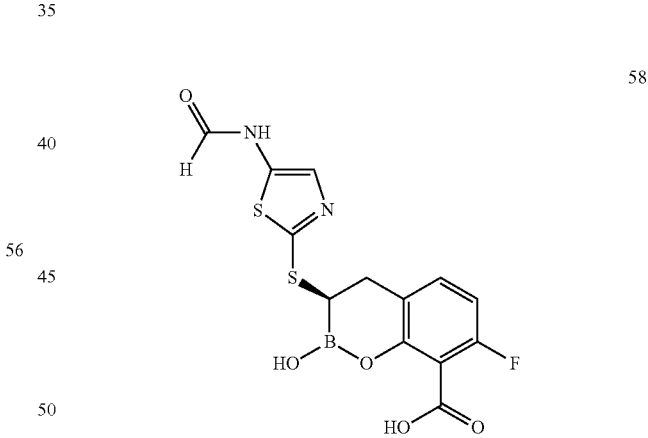

Compound 58 was prepared from 19G (Example 19) following method described in step 5 of Example 1 by replacing 2-mercapto-1,3,4-thiadiazole with 5-aminothiazole-2-thiol (US2013/317021) followed by formylation of the resulting compound with N-formylbenzotriazole as described in Katritzky, *Synthesis*, 1995 (5); 503-505, which is incorporated herein by reference in its entirety.

The final deprotection was done by following the method described in step 6 of Example 1.

$^1$H NMR (300 MHz, CD$_3$OD): δ 8.27 (s, 1H), 7.48 (s, 1H), 7.11 (t, J=7.2 Hz, 1H), 6.60 (t, J=8.4 Hz, 1H), 3.89-3.87 (m, 1H), 2.93-2.88 (m, 2H).

MS calcd for (C$_{13}$H$_{10}$BFN$_2$O$_5$S$_2$): 368.

MS (ESI, positive) found: (M+1): 369.

MS (ESI, negative) found: (M−1): 397.

Example 59: (3R)-7-fluoro-2-hydroxy-3-(1,3,4-thiadiazol-2-ylsulfanyl)-3,4-dihydro-1,2-benzoxaborinine-8-carboxylic acid (59)

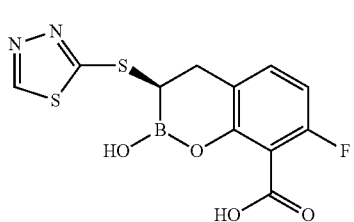

Compound 59 was prepared from 19G (Example 19) following methods described in steps 5 and 6 of Example 1 except replacing 2-mercapto-1,3,4-thiadiazole with 1,3,4-thiadiazole-2-thiol in step 5.

$^1$H NMR (400 MHz, CD$_3$OD): δ 9.23 (s, 1H), 7.12 (t, J=7.2 Hz, 1H), 6.57 (t, J=9.2 Hz, 1H), 3.76 (s, 1H), 3.21-2.95 (m, 2H).

MS calcd for (C$_{11}$H$_8$BFN$_2$O$_4$S$_2$): 326.

MS (ESI, positive) found: (M+1): 327.

Example 60: (3R)-2-hydroxy-7-methoxy-3-(thiadiazol-5-ylsulfanyl)-3,4-dihydro-1,2-benzoxaborinine-8-carboxylic acid (60)

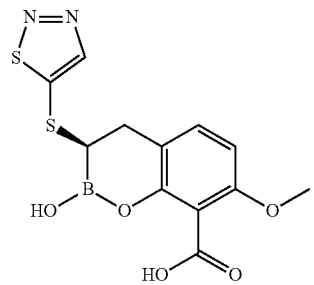

Compound 60 was prepared following the procedure described in Example 26 except replacing 4-amino-4H-1,2,4-triazole-3-thiol in step 5 with 5-mercapto-1,2,3-thiadiazole as described in U.S. Pat. No. 4,758,557, which is incorporated herein by reference in its entirety.

$^1$H NMR (400 MHz, CD$_3$OD): δ 8.58 (s, 1H), 7.19-7.06 (m, 1H), 6.54-6.39 (m, 1H), 3.85-3.30 (m, 3H), 3.14-2.85 (m, 3H).

MS calcd for (C$_{12}$H$_{11}$BN$_2$O$_5$S$_2$): 338.

MS (ESI, positive) found: (2M+1): 677.

MS (ESI, negative) found: (2M−1): 675.

Example 61: (3R)-3-(4-carbamoylthiazol-2-yl)sulfanyl-2-hydroxy-7-methoxy-3,4-dihydro-1,2-benzoxaborinine-8-carboxylic acid (61)

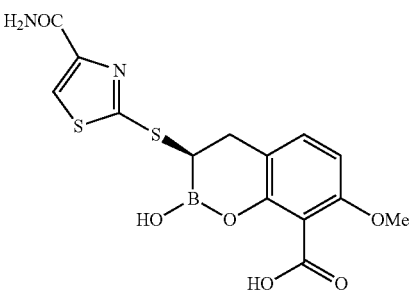

Compound 61 was prepared following the procedure described in Example 26 except replacing 4-amino-4H-1,2,4-triazole-3-thiol in step 5 with 2-sulfanylthiazole-5-carboxamide.

$^1$H NMR (400 MHz, CD$_3$OD): δ 8.11 (s, 1H), 7.03 (d, J=8.4 Hz, 1H), 6.48 (d, J=8.4 Hz, 1H), 3.77 (s, 3H), 3.31-3.29 (m, 2H), 2.91-2.88 (m, 1H).

MS calcd for (C$_{14}$H$_{13}$BN$_2$O$_6$S$_2$): 380.

MS (ESI, positive) found: (M+1): 381.

Example 62: (3R)-2-hydroxy-7-methoxy-3-(1,3,4-thiadiazol-2-ylsulfanyl)-3,4-dihydro-1,2-benzoxaborinine-8-carboxylic acid (62)

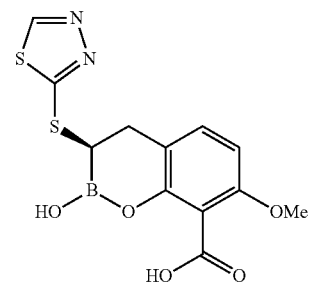

Compound 62 was prepared following the procedure described in Example 26 except replacing 4-amino-4H-1,2,4-triazole-3-thiol in step 5 with 1,3,4-thiadiazole-2-thiol.

$^1$H NMR (300 MHz, CD$_3$OD): δ 9.10 (s, 1H), 6.67 (d, J=8.1 Hz, 1H), 6.49 (d, J=8.4 Hz, 1H), 3.57 (s, 3H), 3.01-2.95 (m, 1H), 2.75-2.66 (m, 2H).

MS calcd for (C$_{12}$H$_{11}$BN$_2$O$_5$S$_2$): 338.

MS (ESI, positive) found: (M+1−H$_2$O): 321.

Example 63: (3R)-3-[(5-acetamido-1,3,4-thiadiazol-2-yl)sulfanyl]-2-hydroxy-7-methoxy-3,4-dihydro-1,2-benzoxaborinine-8-carboxylic acid (63)

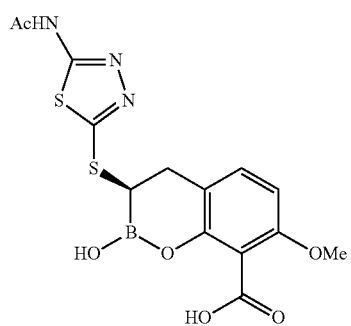

Compound 63 was prepared following the procedure described in Example 26 except replacing 4-amino-4H-1,2,4-triazole-3-thiol in step 5 with N-(5-sulfanyl-1,3,4-thiadiazol-2-yl)acetamide as described in *J. Med Chem.*, 1986, 29, 1488-1494, which is incorporated herein by reference in its entirety.

$^1$H NMR (400 MHz, CD$_3$OD): δ 7.03 (d, J=8.4 Hz, 1H), 6.46 (d, J=8 Hz, 1H), 3.75 (s, 3H), 3.62-3.60 (m, 1H), 3.17-3.14 (m, 1H), 2.89-2.85 (m, 1H), 2.22 (s, 3H).

MS calcd for (C$_{14}$H$_{14}$BN$_3$O$_6$S$_2$): 395.
MS (ESI, positive) found: (M+1): 396.
MS (ESI, negative) found: (M−1): 394.

Example 64: (3R)-3-[[4-amino-5-(trifluoromethyl)-1,2,4-triazol-3-yl]sulfanyl]-2-hydroxy-7-methoxy-3,4-dihydro-1,2-benzoxaborinine-8-carboxylic acid (64)

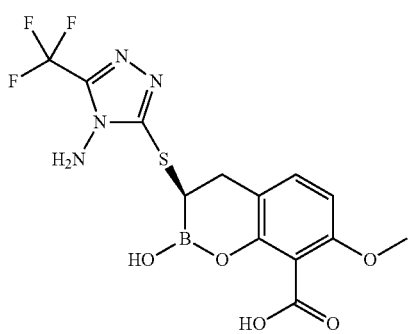

Compound 64 was prepared following the procedure described in Example except replacing 4-amino-4H-1,2,4-triazole-3-thiol in step 5 with 4-amino-5-(trifluoromethyl)-1,2,4-triazole-3-thiol as described in *J. Med. Chem.*, 1971, 14, 335-338, which is incorporated herein by reference in its entirety.

$^1$H NMR (400 MHz, CD$_3$OD): δ 7.02 (d, J=8.4 Hz, 1H), 6.45 (d, J=8.8 Hz, 1H), 3.89-3.67 (m, 4H), 3.19-3.13 (m, 1H), 2.92-2.87 (m, 1H).

MS calcd for (C$_{13}$H$_{12}$BF$_3$N$_4$O$_5$S): 404.
MS (ESI, positive) found: (M+1): 405.
MS (ESI, negative) found: (M−1): 403.

Example 65: (3R)-3-[1-(4,5-dihydrothiazol-2-yl)azetidin-3-yl]sulfanyl-2-hydroxy-7-methoxy-3,4-dihydro-1,2-benzoxaborinine-8-carboxylic acid (65)

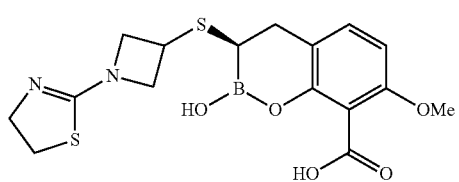

Compound 65 was prepared following the procedure described in Example 26 except replacing 4-amino-4H-1,2,4-triazole-3-thiol in step 5 with 1-(4,5-dihydrothiazol-2-yl)azetidine-3-thiol as described in *J. Antibiot.*, 2006, 59, 241-247, which is incorporated herein by reference in its entirety.

$^1$H NMR (300 MHz, CD$_3$OD): δ 6.76 (d, 1H), 6.25 (d, 1H), 4.55 (m, 1H), 4.30-4.15 (m, 2H), 3.80-3.55 (m, 8H), 3.28-3.15 (m, 2H), 2.65-2.52 (m, 1H), 2.56-2.44 (m, 1H).

MS calcd for (C$_{16}$H$_{19}$BN$_2$O$_5$S$_2$): 394.
MS (ESI, positive) found: (M+1): 395.

Example 66: (3R)-3-[[4-amino-5-(aminomethyl)-1,2,4-triazol-3-yl]sulfanyl]-2-hydroxy-7-methoxy-3,4-dihydro-1,2-benzoxaborinine-8-carboxylic acid (66)

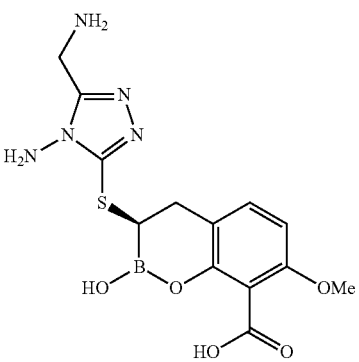

Compound 66 was prepared following the procedure described in Example except replacing 4-amino-4H-1,2,4-triazole-3-thiol in step 5 with 4-amino-5-(aminomethyl)-1,2,4-triazole-3-thiol as described in J Indian. Chem. Soc., 1984, 61, 713-714, which is incorporated herein by reference in its entirety.

$^1$H NMR (400 MHz, CD$_3$OD): δ 7.04 (d, J=8.4 Hz, 1H), 6.45 (d, J=7.6 Hz, 1H), 4.32 (s, 2H), 3.74-3.69 (m, 1H), 3.61 (m, 3H), 3.18-3.13 (m, 1H), 2.90-2.86 (m, 1H).

MS calcd for (C$_{13}$H$_{16}$BN$_5$O$_5$S): 365.
MS (ESI, positive) found: (M+1): 366.

Example 67: (3R)-3-[[5-(2-amino-2-imino-ethyl)sulfanyl-1,3,4-thiadiazol-2-yl]sulfanyl]-2-hydroxy-7-methoxy-3,4-dihydro-1,2-benzoxaborinine-8-carboxylic acid (67)

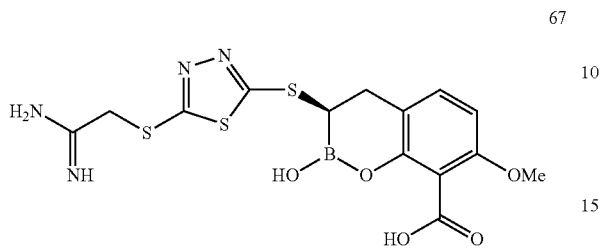

Compound 67 was prepared following the procedure described in Example 26 except replacing 4-amino-4H-1,2,4-triazole-3-thiol in step 5 with 2-[(5-sulfanyl-1,3,4-thiadiazol-2-yl)sulfanyl]acetamidine as described in U.S. Pat. No. 4,971,963, which is incorporated herein by reference in its entirety.

$^1$H NMR (400 MHz, CD$_3$OD): δ 7.05 (d, J=8.8 Hz, 1H), 6.48 (d, J=8 Hz, 1H), 4.36-4.31 (m, 2H), 3.82 (s, 3H), 3.76-3.69 (m, 1H), 3.18-3.14 (m, 1H), 2.94-2.89 (m, 1H).

MS calcd for (C$_{14}$H$_{15}$BN$_4$O$_5$S$_3$): 426.

MS (ESI, positive) found: (M+1): 427.

Example 68: (3R)-2-hydroxy-7-methoxy-3-[[5-(2-piperazin-1-ylethylsulfanyl)-1,3,4-thiadiazol-2-yl]sulfanyl]-3,4-dihydro-1,2-benzoxaborinine-8-carboxylic acid (68)

Compound 68 was prepared as described in Example 107 except replacing 107B with tert-butyl 4-[2-[(5-sulfanyl-1,3,4-thiadiazol-2-yl)sulfanyl]ethyl]piperazine-1-carboxylate, which was made from 107A and tert-butyl 4-(2-bromoethyl)piperazine-1-carboxylate (described in PCT Publication WO2013/64919, incorporated herein by reference in its entirety) as in step 1 of Example 107.

$^1$H NMR (400 MHz, CD$_3$OD): δ 7.05 (d, J=8.4 Hz, 1H), 6.49 (d, J=8.4 Hz, 1H), 3.76 (s, 3H), 3.71-3.53 (m, 3H), 3.41 (m, 4H), 3.27-3.14 (m, 7H), 2.93-2.89 (m, 1H).

MS calcd for (C$_{18}$H$_{23}$BN$_4$O$_5$S$_3$): 482.

MS (ESI, positive) found: (M+1): 483.

Example 69: (3R)-2-hydroxy-7-methoxy-3-thiazol-5-ylsulfanyl-3,4-dihydro-1,2-benzoxaborinine-8-carboxylic acid (69)

Compound 69 was prepared following the procedure described in Example 26 except replacing 4-amino-4H-1,2,4-triazole-3-thiol in step 5 with thiazole-5-thiol as described in U.S. Pat. No. 5,028,601, which is incorporated herein by reference in its entirety.

$^1$H NMR (400 MHz, CD$_3$OD): δ 8.91 (s, 1H), 7.48 (s, 1H), 6.62 (d, J=8.4 Hz, 1H), 6.26 (d, J=8.4 Hz, 1H), 3.74 (s, 3H), 2.95-2.91 (m, 1H), 2.59-2.15 (m, 2H).

MS calcd for (C$_{13}$H$_{12}$BNO$_5$S$_2$): 337.

MS (ESI, positive) found: (M+1): 338.

Example 70: (3R)-2-hydroxy-7-methoxy-3-(4H-1,2,4-triazol-3-ylsulfanyl)-3,4-dihydro-1,2-benzoxaborinine-8-carboxylic acid (70)

Compound 70 was prepared following the procedure described in Example 26 except replacing 4-amino-4H-1,2,4-triazole-3-thiol in step 5 with 4H-1,2,4-triazole-3-thiol.

$^1$H NMR (400 MHz, CD$_3$OD): δ 8.48 (s, 1H), 7.02 (d, J=8.4 Hz, 1H), 6.57 (d, J=8.4 Hz, 1H), 3.74 (s, 3H), 3.68 (s, 1H), 3.13-3.07 (m, 1H), 2.82-2.78 (m, 1H).

MS calcd for (C$_{12}$H$_{12}$BN$_3$O$_5$S): 321.

MS (ESI, positive) found: (M+1): 322.

MS (ESI, negative) found: (M−1): 320.

Example 71: (3R)-3-[[4-amino-5-(piperazin-1-ylmethyl)-1,2,4-triazol-3-yl]sulfanyl]-2-hydroxy-7-methoxy-3,4-dihydro-1,2-benzoxaborinine-8-carboxylic acid (71)

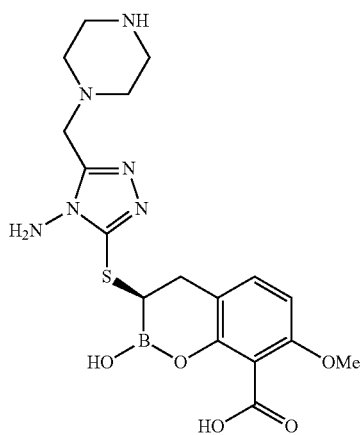

Compound 71 was prepared following the procedure described in Example 26 except replacing 4-amino-4H-1,2,4-triazole-3-thiol in step 5 with tert-butyl 4-[(4-amino-5-sulfanyl-1,2,4-triazol-3-yl)methyl]piperazine-1-carboxylate. The thiol intermediate was made from 2-(4-tert-butoxycarbonylpiperazin-1-yl)acetic acid as described in *J. Indian. Chem. Soc.*, 1984, 61, 713-714, incorporated herein by reference in its entirety, and followed by reprotection with Boc group.

$^1$H NMR (400 MHz, CD$_3$OD): δ 7.07 (d, J=8 Hz, 1H), 6.48 (d, J=8.4 Hz, 1H), 3.91-3.69 (m, 6H), 3.31-3.17 (m, 5H), 2.91-2.83 (m, 5H).

MS calcd for (C$_{17}$H$_{23}$BN$_6$O$_5$S): 434.
MS (ESI, positive) found: (M+1): 435.
MS (ESI, negative) found: (M−1): 433.

Example 72: (3R)-2-hydroxy-7-methoxy-3-(2-piperazin-1-ylethylsulfanyl)-3,4-dihydro-1,2-benzoxaborinine-8-carboxylic acid (72)

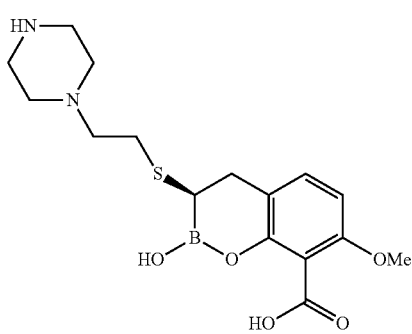

Compound 72 was prepared following the procedure described in Example 26 except replacing 4-amino-4H-1,2,4-triazole-3-thiol in step 5 with 2-piperazin-1-ylethanethiol as described in PCT publication WO 2014/145686, which is incorporated herein by reference in its entirety.

$^1$H NMR (400 MHz, CD$_3$OD): δ 7.06-7.05 (m, 1H), 6.43-6.42 (m, 1H), 3.95-3.84 (m, 4H), 3.62-3.11 (m, 6H), 3.07-2.94 (m, 2H), 2.93-2.44 (m, 6H).

MS calcd for (C$_{16}$H$_{23}$BN$_2$O$_5$S): 366.
MS (ESI, positive) found: (M+1): 367.

Example 73: (3R)-3-[[4-(4-aminobutyl)-1,2,4-triazol-3-yl]sulfanyl]-2-hydroxy-7-methoxy-3,4-dihydro-1,2-benzoxaborinine-8-carboxylic acid (73)

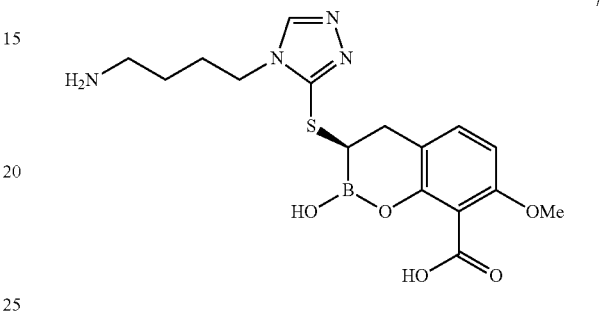

Compound 73 was prepared following the procedure described in Example 26 except replacing 4-amino-4H-1,2,4-triazole-3-thiol in step 5 with tert-butyl N-[4-(3-sulfanyl-1,2,4-triazol-4-yl)butyl]carbamate (prepared starting from tert-butyl N-[4-(aminocarbamothioylamino)butyl]carbamate as described in Chem. Pharm. Bull, 1988, 36, 2968-2976, which is incorporated herein by reference in its entirety).

$^1$H NMR (400 MHz, CD$_3$OD): δ 8.46 (s, 1H), 6.54 (d, J=8 Hz, 1H), 6.23 (d, J=8.4 Hz, 1H), 3.81-3.70 (m, 2H), 3.59 (s, 3H), 3.15-3.03 (m, 2H), 2.98-2.43 (m, 3H), 1.63-1.28 (m, 4H).

MS calcd for (C$_{16}$H$_{21}$13 N$_4$O$_5$S): 392.
MS (ESI, positive) found: (M+1): 393.

Example 74: (3R)-3-[(3-amino-1,2,4-thiadiazol-5-yl)sulfanyl]-2-hydroxy-7-methoxy-3,4-dihydro-1,2-benzoxaborinine-8-carboxylic acid (74)

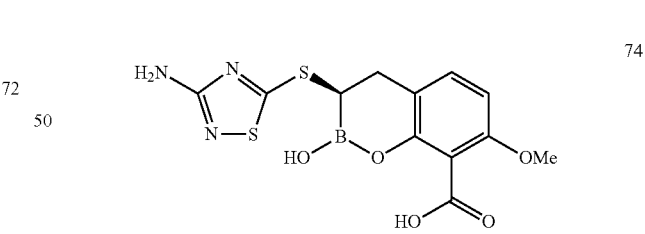

Compound 74 was prepared following the procedure described in Example 26 except replacing 4-amino-4H-1,2,4-triazole-3-thiol in step 5 with tert-butyl N-(5-sulfanyl-1,2,4-thiadiazol-3-yl)carbamate as described in Tetrahedron Lett., 2006, 47, 8039-8042, which is incorporated herein by reference in its entirety.

$^1$H NMR (400 MHz, CD$_3$OD): δ 7.03 (d, J=8.8 Hz, 1H), 6.47 (d, J=8.8 Hz, 1H), 3.82-3.76 (m, 4H), 3.32-3.19 (m, 2H).

MS calcd for (C$_{12}$H$_{12}$BN$_3$O$_5$S$_2$): 353.
MS (ESI, positive) found: (M+1): 354.

Example 75: (3R)-2-hydroxy-7-methoxy-3-(1,2,4-thiadiazol-5-ylsulfanyl)-3,4-dihydro-1,2-benzoxaborinine-8-carboxylic acid (75)

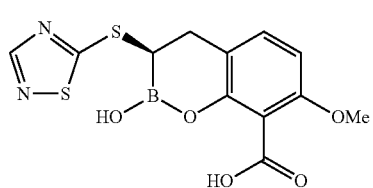

Compound 75 was prepared following the procedure described in Example 26 except replacing 4-amino-4H-1,2,4-triazole-3-thiol in step 5 with 1,2,4-thiadiazole-5-thiolas described in PCT publication WO2005/26139, which is incorporated herein by reference in its entirety.

$^1$H NMR (400 MHz, CD3OD): δ 8.55 (s, 1H), 7.02 (d, J=7.6 Hz, 1H), 6.45 (d, J=8.8 Hz, 1H), 3.82-3.74 (m, 4H), 3.22-3.11 (m, 1H), 2.91-2.86 (m, 1H).

MS calcd for ($C_{12}H_{11}BN_2O_5S_2$): 338.

MS (ESI, positive) found: (M+1): 339.

MS (ESI, negative) found: (M−1): 337.

Example 76: (3R)-2-hydroxy-7-methoxy-3-(1-sulfamoylazetidin-3-yl)sulfanyl-3,4-dihydro-1,2-benzoxaborinine-8-carboxylic acid (76)

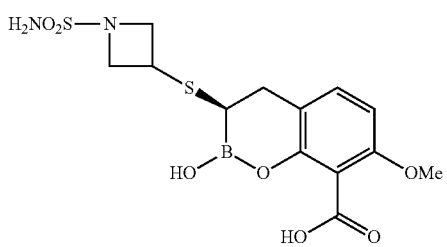

Compound 76 was prepared following the procedure described in Example 26 except replacing 4-amino-4H-1,2,4-triazole-3-thiol in step 5 with (4-nitrophenyl)methyl N-(3-sulfanylazetidin-1-yl)sulfonylcarbamate. The deprotection of p-nitrobenzyl carbamate was done as described in PCT publication WO 2011/097958, which is incorporated herein by reference in its entirety. Final deprotection to 76 was done following procedures as in step 7 of Example 19 and step 6 of Example 1 consecutively and isolated as sodium salt.

$^1$H NMR (400 MHz, CD3OD): δ 6.73 (d, J=8.8 Hz, 1H), 6.26 (d, J=8.4 Hz, 1H), 3.93-3.92 (m, 2H), 3.73-3.72 (m, 6H), 3.53-3.51 (m, 2H), 3.31-3.29 (m, 1H).

MS calcd for ($C_{13}H_{17}BN_2O_7S_2$): 388.

MS (ESI, positive) found: (M+1): 389.

MS (ESI, negative) found: (M−1): 387.

Example 77: (3R)-3-(2-aminothiazol-5-yl)sulfanyl-2-hydroxy-7-methoxy-3,4-dihydro-1,2-benzoxaborinine-8-carboxylic acid (77)

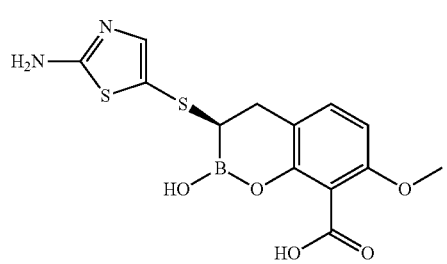

Compound 77 was prepared following the procedure described in Example 26 except replacing 4-amino-4H-1,2,4-triazole-3-thiol in step 5 with 2-aminothiazole-5-thiol as described in J. Med. Chem., 2004, 47, 1719-1728, which is incorporated herein by reference in its entirety.

$^1$H NMR (400 MHz, CD$_3$OD, mixture of isomers) δ 7.30-7.15 (m, 1H), 7.10-6.93 (m, 1H), 6.45-6.41 (m, 1H), 3.86-3.77 (m, 3H), 3.38-3.33 (m, 1H), 3.10-2.90 (m, 1H), 2.80-2.65 (m, 1H).

MS calcd for ($C_{13}H_{13}BN_2O_5S_2$): 352.

MS (ESI, positive) found: (M+1): 353.

MS (ESI, negative) found: (M−1): 351.

Example 78: (3R)-3-[[5-(3-aminoazetidin-1-yl)-1,3,4-thiadiazol-2-yl]sulfanyl]-2-hydroxy-7-methoxy-3,4-dihydro-1,2-benzoxaborinine-8-carboxylic acid (78)

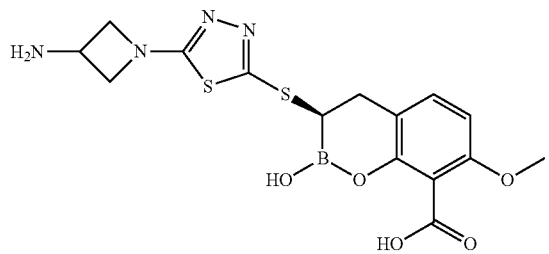

Compound 78 was prepared following the procedures described in Example 96 replacing tert-butyl 3-aminoazetidine-1-carboxylate (96A) in step 1 with tert-butyl N-(azetidin-3-yl)carbamate.

$^1$H NMR (400 MHz, CD3OD): δ 7.03 (d, 1H), 6.48 (d, 1H), 4.57 (dd, 1H), 4.54 (dd, 1H), 4.28 (m, 1H), 4.20 (dd, 1H), 4.15 (dd, 1H), 3.78 (s, 3H), 3.60 (m, 1H), 3.15 (dd, 1H), 2.85 (dd, 1H).

MS calcd for ($C_{15}H_{17}BN_4O_5S_2$): 408.

MS (ESI, positive) found: (M+1): 409.

Example 79: (3R)-7-(2-aminoethoxy)-3-[(5-amino-1,3,4-thiadiazol-2-yl)sulfanyl]-2-hydroxy-3,4-dihydro-1,2-benzoxaborinine-8-carboxylic acid (79)

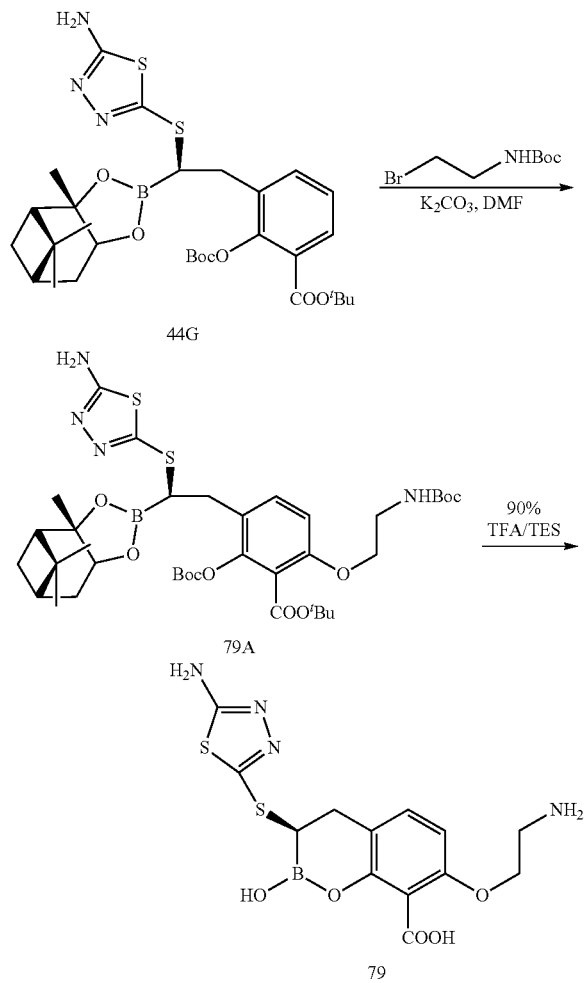

Step 1: Synthesis of 79A

To a solution of compound 44G (305 mg, 0.472) and tert-butyl N-(2-bromoethyl)carbamate as described in J. Org. Chem., 1988, 53, 2226-2232, which is incorporated herein by reference in its entirety (264 mg, 1.18 mmol), potassium carbonate (228 mg, 1.65 mmol) in DMF (2 mL) was stirred at 35° C. overnight under nitrogen atmosphere. The resulting mixture was filtered and the filtrate was concentrated under reduced pressure. The residue was purified by column chromatography to give compound 79A (175 mg, 47%).

1H NMR (400 MHz, CDCl$_3$): δ 9.40 (br. s, 1H), 7.20 (d, J=8.4 Hz, 1H), 6.73 (d, J=8.8 Hz, 1H), 4.46-4.35 (m, 1H), 4.14-4.03 (m, 2H), 3.66-3.64 (m, 2H), 3.25-3.21 (m, 1H), 3.20-3.17 (m, 1H), 2.35-2.32 (m, 2H), 2.29-2.27 (m, 2H), 1.91-1.81 (m, 2H), 1.53 (s, 9H), 1.51 (s, 9H), 1.43 (s, 9H), 1.33 (s, 3H), 1.31 (s, 3H), 1.30-1.07 (m, 1H), 0.85 (s, 3H).

Step 2: Synthesis of 79

To a solution of 79A (170 mg, 0.215 mmol) in 90% TFA/TES (v/v, 6 mL/0.5 mL) was stirred at rt for 1 h. The mixture was concentrated and the residue was purified by prep-HPLC to give 79 (22.1 mg, 27%).

$^1$H NMR (400 MHz, CD3OD): δ 7.14 (d, J=8.4 Hz, 1H), 6.58 (d, J=8.4 Hz, 1H), 5.55 (m, 2H), 4.26-4.24 (m, 2H), 3.55-3.53 (m, 1H), 3.17-3.11 (m, 1H), 2.91-2.86 (m, 1H).

MS calcd for (C$_{13}$H$_{15}$BN$_4$O$_5$S$_2$): 382.

MS (ESI, positive) found: (M+1): 383.

MS (ESI, negative) found: (M−1): 381.

Example 80: (3R)-7-(2-amino-2-oxo-ethoxy)-3-[(5-amino-1,3,4-thiadiazol-2-yl)sulfanyl]-2-hydroxy-3,4-dihydro-1,2-benzoxaborinine-8-carboxylic acid (80)

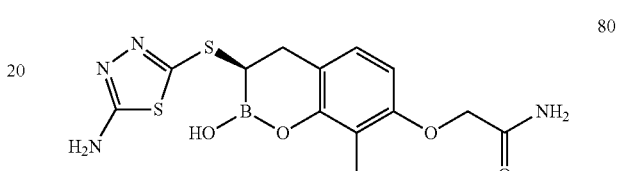

Compound 80 was prepared following the procedures described in Example 79 replacing tert-butyl N-(2-bromoethyl)carbamate in step 1 with 2-bromoacetamide.

$^1$H NMR (400 MHz, CD3OD): δ 7.14 (d, J=8 Hz, 1H), 6.50 (d, J=8 Hz, 1H), 4.50 (s, 2H), 3.57-3.55 (m, 1H), 3.17-3.12 (m, 1H), 2.91-2.86 (m, 1H).

MS calcd for (C$_{13}$H$_{13}$BN$_4$O$_6$S$_2$): 396.

MS (ESI, positive) found: (M+1): 397.

MS (ESI, negative) found: (M−1): 395.

Example 81: (3R)-3-[(5-amino-1,3,4-thiadiazol-2-yl)sulfanyl]-7-[2-(azetidin-3-ylamino)-2-oxo-ethoxy]-2-hydroxy-3,4-dihydro-1,2-benzoxaborinine-8-carboxylic acid (81)

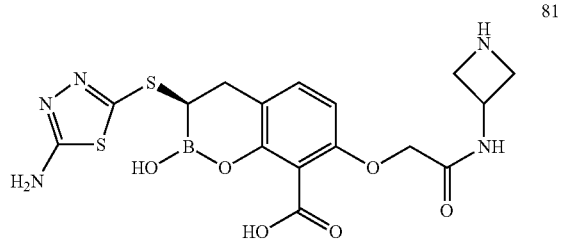 [SMILES: Nc1nnc(S[C@H]2Cc3ccc(OCC(=O)NC4CNC4)c(C(=O)O)c3OB2O)s1]

Compound 81 was prepared following the procedures described in Example 79 replacing tert-butyl N-(2-bromoethyl)carbamate in step 1 with tert-butyl 3-[(2-bromoacetyl)amino]azetidine-1-carboxylate.

$^1$H NMR (400 MHz, CD3OD): δ 7.20 (d, J=8.4 Hz, 1H), 6.56 (d, J=8.8 Hz, 1H), 4.73 (s, 2H), 4.34-4.18 (m, 5H), 3.59-3.57 (m, 1H), 3.17-2.89 (m, 2H).

MS calcd for (C$_{16}$H$_{18}$BN$_5$O$_6$S$_2$): 451.

MS (ESI, positive) found: (M+1): 452.

MS (ESI, negative) found: (M−1): 450.

Example 82: (3R)-3-[(3-amino-1H-1,2,4-triazol-5-yl)sulfanyl]-2-hydroxy-7-methoxy-3,4-dihydro-1,2-benzoxaborinine-8-carboxylic acid (82)

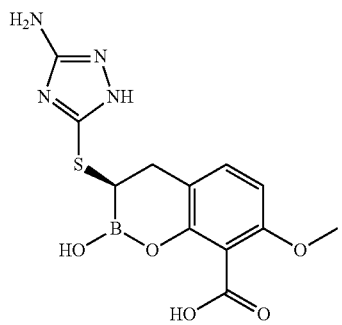

Compound 82 was prepared following the procedure described in Example 26 except replacing 4-amino-4H-1,2,4-triazole-3-thiol in step 5 with 5-amino-4H-1,2,4-triazole-3-thiol.

$^1$H NMR (400 MHz, CD3OD): δ 7.01 (d, J=8.4 Hz, 1H), 6.45 (d, J=8.4 Hz, 1H), 3.80 (s, 3H), 3.55-3.53 (m, 1H), 3.08-3.03 (m, 1H), 2.77-2.72 (m, 1H).

MS calcd for ($C_{12}H_{13}BN_4O_5S$): 336.

MS (ESI, positive) found: (M+1): 337.

MS (ESI, negative) found: (M−1): 335.

Example 83: (3R)-3-[(5-amino-1,3,4-thiadiazol-2-yl)sulfanyl]-7-ethoxy-2-hydroxy-3,4-dihydro-1,2-benzoxaborinine-8-carboxylic acid (83)

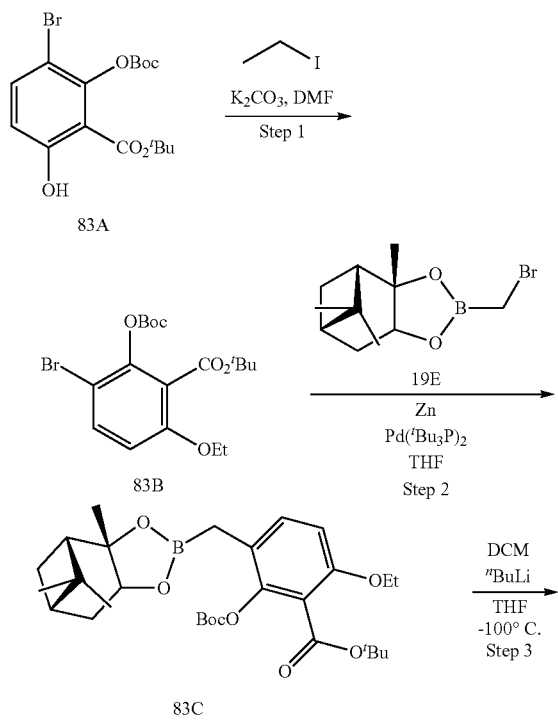

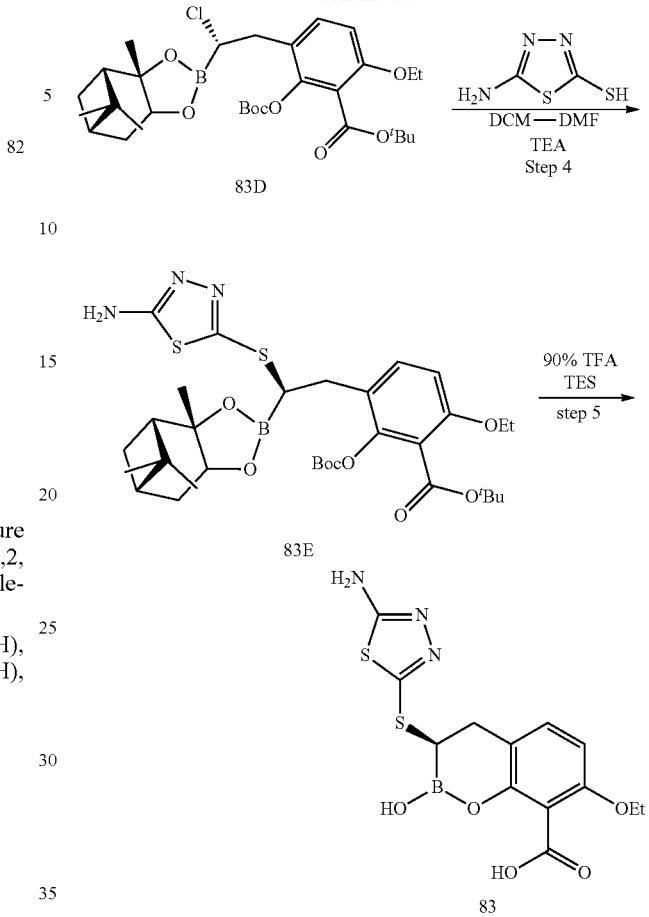

Step 1: Synthesis of 83B

To a mixture of compound 83A (synthesized from 44C by treatment of pyrrolidine in THF as in the preparation of 44G) (150 mg, 0.386 mmol), potassium carbonate (60 mg, 0.386 mmol) in DMF (5 mL) was added iodoethane (60 mg, 0.386 mmol). The reaction mixture was stirred at rt for 1 h. Then the mixture was filtered and the filtrate was concentrated under pressure. The residue was dissolved in dichloromethane, washed with water and brine. The combined organic layer was dried over sodium sulfate, evaporated to dryness to provide compound 83B (160 mg, 99%).

1H NMR (400 MHz, CDCl$_3$): δ 7.48 (d, J=8.8 Hz, 1H), 6.68 (d, J=8.8 Hz, 1H), 4.03 (q, J=6.8 Hz, 2H), 1.54 (s, 9H), 1.53 (s, 9H), 1.37 (t, J=6.8 Hz, 3H).

Compound 83 was prepared in steps 2-5 from 83B following the procedures described in steps 3-6 of Example 26 except replacing 4-amino-4H-1,2,4-triazole-3-thiol in step 5 with 5-amino-1,3,4-thiadiazole-2-thiol.

$^1$H NMR (400 MHz, CD3OD): δ 6.64 (d, J=8.4 Hz, 1H), 6.22 (d, J=8.4 Hz, 1H), 3.97 (q, J=6.4 Hz, 2H), 3.09-3.05 (m, 1H), 2.84-2.76 (m, 2H), 1.32 (t, J=6.8 Hz, 3H).

MS calcd for ($C_{13}H_{14}BN_3O_5S_2$): 367.

MS (ESI, positive) found: (M+1): 368.

MS (ESI, negative) found: (M−1): 366.

Example 84: (3R)-3-[(5-amino-1,3,4-thiadiazol-2-yl)sulfanyl]-7-(difluoromethoxy)-2-hydroxy-3,4-dihydro-1,2-benzoxaborinine-8-carboxylic acid (84)

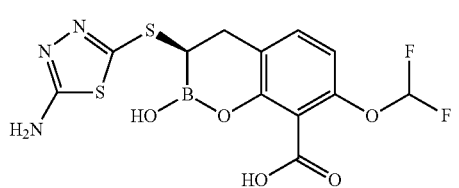

Compound 84 was prepared following the procedures described in Example 83 except replacing iodoethane in step 1 with bromo(difluoro)methane.

$^1$H NMR (300 MHz, CD3OD): δ 7.08 (d, 1H), 6.95-6.40 (m, 2H), 3.53-3.42 (m, 1H), 3.19-3.06 (m, 1H), 2.93-2.85 (m, 1H).

MS calcd for ($C_{12}H_{10}BF_2N_3O_5S_2$): 389.

MS (ESI, positive) found: (M+1-$H_2O$): 372.

Example 85: (3R)-2-hydroxy-7-isopropoxy-3-(1,3,4-thiadiazol-2-ylsulfanyl)-3,4-dihydro-1,2-benzoxaborinine-8-carboxylic acid (85)

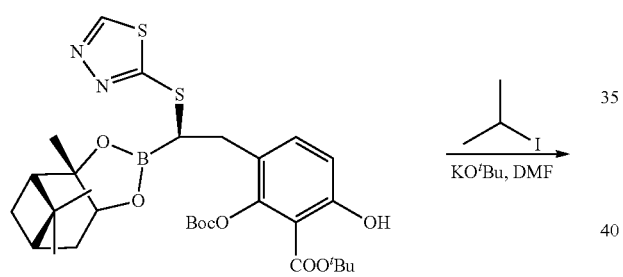

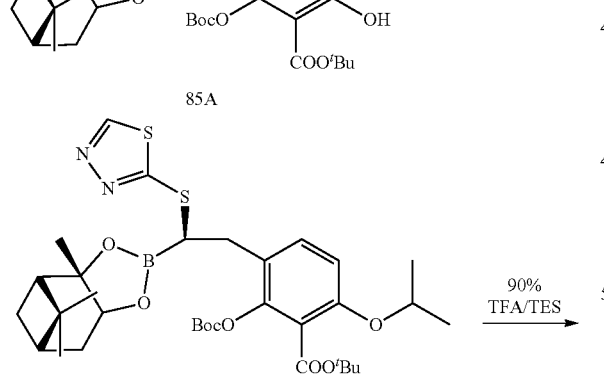

Compound 85A was prepared following the procedures described for 44G of Example 44 except replacing 5-amino-1,3,4-thiadiazole-2-thiol (31J) with 1,3,4-thiadiazole-2-thiol in step 5.

Step 1: Synthesis of 85B

Compound 85B was prepared from 85A following the procedure described in step 1 of Example 79 replacing tert-butyl N-(2-bromoethyl)carbamate with 2-iodopropane and potassium carbonate with potassium t-butoxide.

Step 2: Synthesis of 85

Deprotection of 85B to 85 was done following the method described in step 2 of Example 79.

$^1$H NMR (400 MHz, $CD_3OD$): δ 9.19 (s, 1H), 6.97 (d, J=8.8 Hz, 1H), 6.44 (d, J=8 Hz, 1H), 4.51-4.47 (m, 1H), 3.72-3.71 (m, 1H), 3.18-3.14 (m, 1H), 2.91-2.89 (m, 1H), 1.25-1.23 (m, 6H).

MS calcd for ($C_{14}H_{15}BN_2O_5S_2$): 366.

MS (ESI, positive) found: (M+1): 367.

MS (ESI, negative) found: (M−1): 365.

Example 86: (3R)-7-(cyanomethoxy)-2-hydroxy-3-(1,3,4-thiadiazol-2-ylsulfanyl)-3,4-dihydro-1,2-benzoxaborinine-8-carboxylic acid (86)

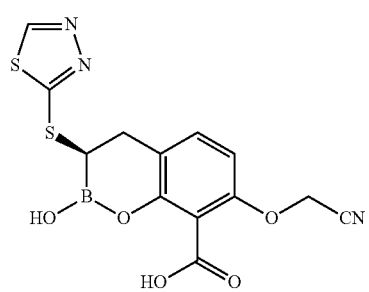

Compound 86 was prepared using similar methods described in Example 85 except replacing 2-iodopropane in step 1 with 2-bromoacetonitrile and potassium t-butoxide with sodium hydride.

$^1$H NMR (400 MHz, $CD_3OD$): δ 9.23 (s, 1H), 7.12 (d, J=8.4 Hz, 1H), 6.58 (d, J=8 Hz, 1H), 4.92-4.89 (m, 2H), 3.76-3.74 (m, 1H), 3.31-3.17 (m, 1H), 2.98-2.94 (m, 1H).

MS calcd for ($C_{13}H_{10}BN_3O_5S_2$): 363.

MS (ESI, positive) found: (M+1): 364.

MS (ESI, negative) found: (M−1): 362.

Example 87: (3R)-7-(2-fluoroethoxy)-2-hydroxy-3-(1,3,4-thiadiazol-2-ylsulfanyl)-3,4-dihydro-1,2-benzoxaborinine-8-carboxylic acid (87)

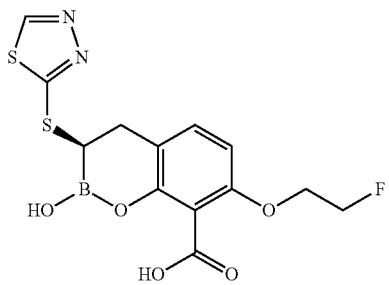

Compound 87 was prepared following the procedures described in Example 83 except replacing iodoethane in step 1 with 1-bromo-2-fluoro-ethane and 5-amino-1,3,4-thiadiazole-2-thiol (31J) with 1,3,4-thiadiazole-2-thiol in step 4.

$^1$H NMR (400 MHz, D$_2$O) δ 9.23 (s, 1H), 6.79 (d, J=8 Hz, 1H), 6.35 (d, J=8 Hz, 1H), 4.78-4.65 (m, 2H), 4.24-4.14 (m, 2H), 3.14-2.84 (m, 3H).

MS calcd for (C$_{13}$H$_{12}$BFN$_2$O$_5$S$_2$): 370.
MS (ESI, positive) found: (M+1): 371.
MS (ESI, negative) found: (M−1): 369.

Example 88: (3R)-2-hydroxy-7-isobutoxy-3-(1,3,4-thiadiazol-2-ylsulfanyl)-3,4-dihydro-1,2-benzoxaborinine-8-carboxylic acid (88)

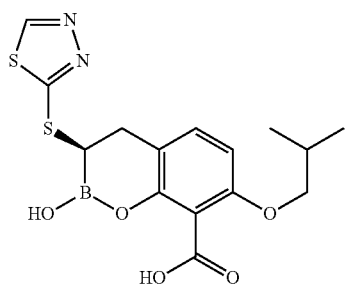

Compound 88 was prepared using similar methods described in Example 85 except replacing 2-iodopropane in step 1 with 1-bromo-2-methyl-propane and potassium t-butoxide in DMF with KOH in DMSO.

$^1$H NMR (400 MHz, CD$_3$OD): δ 9.29 (s, 1H), 6.97 (d, J=8.4 Hz, 1H), 6.39 (d, J=8.4 Hz, 1H), 3.71-3.67 (m, 3H), 3.25-3.15 (m, H), 1.03-0.99 (m, 6H).

MS calcd for (C$_{15}$H$_{17}$BN$_2$O$_5$S$_2$): 380.
MS (ESI, positive) found: (M+1): 381.
MS (ESI, negative) found: (M−1): 379.

Example 89: (3R)-2-hydroxy-7-(2-methoxyethoxy)-3-(1,3,4-thiadiazol-2-ylsulfanyl)-3,4-dihydro-1,2-benzoxaborinine-8-carboxylic acid (89)

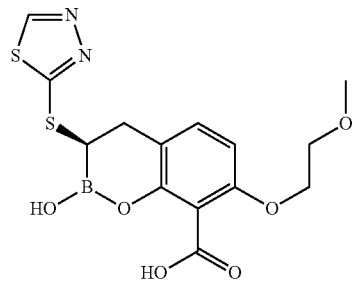

Compound 89 was prepared using similar methods described in Example 85 except replacing 2-iodopropane in step 1 with 1-iodo-2-methoxy-ethane.

$^1$H NMR (400 MHz, CD3OD): δ 9.19 (s, 1H), 7.01 (d, J=8 Hz, 1H), 6.45 (d, J=8 Hz, 1H), 4.07-4.04 (m, 2H), 3.72-3.66 (m, 3H), 338-3.31 (m, 3H), 3.19-3.14 (m, 1H), 2.92-2.90 (m, 1H).

MS calcd for (C$_{14}$H$_{15}$BN$_2$O$_6$S$_2$): 382.
MS (ESI, positive) found: (M+1): 383.
MS (ESI, negative) found: (M−1): 381.

Example 90: (3R)-3-[(5-amino-1,3,4-thiadiazol-2-yl)sulfanyl]-7-(2,2-difluoroethoxy)-2-hydroxy-3,4-dihydro-1,2-benzoxaborinine-8-carboxylic acid (90)

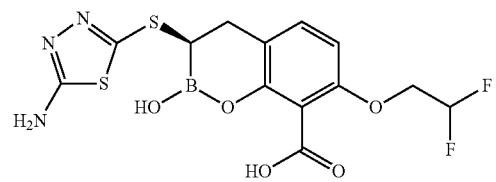

Compound 87 was prepared following the procedures described in Example 83 except replacing iodoethane in step 1 with 2-bromo-1,1-difluoro-ethane.

$^1$H NMR (300 MHz, CD3OD): δ 7.05 (d, 1H), 6.59-6.42 (d, 1H), 6.35-5.86 (m, 1H), 4.22-4.18 (m, 2H), 3.54-3.42 (m, 1H), 3.24-3.08 (m, 1H), 2.95-2.79 (m, 1H).

MS calcd for (C$_{13}$H$_{12}$BF$_2$N$_3$O$_5$S$_2$): 403.
MS (ESI, positive) found: (M+1): 404.

Example 91: (3R)-7-(2,2-difluoroethoxy)-2-hydroxy-3-(1,3,4-thiadiazol-2-ylsulfanyl)-3,4-dihydro-1,2-benzoxaborinine-8-carboxylic acid (91)

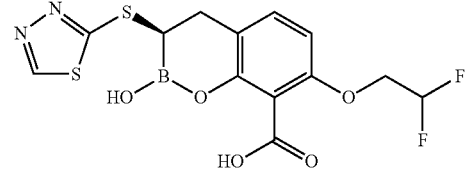

Compound 91 was prepared following the procedures described in Example 83 except replacing iodoethane in step 1 with 2-bromo-1,1-difluoro-ethane and 5-amino-1,3,4-thiadiazole-2-thiol (31J) with 1,3,4-thiadiazole-2-thiol in step 4.

$^1$H NMR (300 MHz, CD$_3$OD): δ 9.22 (s, 1H), 7.03 (d, J=9 Hz, 1H), 6.48 (d, J=8.1 Hz, 1H), 6.08 (dd, d, J=55.5, 4.2 Hz, 1H), 4.21-4.11 (m, 2H), 3.74-3.72 (m, 1H), 3.24-3.14 (m, 1H), 2.95-2.89 (m, 1H).

MS calcd for (C$_{13}$H$_{11}$BF$_2$N$_2$O$_5$S$_2$): 388.
MS (ESI, positive) found: (M+1): 389.

Example 92: (3R)-7-(cyclopropylmethoxy)-2-hydroxy-3-(1,3,4-thiadiazol-2-ylsulfanyl)-3,4-dihydro-1,2-benzoxaborinine-8-carboxylic acid (92)

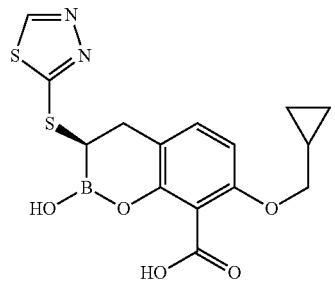

92

Compound 92 was prepared using similar methods described in Example 85 except replacing 2-iodopropane in step 1 with bromomethylcyclopropane.

$^1$H NMR (400 MHz, CD3OD): δ 9.19 (s, 1H), 6.98 (d, J=8 Hz, 1H), 6.41 (d, J=8 Hz, 1H), 3.82-3.71 (m, 3H), 3.18-3.14 (m, 1H), 2.92-2.87 (m, 1H), 1.18-1.16 (m, 1H), 0.56-0.29 (m, 4H).

MS calcd for (C$_{15}$H$_{15}$BN$_2$O$_5$S$_2$): 378.
MS (ESI, positive) found: (M+1): 379.
MS (ESI, negative) found: (M−1): 377.

Example 93: (3R)-2-hydroxy-7-(1,3,4-thiadiazol-2-ylmethoxy)-3-(1,3,4-thiadiazol-2-ylsulfanyl-3,4-dihydro-1,2-benzoxaborinine-8-carboxylic acid (93)

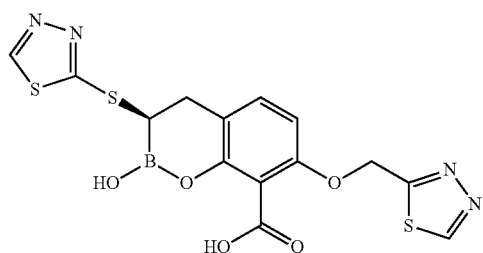

93

Compound 92 was prepared using similar methods described in Example 85 except replacing 2-iodopropane in step 1 with 2-(bromomethyl)-1,3,4-thiadiazole and potassium t-butoxide with cesium carbonate.

$^1$H NMR (400 MHz, CD3OD): δ 9.46 (s, 1H), 9.21 (s, 1H), 7.06 (d, J=7.6 Hz, 1H), 6.60 (d, J=8.0 Hz, 1H), 5.52 (m, 2H), 3.73 (m, 1H), 3.18 (dd, J=15.6, 4.4 Hz, 1H), 2.93 (dd, J=15.6, 2.8 Hz, 1H).

MS calcd for (C$_{14}$H$_{11}$BN$_4$O$_5$S$_3$): 422.
MS (ESI, positive) found: (M+1): 423.

Example 94: (3R)-7-(difluoromethoxy)-2-hydroxy-3-(1,3,4-thiadiazol-2-ylsulfanyl)-3,4-dihydro-1,2-benzoxaborinine-8-carboxylic acid (94)

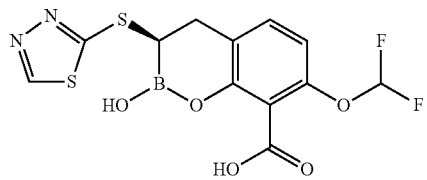

94

Compound 94 was prepared following the procedures described in Example 83 except replacing iodoethane in step 1 with bromo(difluoro)methane and 5-amino-1,3,4-thiadiazole-2-thiol (31J) with 1,3,4-thiadiazole-2-thiol in step 4.

$^1$H NMR (300 MHz, CD3OD): δ 9.22 (s, 1H), 7.11-6.42 (m, 3H), 3.35-2.85 (m, 3H).

MS calcd for (C$_{12}$H$_9$BF$_2$N$_2$O$_5$S$_2$): 374.
MS (ESI, positive) found: (M+1): 375.

Example 95: (3R)-2-hydroxy-7-(2-methylsulfanylethoxy)-3-(1,3,4-thiadiazol-2-ylsulfanyl)-3,4-dihydro-1,2-benzoxaborinine-8-carboxylic acid (95)

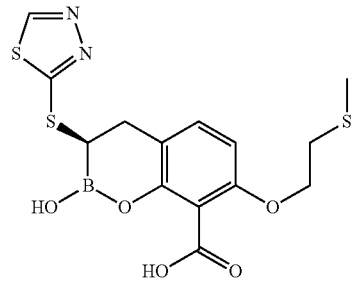

95

Compound 92 was prepared using similar methods described in Example 85 except replacing 2-iodopropane in step 1 with 1-iodo-2-methylsulfanyl-ethane.

$^1$H NMR (400 MHz, CD$_3$OD): δ 9.29 (s, 1H), 7.01 (d, J=8 Hz, 1H), 6.45 (d, J=6.8 Hz, 1H), 4.14-4.08 (m, 2H), 3.74-3.72 (m, 1H), 3.26-3.15 (m, 2H), 2.81-2.77 (m, 2H), 2.15-2.03 (m, 3H).

MS calcd for (C$_{14}$H$_{15}$BN$_2$O$_5$S$_3$): 398.
MS (ESI, positive) found: (M+1): 399.
MS (ESI, negative) found: (M−1): 397.

Example 96: (3R)-3-[[5-(azetidin-3-ylamino)-1,3,4-thiadiazol-2-yl]sulfanyl]-2-hydroxy-7-methoxy-3,4-dihydro-1,2-benzoxaborinine-8-carboxylic acid (96)

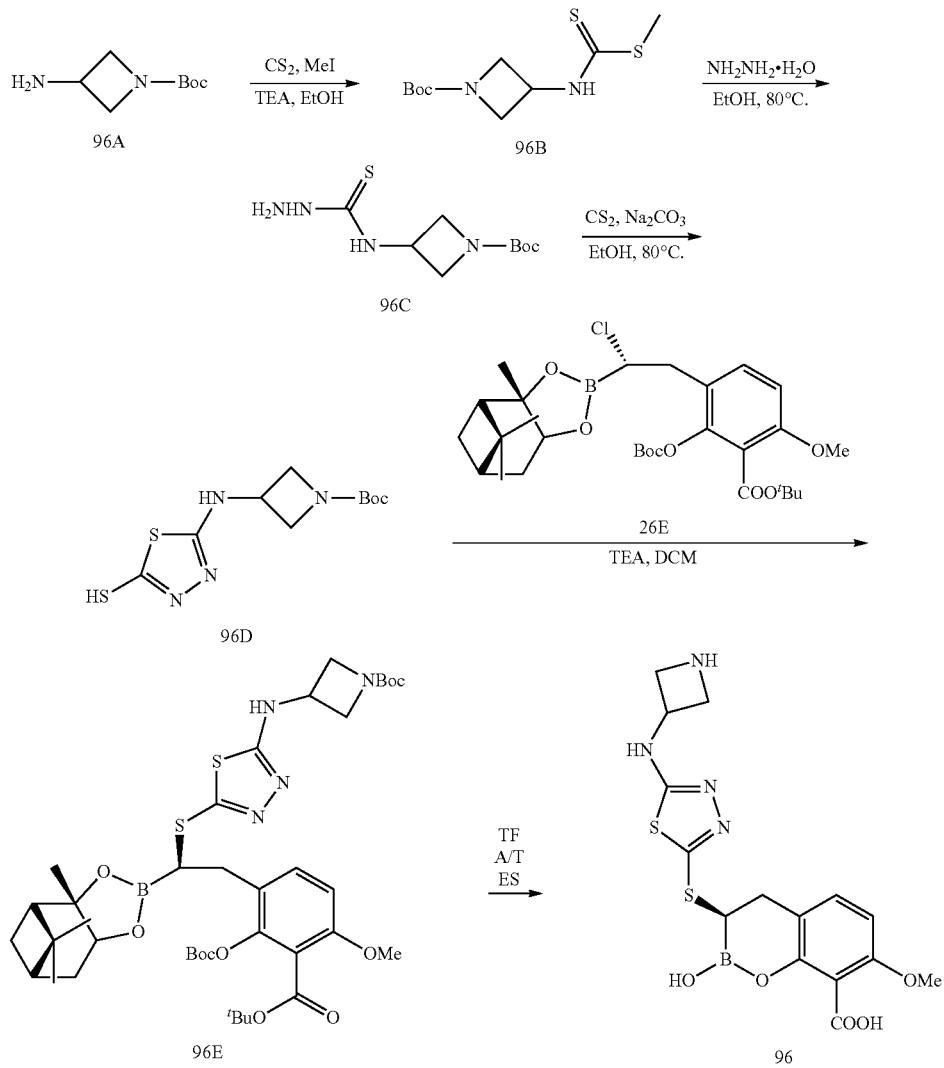

Step 1: Synthesis of 96B

To a mixture of compound 96A (5.0 g, 29.03 mmol) and TEA (5 mL, 35.87 mmol) in ethanol (20 mL) was added $CS_2$ (2 mL, 33.10 mmol) while maintaining the temperature between 20° C. to 25° C. After stirring for 1.5h. Methyl iodide (2 mL, 32.11 mmol) was added and stirred overnight. The reaction was complete as monitored by LCMS. The solvent was removed under reduced pressure. Then the residue was diluted with ethyl acetate and water, the organic phase was collected, dried, concentrated in vacuo to provide compound 96B (8.1 g, 100%) as a yellow solid.

Step 2: Synthesis of 96C

To a mixture of compound 96B (8.1 g, 29.03 mmol), $NH_2NH_2H_2O$ (4 mL, 82.46 mmol) in ethanol (20 mL) was stirred at 80° C. overnight. The mixture was concentrated under reduced pressure. Then the residue was taken up in ethyl acetate and the organic layer was washed with water, dried, filtered and concentrated in vacuo to give compound 96C (6.2 g, 87% for two steps) as a white solid.

Step 3: Synthesis of 96D

To a mixture of compound 96C (6.2 g, 25.17 mmol), $CS_2$ (3 mL, 49.64 mmol), $Na_2CO_3$ (1.4 g, 13.21 mmol) in EtOH (20 mL) was stirred at 80° C. overnight. LC-MS analysis showed the complete consumption of starting material. The mixture was then concentrated under reduced pressure, and the residue was dissolved in ethyl acetate, washed with water, dried and concentrated in vacuo to provide compound 96D (4.0 g, 55%) as a white solid.

Step 4: Synthesis of 96E

To a mixture of compound 96D (1.021 g, 3.54 mmol) and compound 26E (2.0 g, 3.54 mmol) in DCM (10 mL) was added TEA (715.08 mg, 7.08 mmol) and stirred at rt overnight. The reaction was concentrated under pressure and the residue was purified by column chromatography (PE/EA=10:1 to 1:2) to give compound 96E (2.3 g, 79%).

Step 5: Synthesis of 96

A solution of compound 96E (1.2 g, 1.47 mmol) in TFA/TES (v/v, 6 mL/2 mL) was stirred at 30° C. overnight. The mixture was concentrated under reduced pressure and the residue was dissolved in water. The aqueous solution was washed with diethyl ether (3×10 mL) and lyophilized to afford 96 (82 mg, 14%) as a white solid.

$^1$H NMR (300 MHz, CD$_3$OD): δ 7.05 (d, J=6.3 Hz, 1H), 6.49 (d, J=6 Hz, 1H), 4.86-4.59 (m, 2H), 4.48-4.39 (m, 3H), 3.76 (s, 3H), 3.74 (s, 1H), 3.16-3.12 (m, 1H), 2.92-2.88 (m, 1H).

MS calcd for (C$_{15}$H$_{17}$BN$_4$O$_5$S$_2$): 408.
MS (ESI, positive) found: (M+1): 409.
MS (ESI, negative) found: (M-1): 407.

Example 97: (3R)-3-[[5-(2-aminoethylamino)-1,3,4-thiadiazol-2-yl]sulfanyl]-2-hydroxy-7-methoxy-3,4-dihydro-1,2-benzoxaborinine-8-carboxylic acid (97)

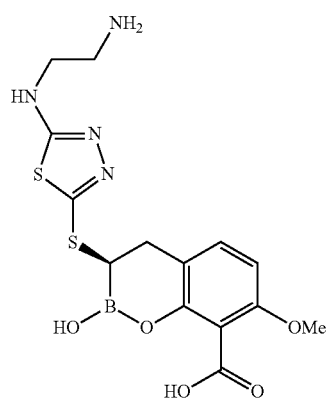

97

Compound 97 was prepared following the procedures described in Example 96 replacing tert-butyl 3-aminoazetidine-1-carboxylate (96A) in step 1 with tert-butyl N-(2-aminoethyl)carbamate as described in J. Org. Chem., 1997, 62, 411-416, which is incorporated herein by reference in its entirety.

$^1$H NMR (400 MHz, CD$_3$OD): δ 7.04 (d, J=8 Hz, 1H), 6.47 (d, J=8 Hz, 1H), 3.76 (s, 3H), 3.75-3.55 (m, 3H), 3.36-3.11 (m, 3H), 2.88-2.85 (m, 1H).

MS calcd for (C$_{14}$H$_{17}$BN$_4$O$_5$S$_2$): 396.
MS (ESI, positive) found: (M+1): 397.
MS (ESI, negative) found: (M-1): 395.

Example 98: (3R)-2-hydroxy-7-methoxy-3-[[5-(2-piperazin-1-ylethylamino)-1,3,4-thiadiazol-2-yl]sulfanyl]-3,4-dihydro-1,2-benzoxaborinine-8-carboxylic acid (98)

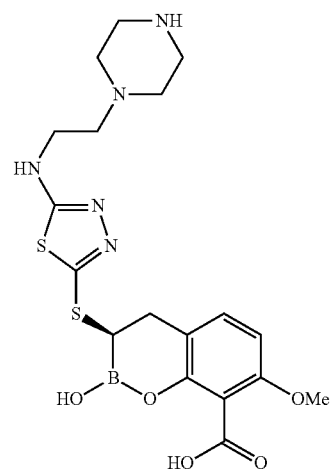

98

Compound 98 was prepared following the procedures described in Example 96 replacing tert-butyl 3-aminoazetidine-1-carboxylate (96A) in step 1 with tert-butyl 4-(2-aminoethyl)piperazine-1-carboxylate as described in U.S. Pat. No. 6,395,737, which is incorporated herein by reference in its entirety.

$^1$H NMR (400 MHz, CD$_3$OD): δ 7.06 (d, J=8.8 Hz, 1H), 6.49 (d, J=8.0 Hz, 1H), 3.87 (m, 1H), 3.77 (s, 3H), 3.66-3.50 (m, 2H), 3.44 (m, 2H), 3.30-2.98 (m, 6H), 2.89-2.58 (m, 4H).

MS calcd for (C$_{18}$H$_{24}$BN$_5$O$_5$S$_2$): 465.
MS (ESI, positive) found: (M+1): 466.
MS (ESI, negative) found: (M-1): 464.

Example 99: (3R)-3-[[5-(azetidin-3-ylamino)-1,3,4-thiadiazol-2-yl]sulfanyl]-2-hydroxy-3,4-dihydro-1,2-benzoxaborinine-8-carboxylic acid (99)

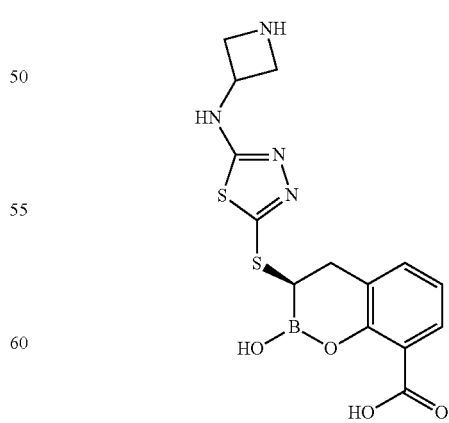

99

Compound 99 was prepared following similar procedure described in example 1 (steps 1-6) replacing 2-mercapto-1,3,4-thiadiazole in step 5 with 108C.

¹H NMR (400 MHz, CD₃OD): δ 7.79 (d, J=8.4 Hz, 1H), 7.36 (d, J=7.2 Hz, 1H), 6.97 (t, J=7.6 Hz, 1H), 4.64-4.60 (m, 1H), 4.43-4.32 (m, 4H), 3.85-3.84 (m, 1H), 3.31-3.05 (m, 2H).
MS calcd for (C$_{14}$H$_{15}$BN$_4$O$_4$S$_2$): 378.
MS (ESI, positive) found: (M+1): 379.
MS (ESI, negative) found: (M-1): 377.

Example 100: (3R)-3-[[5-(3-aminopropylamino)-1,3,4-thiadiazol-2-yl]sulfanyl]-2-hydroxy-7-methoxy-3,4-dihydro-1,2-benzoxaborinine-8-carboxylic acid (100)

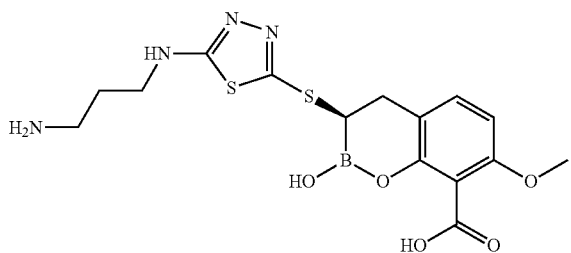

100

Compound 100 was prepared following the procedures described in Example 96 replacing tert-butyl 3-aminoazetidine-1-carboxylate (96A) in step 1 with tert-butyl N-(2-aminopropyl)carbamate as described in *J. Org. Chem.*, 1997, 62, 411-416, which is incorporated herein by reference in its entirety.
¹H NMR (400 MHz, CD₃OD): δ 7.05 (d, J=8.4 Hz, 1H), 6.49 (d, J=8.4 Hz, 1H), 3.76 (s, 3H), 3.63 (m, 1H), 3.60-3.50 (m, 1H), 3.40-3.35 (m, 1H), 3.14 (dd, J=15.6, 4.8 Hz, 1H), 3.07 (t, J=7.2 Hz, 2H), 2.86 (d, J=15.6 Hz, 1H), 2.19-2.00 (m, 2H).
MS calcd for (C$_{15}$H$_{19}$BN$_4$O$_5$S$_2$): 410.
MS (ESI, positive) found: (M+1): 411.
MS (ESI, negative) found: (M-1): 409.

Example 101: (3R)-3-[[5-[bis(2-aminoethyl)amino]-1,3,4-thiadiazol-2-yl]sulfanyl]-2-hydroxy-7-methoxy-3,4-dihydro-1,2-benzoxaborinine-8-carboxylic acid (101)

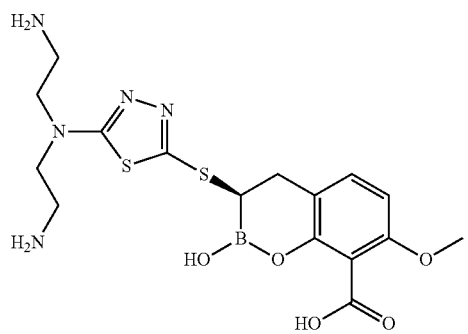

101

Compound 101 was prepared following the procedures described in Example 96 replacing tert-butyl 3-aminoazetidine-1-carboxylate (96A) in step 1 with tert-butyl N-[2-[2-(tert-butoxycarbonylamino)ethylamino]ethyl]carbamate as described in *Org. Lett.*, 2000, 2, 2117-2120, which is incorporated herein by reference in its entirety.
¹H NMR (400 MHz, CD₃OD): δ 7.00 (d, J=8.4 Hz, 1H), 6.45 (d, J=8.4 Hz, 1H), 3.88-3.59 (m, 9H), 3.83 (s, 3H), 3.12 (dd, J=15.6, 4.4 Hz, 1H), 2.88 (d, J=15.6 Hz, 1H).
MS calcd for (C$_{16}$H$_{22}$BN$_5$O$_5$S$_2$): 439.
MS (ESI, positive) found: (M+1): 440.
MS (ESI, negative) found: (M-1): 438.

Example 102: (3R)-3-[[5-[[2-amino-1-(aminomethyl)ethyl]amino]-1,3,4-thiadiazol-2-yl]sulfanyl]-2-hydroxy-7-methoxy-3,4-dihydro-1,2-benzoxaborinine-8-carboxylic acid (102)

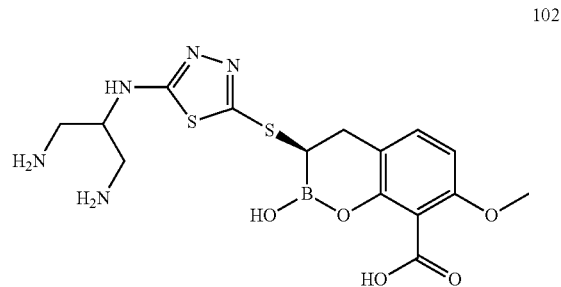 [SMILES: COc1ccc2c(c1C(=O)O)OB(O)[C@@H](Sc1nnc(NC(CN)CN)s1)C2]

102

Compound 102 was prepared following the procedures described in Example 96 replacing tert-butyl 3-aminoazetidine-1-carboxylate (96A) in step 1 with tert-butyl N-[2-amino-3-(tert-butoxycarbonylamino)propyl]carbamate as described in *J. med. Chem.*, 2005, 48, 7781-7788, which is incorporated herein by reference in its entirety.
¹H NMR (400 MHz, D₂O) δ 6.78 (d, J=8.4 Hz, 1H), 6.38 (d, J=8.4 Hz, 1H), 4.08 (m, 1H), 3.73 (s, 3H), 3.62 (d, J=2.0 Hz, 1H), 3.15-2.96 (m, 5H), 2.76 (dd, J=15.6, 6.0 Hz, 1H).
MS calcd for (C$_{15}$H$_{20}$BN$_5$O$_5$S$_2$): 425.
MS (ESI, positive) found: (M+1): 426.
MS (ESI, negative) found: (M-1): 424.

Example 103: (3R)-2-hydroxy-7-methoxy-3-[[5-[[(3S)-pyrrolidin-3-yl]amino]-1,3,4-thiadiazol-2-yl]sulfanyl]-3,4-dihydro-1,2-benzoxaborinine-8-carboxylic acid (103)

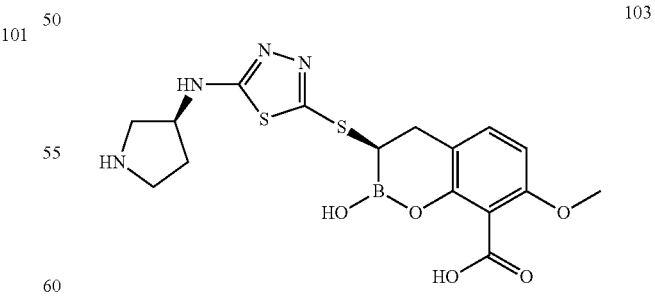

103

Compound 103 was prepared following the procedures described in Example 96 replacing tert-butyl 3-aminoazetidine-1-carboxylate (96A) in step 1 with tert-butyl (3S)-3-aminopyrrolidine-1-carboxylate as described in PCT publication WO 2005/020975, which is incorporated herein by reference in its entirety.

¹H NMR (400 MHz, CD₃OD): δ 7.04 (d, J=8.4 Hz, 1H), 6.48 (d, J=8.4 Hz, 1H), 4.45 (m, 1H), 3.76 (s, 3H), 3.63-3.48 (m, 4H), 3.40-3.35 (m, 1H), 3.13 (dd, J=15.6, 5.2 Hz, 1H), 2.88 (d, J=14.4 Hz, 1H), 2.42-2.38 (m, 1H), 2.27-2.22 (m, 1H).

MS calcd for ($C_{16}H_{19}BN_4O_5S_2$): 422.
MS (ESI, positive) found: (M+1): 423.
MS (ESI, negative) found: (M−1): 421.

Example 104: (3R)-2-hydroxy-7-methoxy-3-[[5-(4-piperidylamino)-1,3,4-thiadiazol-2-yl]sulfanyl]-3,4-dihydro-1,2-benzoxaborinine-8-carboxylic acid (104)

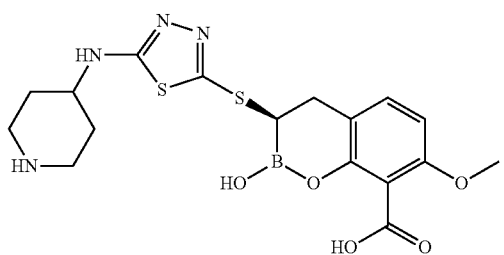

Compound 104 was prepared following the procedures described in Example 96 replacing tert-butyl 3-aminoazetidine-1-carboxylate (96A) in step 1 with tert-butyl 4-aminopiperidine-1-carboxylate as described in PCT publication WO 2006/115353, which is incorporated herein by reference in its entirety.

¹H NMR (400 MHz, CD₃OD): δ 7.05 (d, J=8.4 Hz, 1H), 6.49 (d, J=8.0 Hz, 1H), 3.95-3.90 (m, 1H), 3.83 (s, 3H), 3.77-3.73 (m, 1H), 3.61-3.59 (m, 2H), 3.23-3.10 (m, 3H), 2.88 (d, J=15.2 Hz, 1H), 2.41-2.26 (m, 2H), 1.85-1.76 (m, 2H).

MS calcd for ($C_{17}H_{21}BN_4O_5S_2$): 436.
MS (ESI, positive) found: (M+1): 437.
MS (ESI, negative) found: (M−1): 435.

Example 105: (3R)-3-[[5-[2-(azetidin-3-ylamino)ethylamino]-1,3,4-thiadiazol-2-yl]sulfanyl]-2-hydroxy-7-methoxy-3,4-dihydro-1,2-benzoxaborinine-8-carboxylic acid (105)

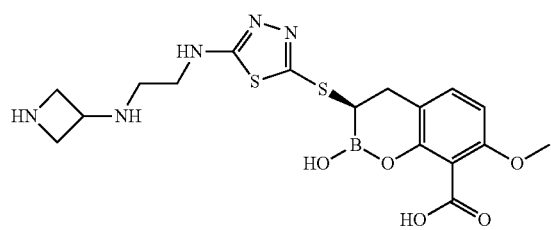

Compound 105 was prepared following the procedures described in Example 96 replacing tert-butyl 3-aminoazetidine-1-carboxylate (96A) in step 1 with tert-butyl 3-(2-aminoethylamino)azetidine-1-carboxylate as described in U.S. Pat. No. 5,846,965, which is incorporated herein by reference in its entirety.

¹H NMR (400 MHz, CD₃OD): δ 7.06 (d, J=8.4 Hz, 1H), 6.50 (d, J=8.0 Hz, 1H), 4.54-4.42 (m, 4H), 3.76 (s, 3H), 3.73-3.60 (m, 3H), 3.39-3.36 (m, 2H), 3.14 (dd, J=16.0, 4.4 Hz, 1H), 2.90 (d, J=15.6 Hz, 1H).

MS calcd for ($C_{17}H_{22}BN_5O_5S_2$): 451.
MS (ESI, positive) found: (M+1): 452.
MS (ESI, negative) found: (M−1): 450.

Example 106: (3R)-3-[(5-guanidino-1,3,4-thiadiazol-2-yl)sulfanyl]-2-hydroxy-7-methoxy-3,4-dihydro-1,2-benzoxaborinine-8-carboxylic acid (106)

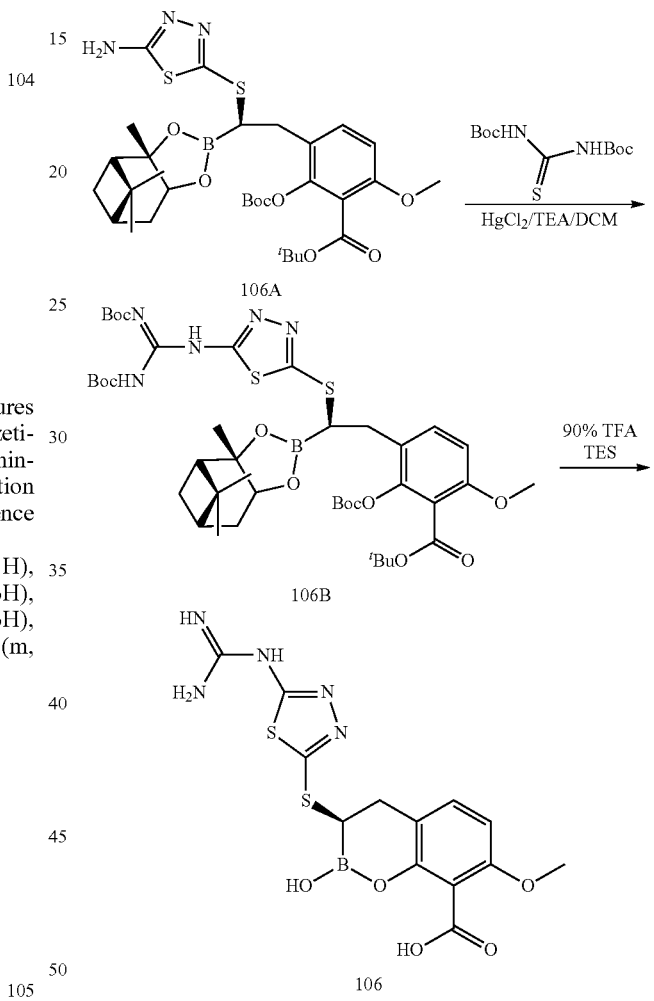

Step 1: Synthesis of 106B

Compound 106B was prepared from the penultimate precursor of Example 27 by treating with N,N'-bis(tert-butoxycarbonyl)-thiourea as described in J. Med. Chem., 2008, 51. 3304-3312, which is incorporated herein by reference in its entirety.

Step 2: Synthesis of 106

Compound 106B was deprotected under the conditions described in step 6 of Example 1.

¹H NMR (400 MHz, CD₃OD): δ 7.05 (d, 1H), 6.48 (d, 1H), 3.76 (s, 3H), 3.61 (m, 1H), 3.17 (dd, 1H), 2.90 (dd, 1H).

MS calcd for ($C_{13}H_{14}BN_5O_5S_2$): 395.
MS (ESI, positive) found: (M+1): 396.
MS (ESI, negative) found: (M−1): 394.

Example 107: (3R)-3-[[5-(2-aminoethylsulfanyl)-1,3,4-thiadiazol-2-yl]sulfanyl]-2-hydroxy-7-methoxy-3,4-dihydro-1,2-benzoxaborinine-8-carboxylic acid (107)

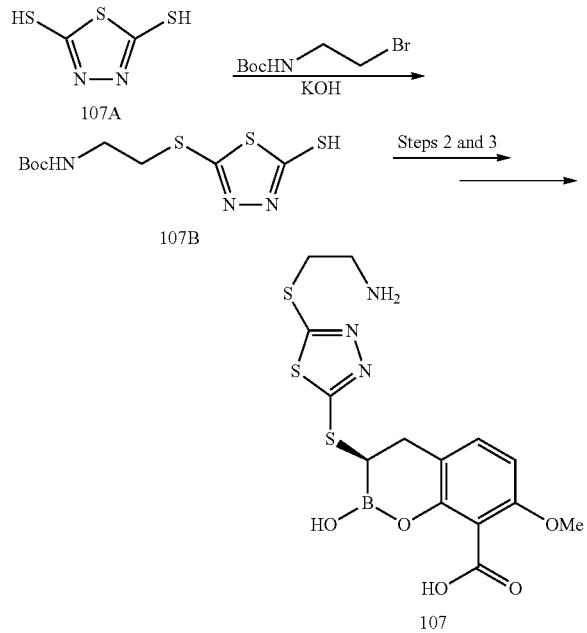

Step 1: Synthesis of 107B

To a solution of compound 107A (1 g, 6.6 mmol) in ethanol (10 mL) was added KOH (410 mg, 7.26 mmol). The resulting mixture was stirred at 70° C. for 1 h and tert-butyl N-(2-bromoethyl)carbamate as described in *J. Org. Chem.*, 1988, 53, 2226-2232, which is incorporated herein by reference in its entirety, (1.6 g, 7.26 mmol, 1.1 eq) was then added to the reaction. The mixture was stirred at 70° C. for additional 2h. The reaction was cooled to room temperature, filtered through Celite and concentrated under reduced pressure. The residue was purified by column chromatography (EA/Hexanes=1:3 to 1:1) to give compound 107B (1.63 g, 84%).

1H NMR (300 MHz, CDCl$_3$): δ 3.42 (t, 2H), 3.15 (t, 2H), 1.45 (s, 9H).

Compound 107 synthesized following the procedures described in Example 26 except replacing 4-amino-4H-1,2,4-triazole-3-thiol in step 5 with 107B.

$^1$H NMR (300 MHz, CD$_3$OD+DMSO-d$_6$) δ 6.51 (d, J=8.1 Hz, 1H), 6.07 (d, J=8.1 Hz, 1H), 4.15 (d, J=6.9 Hz, 1H), 3.55 (s, 3H), 3.20-3.08 (m, 2H), 3.04-2.92 (m, 1H), 2.80-2.65 (m, 3H).

MS calcd for ($C_{14}H_{16}BN3O_5S_3$): 413.
MS (ESI, positive) found: (M+1): 414.

Example 108: (3R)-3-[[5-(azetidin-3-ylsulfanyl)-1,3,4-thiadiazol-2-yl]sulfanyl]-2-hydroxy-7-methoxy-3,4-dihydro-1,2-benzoxaborinine-8-carboxylic acid (108)

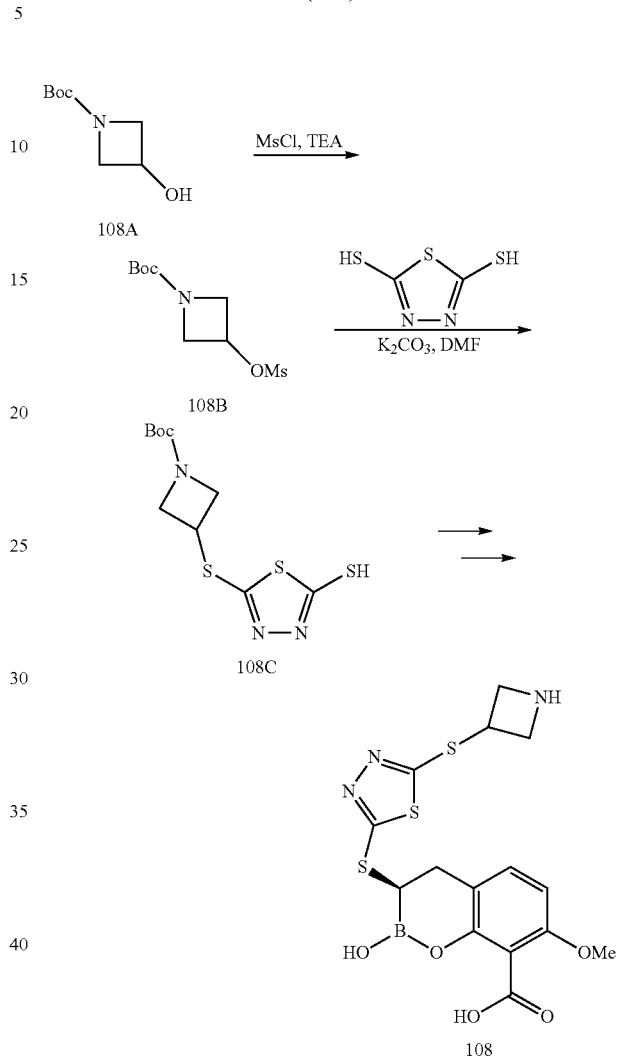

Step 1: Synthesis of 108B

To a solution of compound 108A (2.0 g, 11.55 mmol) in dichloromethane (10 mL) was added MSCl (1.455 g, 12.70 mmol) followed by TEA (1.519 g, 15.01 mmol). The mixture was stirred at rt overnight. The reaction was quenched with water and extracted with additional dichloromethane. The organic layer was washed, dried and concentrated to dryness to afford compound 108B (2.8 g, 96%) as a white solid.

1H NMR (400 MHz, CDCl$_3$): δ 5.22-5.18 (m, 1H), 4.30-4.25 (m, 2H), 4.12-4.08 (m, 2H), 3.06 (s, 3H), 1.45 (s, 9H).

Step 2: Synthesis of 108C

To a solution of compound 108B (200 mg, 0.80 mmol) in DMF (3 mL) were added 1,3,4-thiadiazole-2,5-dithiol (179 mg, 1.20 mmol) and K$_2$CO$_3$ (110 mg, 0.80 mmol). The mixture was stirred at rt overnight. The reaction was then heated to 100° C. for 2 h. The mixture cooled to rt and acidified with aq. citric acid. The mixture was diluted with ethyl acetate, washed with water dried and concentrated. The residue was purified by column chromatography (PE/EA=50:1 to 3:1) to give compound 108C (100 mg, 41%).

1H NMR (400 MHz, CDCl$_3$): δ 11.32 (br. s, 1H), 4.43 (m, 2H), 4.30-4.27 (m, 1H), 3.95-3.91 (m, 2H), 1.45 (s, 9H).

Compound 108 was synthesized following the procedures described in Example 26 except replacing 4-amino-4H-1,2,4-triazole-3-thiol in step 5 with 108C.

$^1$H NMR (400 MHz, CD$_3$OD): δ 7.05 (d, J=8.4 Hz, 1H), 6.49 (d, J=8.4 Hz, 1H), 4.78-4.63 (m, 1H), 4.61-4.57 (m, 2H), 4.46-4.38 (m, 2H), 3.76 (s, 3H), 3.59 (s, 1H), 3.19-3.14 (m, 1H), 2.95-2.91 (m, 1H).

MS calcd for (C$_{15}$H$_{16}$BN$_3$O$_5$S$_3$): 425.

MS (ESI, positive) found: (M+1): 426.

Example 109: (3R)-3-[[5-[2-amino-1-(aminomethyl)ethyl]sulfanyl-1,3,4-thiadiazol-2-yl]sulfanyl]-2-hydroxy-7-methoxy-3,4-dihydro-1,2-benzoxaborinine-8-carboxylic acid (109)

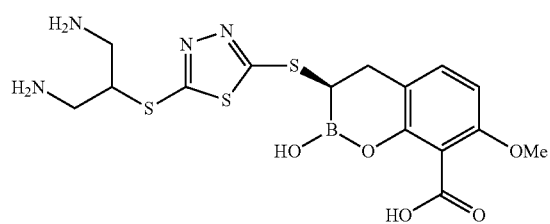

109

Compound 109 was prepared as described in Example 107 replacing 107B with tert-butyl N-[3-(tert-butoxycarbonylamino)-2-[(5-sulfanyl-1,3,4-thiadiazol-2-yl)sulfanyl]propyl]carbamate, which was made from 107A and tert-butyl N-[2-bromo-3-(tert-butoxycarbonylamino)propyl]carbamate (described in US 2011/257406, incorporated herein by reference in its entirety) as in step 1 of Example 107.

$^1$H NMR (400 MHz, CD$_3$OD): δ 7.06 (d, J=8 Hz, 1H), 6.49 (d, J=8 Hz, 1H), 4.25-3.98 (m, 1H), 3.96-3.84 (m, 2H), 3.78 (s, 3H), 3.71-3.37 (m, 3H), 3.31-2.93 (m, 2H).

MS calcd for (C$_{15}$H$_{19}$BN$_4$O$_5$S$_3$): 442.

MS (ESI, positive) found: (M+1): 443.

MS (ESI, negative) found: (M−1): 441.

Example 110: (3R)-2-hydroxy-7-methoxy-3-[[5-(2-morpholinoethylsulfanyl)-1,3,4-thiadiazol-2-yl]sulfanyl]-3,4-dihydro-1,2-benzoxaborinine-8-carboxylic acid (110)

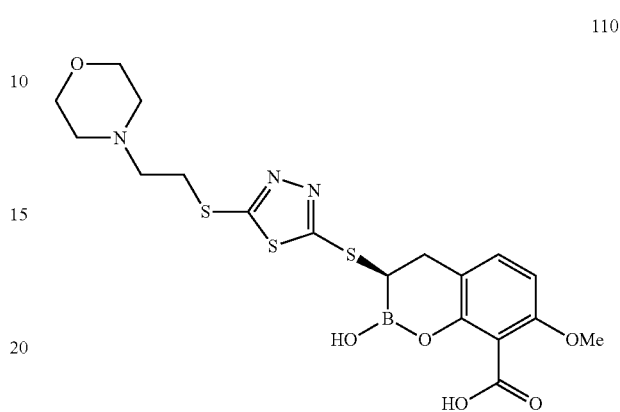

110

Compound 110 was prepared as described in Example 107 replacing 107B with 5-(2-morpholinoethylsulfanyl)-1,3,4-thiadiazole-2-thiol, which was made from 107A and 4-(2-bromoethyl)morpholine (described in PCT publication WO 2013/160810, incorporated herein by reference in its entirety) as in step 1 of Example 107.

$^1$H NMR (400 MHz, CD$_3$OD): δ 7.05 (d, J=8.4 Hz, 1H), 6.49 (d, J=8.4 Hz, 1H), 3.99 (s, 3H), 3.81-3.74 (m, 7H), 3.64-3.53 (m, 6H), 3.19-3.14 (m, 1H), 2.95-2.91 (m, 1H).

MS calcd for (C$_{18}$H$_{22}$BN$_3$O$_6$S$_3$): 483.

MS (ESI, positive) found: (M+1): 484.

MS (ESI, negative) found: (M−1): 482.

Example 111: (3R)-3-[[5-[(5-amino-1,3,4-thiadiazol-2-yl)sulfanyl]-1,3,4-thiadiazol-2-yl]sulfanyl]-2-hydroxy-7-methoxy-3,4-dihydro-1,2-benzoxaborinine-8-carboxylic acid (111)

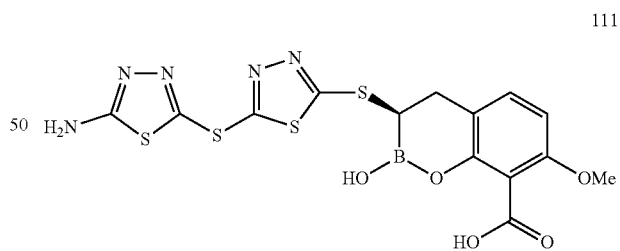

111

Compound 111 was prepared as described in Example 107 replacing 107B with tert-butyl N-[5-[(5-sulfanyl-1,3,4-thiadiazol-2-yl)sulfanyl]-1,3,4-thiadiazol-2-yl]carbamate, which was made from 107A and tert-butyl N-(5-bromo-1,3,4-thiadiazol-2-yl)carbamate as in step 1 of Example 107.

$^1$H NMR (400 MHz, CD$_3$OD): δ 7.02 (d, J=8.4 Hz, 1H), 6.46 (d, J=8.4 Hz, 1H), 3.83 (s, 3H), 3.72-3.63 (m, 1H), 3.30-3.12 (m, 1H), 2.98-2.86 (m, 1H).

MS calcd for (C$_{14}$H$_{12}$BN$_5$O$_5$S$_4$): 469.

MS (ESI, positive) found: (M+1): 470.

Example 112: (3R)-2-hydroxy-7-methoxy-3-[[5-(4-piperidylsulfanyl)-1,3,4-thiadiazol-2-yl]sulfanyl]-3,4-dihydro-1,2-benzoxaborinine-8-carboxylic acid (112)

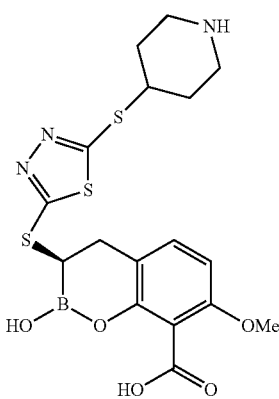

112

Compound 112 was prepared as described in Example 107 replacing 107B with tert-butyl 4-[(5-sulfanyl-1,3,4-thiadiazol-2-yl)sulfanyl]piperidine-1-carboxylate, which was made from 107A and tert-butyl 4-bromopiperidine-1-carboxylate (described in PCT publication WO 2004/084898, incorporated herein by reference in its entirety) as in step 1 of Example 107.

$^1$H NMR (400 MHz, CD$_3$OD): δ 7.06 (d, J=8.4 Hz, 1H), 6.49 (d, J=8.8 Hz, 1H), 4.01-3.97 (m, 1H), 3.76-3.74 (m, 4H), 3.51-3.46 (m, 2H), 3.18-3.14 (m, 3H), 2.95-2.81 (m, 1H), 2.45-2.43 (m, 2H), 2.09-1.98 (m, 2H).

MS calcd for (C$_{17}$H$_{20}$BN$_3$O$_5$S$_3$): 453.
MS (ESI, positive) found: (M+1): 454.
MS (ESI, negative) found: (M−1): 452.

Example 113: (3R)-3-[[5-(3-aminopropylsulfanyl)-1,3,4-thiadiazol-2-yl]sulfanyl]-2-hydroxy-7-methoxy-3,4-dihydro-1,2-benzoxaborinine-8-carboxylic acid (113)

113

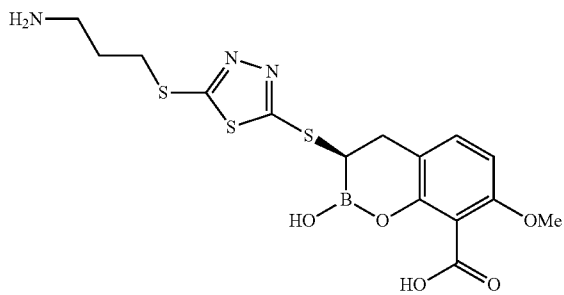

Compound 113 was prepared as described in Example 107 replacing 107B with tert-butyl N-[3-[(5-sulfanyl-1,3,4-thiadiazol-2-yl)sulfanyl]propyl]carbamate, which was made from 107A and 3-(tert-butoxycarbonylamino)propyl methanesulfonate (described in PCT publication WO2013166319, incorporated herein by reference in its entirety) as in step 1 of Example 107.

$^1$H NMR (400 MHz, CD$_3$OD): δ 7.07 (d, J=8.0 Hz, 1H), 6.49 (d, J=8.4 Hz, 1H), 3.76-3.73 (m, 4H), 3.55-3.49 (m, 1H), 3.30-3.18 (m, 4H), 2.91-2.90 (m, 1H), 2.27-2.22 (m, 2H).

MS calcd for (C$_{15}$H$_{18}$BN$_3$O$_5$S$_3$): 427.
MS (ESI, positive) found: (M+1): 428.
MS (ESI, negative) found: (M−1): 426.

Example 114: (3R)-3-[(5-amino-1,3,4-thiadiazol-2-yl)sulfanyl]-6-fluoro-2-hydroxy-7-methoxy-3,4-dihydro-1,2-benzoxaborinine-8-carboxylic acid (114)

114

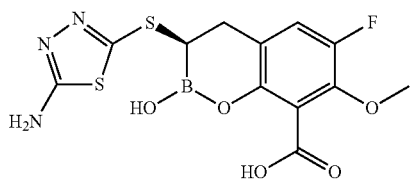

Compound 114 was prepared following procedures described in Example 38 except replacing 3,4,5-trifluorophenol (38A) with 4-fluoro-3-methoxyphenol.

$^1$H NMR (300 MHz, CD$_3$OD): δ 6.93 (d, 1H), 3.84 (s, 3H), 3.52-3.48 (m, 1H), 3.25-3.04 (m, 1H), 2.83-2.76 (m, 1H).

MS calcd for (C$_{12}$H$_{11}$BFN$_3$O$_5$S$_2$): 371.
MS (ESI, positive) found: (M+1): 372.
MS (ESI, negative) found: (M−1): 370.

Example 115: (3R)-3-[(5-amino-1,3,4-thiadiazol-2-yl)sulfanyl]-2-hydroxy-4,8-dihydro-3H-oxaborinino[6,5-f]benzimidazole-9-carboxylic acid (115)

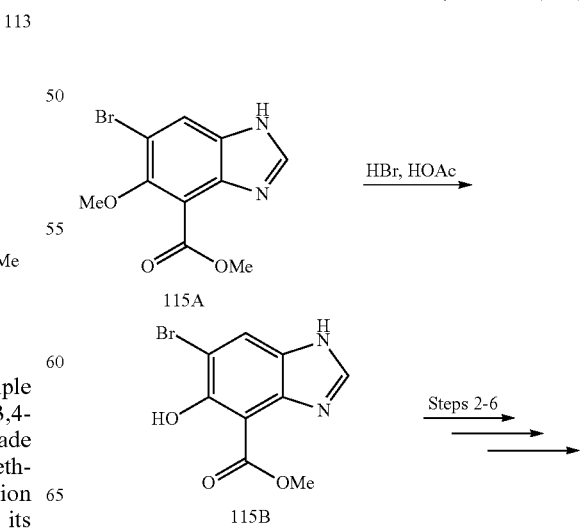

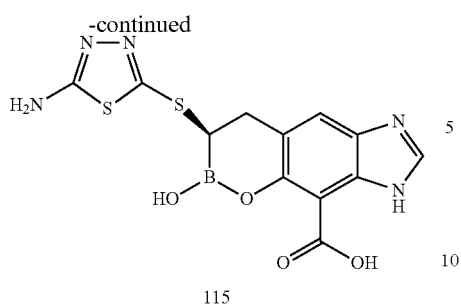

115

Step 1: Synthesis of 115B

To a solution of 115A as described in PCT publication WO 2009/134850, incorporated herein by reference in its entirety, (3.0 g, 10.52 mmol, 1.0 eq) in acetic acid (30 mL) was added hydrobromic acid (30 mL). The reaction mixture was stirred at 110° C. overnight. Then the mixture was filtered and the solid was dried under vacuum to give 115B (3.2 g, 100%).

$^1$H NMR (400 MHz, DMSO-d6): δ 9.01 (s, 1H), 8.08 (s, 1H).

Formation of di-Boc protected t-butyl ester of 115B and conversion to 115 in steps 2-6 was done following methods described in steps 2-6 of Example 26.

$^1$H NMR (400 MHz, CD$_3$OD): δ δ 9.11 (s, 1H), 7.81 (s, 1H), 5.48 (s, 1H), 3.75 (s, 1H), 3.45-3.05 (m, 2H).

MS calcd for (C$_{12}$H$_{10}$BN$_5$O$_4$S$_2$): 363.
MS (ESI, positive) found: (M+1): 364.
MS (ESI, negative) found: (M−1): 362.

Example 116: (3R)-3-[[5-(2-aminoethylsulfanyl)-1,3,4-thiadiazol-2-yl]sulfanyl]-2-hydroxy-3,4-dihydro-1,2-benzoxaborinine-8-carboxylic acid (116)

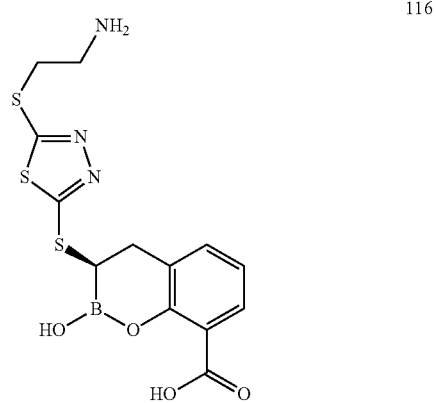 [SMILES: NCCSc1nnc(S[C@H]2Cc3cccc(C(=O)O)c3OB2O)s1]

116

Compound 116 was prepared following similar procedure described in example 1 (steps 1-6) replacing 2-mercapto-1,3,4-thiadiazole in step 5 with thiol 107B.

$^1$H NMR (400 MHz, CD$_3$OD): δ 7.79 (d, J=7.2 Hz, 1H), 7.37 (d, J=7.2 Hz, 1H), 6.98 (t, J=7.6 Hz, 1H), 3.88-3.87 (m, 1H), 3.76-3.69 (m, 1H), 3.46-3.08 (m, 5H).

MS calcd for (C$_{13}$H$_{14}$BN$_3$O$_4$S$_3$): 383.
MS (ESI, positive) found: (M+1): 384.
MS (ESI, negative) found: (M−1): 382.

Example 117: (3R)-3-[[5-(2-aminoethoxy)-1,3,4-thiadiazol-2-yl]sulfanyl]-2-hydroxy-7-methoxy-3,4-dihydro-1,2-benzoxaborinine-8-carboxylic acid (117)

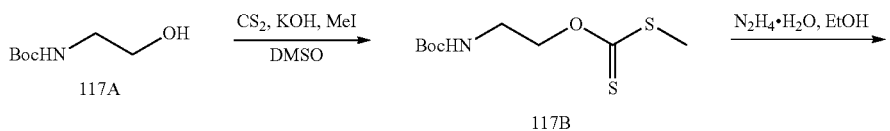

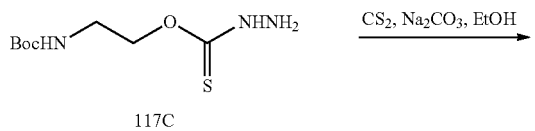

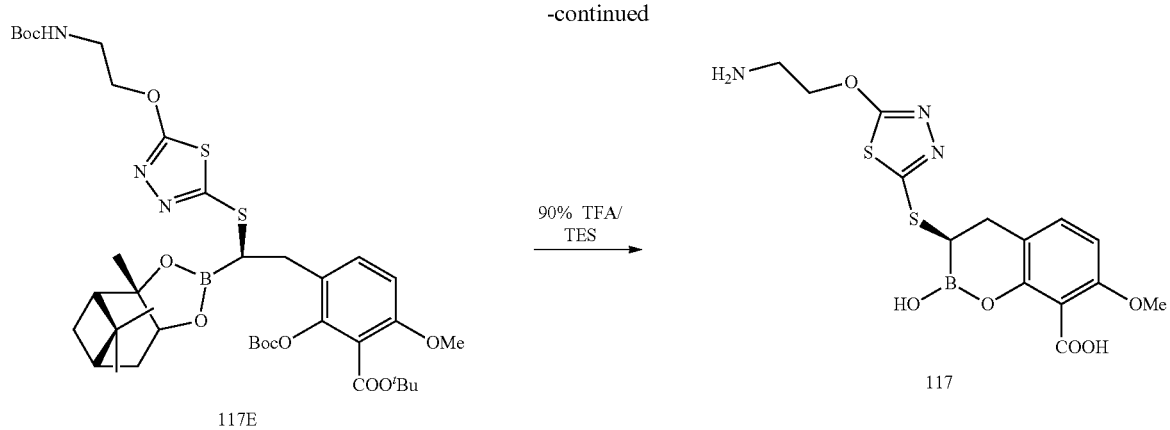

Step 1: Synthesis of 117B

To a mixture of compound 117A (2.0 g, 12.4 mmol), KOH (1.40 g, 24.8 mmol) in DMSO (12 mL) was added $CS_2$ (1 mL, 16.5 mmol) dropwise. After stirring for 1.5 h. MeI (1 mL, 16.1 mmol) was added and stirred for another 1.5 h. Then the mixture was evaporated to dryness. The residue was dissolved in ethyl acetate and washed with water, dried, filtered and concentrated in vacuo to give compound 117B (2.1 g, 67%).

Step 2: Synthesis of 117C

To a solution of compound 117B (2.0 g, 7.96 mmol) in EtOH (20 mL) at 0° C. was added $N_2H_4 \cdot H_2O$ (387 mL, 7.96 mmol). The mixture was stirred at 0° C. for 1 h. The reaction was quenched with water and extracted with ethyl acetate (2×100 mL). The combined organic extract was washed with water, dried, filtered and concentrated to afford compound 117C (2.06 g, 100%).

Step 3: Synthesis of 117D

To a solution of compound 117C (58 mg, 0.247 mmol) in ethanol (2 mL) was added $CS_2$ (18 mL, 0.796 mmol, 1.2 eq) followed by $Na_2CO_3$ (13 mg, 0.124 mmol, 0.5 eq). The resulting mixture was heated to reflux overnight. Then the mixture was concentrated under pressure and the residue was dissolved in ethyl acetate, treated with aq citric acid to pH 3-5. The organic layer was washed by water, dried, filtered and evaporated to dryness to afford compound 117D (50 mg, 73%).

Step 4: Synthesis of 117E

To a mixture of compound 117D (160 mg, 0.578 mmol) and compound 5 (330 mg, 0.58 mmol) in dichloromethane (5 mL) was added TEA (240 mL, 1.733 mmol). The mixture was stirred at rt overnight. Then the mixture was concentrated and the residue was purified by column chromatography to give compound 117E (150 mg, 32%).

Step 5: Synthesis of 117

To a solution of compound 117E (140 mg, 0.17 mmol) in 90% TFA/TES (v/v, 5 mL/0.6 mL) was stirred at rt for 1 h. The mixture was concentrated under reduced pressure. Then the residue was dissolved in water and washed with ether (3×5 mL). The aqueous layer was lyophilized to afford 117 (40 mg, 58%) as white solid.

$^1$H NMR (400 MHz, $CD_3OD$): δ 7.04 (d, J=8.8 Hz, 1H), 6.47 (d, J=8.4 Hz, 1H), 4.81-4.79 (m, 2H), 3.74 (s, 3H), 3.58-3.52 (m, 3H), 3.16-3.11 (m, 1H), 2.91-2.86 (m, 1H).

MS calcd for ($C_{14}H_{16}BN_3O_6S_2$): 397.

MS (ESI, positive) found: (M+1): 398.

Example 118: (3R)-3-[[5-(azetidin-3-ylamino)-1,3,4-thiadiazol-2-yl]sulfanyl]-7-ethoxy-2-hydroxy-3,4-dihydro-1,2-benzoxaborinine-8-carboxylic acid (118)

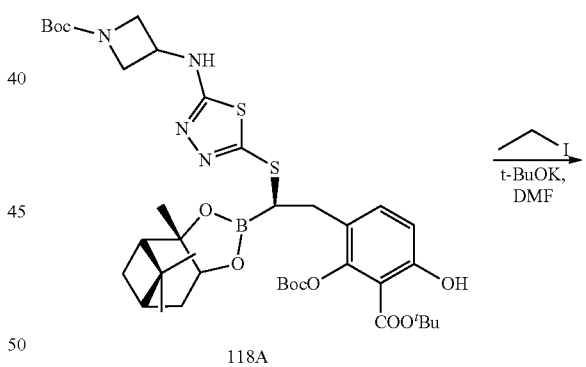

118A

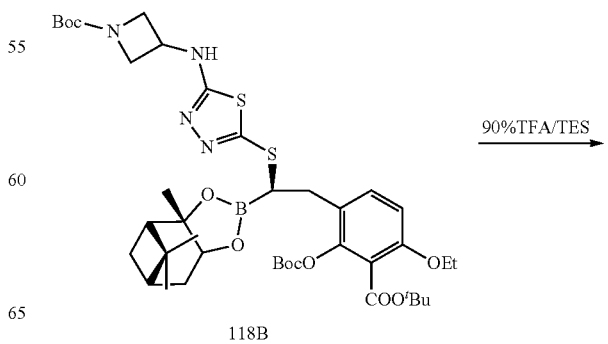

118B

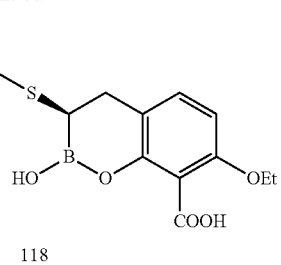

Step 1: Synthesis of 118B

To a solution of compound 118A (270 mg, 0.337 mmol) in DMF (3 mL) were added iodoethane (105 mg, 0.674 mmol) and t-BuOK (75 mg, 0.668 mmol). The resulting mixture was stirred at rt for 1 h. The reaction was quenched by water and the aqueous layer was extracted with ethyl acetate. Then the organic layer was washed with brine, dried and evaporated to dryness. The residue was purified by prep-TLC (DCM/MeOH=20:1) to afford compound 118B (80 mg, 29%) as light yellow solid.

Step 2: Synthesis of 118

To a solution of compound 118B (75 mg, 0.09 mmol) in 90% TFA/TES (v/v, 4 mL/0.5 mL) was stirred at rt for 1 h. The mixture was concentrated under reduced pressure and the residue was dissolved in water. The aqueous solution was washed with ether and lyophilized to afford 118 (38 mg, 99%) as a white solid.

$^1$H NMR (400 MHz, CD$_3$OD): δ 7.02 (d, J=8.4 Hz, 1H), 6.46 (d, J=8.4 Hz, 1H), 4.68-4.61 (m, 2H), 4.59-4.36 (m, 3H), 4.03-3.97 (m, 2H), 3.74-3.73 (m, 1H), 3.16-3.14 (m, 1H), 2.92-2.88 (m, 1H), 1.32 (t, J=7.2 Hz, 3H).

MS calcd for (C$_{16}$H$_{19}$BN$_4$O$_5$S$_2$): 422.
MS (ESI, positive) found: (M+1): 423.
MS (ESI, negative) found: (M−1): 421.

Example 119: (3R)-3-[(5-amino-1,3,4-thiadiazol-2-yl)sulfanyl]-2-hydroxy-7-(triazol-1-yl)-3,4-dihydro-1,2-benzoxaborinine-8-carboxylic acid (119)

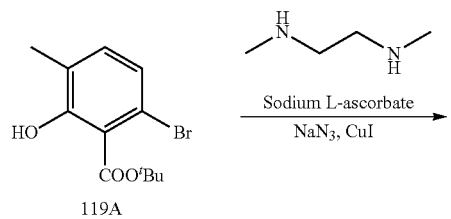

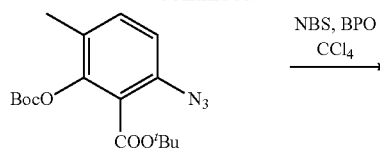

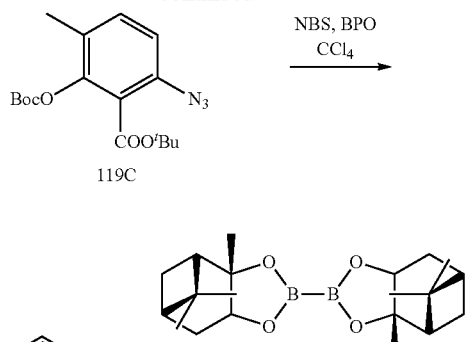

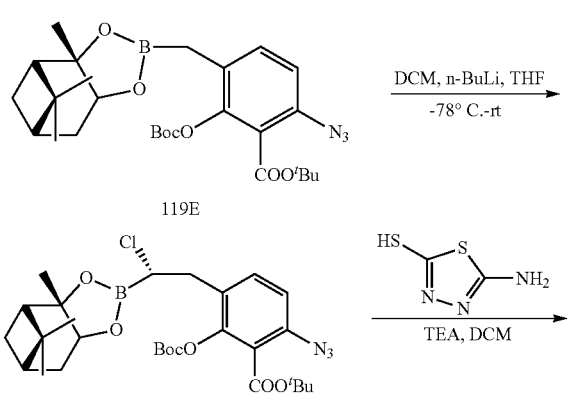

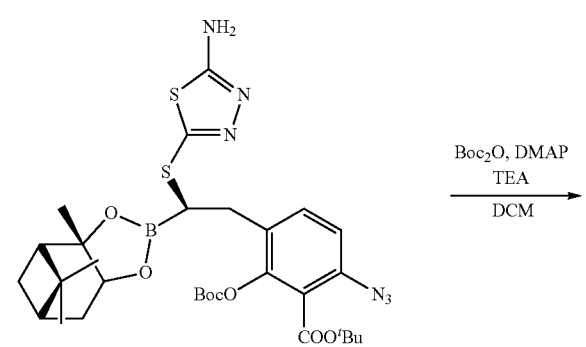

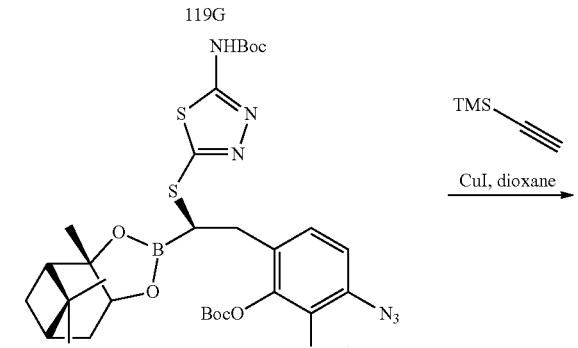

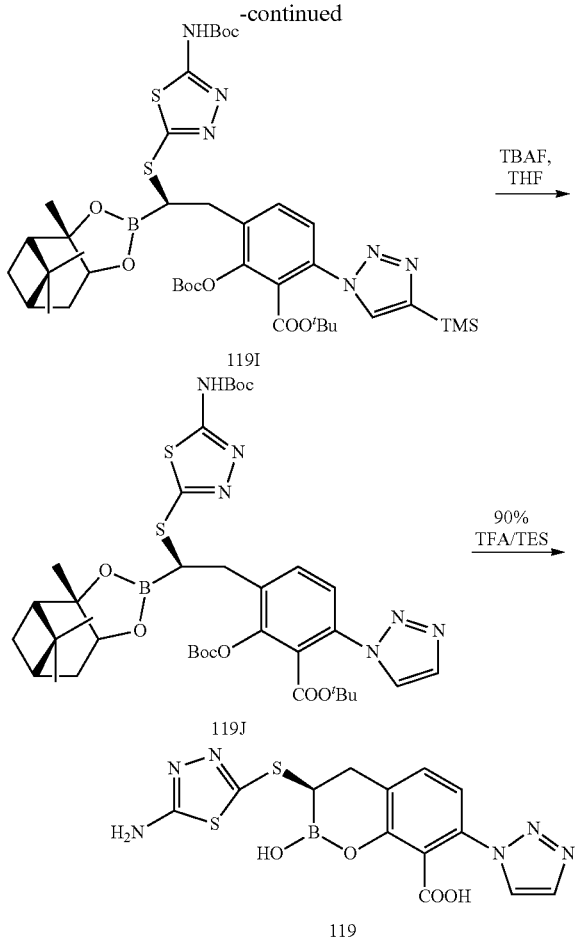

Step 1: Synthesis of 119B

The mixture of compound 119A (900 mg, 3.14 mmol), NaN₃ (406 g, 6.29 mmol), CuI (60 mg, 0.314 mmol), sodium L-ascorbate (31 mg, 0.157 mmol) and N,N'-dimethylethylenediamine (42 mg, 0.471 mmol) in EtOH:H₂O (7:3, 15 mL) was stirred at 80° C. for 2 hours in nitrogen atmosphere. After cooling down, the mixture was diluted with ethyl acetate and washed with 0.1N HCl. The aqueous layers was further extracted with ethyl acetate. The combined organic layers were dried over sodium sulfate, and evaporated to dryness in vacuo. The residue was purified by column chromatography (EA/Hexanes=1:15 to 1:10) to give compound 119B (730 mg, 92%).

1H NMR (300 MHz, CDCl₃): δ 11.61 (s, 1H), 7.23 (d, J=7.8 Hz, 1H), 6.65 (d, J=7.8 Hz, 1H), 2.21 (s, 3H), 1.63 (s, 9H).

Step 2: Synthesis of Compound 119C

To a solution of compound 119B (7.0 g, 28.1 mmol) in dichloromethane (100 mL) were added Boc₂O (6.2 g, 28.1 mmol) and DMAP (342 mg, 2.8 mmol). The resulting mixture was stirred at rt for 30 minutes. Then the mixture was concentrated and the residue was purified by column chromatography (PE/EA=100:1 to 10:1) to give compound 119 C (9.5 g, 93%).

1H NMR (400 MHz, CDCl₃): δ 7.25 (d, J=8.0 Hz, 1H), 6.98 (d, J=8.8 Hz, 1H), 2.18 (s, 3H), 1.57 (s, 9H), 1.53 (s, 9H).

Step 3: Synthesis of Compound 119D

To a stirred mixture of compound 119C (9.8 g, 28.05 mmol), NBS (5.0 g, 28.05 mmol), BPO (678 mg, 2.8 mmol) in CCl₄ (100 mL) was heated to reflux for 12 h. TLC analysis showed the incomplete consumption of raw material, then another batch of NBS (5.0 g, 28.05 mmol) and BPO (678 mg, 2.8 mmol) were added. The mixture was stirred for additional 12 h. The mixture was cooled and filtered. The filtrate was concentrated under reduced pressure. The residue was purified by column chromatography (PE/EA=100:1 to 10:1) to give pure compound 119D (10 g).

1H NMR (400 MHz, CDCl₃): δ 8.11 (d, J=6.8 Hz, 1H), 7.07 (d, J=8.4 Hz, 1H), 4.40 (s, 2H), 1.57 (s, 9H), 1.53 (s, 9H).

Step 4: Synthesis of Compound 119E

To a stirred mixture of compound 119D (10 g, 23.13 mmol), compound bis(pinanediolato)diboran (9.94 g, 27.76 mmol), PdCl₂(dppf) (944 mg, 1.15 mmol), KOAc (6.81 g, 69.39 mmol) in dioxane (100 mL) was degassed with nitrogen. The resulting mixture was heated to 90° C. overnight. Then the solvent was removed under reduced pressure and diluted with water and ethyl acetate, the aqueous layers was extracted with ethyl acetate. The combined organic layers were dried over sodium sulfate, evaporated to dryness in vacuo. The residue was purified by column chromatography (PE/EA=100:1 to 20:1) to give compound 119E (2.3 g, 15% for two steps).

¹H NMR (400 MHz, CDCl₃): δ 7.34 (d, J=8.0 Hz, 1H), 6.99 (d, J=8.4 Hz, 1H), 4.27-4.24 (m, 1H), 2.30-2.27 (m, 1H), 2.17 (s, 2H), 2.01 (t, J=5.2 Hz, 1H), 1.89-1.81 (m, 2H), 1.57 (s, 9H), 1.53 (s, 9H), 1.37 (s, 3H), 1.27 (s, 3H), 1.17 (d, J=10.8 Hz, 1H), 0.84 (s, 3H).

Step 5: Synthesis of Compound 119F

To a 3-neck round-bottom flask, purged and maintained in inert atmosphere of nitrogen, was placed a solution of dichloromethane (927 mg, 10.9 mmol) in anhydrous THF (50 mL). The solution was cooled to −100° C. and n-BuLi (2.5 M, 3.1 mL, 7.85 mmol) was added slowly along the flask wall over 10 minutes. After stirring for 20 minutes, compound 119E (2.3 g, 4.36 mmol) in anhydrous THF (30 mL) was added dropwise over 10 minutes. The resulting mixture was warmed slowly to rt and stirred at that temperature for overnight. The mixture was evaporated to dryness and the residue was dissolved in ethyl acetate, washed with water brine and dried in vacuo to give crude compound 119F (2.7 g, 100%).

¹H NMR (400 MHz, CDCl₃): δ 7.41 (d, J=8.4 Hz, 1H), 7.03 (d, J=8.4 Hz, 1H), 4.37 (d, J=8.4 Hz, 1H), 3.65 (t, J=8.4 Hz, 1H), 3.18-3.12 (m, 1H), 2.97-2.91 (m, 1H), 2.34-2.31 (m, 1H), 2.21-2.17 (m, 1H), 2.08-2.04 (m, 1H), 1.91-1.85 (m, 2H), 1.57 (s, 9H), 1.53 (s, 9H), 1.41 (s, 3H), 1.31 (s, 3H), 1.29-1.22 (m, 3H), 1.08 (d, 1H), 0.85 (s, 3H).

Step 6: Synthesis of Compound 119G

To a solution of compound 119F (2.5 g, 4.34 mmol) in dichloromethane (30 mL) were added compound 5-amino-1,3,4-thiadiazole-2-thiol (751 mg, 5.64 mmol) and TEA (878 mg, 8.7 mmol). The resulting mixture was stirred at rt for 2 h. Then the mixture was quenched with water, separated and the aqueous layer was extracted with dichloromethane. The combined organic layer was washed with brine, dried over sodium sulfate, concentrated under reduced pressure to provide compound 119G (1.9 g, 65%).

¹H NMR (400 MHz, CDCl₃): δ 7.35 (d, J=8.4 Hz, 1H), 7.02 (d, J=8.0 Hz, 1H), 5.23 (br. s, 2H), 4.32 (d, J=7.6 Hz, 1H), 3.26-3.22 (m, 2H), 2.90-2.82 (m, 1H), 2.40-2.31 (m, 1H), 2.30-2.04 (m, 1H), 1.99-1.97 (m, 1H), 1.86-1.84 (m, 2H), 1.57 (s, 9H), 1.52 (s, 9H), 1.46 (s, 3H), 1.43 (d, J=10.4 Hz, 1H), 1.25 (s, 3H), 0.85 (s, 3H).

Step 7: Synthesis of Compound 119H

To a mixture of compound 119G (1.9 g, 2.83 mmol), Boc₂O (740 mg, 3.4 mmol), DMAP (35 mg, 0.283 mmol) and TEA (572 mg, 5.66 mmol) in dichloromethane (20 mL) was stirred at rt for 1 h. The mixture was concentrated and the residue was purified by column chromatography (PE/EA=10:1 to 3:1) to give compound 119H (1.9 g, 87%).

Step 8: Synthesis of Compound 119I

To a mixture of compound 119H (200 mg, 0.26 mmol), ethynyltrimethylsilane (51 mg, 0.52 mmol), CuI (49 mg, 0.26 mmol) in 1,4-dioxane (4 mL) was stirred at 80° C. overnight in a seal tube under nitrogen. The mixture was filtered and the filtrate was concentrated under reduced pressure to afford crude 119I (250 mg) which was used directly to next step without purification.

Step 9: Synthesis of Compound 119J

To a solution of compound 119I (250 mg, 0.26 mmol) in THF (2 mL) was added TBAF (1.0 M in THF, 1.04 mL, 1.04 mmol). The mixture was stirred at 35° C. overnight. The mixture was concentrated under reduced pressure and the residue was dissolved in ethyl acetate. Then the solution was washed with water, dried and evaporated to give crude 119J (300 mg).

Step 10: Synthesis of Compound 119

To a solution of compound 119J (300 mg, 0.26 mmol, 1.0 eq) in 90% TFA/TES (v/v, 5 mL/1 mL) was stirred at 30° C. for 1 h. The mixture was concentrated and the residue was purified by prep-HPLC to give 119 (14 mg).

¹H NMR (400 MHz, CD₃OD): δ 8.18 (s, 1H), 7.82 (s, 1H), 7.29 (d, J=7.6 Hz, 1H), 6.97 (d, J=7.6 Hz, 1H), 3.62-3.59 (m, 1H), 3.28-3.25 (m, 1H), 3.07-3.02 (m, 1H).

MS calcd for (C₁₃H₁₁BN₆O₄S₂): 390.
MS (ESI, positive) found: (M+1): 391.
MS (ESI, negative) found: (M−1): 389.

Example 120: (3R)-3-[(5-amino-1,3,4-thiadiazol-2-yl)sulfanyl]-2-hydroxy-7-(methanesulfonamido)-3,4-dihydro-1,2-benzoxaborinine-8-carboxylic acid (120)

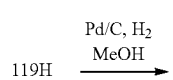

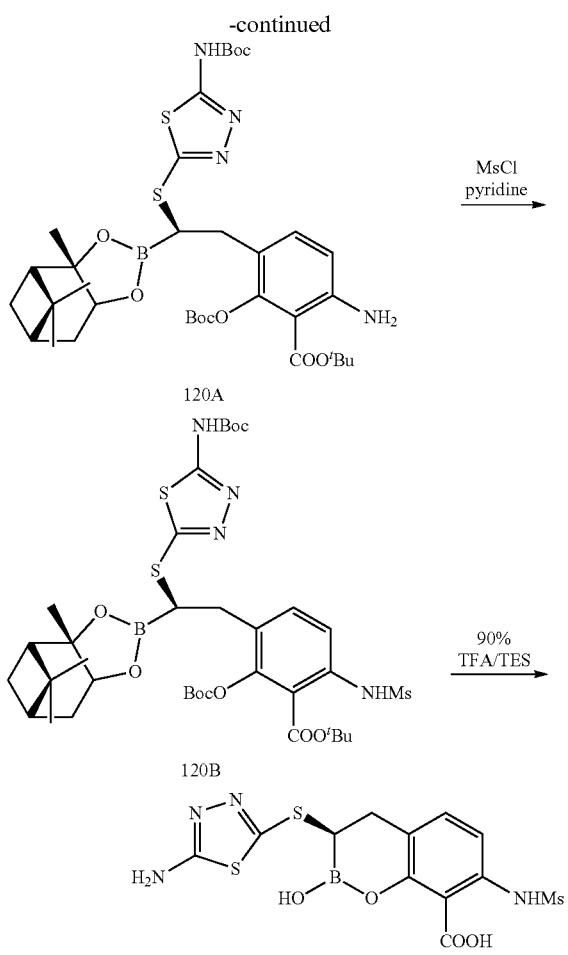

Step 1: Synthesis of Compound 120A

A solution of compound 119H (500 mg, 0.65 mmol) in methanol (5 mL) was added 10% Pd/C (25 mg). The reaction mixture was stirred at rt overnight under hydrogen atmosphere. The catalyst was filtered off and the filtrate was concentrated under reduced pressure. The residue was purified by column chromatography to give compound 120A (317 mg, 66%).

Step 2: Synthesis of Compound 120B

To a solution of compound 120A (150 mg, 0.2 mmol) in pyridine (3 mL) was added MsCl (691 mg, 6.03 mmol). The reaction mixture was stirred at rt overnight. The mixture was concentrated and the residue was purified by prep-HPLC to give compound 120B (10 mg, 6%).

Step 3: Synthesis of Compound 120

To a solution of compound 120B (225 mg, 0.27 mmol, 1.0 eq) in 90% TEA/TES (10 mL) was stirred at rt for 2 h. The mixture was concentrated and the residue was purified by pre-HPLC to give 120 (10 mg, 9%).

¹H NMR (400 MHz, CD₃OD): δ 7.31 (d, J=8 Hz, 1H), 7.22 (d, J=8 Hz, 1H), 3.67-3.66 (m, 1H), 3.31-3.17 (m, 1H), 3.03 (s, 3H), 2.99-2.95 (m, 1H).

MS calcd for ($C_{12}H_{13}BN_4O_6S_3$): 416.

MS (ESI, positive) found: (M+1): 417.

MS (ESI, negative) found: (M−1): 415.

General Procedure (A) for Prodrug Formation:

To a solution of sodium salt of 62 (10 mmol) (prepared by treating 62 in MeCN-water with 1N NaOH to pH7.6-8 and lyophilization) in anhydrous DMF (50 mL) was added prodrug precursor (20 mmol, 2 eq) followed by 0.2 eq of potassium carbonate. The mixture was stirred at 50° C. for overnight. The reaction was cooled to room temperature and DMF was concentrated under reduced pressure. The resulting mixture was diluted with 300 mL EtOAc and washed with 0.2 N HCl, water, dried and concentrated. Prep-HPLC (C18, acetonitrile and water as mobile phases, 0.1% formic acid) of crude product and lyophilization provided pure prodrug as a white solid.

General Procedure (B) for Prodrug Formation:

To the solution of Compound 62 (1 mmol) in DMF (5 mL) was added prodrug precursor (2 mmol), followed by K₂CO₃ (1.5 mmol). The resulting mixture was stirred at 50° C. for 18 h. The reaction was cooled to room temperature and DMF was concentrated under reduced pressure. The resulting mixture was diluted with EtOAc and washed with 0.2 N HCl, water, dried and concentrated. Purification of the residue by prep-HPLC (C18, acetonitrile and water as mobile phases, 0.1% formic acid) and lyophilization gave prodrug as white solid.

Example 121: 2-methylpropanoyloxymethyl (3R)-2-hydroxy-7-methoxy-3-(1,3,4-thiadiazol-2-ylsulfanyl)-3,4-dihydro-1,2-benzoxaborinine-8-carboxylate (121)

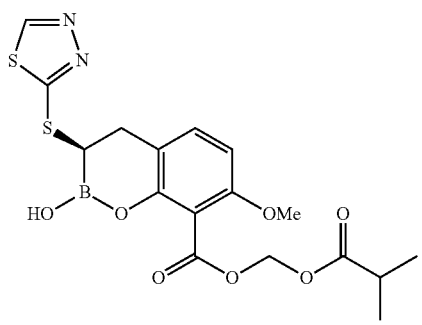

Compound 121 was prepared following procedure A for prodrug formation and using chloromethyl isobutyrate as the prodrug precursor.

¹H NMR (300 MHz, CD₃OD): δ 9.20 (s, 1H), 7.04 (d, J=9 Hz, 1H), 6.42 (d, J=8.4 Hz, 1H), 5.89 (d, J=6.3 Hz, 1H), 5.81 (d, J=5.7 Hz, 1H), 3.74-3.69 (m, 4H), 3.15 (dd, J=15.3, 5.1 Hz, 1H), 2.89 (dd, J=15.6, 2.7 Hz, 1H), 2.69-2.60 (m, 1H), 1.19 (d, J=6.9 Hz, 6H).

MS calcd for ($C_1H_{19}BN_2O_7S_2$): 438.

MS (ESI, negative) found: (M−1): 437.

Example 122: isopropoxycarbonyloxymethyl (3R)-2-hydroxy-7-methoxy-3-(1,3,4-thiadiazol-2-ylsulfanyl)-3,4-dihydro-1,2-benzoxaborinine-8-carboxylate (122)

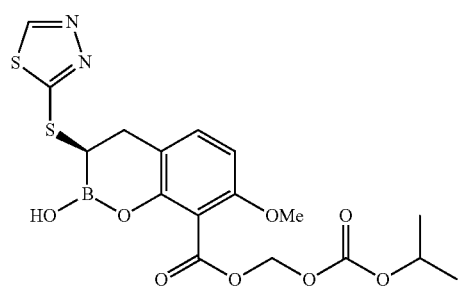

Compound 122 was prepared following procedure A for prodrug formation and using chloromethyl isopropyl carbonate as the prodrug precursor.

¹H NMR (300 MHz, CD₃OD): δ 9.21 (s, 1H), 7.04 (d, J=8.1 Hz, 1H), 6.42 (d, J=8.4 Hz, 1H), 5.87 (d, J=5.7 Hz, 1H), 5.81 (d, J=5.7 Hz, 1H), 3.71-3.70 (m, 4H), 3.35-3.30 (m, 1H), 3.15 (dd, J=14.7, 4.8 Hz, 1H), 2.89 (dd, J=15.6, 2.7 Hz, 1H), 1.32 (d, J=6.3 Hz, 6H).

MS calcd for ($C_1H_{19}BN_2O_8S_2$): 454.

MS (ESI, negative) found: (M−1): 453.

Example 123: acetoxymethyl (3R)-2-hydroxy-7-methoxy-3-(1,3,4-thiadiazol-2-ylsulfanyl)-3,4-dihydro-1,2-benzoxaborinine-8-carboxylate (123)

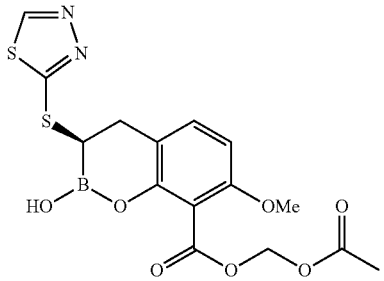

Compound 123 was prepared following procedure B for prodrug formation and using chloromethyl acetate as the prodrug precursor.

¹H NMR (300 MHz, CD₃OD): δ 9.20 (s, 1H), 7.04 (d, J=8.1 Hz, 1H), 6.42 (d, J=8.1 Hz, 1H), 5.87 (d, J=5.7 Hz, 1H), 5.81 (d, J=6 Hz, 1H), 3.72-3.71 (m, 4H), 3.15 (dd, J=15.9, 4.5 Hz, 1H), 2.89 (dd, J=15.6, 2.7 Hz, 1H), 2.14 (t, 3H).

MS calcd for ($C_{15}H_{15}BN_2O_7S_2$): 410.

MS (ESI, negative) found: (M−1): 409.

Example 124: ethoxycarbonyloxymethyl (3R)-2-hydroxy-7-methoxy-3-(1,3,4-thiadiazol-2-ylsulfanyl)-3,4-dihydro-1,2-benzoxaborinine-8-carboxylate (124)

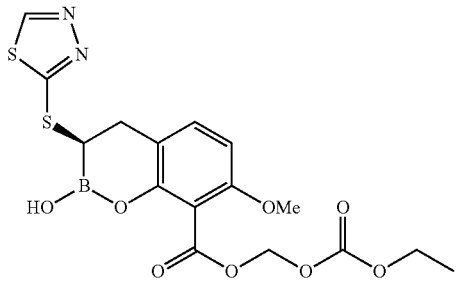

Compound 124 was prepared following procedure B for prodrug formation and using chloromethyl ethyl carbonate as the prodrug precursor.

$^1$H NMR (300 MHz, CD$_3$OD): δ 9.20 (s, 1H), 7.04 (d, J=8.4 Hz, 1H), 6.42 (d, J=8.7 Hz, 1H), 5.87 (q, J=5.7 Hz, 2H), 4.25 (q, J=7.2 Hz, 2H), 3.71-3.70 (m, 4H), 3.15 (dd, J=15, 3.9 Hz, 1H), 2.89 (dd, J=15.6, 2.7 Hz, 1H), 1.31 (t, J=7.2 Hz, 3H).

MS calcd for (C$_{16}$H$_{17}$BN$_2$O$_8$S$_2$): 440.

MS (ESI, negative) found: (M−1): 439.

Example 125: 2,2-dimethylpropanoyloxymethyl (3R)-2-hydroxy-7-methoxy-3-(1,3,4-thiadiazol-2-ylsulfanyl)-3,4-dihydro-1,2-benzoxaborinine-8-carboxylate (125)

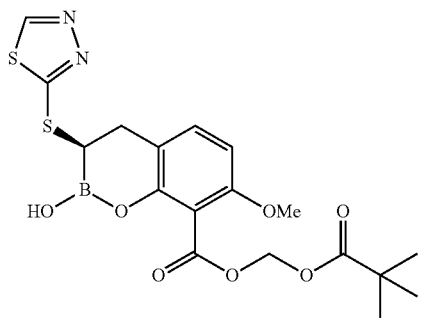

Compound 125 was prepared following procedure B for prodrug formation and using chloromethyl pivalate as the prodrug precursor.

$^1$H NMR (300 MHz, CD$_3$OD): δ 9.22 (s, 1H), 7.03 (d, J=8.4 Hz, 1H), 6.42 (d, J=8.1 Hz, 1H), 5.89 (d, J=5.7 Hz, 1H), 5.82 (d, J=5.7 Hz, 1H), 3.69-3.68 (m, 4H), 3.15 (dd, J=15.6, 4.8 Hz, 1H), 2.89 (dd, J=15.6, 2.7 Hz, 1H), 1.23 (s, 9H).

MS calcd for (C$_{18}$H$_{21}$BN$_2$O$_7$S$_2$): 452.

MS (ESI, negative) found: (M−1): 451.

Example 126: butanoyloxymethyl (3R)-2-hydroxy-7-methoxy-3-(1,3,4-thiadiazol-2-ylsulfanyl)-3,4-dihydro-1,2-benzoxaborinine-8-carboxylate (126)

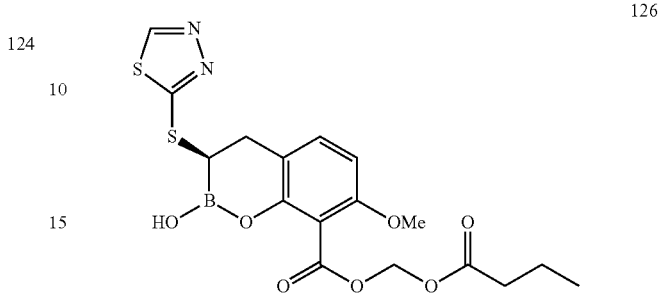

Compound 126 was prepared following procedure A for prodrug formation and using chloromethyl butanoate as the prodrug precursor.

$^1$H NMR (300 MHz, CD$_3$OD): δ 9.20 (s, 1H), 7.03 (d, J=8.4 Hz, 1H), 6.43 (d, J=8.1 Hz, 1H), 5.89 (d, J=5.7 Hz, 1H), 5.82 (d, J=5.7 Hz, 1H), 3.70-3.69 (m, 4H), 3.15 (dd, J=12, 4.8 Hz, 1H), 2.89 (dd, J=15.6, 2.7 Hz, 1H), 2.42 (t, J=7.2 Hz, 2H), 1.69 (m, 2H), 0.97 (t, J=7.5 Hz, 3H).

MS calcd for (C$_1$H$_{19}$BN$_2$O$_7$S$_2$): 438.

MS (ESI, negative) found: (M−1): 437.

Example 127: propanoyloxymethyl (3R)-2-hydroxy-7-methoxy-3-(1,3,4-thiadiazol-2-ylsulfanyl)-3,4-dihydro-1,2-benzoxaborinine-8-carboxylate (127)

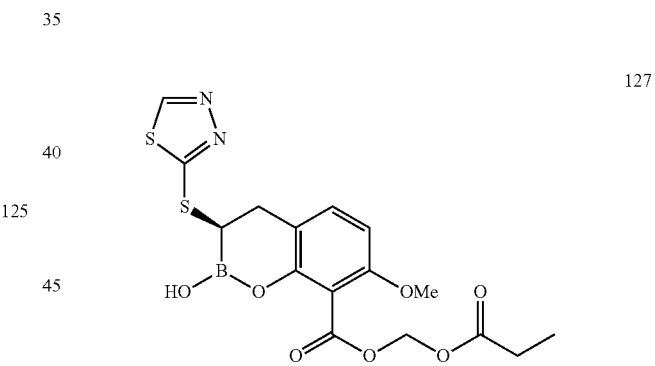

Compound 127 was prepared following procedure B for prodrug formation and using chloromethyl propionate as the prodrug precursor.

$^1$H NMR (300 MHz, CD$_3$OD): δ 9.19 (s, 1H), 7.03 (d, J=8.1 Hz, 1H), 6.43 (d, J=9.0 Hz, 1H), 5.89 (d, J=5.7 Hz, 1H), 5.82 (d, J=5.7 Hz, 1H), 3.71-3.70 (m, 4H), 3.15 (dd, J=15.6, 4.5 Hz, 1H), 2.89 (dd, J=15.6, 2.7 Hz, 1H), 2.46 (q, J=7.8 Hz, 2H), 1.55 (t, J=7.2 Hz, 3H).

MS calcd for (C$_{16}$H$_{17}$BN$_2$O$_7$S$_2$): 424.

MS (ESI, negative) found: (M−1): 423.

Example 128. Inhibition of Carbapenemase Activity of NDM-1

$K_i$ values of inhibition of NDM-1 were determined spectrophotometrically, using imipenem as a substrate for all compounds or using three different carbapenems, imipenem, tebipenem and biapenem for NDM-1 preparation was diluted at 1/512, 1/256 and 1/64 ratios (for imipenem, tebipenem and biapenem/meropenem, respectively) and mixed with various concentrations of beta-lactamase inhibitors (BLIs) in reaction buffer (50 mM sodium phosphate pH7.0, 0.1 mg/ml bovine serum albumin) and incubated for 10 min at 37 C. 100 uM of substrate was added and absorbance profiles were recorded at 294 nm every 1 min for 1h at 37 C. $K_i$ values were calculated by method of Waley S G (Biochem J. 1982 Sep. 1; 205(3):631-3). EDTA was used as a positive control. The results of these experiments are presented in Table 1. These experiments demonstrated that several described compounds are potent inhibitors of NDM-1

TABLE 1

Activity of BLIs ($K_i$, μM) to inhibit cleavage of carbapenems by NDM-1

| Compound # | Imipenem | Meropenem | Tebipenem | Biapenem |
|---|---|---|---|---|
| 1 | Y | Y | Z | Y |
| 2 | X | ND | Y | ND |
| 3 | Z | ND | Z | Z |
| 4 | X | ND | X | X |
| 5 | Y | ND | ND | ND |
| 6 | X | ND | ND | ND |
| 7 | Y | ND | ND | ND |
| 8 | Z | ND | ND | ND |
| 9 | Z | ND | ND | ND |
| 10 | Y | ND | ND | ND |
| 11 | Z | ND | ND | ND |
| 12 | Y | ND | ND | ND |
| 13 | Y | ND | ND | ND |
| 14 | X | X | ND | X |
| 15 | Y | Y | ND | Y |
| 16 | X | ND | ND | ND |
| 17 | Y | Y | ND | Y |
| 18 | Y | X | ND | X |
| 19 | X | ND | ND | ND |
| 20 | X | ND | ND | ND |
| 22 | ND | ND | ND | ND |
| 23 | Y | ND | ND | ND |
| 24 | Y | ND | ND | ND |
| 25 | X | ND | ND | ND |
| 26 | X | ND | ND | ND |
| 27 | Y | X | Y | Y |
| 28 | X | ND | ND | ND |
| 29 | Y | ND | ND | ND |
| 30 | Y | X | Y | Y |
| 31 | Z | ND | ND | ND |
| 32 | Y | ND | ND | ND |
| 33 | Z | ND | ND | ND |
| 34 | Y | ND | ND | ND |
| 35 | Y | ND | ND | ND |
| 36 | Y | ND | ND | ND |
| 37 | Y | ND | ND | ND |
| 38 | Z | ND | ND | ND |
| 39 | Z | ND | ND | ND |
| 40 | Z | ND | ND | ND |
| 41 | X | ND | ND | ND |
| 42 | X | ND | ND | ND |
| 43 | X | ND | ND | ND |
| 44 | X | ND | ND | ND |
| 45 | Y | ND | ND | ND |
| 46 | Z | ND | ND | ND |
| 47 | Z | ND | ND | ND |
| 48 | Z | ND | ND | ND |
| 49 | Z | ND | ND | ND |
| 50 | Z | ND | ND | ND |
| 51 | Z | ND | ND | ND |
| 52 | Z | ND | ND | ND |
| 53 | Z | ND | ND | ND |
| 54 | Z | ND | ND | ND |
| 55 | Z | ND | ND | ND |
| 56 | Z | ND | ND | ND |
| 57 | Y | ND | ND | ND |
| 58 | Z | ND | ND | ND |
| 59 | Z | ND | ND | ND |
| 60 | Z | ND | ND | ND |
| 61 | Z | ND | ND | ND |
| 62 | Z | ND | ND | Y |
| 63 | Z | ND | ND | ND |
| 64 | Z | ND | ND | ND |
| 65 | Z | ND | ND | ND |
| 66 | Y | ND | ND | ND |
| 67 | X | ND | ND | ND |
| 68 | Z | ND | ND | ND |
| 69 | Z | ND | ND | ND |
| 70 | Y | ND | ND | ND |
| 71 | Y | ND | ND | ND |
| 72 | Z | ND | ND | ND |
| 73 | Y | ND | ND | ND |
| 74 | Z | ND | ND | ND |
| 75 | Z | ND | ND | ND |
| 76 | Z | ND | ND | ND |
| 79 | Z | ND | ND | ND |
| 80 | Z | ND | ND | ND |
| 81 | Z | ND | ND | ND |
| 82 | X | ND | ND | ND |
| 83 | X | ND | ND | ND |
| 84 | Y | ND | ND | ND |
| 85 | Z | ND | ND | ND |
| 86 | Z | ND | ND | ND |
| 87 | Z | ND | ND | ND |
| 88 | Y | ND | ND | ND |
| 89 | Y | ND | ND | ND |
| 90 | Y | ND | ND | ND |
| 91 | Y | ND | ND | ND |
| 92 | Y | ND | ND | ND |
| 93 | Z | ND | ND | ND |
| 94 | Z | ND | ND | ND |
| 95 | Y | ND | ND | ND |
| 96 | X | ND | ND | ND |
| 97 | X | ND | ND | ND |
| 98 | Y | ND | ND | ND |
| 99 | X | ND | ND | ND |
| 100 | X | ND | ND | ND |
| 101 | X | ND | ND | ND |
| 102 | X | ND | ND | ND |
| 103 | X | ND | ND | ND |
| 104 | X | ND | ND | ND |
| 105 | X | ND | ND | ND |
| 106 | Z | ND | ND | ND |
| 107 | X | ND | ND | ND |
| 108 | Y | ND | ND | ND |
| 109 | X | ND | ND | ND |
| 110 | Z | ND | ND | ND |
| 111 | Z | ND | ND | ND |
| 112 | Y | ND | ND | ND |
| 113 | X | ND | ND | ND |
| 114 | Y | ND | ND | ND |
| 115 | Z | ND | ND | ND |
| 116 | X | ND | ND | ND |
| 117 | X | ND | ND | ND |
| 118 | Z | ND | ND | ND |
| 119 | X | ND | ND | ND |
| 120 | X | ND | ND | ND |
| EDTA | Y | Y | Y | Y |

X = Less than 0.010 μM
Y = 0.010 μM to 0.1 μM
Z = Greater than 0.1 μM
ND = Not determined Example 129. Inhibition of Activity of VIM-1

$IC_{50}$ values of inhibition of VIM-1 were determined spectrophotometrically using nitrocefin (NCF) as reporter substrate. ECM6711 strain carrying pUCP24-VIM-1 plasmid was grown at 37 C to reach OD600=0.6-0.8. Cell suspension was centrifuged for 10 min at 4000g, supernatant was collected, diluted at 1/64 ratio, mixed with various concentrations of BLIs in reaction buffer and incubated for 10 min at 37 C. 200 uM NCF was added and absorbance profiles were recorded at 490 nm every 30 seconds for 30 min at 37 C. $IC_{50}$ values were calculated as a concentration of BLIs that reduces the rate of NCF degradation by VIM-1 supernatant by 50%. EDTA was used as a positive control. The results of these experiments are presented in Table 2. These experiments demonstrated that several described compounds are potent inhibitors of VIM-1.

TABLE 2

Activity of BLIs (IC50, μM) to inhibit cleavage of Nitrocefin by VIM-1

| Compound | $IC_{50}$, NCF, μM |
|---|---|
| 1 | X |
| 2 | X |
| 3 | Y |
| 4 | X |
| 5 | Y |
| 6 | X |
| 7 | X |
| 8 | X |
| 9 | X |
| 10 | Y |
| 11 | Y |
| 12 | X |
| 13 | X |
| 14 | X |
| 15 | X |
| 16 | X |
| 17 | X |
| 18 | Y |
| 19 | X |
| 20 | Y |
| 23 | Y |
| 24 | Y |
| 25 | X |
| 26 | X |
| 27 | X |
| 28 | X |
| 29 | X |
| 30 | X |
| 31 | Y |
| 32 | Y |
| 33 | Y |
| 34 | X |
| 35 | X |
| 36 | Y |
| 37 | Y |
| 38 | Y |
| 39 | X |
| 40 | Y |
| 41 | X |
| 42 | X |
| 43 | X |
| 44 | X |
| 45 | Y |
| 46 | Y |
| 47 | X |
| 48 | Y |
| 49 | Y |
| 50 | X |
| 51 | Y |
| 52 | X |
| 53 | X |
| 54 | X |
| 55 | Y |
| 56 | Y |
| 57 | X |
| 58 | X |
| 59 | X |
| 60 | X |
| 61 | X |
| 62 | X |
| 63 | X |
| 64 | X |
| 65 | Y |
| 66 | X |
| 67 | X |
| 68 | X |
| 69 | X |
| 70 | X |
| 71 | X |
| 72 | X |
| 73 | X |
| 74 | X |
| 75 | X |
| 76 | Y |
| 79 | Y |
| 80 | X |
| 81 | Y |
| 82 | X |
| 83 | X |
| 84 | X |
| 85 | X |
| 86 | X |
| 87 | X |
| 88 | X |
| 89 | X |
| 90 | X |
| 91 | X |
| 92 | X |
| 93 | X |
| 94 | X |
| 95 | X |
| 96 | X |
| 97 | X |
| 98 | X |
| 99 | X |
| 100 | X |
| 101 | X |
| 102 | X |
| 103 | X |
| 104 | X |
| 105 | X |
| 106 | X |
| 107 | X |
| 108 | X |
| 109 | X |
| 110 | X |
| 111 | X |
| 112 | X |
| 113 | X |
| 114 | X |
| 115 | X |
| 116 | X |
| 117 | X |
| 118 | X |
| 119 | X |
| 120 | X |
| EDTA | X |

X = $IC_{50}$ of less than 1.0 μM
Y = $IC_{50}$ of 1.0 μM and above

Example 130: Inhibition of Carbapenemase Activity of Class A, B and D Carbapenemases $K_i$ values of inhibition of purified class A (KPC-2), B (NDM-1) and D (OXA-48) carbapenemases were determined spectrophotometrically using either imipenem (for NDM-1) or biapenem (for KPC-2 and OXA-48) as substrates. Purified enzymes (6 nM and 145 nM for KPC-2 and OXA-48, respectively, 1/512 of NDM-1 enzyme preparation) were mixed with various concentrations of inhibitors in reaction buffer and incubated for 10 min at room temperature. 100 μM of substrate was added and absorbance profiles were recorded at 294 nm every 1 min for 1 hour at 37 C. $K_i$ values were calculated by method of Waley S G (Biochem J. 1982 Sep. 1; 205(3):631-3). The results of these experiments are presented in Table 3. These experiments demonstrated that the described compounds are inhibitors with activity towards carbapenemases from various classes.

TABLE 3

Activity of BLIs (Ki, μM) to inhibit cleavage of carbapenems by purified class A, B and D carbapenemases

| Compound | $K_i$ KPC-2, Biapenem (μM) | $K_i$ OXA-48, Biapenem (μM) | $K_i$ NDM-1, Imipenem (μM) |
|---|---|---|---|
| 1 | Y | Y | Y |
| 2 | Y | Y | X |
| 3 | Y | X | Z |
| 4 | Y | X | X |
| 5 | ND | ND | Y |
| 6 | Y | X | X |
| 7 | ND | X | Y |
| 8 | ND | X | Z |
| 9 | ND | Y | Z |
| 10 | ND | ND | Y |
| 11 | ND | ND | Z |
| 12 | ND | ND | Y |
| 13 | ND | ND | Y |
| 14 | ND | ND | Y |
| 15 | Y | X | X |
| 16 | Y | X | Z |
| 17 | ND | ND | Y |
| 18 | ND | X | Y |
| 19 | ND | ND | Z |
| 20 | ND | ND | X |
| 23 | ND | ND | Y |
| 24 | ND | ND | Y |
| 25 | ND | ND | X |
| 26 | ND | ND | X |
| 27 | Y | Y | Y |
| 28 | ND | ND | X |
| 29 | ND | ND | Y |
| 30 | Y | Y | Y |
| 31 | ND | ND | Z |
| 32 | ND | ND | Y |
| 33 | ND | ND | Y |
| 34 | ND | ND | Y |
| 35 | ND | ND | Y |
| 36 | ND | ND | Y |
| 37 | ND | ND | Y |
| 38 | ND | ND | Z |
| 39 | ND | ND | Z |
| 40 | ND | ND | Z |
| 41 | ND | ND | X |
| 42 | ND | ND | X |
| 43 | ND | ND | X |
| 44 | ND | ND | X |
| 45 | ND | ND | Y |
| 46 | ND | ND | Z |
| 47 | ND | ND | Y |
| 48 | ND | ND | Z |
| 49 | ND | ND | Z |
| 50 | ND | ND | Z |
| 51 | ND | ND | Z |
| 52 | ND | ND | Z |
| 53 | ND | ND | Z |
| 54 | ND | ND | Z |
| 55 | ND | ND | Z |
| 56 | ND | ND | Z |
| 57 | ND | ND | Y |
| 58 | ND | ND | Z |
| 59 | ND | ND | Z |
| 60 | ND | ND | Z |
| 61 | ND | ND | Z |
| 62 | 0.0039 | 0.0056 | Z |
| 63 | ND | ND | Z |
| 64 | ND | ND | Z |
| 65 | ND | ND | Z |
| 66 | ND | ND | Y |
| 67 | ND | ND | X |
| 68 | ND | ND | Z |
| 69 | ND | ND | Z |
| 70 | ND | ND | Y |
| 71 | ND | ND | Y |
| 72 | ND | ND | Z |
| 73 | ND | ND | Y |
| 74 | ND | ND | Z |
| 75 | ND | ND | Z |
| 76 | ND | ND | Z |
| 79 | ND | ND | Z |
| 80 | ND | ND | Z |
| 81 | ND | ND | Z |
| 82 | ND | ND | X |
| 83 | ND | ND | X |
| 84 | ND | ND | Y |
| 85 | ND | ND | Z |
| 86 | ND | ND | Z |
| 87 | ND | ND | Y |
| 88 | ND | ND | Y |
| 89 | ND | ND | Y |
| 90 | ND | ND | Y |
| 91 | ND | ND | Y |
| 92 | ND | ND | Y |
| 93 | ND | ND | Z |
| 94 | ND | ND | Z |
| 95 | ND | ND | Y |
| 96 | ND | ND | X |
| 97 | ND | ND | X |
| 98 | ND | ND | Y |
| 99 | ND | ND | X |
| 100 | ND | ND | X |
| 101 | ND | ND | X |
| 102 | ND | ND | X |
| 103 | ND | ND | X |
| 104 | ND | ND | X |
| 105 | ND | ND | X |
| 106 | ND | ND | Z |
| 107 | ND | ND | X |
| 108 | ND | ND | Y |
| 109 | ND | ND | X |
| 110 | ND | ND | Z |
| 111 | ND | ND | Z |
| 112 | ND | ND | Y |
| 113 | ND | ND | X |
| 114 | ND | ND | Y |
| 115 | ND | ND | Z |
| 116 | ND | ND | X |
| 117 | ND | ND | X |
| 118 | ND | ND | Z |
| 119 | ND | ND | X |
| 120 | ND | ND | X |

X = Less than 0.01 μM
Y = 0.01 μM to 0.1 μM
Z = Greater than 0.1 μM
ND = Not Determined For several compounds, the Ki of inhibition of multiple carbapenems by KPC-2 (Table 4) and OXA-48 (Table 5) were determined.

TABLE 4

Activity of BLIs ($K_i$, μM) to inhibit cleavage of carbapenems by KPC-2

| Compound | Biapenem | Tebipenem | Meropenem | Doripenem | Imipenem |
|---|---|---|---|---|---|
| 4 | Y | X | X | X | Y |
| 14 | Y | Y | Y | Y | Y |
| 23 | X | X | X | X | Y |
| 27 | X | X | X | X | Y |
| 30 | X | X | X | X | Y |
| 62 | X | ND | X | X | Y |

X = Less than 0.010 μM
Y = 0.010 μM to 0.1 μM
Z = Greater than 0.1 μM
ND = Not Determined

TABLE 5

Activity of BLIs ($K_i$, μM) to inhibit cleavage of carbapenems by OXA-48

| Compound | Biapenem | Tebipenem | Meropenem | Doripenem | Imipenem |
|---|---|---|---|---|---|
| 4 | X | Y | Z | Y | X |
| 14 | Y | Z | Z | ND | Y |
| 23 | X | X | X | X | X |
| 27 | X | X | X | X | X |
| 30 | X | X | X | X | X |
| 62 | X | ND | X | X | X |

X = Less than 0.01 μM
Y = 0.010 μM to 0.1 μM
Z = Greater than 0.1 μM
ND = Not Determined

Example 131: Inhibition of Activity of Various Beta-Lactamases $K_i$ values of inhibition of multiple purified class A, C and D enzymes were determined spectrophotometrically using nitrocefin as reporter substrate. Purified enzymes were mixed with various concentrations of inhibitors in reaction buffer and incubated for 10 min at room temperature. Nitrocefin was added and substrate cleavage profiles were recorded at 490 nm every 10 sec for 10 min. The results of these experiments are presented in Table 6. These experiments confirmed that the described compounds are inhibitors with a broad-spectrum of activity towards various β-lactamases.

TABLE 6

Activity of BLIs ($K_i$, μM) to inhibit cleavage of nitrocefin by purified class A, C and D enzymes

| Compound | Ki (CTX-M-14, NCF), μM | Ki (SHV-12, NCF), μM | Ki (TEM-10, NCF), μM | Ki (KPC-2, NCF), μM | Ki (P99/AmpC of ECL, NCF), μM | Ki (CMY-2, NCF), μM | Ki (OXA-48, NCF), μM |
|---|---|---|---|---|---|---|---|
| 1 | X | X | X | Y | X | X | X |
| 2 | Y | X | Z | Y | Y | Y | X |
| 3 | X | Y | Z | X | X | X | X |
| 4 | X | X | Y | Y | X | X | X |
| 5 | X | X | X | X | X | X | X |
| 6 | X | X | X | X | X | X | X |
| 7 | X | X | Y | Y | X | X | X |
| 8 | X | X | X | X | X | X | X |
| 9 | X | Y | Z | X | X | X | X |
| 10 | X | X | X | Y | X | X | X |
| 11 | Y | X | Y | Y | X | X | X |
| 12 | X | X | X | Y | X | ND | X |
| 13 | X | X | X | X | X | ND | X |
| 14 | X | X | Y | Y | X | ND | X |
| 15 | X | X | Y | Y | X | X | X |
| 16 | X | Y | Y | X | X | ND | X |
| 17 | X | X | X | X | X | ND | X |
| 18 | Y | X | Y | Y | Y | ND | X |
| 19 | X | X | X | X | X | ND | X |
| 20 | X | X | X | Y | Y | ND | Y |
| 22 | X | X | X | X | X | X | X |
| 23 | X | X | X | X | X | ND | X |
| 24 | X | X | X | Y | Y | ND | X |
| 25 | X | X | X | Y | Y | ND | X |
| 26 | X | X | X | Y | Y | ND | X |
| 27 | X | X | X | X | Y | ND | X |
| 28 | X | X | X | Y | Y | ND | X |
| 29 | X | X | Y | Y | Y | ND | X |
| 30 | X | X | X | X | X | ND | X |
| 31 | X | X | X | Y | Y | ND | X |
| 32 | X | X | Y | X | X | ND | X |
| 33 | X | X | Y | Y | X | ND | X |
| 34 | X | X | X | Y | X | ND | X |
| 35 | X | X | X | X | Y | ND | X |

TABLE 6-continued

Activity of BLIs (Ki, μM) to inhibit cleavage of nitrocefin by purified class A, C and D enzymes

| Compound | Ki (CTX-M-14, NCF), μM | Ki (SHV-12, NCF), μM | Ki (TEM-10, NCF), μM | Ki (KPC-2, NCF), μM | Ki (P99/AmpC of ECL, NCF), μM | Ki (CMY-2, NCF), μM | Ki (OXA-48, NCF), μM |
|---|---|---|---|---|---|---|---|
| 36 | X | X | X | X | Z | ND | X |
| 37 | X | X | X | X | Z | ND | X |
| 38 | X | X | Y | Z | Y | ND | X |
| 39 | X | X | X | X | Y | ND | X |
| 40 | X | X | X | X | X | ND | X |
| 41 | X | X | X | X | X | ND | X |
| 42 | X | X | X | Y | Y | ND | X |
| 43 | X | X | X | X | X | ND | X |
| 44 | X | X | X | X | X | ND | X |
| 45 | X | X | X | Y | Z | ND | X |
| 46 | X | X | X | Y | Z | ND | X |
| 47 | X | X | X | Y | Y | ND | X |
| 48 | X | X | Y | Y | Z | ND | X |
| 49 | X | X | X | X | Y | ND | X |
| 50 | X | X | X | X | X | ND | X |
| 51 | X | X | X | X | Z | ND | X |
| 52 | X | X | X | X | Y | ND | X |
| 53 | X | X | X | X | Y | ND | X |
| 54 | X | X | X | X | Y | ND | X |
| 55 | Y | Y | Y | Y | Y | ND | X |
| 56 | Y | Y | X | Y | Z | ND | X |
| 57 | X | X | Y | Y | Z | ND | X |
| 58 | X | X | X | Y | Y | ND | X |
| 59 | X | X | X | X | Y | ND | X |
| 60 | X | X | X | X | Z | ND | X |
| 61 | X | X | X | X | Y | ND | X |
| 62 | X | X | X | X | Y | ND | X |
| 63 | X | X | X | Y | X | ND | X |
| 64 | X | X | Y | Y | Z | ND | X |
| 65 | X | X | X | X | Z | ND | X |
| 66 | X | X | Y | Y | Z | ND | Y |
| 67 | X | X | X | Y | Y | ND | X |
| 68 | X | X | Y | Y | Y | ND | X |
| 69 | X | X | X | X | Y | ND | X |
| 70 | X | X | X | Y | Y | ND | X |
| 71 | X | X | Y | Y | Z | ND | Y |
| 72 | X | X | X | X | Y | ND | X |
| 73 | X | X | Y | Y | Z | ND | X |
| 74 | X | X | X | X | Y | ND | X |
| 75 | X | X | X | X | Y | ND | X |
| 76 | X | ND | X | Y | Y | ND | X |
| 79 | X | X | Y | Z | Y | ND | X |
| 80 | X | X | X | Y | Y | ND | X |
| 81 | X | X | Y | Z | Y | ND | X |
| 82 | X | X | X | Y | Y | ND | X |
| 83 | X | X | X | Y | Y | ND | X |
| 84 | X | X | Y | Y | Y | ND | X |
| 85 | X | X | X | Y | Y | ND | X |
| 86 | X | X | Y | Y | Z | ND | X |
| 87 | X | X | Y | Y | Y | ND | X |
| 88 | X | X | Y | Y | Y | ND | X |
| 89 | X | X | Y | Y | Z | ND | X |
| 90 | X | X | Y | X | Z | ND | X |
| 91 | X | X | Y | Y | Y | ND | X |
| 92 | X | ND | Y | Y | Y | ND | X |
| 93 | X | ND | Y | Y | Y | ND | X |
| 94 | X | ND | Y | Y | Z | ND | X |
| 95 | X | ND | X | Y | Y | ND | X |
| 96 | X | X | X | Y | Y | ND | X |
| 97 | X | X | X | Y | Y | ND | X |
| 98 | X | X | X | Y | Y | ND | X |
| 99 | X | X | Y | Y | X | ND | X |
| 100 | X | X | Y | Y | X | ND | X |
| 101 | X | X | Y | Y | Z | ND | X |
| 102 | X | X | Z | Z | Z | ND | Y |
| 103 | X | X | X | Y | Y | ND | X |
| 104 | X | X | X | X | Y | ND | X |
| 105 | X | X | X | Y | Y | ND | X |
| 106 | X | ND | X | Y | X | ND | X |
| 107 | X | X | Y | Y | Y | ND | X |
| 108 | X | X | Y | Y | Y | ND | X |
| 109 | X | X | Y | Y | Y | ND | X |
| 110 | X | X | X | X | Y | ND | X |

TABLE 6-continued

Activity of BLIs (Ki, µM) to inhibit cleavage of nitrocefin by purified class A, C and D enzymes

| Compound | Ki (CTX-M-14, NCF), µM | Ki (SHV-12, NCF), µM | Ki (TEM-10, NCF), µM | Ki (KPC-2, NCF), µM | Ki (P99/AmpC of ECL, NCF), µM | Ki (CMY-2, NCF), µM | Ki (OXA-48, NCF), µM |
|---|---|---|---|---|---|---|---|
| 111 | X | X | X | Y | Y | ND | Z |
| 112 | X | X | X | X | X | ND | X |
| 113 | X | X | X | X | X | ND | X |
| 114 | X | X | X | Y | Y | ND | X |
| 115 | X | X | X | Y | X | ND | X |
| 116 | X | X | X | X | X | ND | X |
| 117 | X | X | X | Y | Y | ND | X |
| 118 | X | X | Y | Y | Y | ND | X |
| 119 | X | Y | Y | Z | Y | ND | X |
| 120 | X | ND | X | Y | X | ND | X |
| Tazobactam | X | X | X | Z | Z | Y | Y |
| Clavulanic acid | X | X | X | Z | Z | Z | Z |

X = Less than 0.1 µM
Y = 0.1 µM to 1 µM
Z = Greater than 1 µM
ND = Not Determined

Example 132: Potentiation of Imipenem by Compound 1 Against E. coli Strains Expressing Cloned NDM-1 and VIM-1

Carbapenem popentiation activity of Compound 1 was first assessed as its ability to decrease MIC of imipenem of engineered strains of *E. coli* containing plasmids carrying either NDM-1 or VIM-1 genes. Both NDM-1 and VIM-1 expressing strains had increased MIC for imipenem as compared to the strain that contained the vector plasmid alone (Table 7). In the presence of Compound 1 at fixed 4 µg/ml or 8 µg/ml, imipenem MIC of NDM-1 and VIM-1 producing strains was decreased to the level of the strain containing empty vector (Table 7).

TABLE 7

Imipenem Potentiation Activity of Compound 1 against the Strains of *E. coli* Expressing Cloned NDM-1 or VIM-1 Metallo-Beta-lactamases

| Strain | Plasmid | Imipenem MIC (µg/ml) Alone | w/1 at 4 µg/ml |
|---|---|---|---|
| ECM6704 | pUCP24 | X | X |
| ECM6703 | pUCP24-NDM-1 | Y | X |
| ECM6711 | pUCP24-VIM-1 | Y | X |

X = MIC of less than 1.0 µg/mL
Y = MIC of 1.0 µ/mL or above

Example 133: Potentiation of Carbapenems by Compound 1 Against Clinical Isolates Strains Expressing Various Class A, B and D Carbapenemases The panel of clinical isolates expressing class A, B and D carbapenemases alone or in combination with other beta-lactamases was used to evaluate carbapenem potentiation activity of Compound 1. MIC for biapenem, doripenem, imipenem and meropenem of these strains was determined either alone or in the presence of Compound 1 at fixed 5 µg/ml in the growth media. The results are present in Table 8. Compound 1 significantly reduced carbapenem MIC of all the strains expressing various carbapenemases.

TABLE 8

Carbapenem Potentiation Activity of Compound 1 against Clinical Isolates Expressing Class A, B and D Carbapenemases

| Strain | Organism | Beta-Lactamases | Biapenem Alone | Biapenem w/1 at 5 µg/ml | Doripenem Alone | Doripenem w/1 at 5 µg/ml | Imipenem Alone | Imipenem w/1 at 5 µg/ml | Meropenem Alone | Meropenem w/1 at 5 µg/ml |
|---|---|---|---|---|---|---|---|---|---|---|
| EC1064 | *Escherichia coli* | NDM-1, CMY-6, CTX-M-15 | Z | X | Z | Y | Z | Y | Z | Z |
| KP1081 | *Klebsiella pneumoniae* | NDM-1, TEM-1, SHV-11, CMY-6, CTX-M-15 | Z | X | Z | Y | Z | Y | Z | Y |

TABLE 8-continued

Carbapenem Potentiation Activity of Compound 1 against Clinical Isolates Expressing Class A, B and D Carbapenemases

| Strain | Organism | Beta-Lactamases | Biapenem | | Doripenem | | Imipenem | | Meropenem | |
|---|---|---|---|---|---|---|---|---|---|---|
| | | | Alone | w/1 at 5 μg/ml | Alone | w/1 at 5 μg/ml | Alone | w/1 at 5 μg/ml | Alone | w/1 at 5 μg/ml |
| AB1144 | *Acinetobacter baumannii* | NDM-1 | Y | X | Z | Y | Z | Z | Z | Y |
| EA1019 | *Enterobacter aerogenes* | SHV-5, VIM-1 | Z | X | Z | Y | Z | Y | Z | X |
| KP1014 | *Klebsiella pneumoniae* | VIM-1 | Z | Y | Z | Y | Z | Y | Y | X |
| KP1054 | *Klebsiella pneumoniae* | VIM-1, SHV-11 | Z | X | Z | X | Y | Y | Z | X |
| KP1064 | *Klebsiella pneumoniae* | KPC-2, SHV-11, TEM-1 | Z | X | Z | Y | Z | Y | Z | Z |
| KP1074 | *Klebsiella pneumoniae* | KPC-3, SHV-11, TEM | Z | Y | Z | Y | Z | Y | Z | Y |
| KP1084 | *Klebsiella pneumoniae* | KPC-3, SHV-11, TEM-1 | Z | Y | Z | Y | Z | Y | Z | Y |
| KP1004 | *Klebsiella pneumoniae* | KPC-2, TEM-1, SHV-11 | Y | X | Y | X | Z | X | Y | X |
| KP1087 | *Klebsiella pneumoniae* | KPC-2, CTX-M-15, SHV-11, TEM-1 | Z | X | Z | Y | Y | X | Z | Y |
| KP1086 | *Klebsiella pneumoniae* | TEM, SHV, CTX-M-15, OXA-48 | Z | X | Z | Y | Z | Y | Z | Y |

X = MIC of less than 1 μg/mL
Y = MIC of 1 μg/mL to 10 μg/mL
Z = MIC of greater than 10 μg/mL Example 134: Potentiation of Biapenem Against Clinical Isolates Strains Expressing Various Class A, B and D Carbapenemases The same panel of clinical strains was used to evaluate biapenem potentiation activity of two other compounds, Compound 3 and Compound 4. The results are present in Table 9. The results indicate that several compounds are capable to potentiate biapenem against clinical strains expressing various carbapenemases.

TABLE 9

Biapenem Potentiation Activity of several BLIs against Clinical Isolates Expressing Class A, B and D Carbapenemases

| Strain | Organism | Beta-Lactamases | Biapenem MIC (μg/ml) | | | |
|---|---|---|---|---|---|---|
| | | | Alone | w/1 at 5 μg/ml | w/4 at 5 μg/ml | w/3 at 5 μg/ml |
| EC1064 | *Escherichia coli* | NDM-1, CMY-6, CTX-M-15 | Z | X | X | X |
| KP1081 | *Klebsiella pneumoniae* | NDM-1, TEM-1, SHV-11, CMY-6, CTX-M-15 | Z | X | X | X |

TABLE 9-continued

Biapenem Potentiation Activity of several BLIs against Clinical Isolates Expressing Class A, B and D Carbapenemases

| Strain | Organism | Beta-Lactamases | Biapenem MIC (μg/ml) | | | |
|---|---|---|---|---|---|---|
| | | | Alone | w/1 at 5 μg/ml | w/4 at 5 μg/ml | w/3 at 5 μg/ml |
| AB1144 | *Acinetobacter baumannii* | NDM-1 | Z | X | X | Y |
| EA1019 | *Enterobacter aerogenes* | SHV-5, VIM-1 | Z | X | X | Y |
| KP1014 | *Klebsiella pneumoniae* | VIM-1 | Z | Y | Y | Y |
| KP1059 | *Klebsiella pneumoniae* | VIM-1, SHV-11 | Z | Y | Y | Y |
| KP1054 | *Klebsiella pneumoniae* | VIM-1, SHV-11 | Z | X | X | X |
| KP1064 | *Klebsiella pneumoniae* | KPC-2, SHV-11, TEM-1 | Z | X | Y | X |
| KP1074 | *Klebsiella pneumoniae* | KPC-3, SHV-11, TEM | Z | Y | Y | Y |
| KP1084 | *Klebsiella pneumoniae* | KPC-3, SHV-11, TEM-1 | Z | Y | Y | Y |

TABLE 9-continued

Biapenem Potentiation Activity of several BLIs against Clinical Isolates Expressing Class A, B and D Carbapenemases

| | | | Biapenem MIC (µg/ml) | | | |
|---|---|---|---|---|---|---|
| Strain | Organism | Beta-Lactamases | Alone | w/1 at 5 µg/ml | w/4 at 5 µg/ml | w/3 at 5 µg/ml |
| KP1004 | Klebsiella pneumoniae | KPC-2, TEM-1, SHV-11 | Z | X | X | X |
| KP1087 | Klebsiella pneumoniae | KPC-2, CTX-M-15, SHV-11, TEM-1 | Z | X | Y | X |
| KP1086 | Klebsiella pneumoniae | TEM, SHV, CTX-M-15, OXA-48 | Z | X | Y | X |

X = MIC of less than 1 µg/mL
Y = MIC of 1 µg/mL to 10 µg/mL
Z = MIC of greater than 10 µg/mL Example 135. Potentiation of Meropenem and Imipenem by Compound 14 Against the Strains of Enterobacteriaceae Overexpressing Various Carbapenemases The larger panel of clinical isolates expressing class A and B carbapenemases alone or in combination with other beta-lactamases was used to evaluate carbapenem potentiation activity of Compound 14. Several strains simultaneously expressing both class A and class B carbapenemases, which were constructed using conjugation, were also included in the panel. MIC for imipenem and meropenem of these strains was determined either alone or in the presence of Compound 14 at a fixed concentration of 4 µg/ml in the growth media. The results are present in Table 10 below. As shown in the table, Compound 14 significantly reduced carbapenem MIC of the strains expressing various carbapenemases, including those strains that expressed class A and class B enzymes simultaneously.

TABLE 10

Meropenem and Imipemen Potentiation Activity of Compound 14 against the strains of Enterobacteriaceaea producing various carbapenemases

| Strain | Organism | Enzymes | Meropenem | Meropenem + 14 | Imipenem | Imipenem + 14 |
|---|---|---|---|---|---|---|
| EA1019 | Enterobacter aerogenes | SHV-5, VIM-1 | Z | X | Z | Y |
| ECL1045 | Enterobacter cloacae | VIM-1 | Y | X | Y | X |
| KP1054 | Klebsiella pneumoniae | VIM-1, SHV-11 | Z | X | Y | X |
| KP1059 | Klebsiella pneumoniae | VIM-1, SHV-11 | Z | Y | Z | Y |
| KP1065 | Klebsiella pneumoniae | VIM-1, SHV-11 | Y | Z | Y | X |
| ECL1057 | Enterobacter cloacae | NDM-1, TEM-1, CTX-M-15 | Z | Z | Z | Y |
| EC1061 | Escherichia coli | NDM-1, CMY-6 | Z | X | Y | X |
| KP1081 | Klebsiella pneumoniae | NDM-1, TEM-1, SHV-11, CMY-6, CTX-M-15 | Z | X | Z | X |
| KP1014 | Klebsiella pneumoniae | Vim-1, TEM, SHV | Z | X | Z | X |
| EC1064 | Escherichia coli | NDM-1, CMY-6, CTX-M-15 | Z | Y | Z | X |
| KPM1344 | Klebsiella pneumoniae | VIM-1 | Z | Y | Z | X |
| KPM1345 | Klebsiella pneumoniae | VIM-1 SHV | Y | X | Y | X |
| KPM1346 | Klebsiella pneumoniae | NDM-1 TEM SHV CTX-M-15 CMY | Z | Z | Z | Y |
| KPM1347 | Klebsiella pneumoniae | NDM-1 SHV CTX-M-15 | Z | X | Z | X |
| EC1065 | Escherichai coli | IMP-1 CMY-2 | Y | X | Y | X |
| KP1097 | Klebsiella pneumoniae | IMP-1 SHV | Z | Y | Y | X |
| KP1098 | Klebsiella pneumoniae | IMP-26 TEM SHV | Z | Z | Y | Y |

TABLE 10-continued

Meropenem and Imipemen Potentiation Activity of Compound 14 against the strains of Enterobacteriaceaea producing various carbapenemases

| Strain | Organism | Enzymes | Meropenem | Meropenem + 14 | Imipenem | Imipenem + 14 |
|---|---|---|---|---|---|---|
| ECL1082 | Enterobacter cloacae | VIM-1 | Y | X | Z | X |
| EC1068 | Escherichia coli | VIM-1 | Z | X | Y | X |
| ECL1026 | Enterobacter cloacae | KPC | Y | X | Y | X |
| ECL1036 | Enterobacter cloacae | KPC | Y | X | Y | X |
| ECL1055 | Enterobacter cloacae | KPC | Y | X | Y | X |
| KPM1123 | Klebsiella pneumoniae | KPC-2 TEM SHV | Z | X | Z | X |
| ECLM1013 | Enterobacter cloacae | NDM, KPC | Z | X | Z | X |
| ECLM1014 | Enterobacter cloacae | NDM, KPC | Z | X | Y | X |
| ECLM1015 | Enterobacter cloacae | NDM, KPC | Z | X | Z | X |
| ECLM1016 | Enterobacter cloacae | NDM, KPC | Z | X | Z | X |
| ECLM1017 | Enterobacter cloacae | VIM, KPC | Z | X | Z | X |
| ECLM1018 | Enterobacter cloacae | VIM, KPC | Z | X | Z | Y |
| ECLM1019 | Enterobacter cloacae | VIM, KPC | Z | X | Z | X |
| KP1004 | Klebsiella pneumoniae | KPC TEM SHV | Z | X | Z | X |
| KP1061 | Klebsiella pneumoniae | KPC TEM SHV | Y | X | Z | X |
| KP1064 | Klebsiella pneumoniae | KPC TEM SHV | Z | Y | Z | X |
| KP1070 | Klebsiella pneumoniae | KPC TEM SHV | Z | X | Z | X |
| KP1084 | Klebsiella pneumoniae | KPC-3, SHV-11, TEM-1 | Z | Y | Z | Y |
| KPM1097 | Klebsiella pneumoniae | NDM, KPC | Z | X | Z | X |
| KPM1099 | Klebsiella pneumoniae | NDM, KPC | Z | Y | Z | Y |
| KPM1107 | Klebsiella pneumoniae | NDM, KPC | Z | X | Z | X |
| KPM1108 | Klebsiella pneumoniae | NDM, KPC | Z | Z | Z | Y |
| KPM1109 | Klebsiella pneumoniae | NDM, KPC | Z | Y | Z | X |
| KPM1110 | Klebsiella pneumoniae | NDM, KPC | Z | X | Z | X |
| KPM1111 | Klebsiella pneumoniae | NDM, KPC | Z | X | Z | X |
| KPM1122 | Klebsiella pneumoniae | NDM, VIM | Z | Y | Z | Y |

X = MIC of less than 1 μg/mL
Y = MIC of 1 μg/mL to 10 μg/mL
Z = MIC of greater than 10 μg/mL Example 136. Potentiation of Meropenem and Imipenem by Compound 27 Against the Strains of Enterobacteriaceae Overexpressing Various Carbapenemases The large panel of clinical isolates expressing class A, D and B carbapenemases alone or in combination with other beta-lactamases (104 strains) was used to evaluate carbapenem potentiation activity of Compound 27. MIC for meropenem, doripenem, ertapenem and cefepime of these strains was determined either alone or in the presence of Compound 27 at a fixed concentration of 4 μg/ml in the growth media. The results are present in Table 11 below. As shown in the table, Compound 27 significantly reduced antibiotics MIC of the strains expressing various carbapenemases.

TABLE 11

Antibiotics Potentiation Activity of Compound 27 against the strains of Enterobacteriaceaea producing various carbapenemases

| Strain | Organism | Enzymes | M | M + 27 | D | D + 27 | E | E + 27 | C | C + 27 |
|---|---|---|---|---|---|---|---|---|---|---|
| CL1080 | *Enterobacter cloacae* | IMP-1 | Y | X | X | X | Y | Y | Z | Y |
| KP1097 | *Klebsiella pneumonias* | IMP-1 | Z | X | Z | X | Z | X | Z | X |
| KP1098 | *Klebsiella pneumoniae* | IMP-26 | Z | Y | Z | Y | Z | Y | Z | Y |
| EC1065 | *Escherichia coli* | IMP-1 | Y | X | Y | X | Y | X | Z | X |
| KP1159 | *Klebsiella pneumoniae* | SHV-1(2b); CTX-M-15; IMP-4; | Z | X | Z | X | Z | Y | Z | X |
| KP1160 | *Klebsiella pneumoniae* | SHV-28(2be); CTX-M-15; IMP-26; | Z | X | Z | X | Z | Y | Z | X |
| KP1173 | *Klebsiella pneumoniae* | TEM-33(2br); CTX-M-15; IMP-1 | Y | X | Y | X | Y | X | Z | X |
| KP1174 | *Klebsiella pneumoniae* | CTX-M-14; IMP-1; | Y | X | Z | X | Z | X | Z | X |
| ECL1089 | *Enterobacter cloacae* | ACT-type; IMP-1; | Z | Y | Z | Y | Z | Z | Z | Z |
| ECL1090 | *Enterobacter cloacae* | TEM-1(2b); CTX-M-22; ACT-type; IMP-8; | Y | X | Y | X | Y | X | Z | Y |
| CF1022 | *Citrobacter freundii* | SHV-12(2be); TEM-OSBL(2b); IMP-8; | Y | X | Y | X | Y | X | Z | X |
| PM1026 | *Proteus mirabilis* | DHA-1; IMP-26; | Z | X | Z | Y | Y | X | Y | X |
| KP1180 | *Klebsiella pneumoniae* | SHV-OSBL(2b); TEM-OSBL(2b); CTX-M-15; DHA-1; IMP-26; | Y | X | Y | X | Y | X | Z | X |
| KP1181 | *Klebsiella pneumoniae* | SHV-OSBL(2b); CTX-M-15; IMP-26; | Y | X | Y | X | Y | X | Z | X |
| KP1184 | *Klebsiella pneumoniae* | SHV-OSBL(2b); IMP-1; | Y | X | Y | X | Y | X | Y | X |
| KP1185 | *Klebsiella pneumoniae* | SHV-OSBL(2b); TEM-OSBL(2b); IMP-4; | Z | Y | Z | X | Z | Y | Z | Y |
| CF1012 | *Citrobacter freundii* | KPC-2 | Y | X | Y | X | Z | X | Z | X |
| ECL1026 | *Enterobacter cloacae* | KPC-2, TEM-1 | Y | X | Y | X | Z | X | Y | X |
| ECL1036 | *Enterobacter cloacae* | KPC-3, TEM-1 | Y | X | Y | X | Y | X | Z | X |
| ECL1055 | *Enterobacter cloacae* | KPC-3, TEM | Y | X | Y | X | Z | X | Z | X |
| KP1061 | *Klebsiella pneumoniae* | KPC-3, SHV-11, TEM-1 | Z | X | Z | X | Z | X | Z | X |
| KP1070 | *Klebsiella pneumoniae* | KPC-2, SHV-11, TEM-1 | Z | X | Y | X | Z | X | Y | X |
| ECL1059 | *Enterobacter cloacae* | KPC-3, SHV-12, TEM-1 | Y | X | Y | X | Y | X | Y | X |
| KX1017 | *Klebsiella oxytoca* | KPC-2, OXA-2, SHV-30 | Y | X | Y | X | Z | X | Z | X |
| KX1018 | *Klebsiella oxytoca* | KPC-2, SHV-40, OXY-1 | Y | X | Y | X | Y | X | Y | X |
| KP1082 | *Klebsiella pneumoniae* | KPC-2, SHV-1 | Y | X | Y | X | Z | X | Z | X |
| KP1083 | *Klebsiella pneumoniae* | KPC-3, SHV-1, TEM-1 | Y | X | Y | X | Z | X | Z | X |
| KP1088 | *Klebsiella pneumoniae* | KPC-3, SHV-11, TEM-1 | Y | X | Y | X | Z | X | Z | X |

TABLE 11-continued

Antibiotics Potentiation Activity of Compound 27 against the strains of Enterobacteriaceaea producing various carbapenemases

| Strain | Organism | Enzymes | M | M + 27 | D | D + 27 | E | E + 27 | C | C + 27 |
|---|---|---|---|---|---|---|---|---|---|---|
| KPM1202 | Klebsiella pneumoniae | KPC SHV TEM | Y | X | Y | X | Z | X | Z | X |
| KPM1203 | Klebsiella pneumoniae | KPC SHV TEM | Y | X | Y | X | Y | X | Y | X |
| KP1095 | Klebsiella pneumoniae | KPC-2 TEM-1 SHV-1 | Y | X | Y | X | Y | X | Y | X |
| KP1096 | Klebsiella pneumoniae | KPC-2 TEM-181 SHV-11 | Y | X | Y | X | Z | X | Y | X |
| KP1104 | Klebsiella pneumoniae | KPC TEM | Z | X | Z | X | Z | X | Z | X |
| KP1105 | Klebsiella pneumoniae | KPC TEM SHV | Z | X | Y | X | Z | X | Z | X |
| KP1002 | Klebsiella pneumoniae | KPC TEM SHV | Y | X | Y | X | Y | X | Y | X |
| KP1003 | Klebsiella pneumoniae | KPC TEM SHV | Y | X | Y | X | Z | X | Z | X |
| EC1007 | Escherichia coli | KPC-3 | X | X | X | X | X | X | Y | X |
| KP1004 | Klebsiella pneumoniae | KPC-2, TEM-1, SHV-11 | Z | X | Y | X | Z | X | Z | X |
| KP1008 | Klebsiella pneumoniae | KPC-2 | Y | X | X | X | Y | X | Y | X |
| KPM1123 | Klebsiella pneumoniae | KPC-2 TEM SHV | Z | X | Y | X | Z | X | Z | X |
| KX1019 | Klebsiella oxytoca | KPC-2, OXA-2 | Y | X | Y | X | Z | X | Z | X |
| ECL1058 | Enterobacter cloacae | KPC-3, SHV-11, TEM-1 | Z | X | Z | X | Z | Y | Z | X |
| ECL1061 | Enterobacter cloacae | KPC-3, Hyper AmpC expression | Z | X | Y | X | Z | Y | Z | Y |
| KP1084 | Klebsiella pneumoniae | KPC-3, SHV-11, TEM-1 | Z | Y | Z | Y | Z | Z | Z | Y |
| KP1087 | Klebsiella pneumoniae | KPC-2, CTX-M-15, SHV-11, TEM-1 | Z | Y | Z | Y | Z | Y | Z | Y |
| KP1001 | Klebsiella pneumoniae | KPC TEM SHV | Z | Y | Z | Y | Z | Z | Z | Y |
| KP1064 | Klebsiella pneumoniae | KPC-2, SHV-11, TEM-1 | Z | Y | Z | Y | Z | Z | Z | Y |
| KP1074 | Klebsiella pneumoniae | KPC-3, SHV-11, TEM | Z | Z | Z | Y | Z | Z | Z | Z |
| EC1061 | Escherichia coli | NDM-1, CMY-6 | Z | X | Z | X | Z | X | Z | X |
| ECL1057 | Enterobacter cloacae | NDM-1, TEM-1, CTX-M-15 | Z | Z | Z | Z | Z | Z | Z | Z |
| KP1081 | Klebsiella pneumoniae | NDM-1, TEM-1, SHV-11, CMY-6, CTX-M-15 | Z | X | Z | X | Z | Y | Z | Y |
| EC1064 | Escherichia coli | NDM-1, CMY-6, CTX-M-15 | Z | Y | Z | Y | Z | Z | Z | Z |
| KPM1347 | Klebsiella pneumoniae | NDM-1 SHV CTX-M-15 | Z | X | Z | X | Z | X | Z | X |

TABLE 11-continued

Antibiotics Potentiation Activity of Compound 27 against the strains of Enterobacteriaceaea producing various carbapenemases

| Strain | Organism | Enzymes | M | M + 27 | D | D + 27 | E | E + 27 | C | C + 27 |
|---|---|---|---|---|---|---|---|---|---|---|
| ECL1084 | Enterobacter cloacae | CTX-M-15; ACT-16; NDM-1; | Z | X | Z | X | Z | X | Z | X |
| KP1161 | Klebsiella pneumoniae | NDM-1; | Z | X | Z | X | Z | X | Z | X |
| ECL1085 | Enterobacter cloacae | SHV-31(2be); TEM-1(2b); CTX-M-15; NDM-1; | Z | X | Z | X | Z | X | Z | X |
| KP1170 | Klebsiella pneumoniae | SHV-11(2b); CTX-M-15; NDM-1; | Z | X | Z | X | Z | X | Z | X |
| EC1069 | Escherichia coli | CTX-M-27; NDM-1; | Z | X | Z | X | Z | X | Z | X |
| KP1177 | Klebsiella pneumoniae | SHV-OSBL(2b); TEM-OSBL(2b); CTX-M-15; NDM-1; | Z | X | Z | X | Z | X | Z | X |
| EC1070 | Escherichia coli | TEM-OSBL(2b); CMY-42; NDM-5; | Z | X | Z | X | Z | X | Z | X |
| ECL1097 | Enterobacter cloacae | SHV-31(2be); TEM-OSBL(2b); CTX-M-15; ACT-31; NDM-1; | Z | X | Z | X | Z | X | Z | X |
| KP1178 | Klebsiella pneumoniae | SHV-OSBL(2b;) TEM-OSBL(2b); CTX-M-15; NDM-1; | Z | X | Z | X | Z | X | Z | X |
| KP1179 | Klebsiella pneumoniae | SHV-12(2be); TEM-OSBL(2b) ; CTX-M-15; NDM-7; | Z | X | Z | X | Z | X | Z | X |
| ECL1098 | Enterobacter cloacae | TEM-OSBL(2b); DHA-1; ACT-16; NDM-1; | Z | X | Z | X | Z | X | Z | X |
| CF1023 | Citrobacter freundii | SHV-12(2be); TEM-OSBL(2b); CTX-M-3; CMY-34; NDM-1; | Z | X | Z | X | Z | X | Z | X |
| KP1183 | Klebsiella pneumoniae | SHV-OSBL(2b); TEM-OSBL(2b); CTX-M-15; NDM-1; | Z | X | Z | X | Z | X | Z | X |
| EC1072 | Escherichia coli | CTX-M-3; NDM-1; | Z | X | Z | X | Z | X | Z | Y |
| KP1186 | Klebsiella pneumoniae | CTX-M-15; NDM-1; | Z | X | Z | X | Z | X | Z | Y |
| KP1187 | Klebsiella pneumoniae | SHV-55(2be); TEM-OSBL(2b); CTX-M-15; NDM-1; | Z | X | Z | X | Z | X | Z | X |
| KP1188 | Klebsiella pneumoniae | SHV-OSBL(2b); CTX-M-15; NDM-1; | Z | Y | Z | Y | Z | Y | Z | Y |
| KP1189 | Klebsiella pneumoniae | TEM-OSBL(2b); CTX-M-15; CTX-M-27; NDM-1; | Z | X | Z | X | Z | X | Z | X |
| ECL1004 | Enterobacter cloacae | NMC-A | Y | X | Y | X | Z | X | X | X |
| KP1089 | Klebsiella pneumonias | OXA-181, CTX-M-15, TEM, SHV | Y | X | Y | X | Z | X | Z | Y |
| EC1062 | Escherichia coli | OXA-48, CTX-M-15 | X | X | X | X | Y | X | Z | X |
| KP1086 | Klebsiella pneumoniae | OXA-48, CTX-M-15, TEM, SHV | Z | Y | Z | Y | Z | Z | Z | Z |

TABLE 11-continued

Antibiotics Potentiation Activity of Compound 27 against the strains of Enterobacteriaceaea producing various carbapenemases

| Strain | Organism | Enzymes | M | M + 27 | D | D + 27 | E | E + 27 | C | C + 27 |
|---|---|---|---|---|---|---|---|---|---|---|
| EA1019 | *Enterobacter aerogenes* | SHV-5, VIM-1 | Z | X | Z | X | Z | X | Z | Y |
| ECL1045 | *Enterobacter cloacae* | VIM-1 | Y | X | Y | Y | Z | Y | Z | Y |
| KP1054 | *Klebsiella pneumoniae* | VIM-1, SHV-11 | Z | X | Z | X | Y | X | Z | X |
| KP1059 | *Klebsiella pneumoniae* | VIM-1, SHV-11 | Z | Y | Z | Y | Z | Y | Z | Y |
| KP1065 | *Klebsiella pneumoniae* | VIM-1, SHV-11 | Y | X | Y | X | Y | X | Z | X |
| KPM1344 | *Klebsiella pneumoniae* | VIM-1 | Y | X | Y | X | Y | X | Z | X |
| KPM1345 | *Klebsiella pneumoniae* | VIM-1 SHV | Z | X | Z | X | Y | X | Z | X |
| ECL1082 | *Enterobacter cloacae* | VIM-1 | Z | X | Z | X | Y | X | Z | Y |
| EC1068 | *Escherichia coli* | VIM-1 | Z | X | Z | X | Z | X | Z | Y |
| SM1023 | *Serratia marcescens* | VIM-4; | Z | Y | Z | Y | Z | Y | Y | Y |
| KP1164 | *Klebsiella pneumoniae* | SHV-12(2be); VIM-1; | Z | X | Z | X | Z | X | Z | X |
| KP1165 | *Klebsiella pneumoniae* | SHV-11(2b); CTX-M-15; VIM-27; | Z | Z | Z | Z | Z | Z | Z | Z |
| KP1166 | *Klebsiella pneumoniae* | SHV-5(2be); VIM-26; | Z | Y | Z | Y | Z | Y | Z | Z |
| KP1167 | *Klebsiella pneumoniae* | SHV-12(2be); VIM-1; | X | X | X | X | Y | X | Z | X |
| PM1024 | *Proteus mirabilis* | TEM-1(2b); CMY-16; VIM-1; | Y | X | Z | X | Y | X | Z | X |
| CF1021 | *Citrobacter freundii* | CMY-type; VIM-1; | Y | X | Y | X | Y | X | Z | X |
| KP1169 | *Klebsiella pneumoniae* | SHV-11(2b); VIM-1; | Z | X | Z | X | Y | X | Z | X |
| KP1172 | *Klebsiella pneumoniae* | SHV-31(2be); DHA-1; VIM-1; | Y | X | Z | X | Y | X | Z | X |
| ECL1087 | *Enterobacter cloacae* | VIM-1; | Z | X | Z | X | Z | X | Z | Y |
| ECL1088 | *Enterobacter cloacae* | TEM-1(2b); CTX-M-14; ACT-type; VIM-1; | Z | X | Z | X | Z | X | Z | Y |
| KP1175 | *Klebsiella pneumoniae* | SHV-OSBL(2b); VIM-1; | Z | X | Z | X | Z | X | Z | X |
| ECL1091 | *Enterobacter cloacae* | VIM-1; | Z | X | Z | Y | Y | X | Z | Y |
| ECL1092 | *Enterobacter cloacae* | TEM-OSBL(2b); ACT-32; VIM-1; | Y | X | Y | X | Y | X | Z | X |
| ECL1093 | *Enterobacter cloacae* | TEM-OSBL(2b); ACT-32; VIM-1; | Y | X | Y | X | Y | X | Z | X |
| ECL1094 | *Enterobacter cloacae* | VIM-1; | Z | X | Z | X | Z | Y | Z | Y |
| PM1027 | *Proteus mirabilis* | VIM-5; | Z | X | Y | X | Z | X | X | X |
| KP1014 | *Klebsiella pneumoniae* | VIM-1, TEM, SHV | Y | X | Z | Y | Y | X | Z | X |
| ECL1086 | *Enterobacter cloacae* | VIM-31; OXA-48(c) | Y | X | Y | X | Z | Y | Y | Y |
| ECL1096 | *Enterobacter cloacae* | CMY-4; VIM-4; OXA-48(c) | Y | X | Y | X | Z | X | Z | X |

X = MIC of less than 1 μg/mL
Y = MIC of 1 μg/mL to 10 μg/mL
Z = MIC of greater than 10 μg/mL
"M" means Meropenem
"D" means Doripenem
"E" means Ertapenem
"C" means Cefepime The largest panel of clinical isolates expressing class A, D and B carbapenemases alone or in combination with other beta-lactamases (169 strains) was used to evaluate carbapenem potentiation activity of Compounds 97 and 62. MIC for meropenem and tebipenem of these strains were determined either alone or in the presence of Compounds 97 or 62, respectively, at a fixed concentration of 8 µg/ml in the growth media. The results are present in Table 12 below. As shown in the table, both compounds significantly reduced antibiotics MIC of the strains expressing various carbapenemases.

TABLE 12

Meropenem or Tebipenem Potentiation Activity of Compounds 97 or 62, respectively, against the strains of Enterobacteriaceaea producing various carbapenemases

| Strain | Organism | Description | M | M + 97 | T | T + 62 |
|---|---|---|---|---|---|---|
| CF1012 | Citrobacter freundii | KPC-2 | Y | X | Z | X |
| EA1019 | Enterobacter aerogenes | SHV-5, VIM-1 | Z | X | Z | Y |
| ECL1026 | Enterobacter cloacae | KPC-2, TEM-1 | Y | X | Z | X |
| ECL1036 | Enterobacter cloacae | KPC-3, TEM-1 | Y | X | Z | X |
| ECL1045 | Enterobacter cloacae | VIM-1 | Z | X | Y | Y |
| ECL1055 | Enterobacter cloacae | KPC-3, TEM | Y | X | Z | X |
| KP1054 | Klebsiella pneumoniae | VIM-1, SHV-11 | Y | X | Z | X |
| KP1059 | Klebsiella pneumoniae | VIM-1, SHV-11 | Z | X | Z | Z |
| KP1061 | Klebsiella pneumoniae | KPC-3, TEM-1, SHV-11 | Z | X | Z | X |
| KP1064 | Klebsiella pneumoniae | KPC-2, TEM-1, SHV-11 | Z | Y | Z | Y |
| KP1065 | Klebsiella pneumoniae | VIM-1, SHV-11 | Y | X | Y | X |
| KP1070 | Klebsiella pneumoniae | KPC-2, SHV-11, TEM-1 | Z | X | Z | X |
| KP1074 | Klebsiella pneumoniae | KPC-3, SHV-11, TEM | Z | Y | Z | Y |
| ECL1057 | Enterobacter cloacae | NDM-1, TEM-1, CTX-M-15 | Z | Y | Z | Z |
| EC1061 | Escherichia coli | NDM-1, CMY-6 | Z | X | Z | X |
| KP1081 | Klebsiella pneumoniae | NDM-1, TEM-1, SHV-11, CMY-6, CTX-M-15 | Z | X | Z | X |
| ECL1004 | Enterobacter cloacae | NMC-A | Z | X | Z | X |
| EC1007 | Escherichia coli | KPC-3 | Y | X | Y | X |
| KP1004 | Klebsiella pneumoniae | KPC-2, TEM-1, SHV-11 | Z | X | Z | X |
| KP1008 | Klebsiella pneumoniae | KPC-2 | Y | X | Z | X |
| KP1014 | Klebsiella pneumoniae | Vim-1, TEM, SHV | Z | X | Z | X |
| KP1015 | Klebsiella pneumoniae | VIM-1, SHV | Z | Y | Z | Z |
| KP1087 | Klebsiella pneumoniae | KPC-2, CTX-M-15, SHV-11, TEM-1 | Z | X | Z | Y |
| KX1019 | Klebsiella oxytoca | KPC-2, OXA-2 | Y | X | Z | X |
| KX1017 | Klebsiella oxytoca | KPC-2, OXA-2, SHV-30 | Y | X | Z | X |
| KP1082 | Klebsiella pneumoniae | KPC-2, SHV-1 | Z | X | Z | X |
| KX1018 | Klebsiella oxytoca | KPC-2, SHV-40, OXY-1 | Y | X | Z | X |
| KP1083 | Klebsiella pneumoniae | KPC-3, SHV-1, TEM-1 | Z | X | Z | X |
| ECL1058 | Enterobacter cloacae | KPC-3, SHV-11, TEM-1 | Y | X | Z | X |
| KP1084 | Klebsiella pneumoniae | KPC-3, SHV-11, TEM-1 | Z | Y | Z | Y |
| KP1088 | Klebsiella pneumoniae | KPC-3, SHV-11, TEM-1 | Z | X | Z | X |
| ECL1059 | Enterobacter cloacae | KPC-3, SHV-12, TEM-1 | Y | X | Y | X |
| KP1086 | Klebsiella pneumoniae | TEM, SHV, CTX-M-15, OXA-48 | Z | Y | Z | Y |
| EC1064 | Escherichia coli | NDM-1, CMY-6, CTX-M-15 | Z | Y | Z | Y |
| KP1089 | Klebsiella pneumoniae | TEM, SHV, CTX-M-15, OXA-181 | Y | X | Y | X |
| ECL1061 | Enterobacter cloacae | KPC-3, Hyper AmpC expression | Y | X | Z | X |
| KP1092 | Klebsiella pneumoniae | SHV-11, SHV-12, TEM-1, KPC | Z | Z | Z | Z |
| KPM1123 | Klebsiella pneumoniae | KPC-2 TEM SHV | Z | X | Z | X |
| ECL1079 | Enterobacter cloacae | KPC TEM | Z | Z | Z | Z |
| KP1093 | Klebsiella pneumoniae | KPC-3 TEM SHV-11 | Z | Y | Z | Z |
| KP1094 | Klebsiella pneumoniae | KPC-2 TEM-1 LEN-17 | Z | Z | Z | Z |

TABLE 12-continued

Meropenem or Tebipenem Potentiation Activity of Compounds 97 or 62, respectively, against the strains of Enterobacteriaceaea producing various carbapenemases

| Strain | Organism | Description | M | M + 97 | T | T + 62 |
|---|---|---|---|---|---|---|
| KP1095 | Klebsiella pneumoniae | KPC-2 TEM-1 SHV-1 | Y | X | Z | X |
| KP1096 | Klebsiella pneumoniae | KPC-2 TEM-181 SHV-11 | Z | Z | Z | Z |
| KPM1202 | Klebsiella pneumoniae | KPC SHV TEM | Z | X | Z | X |
| KPM1203 | Klebsiella pneumoniae | KPC SHV TEM | Y | X | Z | X |
| KPM1344 | Klebsiella pneumoniae | VIM-1 | Y | X | Y | X |
| KPM1345 | Klebsiella pneumoniae | VIM-1 SHV | Z | X | Y | X |
| KPM1346 | Klebsiella pneumoniae | NDM-1 TEM SHV CTX-M-15 CMY | Z | Y | Z | Z |
| KPM1347 | Klebsiella pneumoniae | NDM-1 SHV CTX-M-15 | Z | X | Z | X |
| EC1065 | Escherichai coli | IMP-1 CMY-2 | Y | X | Y | X |
| KP1097 | Klebsiella pneumoniae | IMP-1 SHV | Z | X | Y | X |
| KP1098 | Klebsiella pneumoniae | IMP-26 TEM SHV | Z | Y | Z | Y |
| KP1099 | Klebsiella pneumoniae | KPC-2 SHV | Z | Y | Z | Z |
| KP1100 | Klebsiella pneumoniae | KPC-3 TEM SHV | Z | Y | Z | Z |
| KP1101 | Klebsiella pneumoniae | KPC-2 TEM SHV | Z | Y | Z | Y |
| KP1102 | Klebsiella pneumoniae | KPC-3 TEM SHV | Z | Y | Z | Z |
| ECL1082 | Enterobacter cloacae | VIM-1 | Y | X | Y | X |
| KP1104 | Klebsiella pneumoniae | KPC, TEM | Z | X | Z | X |
| KP1105 | Klebsiella pneumoniae | KPC, SHV, TEM | Z | X | Z | X |
| KP1001 | Klebsiella pneumoniae | KPC TEM SHV | Z | Y | Z | Y |
| KP1002 | Klebsiella pneumoniae | KPC TEM SHV | Z | X | Z | X |
| KP1003 | Klebsiella pneumoniae | KPC TEM SHV | Z | X | Z | X |
| EC1068 | Escherichia coli | VIM-1 | Z | X | Y | X |
| CF1021 | Citrobacter freundii | CMY-type; VIM-1; | Y | X | Y | X |
| CF1022 | Citrobacter freundii | SHV-12(2be); TEM-OSBL(2b); IMP-8; | Y | X | Y | X |
| CF1023 | Citrobacter freundii | SHV-12(2be); TEM-OSBL(2b); CTX-M-3; CMY-34; NDM-1; | Z | X | Z | X |
| EC1069 | Escherichia coli | CTX-M-27; NDM-1; | Z | X | Z | X |
| EC1070 | Escherichia coli | TEM-OSBL(2b); CMY-42; NDM-5; | Z | X | Z | X |
| EC1072 | Escherichia coli | CTX-M-3; NDM-1; | Z | X | Z | X |
| ECL1084 | Enterobacter cloacae | CTX-M-15; ACT-16; NDM-1; | Z | X | Z | X |
| ECL1085 | Enterobacter cloacae | SHV-31(2be); TEM-1(2b); CTX-M-15; NDM-1; | Z | X | Z | X |
| ECL1087 | Enterobacter cloacae | VIM-1; | Z | X | Y | X |
| ECL1090 | Enterobacter cloacae | TEM-1(2b); CTX-M-22; ACT-type; IMP-8; | Y | X | Y | X |
| ECL1092 | Enterobacter cloacae | TEM-OSBL(2b); ACT-32; VIM-1; | Y | X | Y | X |
| ECL1093 | Enterobacter cloacae | TEM-OSBL(2b); ACT-32; VIM-1; | Y | X | Y | X |
| ECL1094 | Enterobacter cloacae | VIM-1; | Z | X | Z | X |
| ECL1095 | Enterobacter cloacae | SHV-12(2be); TEM-OSBL(2b); CMY-4; ACT-16; VIM-4; OXA-48(c) | Z | X | Z | X |
| ECL1096 | Enterobacter cloacae | CMY-4; VIM-4; OXA-48(c) | Z | X | Z | X |
| ECL1097 | Enterobacter cloacae | SHV-31(2be); TEM-OSBL(2b); CTX-M-15; ACT-31; NDM-1; | Z | X | Z | X |
| ECL1098 | Enterobacter cloacae | TEM-OSBL(2b); DHA-1; ACT-16; NDM-1; | Z | X | Z | X |
| KP1158 | Klebsiella pneumoniae | KPC-2; VIM-1; | Z | Y | Z | Y |
| KP1159 | Klebsiella pneumoniae | SHV-1(2b); CTX-M-15; IMP-4; | Z | X | Y | X |
| KP1160 | Klebsiella pneumoniae | SHV-28(2be); CTX-M-15; IMP-26; | Z | X | Y | X |
| KP1161 | Klebsiella pneumoniae | NDM-1; | Z | X | Z | X |
| KP1162 | Klebsiella pneumoniae | SHV-1(2b); CTX-M-15; IMP-4; | Z | Y | Z | Z |

TABLE 12-continued

Meropenem or Tebipenem Potentiation Activity of Compounds 97 or 62, respectively, against the strains of Enterobacteriaceaea producing various carbapenemases

| Strain | Organism | Description | M | M + 97 | T | T + 62 |
|---|---|---|---|---|---|---|
| KP1163 | Klebsiella pneumoniae | SHV-11(2b); MOX-1; KPC-2; VIM-1; | Z | Y | Z | Z |
| KP1164 | Klebsiella pneumoniae | SHV-12(2be); VIM-1; | Z | X | Z | X |
| KP1165 | Klebsiella pneumoniae | SHV-11(2b); CTX-M-15; VIM-27; | Z | Y | Z | Z |
| KP1166 | Klebsiella pneumoniae | SHV-5(2be); VIM-26; | Z | X | Z | Z |
| KP1168 | Klebsiella pneumoniae | SHV-11(2b); CTX-M-15; VIM-27; | Z | Y | Z | Z |
| KP1169 | Klebsiella pneumoniae | SHV-11(2b); VIM-1; | Z | X | Y | X |
| KP1170 | Klebsiella pneumoniae | SHV-11(2b); CTX-M-15; NDM-1; | Z | X | Z | X |
| KP1172 | Klebsiella pneumoniae | SHV-31(2be); DHA-1; VIM-1; | Z | X | Y | X |
| KP1173 | Klebsiella pneumoniae | TEM-33(2br); CTX-M-15; IMP-1 | Y | X | Y | X |
| KP1174 | Klebsiella pneumoniae | CTX-M-14; IMP-1; | Y | X | Y | X |
| KP1175 | Klebsiella pneumoniae | SHV-OSBL(2b); VIM-1; | Z | X | Z | X |
| KP1176 | Klebsiella pneumoniae | SHV-12(2be); TEM-OSBL(2b); CMY-13; KPC-2; VIM-1; | Z | Y | Z | Z |
| KP1177 | Klebsiella pneumoniae | SHV-OSBL(2b); TEM-OSBL(2b); CTX-M-15; NDM-1; | Z | X | Z | X |
| KP1178 | Klebsiella pneumoniae | SHV-OSBL(2b); TEM-OSBL(2b); CTX-M-15; NDM-1; | Z | X | Z | X |
| KP1179 | Klebsiella pneumoniae | SHV-12(2be); TEM-OSBL(2b); CTX-M-15; NDM-7; | Z | X | Z | X |
| KP1180 | Klebsiella pneumoniae | SHV-OSBL(2b); TEM-OSBL(2b); CTX-M-15; DHA-1; IMP-26; | Y | X | Y | X |
| KP1181 | Klebsiella pneumoniae | SHV-OSBL(2b); CTX-M-15; IMP-26; | Z | X | Y | X |
| KP1182 | Klebsiella pneumoniae | SHV-OSBL(2b); NDM-1; OXA-232(c) | Z | Y | Z | Y |
| KP1183 | Klebsiella pneumoniae | SHV-OSBL(2b); TEM-OSBL(2b); CTX-M-15; NDM-1; | Z | X | Z | X |
| KP1184 | Klebsiella pneumoniae | SHV-OSBL(2b); IMP-1; | Y | X | Y | X |
| KP1185 | Klebsiella pneumoniae | SHV-OSBL(2b); TEM-OSBL(2b); IMP-4; | Z | X | Z | Y |
| KP1186 | Klebsiella pneumoniae | CTX-M-15; NDM-1; | Z | X | Z | X |
| KP1187 | Klebsiella pneumoniae | SHV-55(2be); TEM-OSBL(2b); CTX-M-15; NDM-1; | Z | X | Z | X |
| KP1188 | Klebsiella pneumoniae | SHV-OSBL(2b); CTX-M-15; NDM-1; | Y | X | Z | Y |
| KP1189 | Klebsiella pneumoniae | TEM-OSBL(2b); CTX-M-15; CTX-M-27; NDM-1; | Z | X | Z | X |
| PM1024 | Proteus mirabilis | TEM-1(2b); CMY-16; VIM-1; | Z | X | Z | X |
| PM1025 | Proteus mirabilis | SHV-5(2be); TEM-OSBL(2b); VEB-2; VIM-1; | Y | X | Y | X |
| PM1026 | Proteus mirabilis | DHA-1; IMP-26; | Z | X | Y | Y |
| PM1027 | Proteus mirabilis | VIM-5; | Z | X | Z | X |
| SM1023 | Serratia marcescens | VIM-4; | Z | X | Z | Y |
| SM1024 | Serratia marcescens | TEM-1(2b); IMP-47; | Y | X | Y | Y |
| KP1190 | Klebsiella pneumoniae | KPC-4 VIM-4 TEM SHV | Z | Z | Z | Z |
| KP1191 | Klebsiella pneumoniae | KPC-2 | Z | Y | Z | Y |
| KP1192 | Klebsiella pneumoniae | KPC-2 TEM SHV | Z | Z | Z | Z |
| KP1193 | Klebsiella pneumoniae | KPC-3 TEM SHV | Z | Y | Z | Y |

TABLE 12-continued

Meropenem or Tebipenem Potentiation Activity of Compounds 97 or 62, respectively, against the strains of Enterobacteriaceaea producing various carbapenemases

| Strain | Organism | Description | M | M + 97 | T | T + 62 |
|---|---|---|---|---|---|---|
| KP1194 | Klebsiella pneumoniae | KPC TEM SHV | Z | Z | Z | Z |
| KP1195 | Klebsiella pneumoniae | KPC TEM CTX-M-15 | Z | Z | Z | Z |
| KP1196 | Klebsiella pneumoniae | KPC TEM SHV CTX-M-15 CMY | Z | Y | Z | Z |
| KP1197 | Klebsiella pneumoniae | KPC-3, VIM-1 TEM SHV | Z | Y | Z | Z |
| KP1198 | Klebsiella pneumoniae | KPC-3, VIM-1 TEM SHV | Z | Y | Z | Y |
| KP1199 | Klebsiella pneumoniae | KPC-3 TEM SHV | Z | Z | Z | Z |
| KP1200 | Klebsiella pneumoniae | KPC-3 TEM SHV | Z | Z | Z | Z |
| KP1210 | Klebsiella pneumoniae | KPC SHV TEM | Z | X | Z | X |
| KP1211 | Klebsiella pneumoniae | KPC SHV TEM CTX-M-15 | Z | Y | Z | Y |
| KP1212 | Klebsiella pneumoniae | KPC SHV TEM CTX-M-15 | Z | Y | Z | Z |
| KP1213 | Klebsiella pneumoniae | KPC SHV TEM CTX-M-15 | Z | X | Z | X |
| KP1214 | Klebsiella pneumoniae | KPC SHV TEM + 1.9 kb | Z | Y | Z | Z |
| KP1215 | Klebsiella pneumoniae | KPC SHV | Z | Y | Z | Z |
| KP1216 | Klebsiella pneumoniae | KPC SHV TEM + 1.9 kb | Z | Y | Z | Y |
| KP1217 | Klebsiella pneumoniae | KPC SHV TEM + 1.9 kb | Z | Y | Z | Y |
| KP1218 | Klebsiella pneumoniae | KPC SHV TEM + 1.9 kb | Z | Y | Z | Y |
| KP1219 | Klebsiella pneumoniae | KPC SHV TEM + 1.9 kb | Z | X | Z | X |
| KP1220 | Klebsiella pneumoniae | KPC SHV TEM + 1.9 kb | Z | Y | Z | Y |
| KP1221 | Klebsiella pneumoniae | KPC SHV TEM + 1.9 kb | Z | Y | Z | Y |
| KP1222 | Klebsiella pneumoniae | KPC SHV TEM IMP | Z | X | Z | X |
| KP1223 | Klebsiella pneumoniae | KPC SHV TEM | Z | Z | Z | Z |
| KP1224 | Klebsiella pneumoniae | KPC SHV TEM | Z | Z | Z | Z |
| KP1225 | Klebsiella pneumoniae | KPC SHV TEM + 1.9 kb CMY | Z | X | Z | X |
| KP1226 | Klebsiella pneumoniae | KPC SHV TEM + 1.9 kb | Z | Y | Z | Z |
| KP1227 | Klebsiella pneumoniae | KPC SHV TEM CTX-M-15 | Z | X | Z | X |
| KP1228 | Klebsiella pneumoniae | OXA-48 TEM SHV CTX-M-15 | Y | X | Y | X |
| KP1229 | Klebsiella pneumoniae | OXA-48 TEM SHV CTX-M-15 | Z | X | Z | X |
| KP1230 | Klebsiella pneumoniae | OXA-48 TEM SHV CTX-M-15 | Y | X | Y | X |
| KP1231 | Klebsiella pneumoniae | OXA-48 TEM SHV CTX-M-15 | Y | X | Y | X |
| KP1232 | Klebsiella pneumoniae | OXA-48 TEM SHV CTX-M-15 | Z | Y | Z | Y |
| KP1234 | Klebsiella pneumoniae | OXA-48 TEM SHV CTX-M-15 | Z | Y | Z | Y |
| KP1236 | Klebsiella pneumoniae | OXA-48 TEM SHV CTX-M-15 | Z | Y | Z | Y |
| KP1237 | Klebsiella pneumoniae | OXA-48 TEM SHV CTX-M-15 | Z | Y | Z | Y |
| KP1239 | Klebsiella pneumoniae | OXA-48 SHV | Z | Y | Z | Y |
| KP1240 | Klebsiella pneumoniae | OXA-181 SHV CTX-M-15 | Z | X | Y | X |
| KP1241 | Klebsiella pneumoniae | OXA-181 TEM SHV CTX-M-15 | Z | Y | Z | Y |
| EC1073 | Escherichia coli | OXA-48 | Z | Y | Z | Y |
| EC1074 | Escherichia coli | KPC-2, SHV-12 | Z | X | Z | |
| KP1242 | Klebsiella pneumoniae | KPC-2, SHV-12 TEM | Z | X | Z | |
| KP1243 | Klebsiella pneumoniae | KPC-2 SHV VIM-1 | Z | Y | Z | |
| KP1244 | Klebsiella pneumoniae | KPC SHV TEM + 1.9 kb | Z | Z | Z | Z |
| KP1245 | Klebsiella pneumoniae | KPC SHV TEM + 1.9 kb | Z | X | Z | X |

TABLE 12-continued

Meropenem or Tebipenem Potentiation Activity of Compounds 97 or 62, respectively, against the strains of Enterobacteriaceaea producing various carbapenemases

| Strain | Organism | Description | M | M + 97 | T | T + 62 |
|---|---|---|---|---|---|---|
| KP1246 | *Klebsiella pneumoniae* | KPC SHV TEM + 1.9 kb | Z | X | Z | X |
| KP1247 | *Klebsiella pneumoniae* | IMP TEM SHV | Z | Y | Z | Y |
| KP1248 | *Klebsiella pneumoniae* | OXA-232 SHV CTX-M-15 | Z | Y | Z | Y |
| KP1249 | *Klebsiella pneumoniae* | OXA-232 SHV | Z | Y | Z | Y |
| KP1250 | *Klebsiella pneumoniae* | NDM-1 TEM SHV SMY-2 CTX-M-15 | Z | X | Z | X |
| EC1076 | *Escherichia coli* | NDM-1 CMY-2 | Z | X | Z | X |
| KP1252 | *Klebsiella pneumoniae* | KPC TEM SHV | Z | Y | Z | X |

X = MIC of less than 1 µg/mL
Y = MIC of 1 µg/mL to 10 µg/mL
Z = MIC of greater than 10 µg/mL
"M" means Meropenem
"T" means Tebipenem Example 137: Serum Stability of Prodrugs Prodrug strategy is one of the ways to achieve or increase oral bioavailability for therapeutic drugs. Compound 62 was used as a template for various ester prodrugs. After a prodrug molecule is absorbed into systemic circulation, it should be hydrolyzed in the blood in order to release the active form. Hydrolysis of several prodrugs by rat and human serum were evaluated.

For all stability experiments the test compounds were treated with rat or human serum in Eppendorf tubes. Typically, 980 µl of serum was prewarmed at 37 degrees for 2 minutes and then 20 µl of a compound (at 1 mg/ml, 50×) was added to it to get a final concentration of 20 µg/ml and immediately mixed. Duplicate samples were tested. The tubes were sampled immediately (100 µl) and then placed back in a 37 degree water bath and samples were taken at designated times and transferred directly into Eppendorf tubes containing 400 µl of precipitant solution (a 4.00 µg/mL solution of a standard compound, RPX7479, in 10% water, 45% methanol and 45% acetonitrile). After vortexing for 30 seconds, the tube was centrifuged in a microcentrifuge for 10 minutes at 15K rpm. Next, 100 µl of the supernatant was combined with 600 µl of water and injected on LC-MS using 0.1% formic acid in water for mobile phase A and 0.1% formic acid in methanol for mobile phase B on an ACE 5 C18 2.1×100 mm column with a 10 µL it injection. The flow rate and gradient were adjusted as needed to give the desired resolution and run time. The pH of the mobile phase was adjusted if needed to improve the chromatography.

The time course of both the disappearance of a prodrug and the appearance of the active form of that prodrug is presented in Table 13 and Table 14. The active metabolites for all of the listed prodrugs are corresponding parent drugs

TABLE 13

Time-course of prodrug hydrolysis by human serum

| Example # | Theoretical Initial Conc. in Serum (uM) | Measured Initial Conc. in Serum (uM) | Conc. at t = 1 hr (uM) | Conc. at t = 3 hr (uM) | Active Metabolite Initial Conc. in Serum (uM) | Active Metabolite Conc. at t = 1 hr (uM) | Active Metabolite Conc. at t = 3 hr (uM) |
|---|---|---|---|---|---|---|---|
| 121 | 45.7 | 51.4 | 38.6 | 24.8 | 0.3 | 7.9 | 17.0 |
| 122 | 44.0 | 44.3 | 34.1 | 47.1 | 0.4 | 1.1 | 2.8 |
| 123 | 48.8 | 51.7 | 43.4 | 30.7 | 6.4 | 16.5 | 27.4 |
| 124 | 45.4 | 48.3 | 38.3 | 45.9 | 1.0 | 4.1 | 8.4 |
| 125 | 44.2 | 41.8 | 27.4 | 41.4 | 0 | 0.8 | 2.7 |

TABLE 14

Time-course of prodrug hydrolysis by rat serum

| Example # | Theoretical Initial Conc. in Serum (uM) | Measured Initial Conc. in Serum (uM) | Conc. at t = 1 hr (uM) | Conc. at t = 3 hr (uM) | Active Metabolite Initial Conc. in Serum (uM) | Active Metabolite Conc. at t = 1 hr (uM) | Active Metabolite Conc. at t = 3 hr (uM) |
|---|---|---|---|---|---|---|---|
| 121 | 45.7 | 31.3 | 40.7 | 24.3 | 0.3 | 8.6 | 20.5 |
| 122 | 44.0 | 37.7 | 26.6 | 39.0 | 0.6 | 3.8 | 7.7 |
| 123 | 48.8 | 51.5 | 26.1 | 8.6 | 10.5 | 28.7 | 45.6 |
| 124 | 45.4 | 44.9 | 36.8 | 41.2 | 1.9 | 5.7 | 11.9 |
| 125 | 44.2 | 37.6 | 28.5 | 48.2 | 0 | 0.7 | 2.4 |

The data showed that different prodrugs differ significantly in serum stability. Compound 123 appeared to be completely converted to active metabolite over the course of 4 hour experiment.

Example 138: Oral Pharmacokinetics of Prodrugs of Compound 62

The prodrugs of compound 62, including compounds 121, 122, 123, 124, 125, 126 and 127 were tested for their oral pharmacokinetics. Rats (n=3 per compound) were administered a single oral dose. Oral doses were administered as a single dose. Plasma (~0.3 mL) samples were collected from each rat at designated time points up to 24 hours. Blood samples were centrifuged within 5 min of collection at 12000 g for 5 min to obtain plasma. The plasma samples were stored at −80° C. until analyzed. Data were analyzed using WinNonlin and the results are presented in Table 15.

TABLE 15

Bioavailability of Prodrugs of Compound 62

| Example # | Dose of Compound 62 from Prodrug (mg/kg) | Range of % Oral Bioavailability (Average) |
|---|---|---|
| 121 | 20 | 73-85 (81.0) |
| 121 | 75 | 82-100 (96.9) |
| 122 | 50 | 39-76 (59.3) |
| 123 | 30 | 38-73 (52.4) |
| 124 | 50 | 56-70 (73.9) |
| 125 | 50 | 100 |
| 126 | 50 | 66-103 (78.6) |
| 127 | 50 | 43-79 (58.9) |

Although the invention has been described with reference to embodiments and examples, it should be understood that numerous and various modifications can be made without departing from the spirit of the invention. Accordingly, the invention is limited only by the following claims.

What is claimed is:

1. A compound having the structure of Formula I-(1) or Formula (I-2):

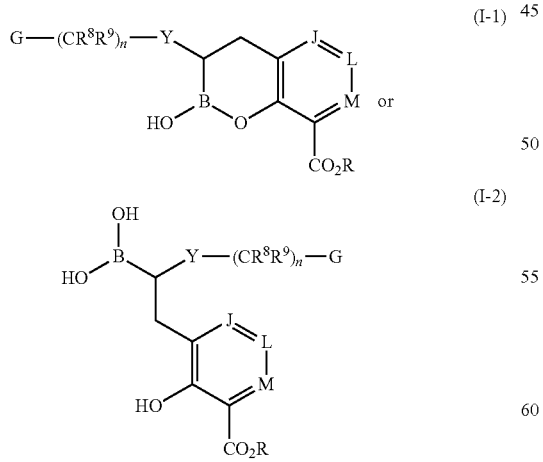

or pharmaceutically acceptable sales thereof, wherein:
Y is selected from the group consisting of —S—, —S(O)—, —S(O)$_2$—, —O—, —CH$_2$— and —NR$^2$—;

G is selected from the group consisting of —NR$^1$R$^2$, —N$_3$, —C(O)NR$^1$R$^2$, —S(O)$_2$NR$^1$R$^2$, —SR$^3$, —OR$^3$, —CH$_2$NR$^1$C(O)R$^5$, —C(=NOR$^3$)—X, C(=NOR$^3$)—Z, —C(O)OR$^3$, —C(O)NR$^1$(OR$^3$), —NR$^1$(OR$^3$), —NR$^1$C(O)R$^5$, —NR$^1$C(O)NR$^2$R$^{1a}$, —NR$^1$C(O)OR$^3$, —NR$^1$S(O)$_2$R$^3$, —NR$^1$S(O)$_2$NR$^2$R$^{1a}$, —NR$^1$NR$^2$R$^{1a}$, —C(O)NR$^1$NR$^2$R$^{1a}$, —S(O)$_2$NR$^1$NR$^2$R$^{1a}$, —C(=NR$^1$)R$^5$, —C(=NR$^1$)NR$^2$R$^{1a}$, —NR$^1$CR$^5$(=NR$^2$), —NR$^1$C(=NR$^2$)NR$^{1a}$R$^{2a}$, —CN, C$_{1-10}$ alkyl optionally substituted by one or more R$^{10}$, C$_{2-10}$ alkenyl optionally substituted by one or more R$^{10}$, C$_{2-10}$alkynyl optionally substituted by one or more R$^{10}$, C$_{3-7}$ carbocyclyl optionally substituted by one or more R$^{10}$, 3-10 membered heterocyclyl optionally substituted by one or more R$^{10}$, C$_{6-10}$aryl optionally substituted by one or more R$^{10}$, 5-10 membered heteroaryl optionally substituted by one or more R$^{10}$, C$_{1-6}$alkylene-C$_{3-7}$ carbocyclyl optionally substituted by one or more R$^{10}$, C$_{1-6}$alkylene-3-10 membered heterocyclyl optionally substituted by one or more R$^{10}$, C$_{1-6}$alkylene-C$_{6-10}$aryl optionally substituted by one or more R$^{10}$, and C$_{1-6}$alkylene-5-10 membered heteroaryl optionally substituted by one or more R$^{10}$;

J, L, and M are each independently selected from the group consisting of CR$^7$ and N;

each R$^7$ is independently selected from the group consisting of —H, —OH, halogen, —CH$_3$, —CF$_3$, C$_1$-C$_6$ alkenyl, C$_1$-C$_6$ alkynyl, C$_1$-C$_6$ heteroalkyl, C$_3$-C$_7$ carbocyclyl, 3-10 membered heterocyclyl, aryl, 5-10 membered heteroaryl, cyano, C$_1$-C$_6$ alkoxy(C$_1$-C$_6$)alkyl, aryloxy, sulfhydryl (mercapto), and —(CH$_2$)$_m$—Y'—(CH$_2$)$_p$M', or two adjacent R$^7$ together with any intervening atoms form a 5-10 membered heteroaryl;

m and p are independently 0 to 3;

Y' is selected from the group consisting of —S—, —S(O)—, —S(O)$_2$—, —O—, —CR$^5$R$^6$—, and —NR$^1$—;

M' is selected from the group consisting of —C(O)NR$^1$R$^2$; —C(O)NR$^1$OR$^3$; —NR$^1$C(O)R$^5$; —NR$^1$C(O)NR$^2$R$^{1a}$; —NR$^1$C(O)OR$^3$; —NR$^1$S(O)$_2$R$^3$; —NR$^1$S(O)$_2$NR$^2$R$^{1a}$; —C(=NR$^1$)R$^5$; —C(=NR$^1$)NR$^2$R$^{1a}$; —NR$^1$CR$^5$(=NR$^2$); —NR$^1$C(=NR$^2$)NR$^{1a}$R$^{2a}$; NR$^1$R$^2$; —SO$_3$R$^3$; —CN; C$_{1-4}$ alkyl optionally substituted with 0-2 substituents selected from the group consisting, —OR$^3$, —NR$^1$R$^2$, halogen, —C(O)NR$^1$R$^2$, and —NR$^1$C(O)R$^5$; C$_{3-10}$ cycloalkyl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; C$_{6-10}$ aryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; 5 to 10 membered heteroaryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; and 4 to 10 membered heterocyclyl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$;

X is hydrogen or optionally substituted C$_{1-9}$alkyl;

Z is selected from optionally substituted C$_{3-8}$ cycloalkyl, optionally substituted heterocyclyl, optionally substituted aryl, optionally substituted heteroaryl;

R is selected from the group consisting of —H, —C$_{1-9}$alkyl, —CR$^5$R$^6$OC(O)C$_{1-9}$alkyl, —CR$^5$R$^6$OC(O)OC$_{1-9}$alkyl, CR$^6$R$^7$OC(O)C$_{6-10}$aryl, CR$^6$R$^7$OC(O)OC$_{6-10}$aryl, and

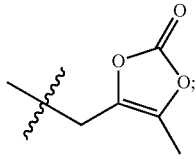 [SMILES: *Cc1oc(=O)oc1C]

each R$^1$, R$^2$, R$^{1a}$ and R$^{2a}$ are independently selected from the group consisting of —H, optionally substituted —C$_{1-10}$alkyl, optionally substituted C$_{2-10}$alkenyl, optionally substituted C$_{2-10}$alkynyl, optionally substituted C$_{3-7}$ cycloalkyl, optionally substituted 3-8 membered heterocyclyl, optionally substituted C$_{6-10}$aryl, and optionally substituted 5-10 membered heteroaryl;

R$^3$ is hydrogen, optionally substituted C$_{1-10}$alkyl, -optionally substituted C$_{1-10}$alkyl-COOH, optionally substituted C$_{2-10}$alkenyl, optionally substituted C$_{2-10}$alkynyl, optionally substituted C$_{3-7}$ cycloalkyl, optionally substituted 3-8 membered heterocyclyl, optionally substituted C$_{6-10}$aryl, and optionally substituted 5-10 membered heteroaryl;

each R$^5$, R$^6$, R$^8$ and R$^9$ are independently selected from the group consisting of —H, —OH, —NH$_2$, -optionally substituted alkoxyl, optionally substituted —C$_{1-10}$alkyl, optionally substituted C$_{2-10}$alkenyl, optionally substituted C$_{2-10}$alkynyl, optionally substituted C$_{3-7}$ cycloalkyl, optionally substituted 3-8 membered heterocyclyl, optionally substituted C$_{6-10}$aryl, and optionally substituted 5-10 membered heteroaryl;

each n is independently 0-3;

each R$^{10}$ is independently (CH$_2$)$_{0-6}$R$^{11}$; and each R$^{11}$ is independently selected from C$_1$-C$_6$ alkyl; C$_2$-C$_6$ alkenyl; C$_2$-C$_6$ alkynyl; C$_1$-C$_6$ heteroalkyl; C$_3$-C$_7$ carbocyclyl optionally substituted with halo, amine, cyano, C1-C6 alkyl, C1-C6 alkoxy, C1-C6 haloalkyl, and C1-C6 haloalkoxy; C3-C7-carbocyclyl-C1-C6-alkyl optionally substituted with halo, amine, cyano, C1-C6 alkyl, C1-C6 alkoxy, C1-C6 haloalkyl, and C1-C6 haloalkoxy; 3-10 membered heterocyclyl optionally substituted with halo, amine, cyano, C1-C6 alkyl, C1-C6 alkoxy, C1-C6 haloalkyl, and C1-C6 haloalkoxy; 3-10 membered heterocyclyl-C1-C6-alkyl optionally substituted with halo, amine, cyano, C1-C6 alkyl, C1-C6 alkoxy, C1-C6 haloalkyl, and C1-C6 haloalkoxy; aryl optionally substituted with halo, amine, cyano, C1-C6 alkyl, C1-C6 alkoxy, C1-C6 haloalkyl, and C1-C6 haloalkoxy; aryl(C1-C6)alkyl optionally substituted with halo, amine, cyano, C1-C6 alkyl, C1-C6 alkoxy, C1-C6 haloalkyl, and C1-C6 haloalkoxy; 5-10 membered heteroaryl optionally substituted with halo, amine, cyano, C1-C6 alkyl, C1-C6 alkoxy, C1-C6 haloalkyl, and C1-C6 haloalkoxy; 5-10 membered heteroaryl(C$_1$-C$_6$)alkyl optionally substituted with halo, amine, cyano, C$_1$-C$_6$ alkyl, C$_1$-C$_6$ alkoxy, C$_1$-C$_6$ haloalkyl, and C$_1$-C$_6$ haloalkoxy; C$_{1-6}$alkylene-C$_{3-7}$carbocyclyl optionally substituted with halo, amine, cyano, C$_1$-C$_6$ alkyl, C$_1$-C$_6$ alkoxy, C$_1$-C$_6$ haloalkyl, and C$_1$-C$_6$ haloalkoxy; C$_{1-6}$alkylene-3-10 membered heterocyclyl optionally substituted with halo, amine, cyano, C$_1$-C$_6$ alkyl, C$_1$-C$_6$ alkoxy, C$_1$-C$_6$ haloalkyl, and C$_1$-C$_6$ haloalkoxy; C$_{1-6}$alkylene-C$_{6-10}$aryl optionally substituted with halo, amine, cyano, C$_1$-C$_6$ alkyl, C$_1$-C$_6$ alkoxy, C$_1$-C$_6$ haloalkyl, and C$_1$-C$_6$ haloalkoxy; C$_{1-6}$alkylene-5-10 membered heteroaryl optionally substituted with halo, amine, cyano, C$_1$-C$_6$ alkyl, C$_1$-C$_6$ alkoxy, C$_1$-C$_6$ haloalkyl, and C$_1$-C$_6$ haloalkoxy; halo; cyano; hydroxy; C$_1$-C$_6$ alkoxy(C$_1$-C$_6$)alkyl (ether); aryloxy; halo(C$_1$-C$_6$)alkyl; halo(C$_1$-C$_6$)alkoxy; amino; amino(C$_1$-C$_6$)alkyl; nitro; O-carbamyl; N-carbamyl; O-thiocarbamyl; N-thiocarbamyl; C-amido; N-amido; S-sulfonamido; N-sulfonamido; C-carboxy; O-carboxy; acyl; cyanate; isocyanate; thiocyanato; isothiocyanato; sulfonyl; —OR$^3$; —C$_{1-6}$alkylene-COOR$^3$; —SR$^3$; —C(O)NR$^1$R$^2$; —NR$^1$R$^2$; —NR$^1$(CH$_2$)$_{0-4}$COR$^5$; —NR$^1$(CH$_2$)$_{0-4}$C(=NR$^2$)R$^5$; —NR$^1$—CH—[(CH$_2$)$_{0-4}$—NR$^{1a}$R$^{2a}$]$_2$; —NR$^1$—(CH$_2$)$_{1-5}$—R$^3$; —NR$^1$(CH$_2$)$_{1-4}$—NR$^{1a}$R$^{2a}$; —N[(CH$_2$)$_{1-4}$—NR$^1$R$^2$]$_2$; —S(CH$_2$)$_{0-4}$C(=NR$^1$)R$^5$; —S(CH$_2$)$_{1-4}$—R$^3$; —S(CH$_2$)$_{0-4}$—NR$^1$R$^2$; —S—CH—[(CH$_2$)$_{0-4}$—NR$^1$R$^2$]$_2$; —S[(CH$_2$)$_{1-4}$—NR$^1$R$^2$]$_2$; —S(CH$_2$)$_{0-4}$-3-10 membered heterocyclyl; —S(CH$_2$)$_{0-4}$-3-10 membered heterocyclyl-NR$^1$R$^2$; —S(CH$_2$)$_{0-4}$-5-10 membered heteroaryl-NR$^1$R$^2$; —S(O)$_2$NR$^1$R$^2$; and —O—C$_{1-6}$alkylene-NR$^1$R$^2$.

2. The compound of claim 1, wherein:

G is selected from the group consisting of —NR$^1$R$^2$, —N$_3$, —C(O)NR$^1$R$^2$, —S(O)$_2$NR$^1$R$^2$, —SR$^3$, —OR$^3$, —CH$_2$NR$^1$C(O)R$^5$, —C(=NOR$^3$)—X, C(=NOR$^3$)—Z, —C(O)OR$^3$, —C(O)NR$^1$(OR$^3$), —NR$^1$(OR$^3$), —NR$^1$C(O)R$^5$, —NR$^1$C(O)NR$^2$R$^{1a}$, —NR$^1$C(O)OR$^3$, —NR$^1$S(O)$_2$R$^3$, —NR$^1$S(O)$_2$NR$^2$R$^{1a}$, —NR$^1$NR$^2$R$^{1a}$, —C(O)NR$^1$NR$^2$R$^{1a}$, —S(O)$_2$NR$^1$NR$^2$R$^{1a}$, —C(=NR$^1$)R$^5$, —C(=NR$^1$)NR$^2$R$^{1a}$, —NR$^1$CR$^5$(=NR$^2$), —NR$^1$C(=NR$^2$)NR$^{1a}$R$^{2a}$, optionally substituted C$_{1-10}$ alkyl, optionally substituted C$_{2-10}$alkenyl, optionally substituted C$_{2-10}$alkynyl, optionally substituted C$_{3-7}$ carbocyclyl, optionally substituted 5-10 membered heterocyclyl, optionally substituted C$_{6-10}$aryl, optionally substituted 5-10 membered heteroaryl, optionally substituted C$_{1-6}$alkylene-C$_{3-7}$carbocyclyl, optionally substituted C$_{1-6}$alkylene-5-10 membered heterocyclyl, optionally substituted C$_{1-6}$alkylene-C$_{6-10}$aryl, and optionally substituted C$_{1-6}$alkylene-5-10 membered heteroaryl;

each R$^7$ is independently selected from the group consisting of —H, —OH, halogen, —CF$_3$, C$_1$-C$_6$ alkenyl, C$_1$-C$_6$ alkynyl, C$_1$-C$_6$ heteroalkyl, C$_3$-C$_7$ carbocyclyl, 5-10 membered heterocyclyl, aryl, 5-10 membered heteroaryl, cyano, C$_1$-C$_6$ alkoxy(C$_1$-C$_6$)alkyl, aryloxy, sulfhydryl (mercapto), and —(CH$_2$)$_m$—Y'—(CH$_2$)$_p$M';

M' is selected from the group consisting of —C(O)NR$^1$R$^2$; —C(O)NR$^1$OR$^3$; —NR$^1$C(O)R$^5$; —NR$^1$C(O)NR$^2$R$^{1a}$; —NR$^1$C(O)OR$^3$; —NR$^1$S(O)$_2$R$^3$; —NR$^1$S(O)$_2$NR$^2$R$^{1a}$; —C(=NR$^1$)R$^5$; —C(=NR$^1$)NR$^2$R$^{1a}$; —NR$^1$CR$^5$(=NR$^2$); —NR$^1$C(=NR$^2$)NR$^{1a}$R$^{2a}$; CF$_3$, C$_{1-4}$ alkyl optionally substituted with 0-2 substituents selected from the group consisting, —OR$^3$, —NR$^1$R$^2$, halogen, —C(O)NR$^1$R$^2$, and —NR$^1$C(O)R$^5$; C$_{3-10}$ cycloalkyl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; C$_{6-10}$ aryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$; 5 to 10 membered heteroaryl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O) R$^5$; and 4 to 10 membered heterocyclyl optionally substituted with 0-2 substituents selected from the group consisting of C$_{1-4}$ alkyl, —OR$^3$, —NR$^1$R$^2$, halogen, —C(O)NR$^1$R$^2$, and —NR$^1$C(O)R$^5$;

R is selected from the group consisting of —H, —C$_{1-9}$alkyl, —CR$^5$R$^6$OC(O)C$_{1-9}$alkyl, —CR$^5$R$^6$OC(O)OC$_{1-9}$alkyl, and

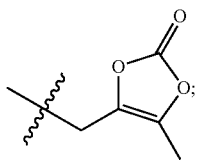 [SMILES: *Cc1oc(=O)oc1C]

each R$^1$, R$^2$, R$^{1a}$ and R$^{ea}$ are independently selected from the group consisting of —H, optionally substituted —C$_{1-10}$alkyl, optionally substituted C$_{2-10}$alkenyl, optionally substituted C$_{2-10}$alkynyl, optionally substituted C$_{3-7}$ cycloalkyl, optionally substituted 3-8 membered heterocyclyl, optionally substituted C$_{6-10}$aryl, and optionally substituted 5-10 membered heteroaryl; and each R$^5$, R$^6$, R$^8$ and R$^9$ are independently selected from the group consisting of —H, —OH, -optionally substituted alkoxyl, optionally substituted —C$_{1-10}$alkyl, optionally substituted C$_{2-10}$alkenyl, optionally substituted C$_{2-10}$alkynyl, optionally substituted C$_{3-7}$ cycloalkyl, optionally substituted 3-8 membered heterocyclyl, optionally substituted C$_{6-10}$aryl, and optionally substituted 5-10 membered heteroaryl.

3. The compound of claim 1, wherein G is selected from the group consisting of —NR$^1$R$^2$, —N$_3$, —C(O)NR$^1$R$^2$, —S(O)$_2$NR$^1$R$^2$, —SR$^3$, —OR$^3$, —CH$_2$NR$^1$C(O)R$^5$, —C(=NOR$^3$)—X, C(=NOR$^3$)—Z, —C(O) OR$^3$, —C(O)NR$^1$(OR$^3$), —NR$^1$(OR$^3$), —NR$^1$C(O)R$^5$, —NR$^1$C(O)NR$^2$R$^{1a}$, —NR$^1$C(O)OR$^3$, —NR$^1$S(O)$_2$R$^3$; —NR$^1$S(O)$_2$NR$^2$R$^{1a}$, —NR$^1$NR$^2$R$^{1a}$, —C(O)NR$^1$NR$^2$R$^{1a}$, —S(O)$_2$NR$^1$NR$^2$R$^{1a}$, —C(=NR$^1$)R$^5$, —C(=NR$^1$)NR$^2$R$^{1a}$, —NR$^1$CR$^5$(=NR$^2$), —NR$^1$C(=NR$^2$)NR$^{1a}$R$^{2a}$, optionally substituted C$_{1-10}$ alkyl, optionally substituted C$_{2-10}$alkenyl, optionally substituted C$_{2-10}$alkynyl, optionally substituted C$_{3-7}$ carbocyclyl, optionally substituted 5-10 membered heterocyclyl, optionally substituted C$_{6-10}$aryl, and optionally substituted 5-10 membered heteroaryl.

4. The compound of claim 1, wherein each R$^{11}$ is independently selected from C$_1$-C$_6$ alkyl; haloC$_{1-6}$alkyl; —OR$^3$; —C$_{1-6}$alkylene-COOR$^3$; —SR$^3$; halogen; —CO—C$_{1-4}$ alkyl; C(O)NR$^1$R$^2$; —NR$^1$R$^2$; —NR$^1$(CH$_2$)$_{0-4}$COR$^5$; —NR$^1$(CH$_2$)$_{0-4}$C(=NR$^2$)R$^5$; —NR$^1$—CH—[(CH$_2$)$_{0-4}$—NR$^{1a}$R$^{2a}$]$_2$; —NR$^1$—(CH$_2$)$_{1-5}$—R$^3$; —NR$^1$(CH$_2$)$_{1-4}$—NR$^{1a}$R$^{2a}$; —N[(CH$_2$)$_{1-4}$—NR$^1$R$^2$]$_2$; —S(CH$_2$)$_{0-4}$C(=NR$^1$) R$^5$; —S(CH$_2$)$_{1-4}$—R$^3$; —S(CH$_2$)$_{0-4}$—NR$^1$R$^2$; —S—CH—[(CH$_2$)$_{0-4}$—NR$^1$R$^2$]$_2$; —S[(CH$_2$)$_{1-4}$—NR$^1$R$^2$]$_2$; —S(CH$_2$)$_{0-4}$-3-10 membered heterocyclyl; —S(CH$_2$)$_{0-4}$-3-10 membered heterocyclyl-NR$^1$R$^2$; —S(CH$_2$)$_{0-4}$-5-10 membered heteroaryl-NR$^1$R$^2$; —S(O)$_2$NR$^1$R$^2$; and —O—C$_{1-6}$ alkylene-NR$^1$R$^2$; C$_{3-7}$ carbocyclo optionally substituted with halo, amine, cyano, C$_1$-C$_6$ alkyl; C$_1$-C$_6$ alkoxy, C$_1$-C$_6$ haloalkyl, and C$_1$-C$_6$ haloalkoxy; 3-10 membered heterocyclyl optionally substituted with halo, amine, cyano, C$_1$-C$_6$ alkyl, C$_1$-C$_6$ alkoxy, C$_1$-C$_6$ haloalkyl, and C$_1$-C$_6$ haloalkoxy; 6 to 10 membered aryl optionally substituted with halo, amine, cyano, C$_1$-C$_6$ alkyl, C$_1$-C$_6$ alkoxy, C$_1$-C$_6$ haloalkyl, and C$_1$-C$_6$ haloalkoxy; and 5-10 membered heteroaryl optionally substituted with halo, amine, cyano, C$_1$-C$_6$ alkyl, C$_1$-C$_6$ alkoxy, C$_1$-C$_6$ haloalkyl, and C$_1$-C$_6$ haloalkoxy.

5. The compound of claim 1, wherein Y is —CH$_2$—, —S(O)—, —S(O)$_2$—, —O—, —NH—, or —S—.

6. The compound of claim 1, wherein the two adjacent R$^7$ together with any intervening atoms form a 5-8 membered heteroaryl ring or wherein the two adjacent R$^7$ together with any intervening atoms form an imidazole ring.

7. The compound of claim 1, wherein R$^8$ is H and R$^9$ is H and n is 0 or 1.

8. The compound of claim 1, wherein:

Y is selected from the group consisting of —S—, —O—, —CH$_2$—, and —NH—;

G is selected from the group consisting of —C(O)NR$^1$R$^2$; —C(O)NR$^1$OR$^3$; NR$^1$C(O)R$^5$; —NR$^1$C(O)NR$^2$R$^{2a}$; —NR$^1$C(O)OR$^3$; —NR$^1$S(O)$_2$R$^3$; —NR$^1$S(O)$_2$NR$^2$R$^{1a}$; —C(=NR$^1$)R$^5$; —C(=NR$^1$)NR$^2$R$^{1a}$; —NR$^1$CR$^5$(=NR$^5$); —NR$^1$C(=NR$^2$)NR$^{1a}$R$^{2a}$; C$_{6-10}$aryl optionally substituted with 0-2 substituents selected from the group consisting of C$_{1-4}$ alkyl, —OR$^3$, —C$_{1-6}$alkylene-COOR$^3$, —SR$^3$, —NR$^1$R$^2$, halogen, —C(O)NR$^1$R$^2$, and —NR$^1$C(O)R$^5$; 5-10 membered heteroaryl optionally substituted with 0-2 substituents selected from the group consisting of C$_{1-4}$ alkyl, —OR$^3$, —C$_{1-6}$alkylene-COOR$^3$, —SR$^3$, —NR$^1$R$^2$, halogen, —C(O)NR$^1$R$^2$, and —NR$^1$C(O) R$^5$; and 5-10 membered heterocyclyl optionally substituted with 0-2 substituents selected from the group consisting of C$_{1-4}$ alkyl, —OR$^3$, —C$_{1-6}$alkylene-COOR$^3$, —SR$^3$, —NR$^1$R$^2$, halogen, —C(O)NR$^1$R$^2$, and —NR$^1$C(O)R$^5$;

R is selected from a group consisting of —H, —C$_{1-9}$alkyl, —CR$^5$R$^6$OC(O)C$_{1-9}$alkyl, and

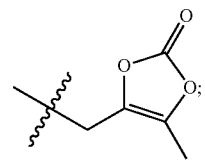 [SMILES: *Cc1oc(=O)oc1C]

each R$^1$, R$^2$, R$^{1a}$, R$^{2a}$, R$^3$, R$^5$ and R$^6$ are independently selected from —H and —C$_{1-4}$alkyl; and R$^7$ is selected from the group consisting of —H, —C$_{1-4}$ alkyl, —OH, —OC$_{1-4}$alkyl, —SC$_{1-4}$alkyl and halogen.

9. The compound of claim 7, having the structure of Formula (Ia), (Ib), (Ic), or (Id)

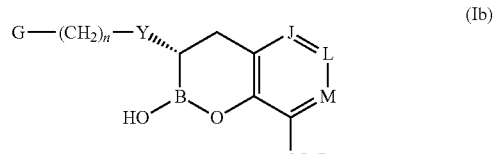

(Ib)

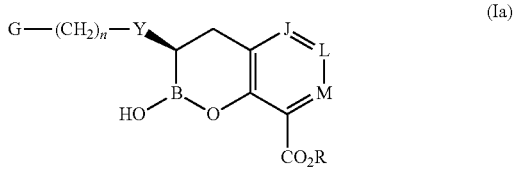

(Ia)

-continued

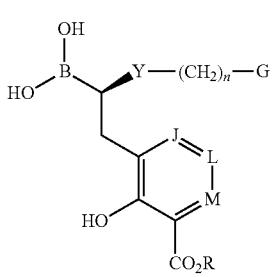
(Ic)

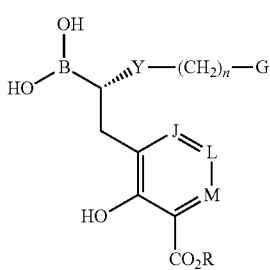
(Id)

or pharmaceutically acceptable salts thereof.

10. The compound of claim 1, wherein:
Y is —O— or —S—;
G is selected from the group consisting of phenyl, imidazole, pyrazole, triazole, tetrazole, thiazole, thiadiazole, oxazole, oxadiazole, isoxazole, isothiazole, pyridine, pyrazine, pyrimidine, pyridazine, azetidine, and pyrazine, each optionally substituted by 0-2 substituents selected from the group consisting of $C_{1-4}$ alkyl, —$OR^3$, —$C_{1-6}$alkylene-$COOR^3$, —$SR^3$, —$NR^1R^2$, halogen, —C(O)$NR^1R^2$, and —$NR^1$C(O)$R^5$, wherein $R^1$, $R^2$ and $R^5$ in G are independently selected from —H and —$C_{1-4}$alkyl; and
J, L and M are $CR^7$.

11. The compound of claim 1, wherein the compound of formula (I) has the structure of formula (Ie) or (If):

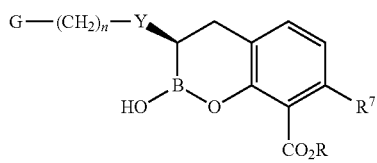
(Ie)

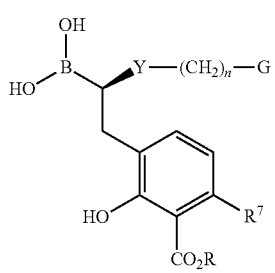
(If)

or pharmaceutically acceptable salts thereof,
wherein n is 0;
$R^7$ is selected from H, F, Cl, —$CH_3$, —$CF_3$, and —Y'—$(CH_2)_pM'$; and
p is 0 or 1.

12. The compound of claim 1, wherein G is a 5-10 membered heteroaryl or a 3-10 membered heterocyclyl, and the heteroaryl or heterocyclyl is optionally substituted with one or more $R^{10}$.

13. The compound of claim 12, wherein G is selected from thiadiazole, thiazole, imidazole, triazole, azetidine or piperazine, each optionally substituted with one or more $R^{10}$.

14. The compound of claim 1, wherein G is selected from

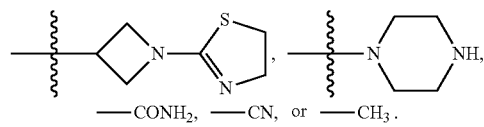

—$CONH_2$, —CN, or —$CH_3$.

15. The compound of claim 1, wherein $R^{10}$ is $R^{11}$, $CH_2R^{11}$, $(CH_2)_2R^{11}$, $(CH_2)_3R^{11}$, or $(CH_2)_4R^{11}$.

16. The compound of claim 1, wherein G is thiadiazole; thiadiazole optionally substituted with —$NR^1R^2$ or —$NR^1$C(O)$R^5$, wherein $R^1$, $R^2$ and $R^5$ in G are independently —H or —$C_{1-4}$alkyl; triazole optionally substituted with —$NR^1R^2$, wherein $R^1$ and $R^2$ in G are independently —H or —$C_{1-4}$alkyl; triazole optionally substituted with a $C_{1-4}$ alkyl; triazole optionally substituted with —$C_{1-6}$alkylene-COOH; triazole optionally substituted with —$(CH_2)_3$—COOH; tetrazole optionally substituted with methyl; pyridine; thiazole; phenyl; or azetidine.

17. The compound of claim 1, wherein:
Y is —S— or —$CH_2$—;
n is 1 or 2;
G is —C(O)$NR^1R^2$; and
J, L and M are $CR^7$.

18. The compound of claim 1, wherein the compound of formula (I) has the structure of formula (Ig) or (Ih):

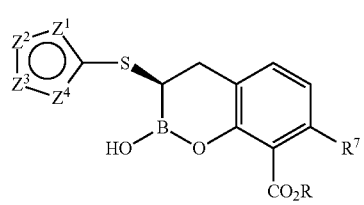
(Ig)

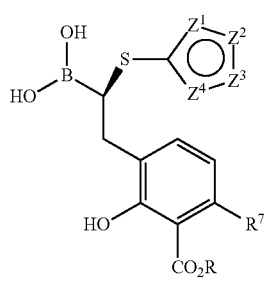
(Ih)

or pharmaceutically acceptable salts thereof, wherein n is 0;
each $Z^1$, $Z^2$, $Z^3$ and $Z^4$ are independently selected from N, $NR^{12}$, O, S, and $CR^{12}$ provided that $Z^1$ to $Z^4$ are selected such that a five membered aromatic ring is formed;
each $R^{12}$ is independently H or $(CH_2)_{0-5}R^{11}$; and each $R^{11}$ is independently selected from $C_1$-$C_6$ alkyl; halo$C_{1-6}$alkyl; —$OR^3$; —$C_{1-6}$alkylene-COO$R^3$; —$SR^3$; halogen; —CO—$C_{1-4}$alkyl; $C(O)NR^1R^2$; —$NR^1R^2$; —$NR^1(CH_2)_{0-4}COR^5$; —$NR^1(CH_2)_{0-4}C(=NR^2)R^5$; —$NR^1$—CH—[$(CH_2)_{0-4}$—$NR^{1a}R^{2a}$]$_2$; —$NR^1$—$(CH_2)_{1-5}$—$R^3$; —$NR^1(CH_2)_{1-4}$—$NR^{1a}R^{2a}$; —$N[(CH_2)_{1-4}$—$NR^1R^2]_2$; —$S(CH_2)_{0-4}C(=NR^1)R^5$; —$S(CH_2)_{1-4}$—$R^3$; —$S(CH_2)_{0-4}$—$NR^1R^2$; —S—CH—[$(CH_2)_{0-4}$—$NR^1R^2]_2$; —$S[(CH_2)_{1-4}$—$NR^1R^2]_2$; —$S(CH_2)_{0-4}$-3-10 membered heterocyclyl; —$S(CH_2)_{0-4}$-3-10 membered heterocyclyl-$NR^1R^2$; —$S(CH_2)_{0-4}$-5-10 membered heteroaryl-$NR^1R^2$; —$S(O)_2NR^1R^2$; and —O—$C_{1-6}$alkylene-$NR^1R^2$; $C_{3-7}$ carbocyclyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 3-10 membered heterocyclyl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; 6 to 10 membered aryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy; and 5-10 membered heteroaryl optionally substituted with halo, amine, cyano, $C_1$-$C_6$ alkyl, $C_1$-$C_6$ alkoxy, $C_1$-$C_6$ haloalkyl, and $C_1$-$C_6$ haloalkoxy.

19. The compound of claim 18, wherein $Z^1$ is S; wherein each $Z^2$ and $Z^3$ are independently N, $NR^{12}$, or $CR^{12}$; and wherein $Z^4$ is N or $CR^{12}$.

20. The compound of claim 18, wherein $Z^1$ to $Z^4$ are selected to form a five membered aromatic ring selected from the group consisting of

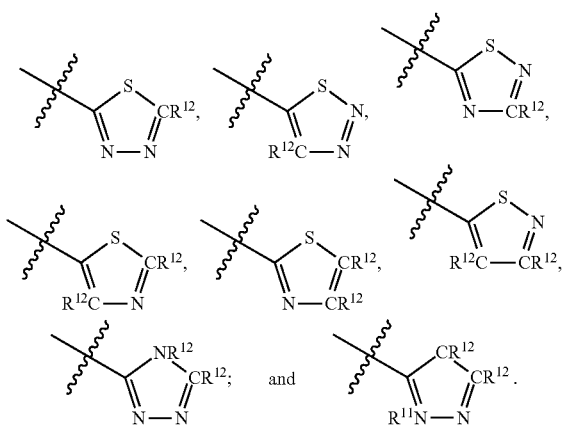

21. The compound of claim 18, wherein $R^{12}$ is H or $R^{12}$ is $R^{11}$; and wherein $R^{11}$ is $C_1$-$C_6$ alkyl, $C_{1-4}$ alkyl optionally substituted with a 3-10 membered heterocyclyl, an optionally substituted $C_{1-6}$alkylene-3-10 membered heterocyclyl, azetidine optionally substituted with one or more $NH_2$, or —$(CH_2)_{0-4}NR^1R^2$.

22. The compound of claim 18, wherein $R^{11}$ is $CH_3$, —$CF_3$, $CHF_2$, $CH_2F$, —$CH_2$-piperazine,

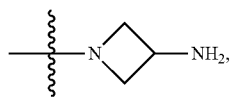

$NH_2$, —$CH_2NH_2$, —$(CH_2)_4NH_2$, or

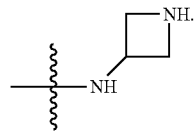 [SMILES: *NC1CNC1]

23. The compound of claim 21, wherein $R^{11}$ is $NR^1R^2$, $R^1$ is H, and $R^2$ is an optionally substituted —$C_{1-4}$alkyl or an optionally substituted 3-8 membered heterocyclyl.

24. The compound of claim 23, wherein $R^2$ is azetidine,

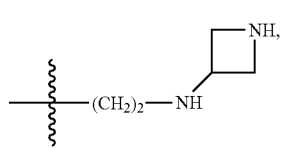

—$(CH_2)_2$-piperazine, pyrrolidine, —$(CH_2)_2$—$NH_2$ or —$(CH_2)_3$—$NH_2$.

25. The compound of claim 1, wherein $R^{11}$ is —C(O)$NR^1R^2$, —$NR^1C(O)R^5$, —$N((CH_2)_{0-4}$—$NR^1R^2)_2$, —$NR^1$—CH—[$(CH_2)_{0-4}$—$NR^{1a}R^{2a}$]$_2$, —$NH(CH_2)_{1-4}$—$NR^1R^2$, is —$NR^1(CH_2)_{0-4}C(=NR^2)R^5$, —$S(CH_2)_{0-4}C(=NR^1)R^5$, —$S(CH_2)_{0-4}$-3-10 membered heterocyclyl, —$S(O)_2NR^1R^2$, —$S(CH_2)_{0-4}$—$NR^1R^2$, —$SR^3$, —$S(CH_2)_{1-4}$-3-10 membered heterocyclyl, —$S(CH_2)_{1-4}$—$R^3$, —$S(CH_2)_{0-4}$-5-10 membered heteroaryl-$NH_2$, —$OR^3$, —$O(CH_2)_{0-4}$—$NR^1R^2$, or —$O(CH_2)_2NH_2$.

26. The compound of claim 1, wherein $R^{11}$ is —$CONH_2$, —NHCOH, —$NHCOCH_3$, —$N((CH_2)_2$—$NH_2)_2$, —NHCH($CH_2$—$NH_2)_2$, —$NH(CH_2)_2$—NH-azetidine, —NHC(=NH)$NH_2$, —$SCH_2C(=NH)NH_2$, —$S(CH_2)_2$-piperazine, —$S(O)_2NH_2$, —$S(CH_2)_2NH_2$ or —$S(CH_2)_3NH_2$, azetidine, piperidine, —$S(CH_2)_2$-morpholine, or

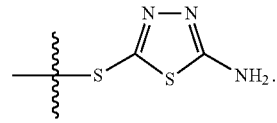 [SMILES: *Sc1nnc(N)s1]

27. The compound of claim 1, wherein $R^7$ is independently selected from the group consisting of —H, —OH, —$C_{1-4}$alkyl, —O—$C_{1-4}$alkyl, —S—$C_{1-4}$alkyl, halogen, —$CF_3$, and cyano.

28. The compound of claim 1, wherein each $R^7$ is independently selected from the group consisting of H, F, Cl, Me, —$CF_3$, SMe, —S(O)Me, and —OMe.

29. The compound of claim 1, wherein $R^7$ is present 1 to 3 times and each $R^7$ is triazole.

30. The compound of claim 1, wherein:
each $R^7$ is independently —$(CH_2)_m$—Y'—$(CH_2)_pM'$;
m and p are independently 0 to 3;
Y' is selected from the group consisting of —S—, —O— and —$NR^1$—;
M' is selected from the group consisting of $NR^1R^2$, —$SO_3R^3$, —CN, —$C(O)NR^1R^2$; $CF_3$, —$C_{1-4}$ alkyl optionally substituted with 1-2 substituents selected from the group consisting, —$OR^3$, —$NR^1R^2$, halogen, —$C(O)NR^1R^2$, and —$NR^1C(O)R^5$; $C_{3-10}$ cycloalkyl optionally substituted with 1-2 substituents selected from the group consisting of $C_{1-4}$ alkyl, —$OR^3$, —$NR^1R^2$, halogen, —$C(O)NR^1R^2$, and —$NR^1C(O)$ $R^5$; $C_{6-10}$ aryl optionally substituted with 1-2 substituents selected from the group consisting of $C_{1-4}$ alkyl, —$OR^3$, —$NR^1R^2$, halogen, —$C(O)NR^1R^2$, and —$NR^1C(O)R^5$; 5 to 10 membered heteroaryl optionally substituted with 1-2 substituents selected from the group consisting of $C_{1-4}$ alkyl, —$OR^3$, —$NR^1R^2$, halogen, —$C(O)NR^1R^2$, and —$NR^1C(O)R^5$; and 4 to 10 membered heterocyclyl optionally substituted with 1-2 substituents selected from the group consisting of $C_{1-4}$ alkyl, —$OR^3$, —$NR^1R^2$, halogen, —$C(O)NR^1R^2$, and —$NR^1C(O)R^5$.

31. The compound of claim 30, wherein Y' is O or NH; and p is 0, 1, or 2.

32. The compound of claim 30, wherein M' is cyclopropyl, —$SO_3CH_3$, $SCH_3$, —$NH_2$, CN, $CHF_2$, $(CH_2)_2F$, $(CH_2)_2OCH_3$, $CH_3$, $CH_2CH_3$, $CH(CH_3)_2CH_2CH(CH_3)_2$,

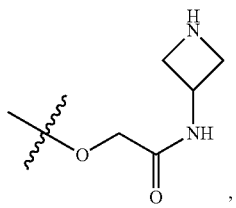 [SMILES: *OCC(=O)NC1CNC1]

or —$O(CH_2)CONH_2$.

33. The compound of claim 30, wherein M' is $C_{1-4}$ alkyl optionally substituted with 0-2 substituents selected from the group consisting, —$OR^3$, —$NR^1R^2$, halogen, —$C(O)NR^1R^2$, and —$NR^1C(O)R^5$; $C(O)NR^1R^2$ wherein $R^1$ is H; azetidine; a 5 to 10 membered heteroaryl; or a thiadiazole.

34. The compound of claim 1, wherein
each $R^7$ is independently selected from the group consisting of —OH, halogen, —$CF_3$, $C_1$-$C_6$ alkenyl, $C_1$-$C_6$ alkynyl, $C_1$-$C_6$ heteroalkyl, $C_3$-$C_7$ carbocyclyl, 5-10 membered heterocyclyl, aryl, 5-10 membered heteroaryl, cyano, $C_1$-$C_6$ alkoxy($C_1$-$C_6$)alkyl, aryloxy, sulfhydryl (mercapto), and —$(CH_2)_m$—Y'—$(CH_2)_p$M';
m and p are independently 0 to 3;
Y' is selected from the group consisting of —S—, —S(O)—, —$S(O)_2$—, —O—, —$CR^5R^6$—, and —$NR^1$—;
M' is selected from the group consisting of —$C(O)NR^1R^2$; —$C(O)NR^1OR^3$; —$NR^1C(O)R^5$; —$NR^1C(O)NR^2R^{1a}$; —$NR^1C(O)OR^3$; —$NR^1S(O)_2R^3$; —$NR^1S(O)_2NR^2R^{1a}$; —$C(=NR^1)R^5$; —$C(=NR^1)NR^2R^{1a}$; $NR^1CR^5(=NR^2)$; —$NR^1C(=NR^2)NR^{1a}R^{2a}$; $C_{1-4}$ alkyl optionally substituted with 0-2 substituents selected from the group consisting, —$OR^3$, —$NR^1R^2$, halogen, —$C(O)NR^1R^2$, and —$NR^1C(O)R^5$; $C_{3-10}$ cycloalkyl optionally substituted with 0-2 substituents selected from the group consisting of $C_{1-4}$ alkyl, —$OR^3$, —$NR^1R^2$, halogen, —$C(O)NR^1R^2$, and —$NR^1C(O)R^5$; 5 to 10 membered heteroaryl optionally substituted with 0-2 substituents selected from the group consisting of $C_{1-4}$ alkyl, —$OR^3$, —$NR^1R^2$, halogen, —$C(O)NR^1R^2$, and —$NR^1C(O)R^5$; and 4 to 10 membered heterocyclyl optionally substituted with 0-2 substituents selected from the group consisting of $C_{1-4}$ alkyl, —$OR^3$, —$NR^1R^2$, halogen, —$C(O)NR^1R^2$, and —$NR^1C(O)R^5$— with the proviso that the compound does not have the structure selected from the group consisting of

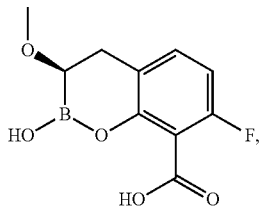

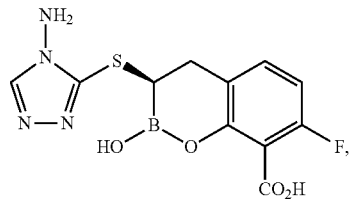

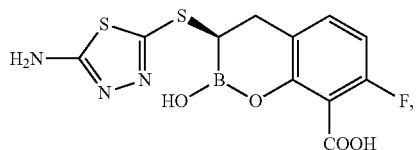

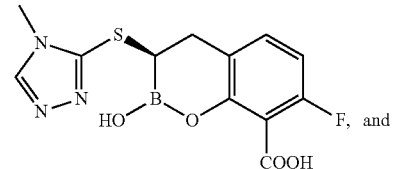

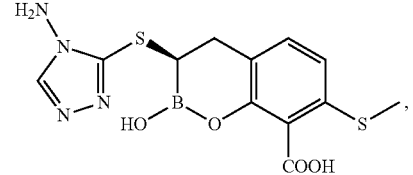

or pharmaceutically acceptable salts thereof.

35. The compound of claim 34, wherein each $R^7$ is independently selected from —OH, —O—$C_{1-4}$alkyl, —S—$C_{1-4}$alkyl, —S(O)—$C_{1-4}$alkyl, and halogen; and wherein R is —$CR^5R^6OC(O)C_{1-9}$alkyl or —$CR^5R^6OC(O)OC_{1-9}$alkyl.

36. The compound of claim 34, wherein $R^1$ is H and $R^2$ is H.

37. The compound of claim 1, having the structure selected from the group consisting of:

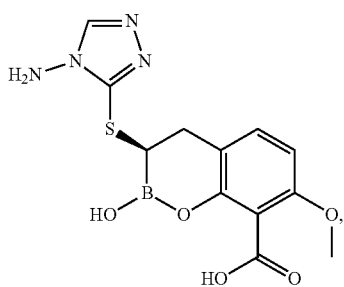

-continued
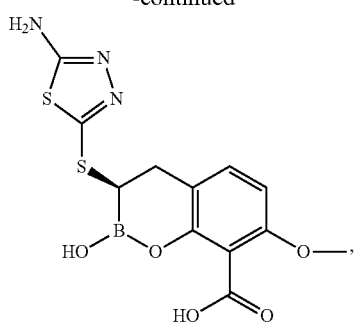
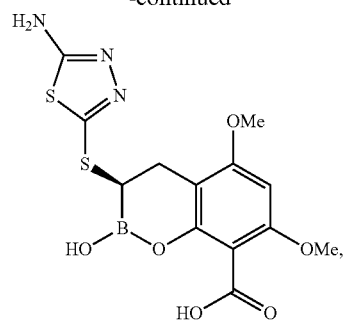
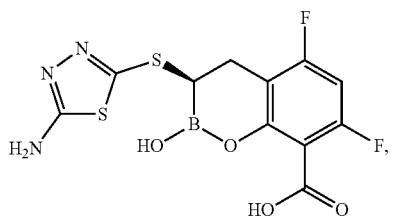
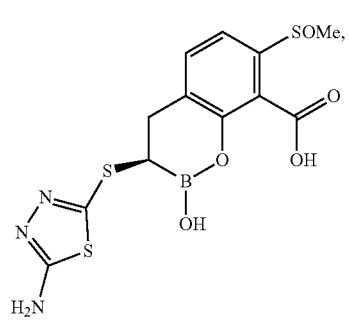
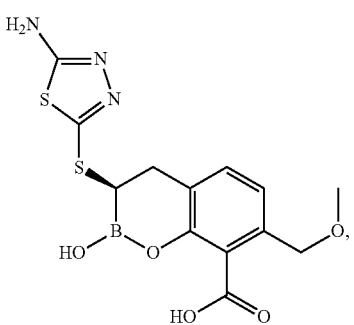
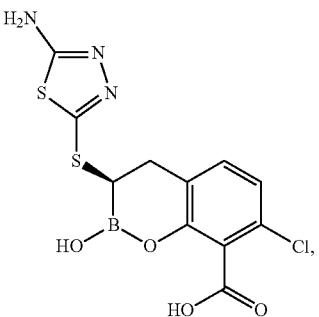

-continued
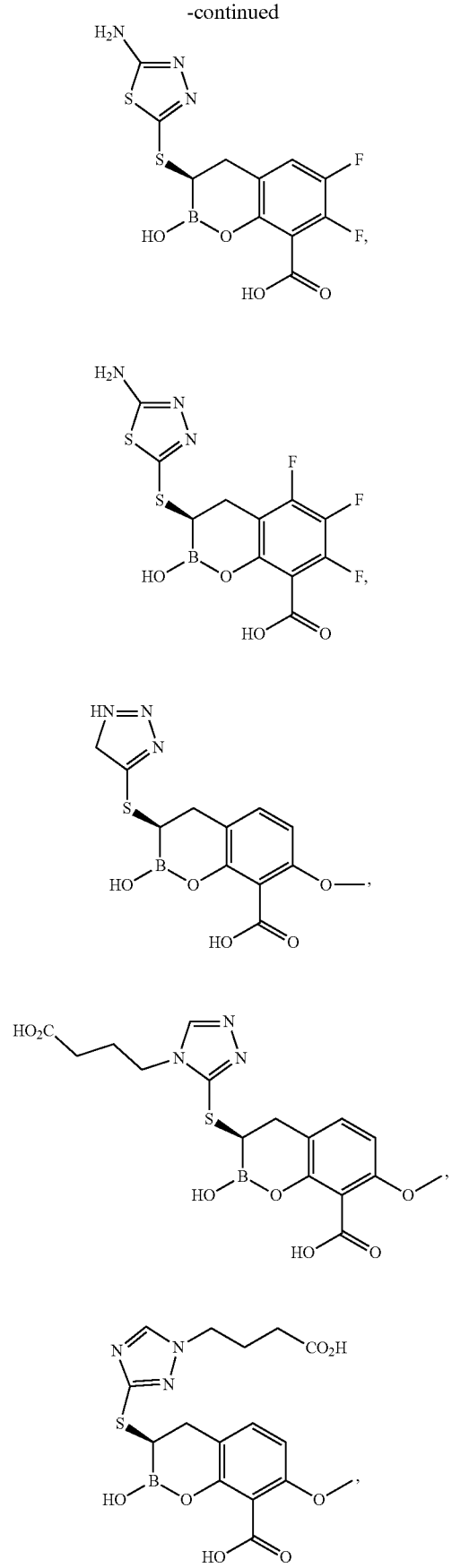
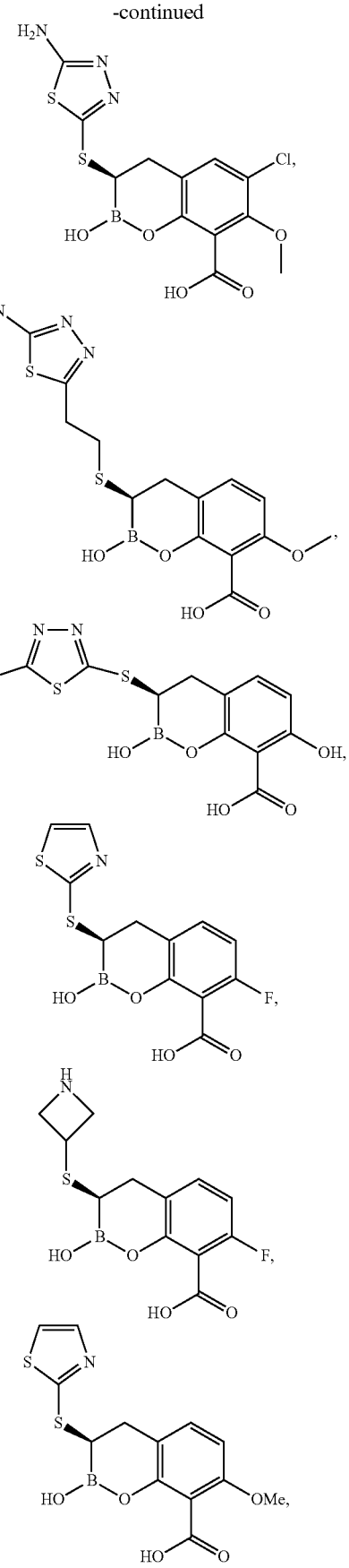

235
-continued
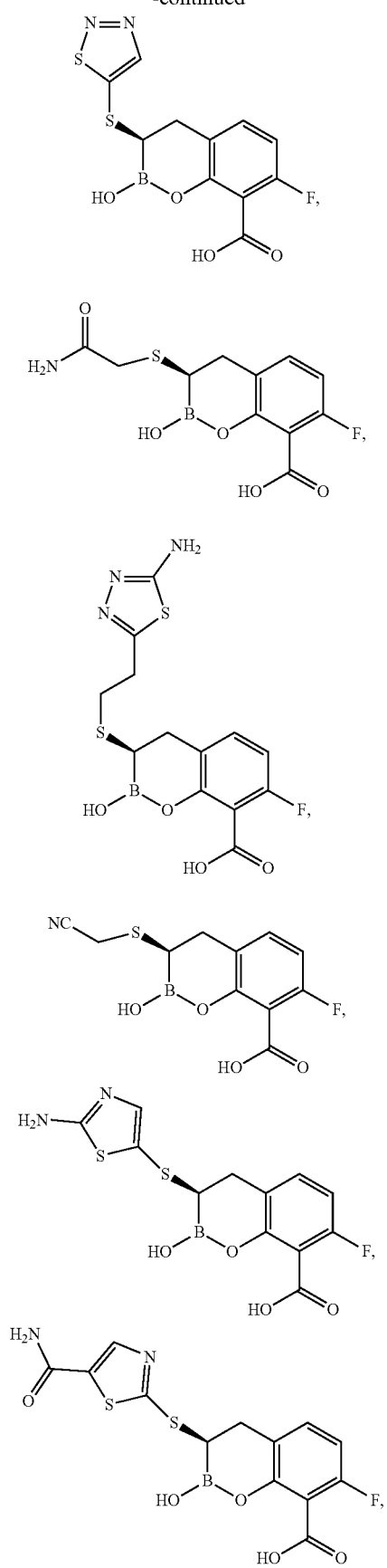
236
-continued
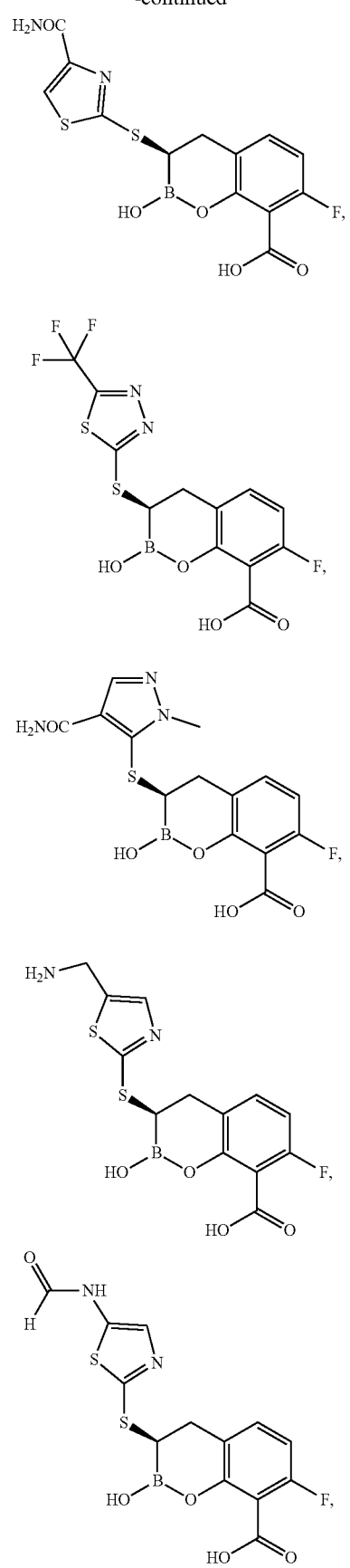

-continued
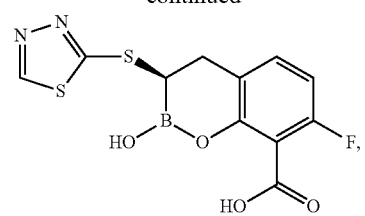
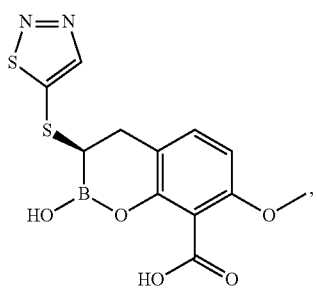
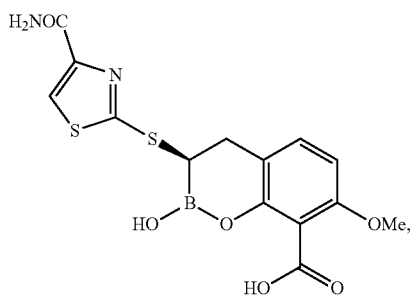
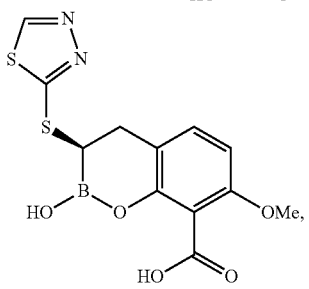
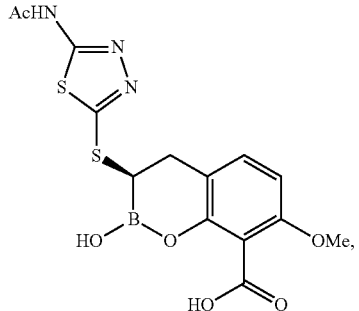
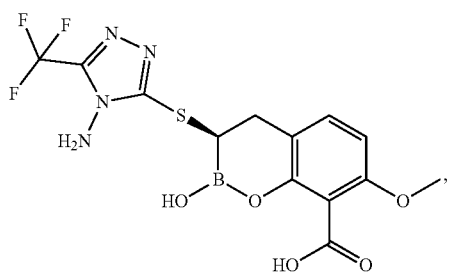
-continued
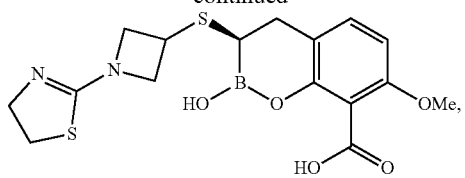
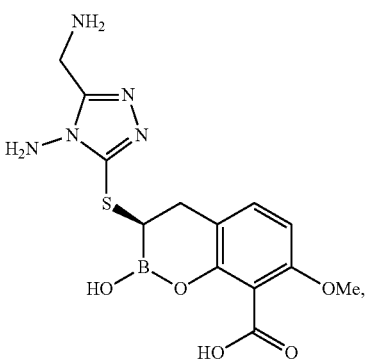
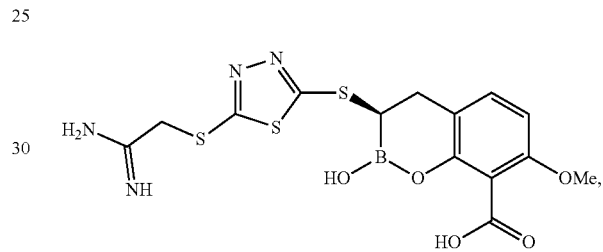
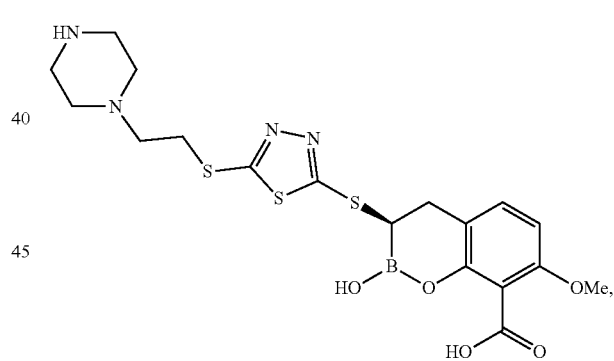
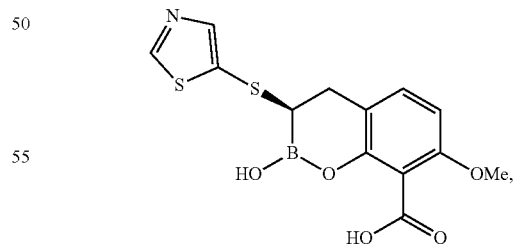
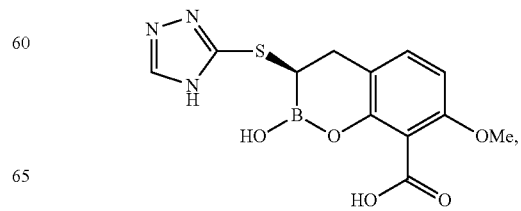

-continued
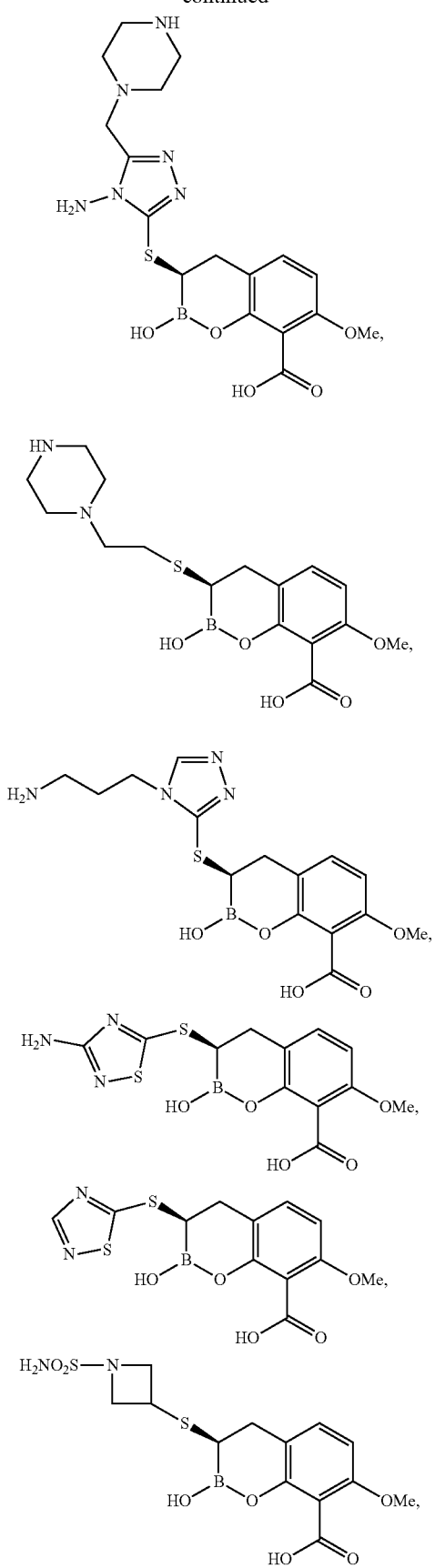
-continued
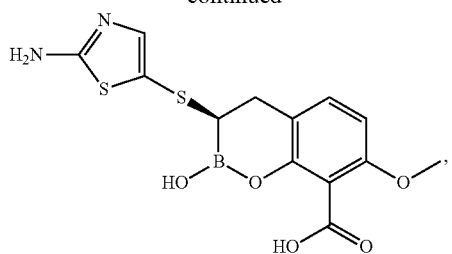
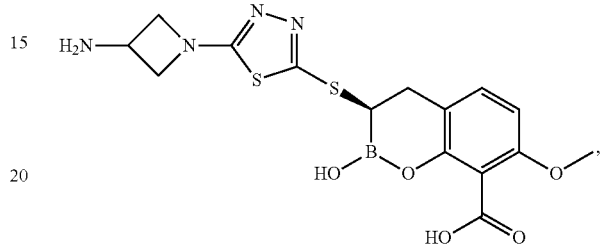
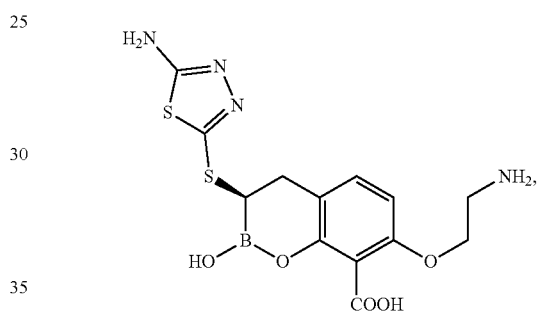

-continued
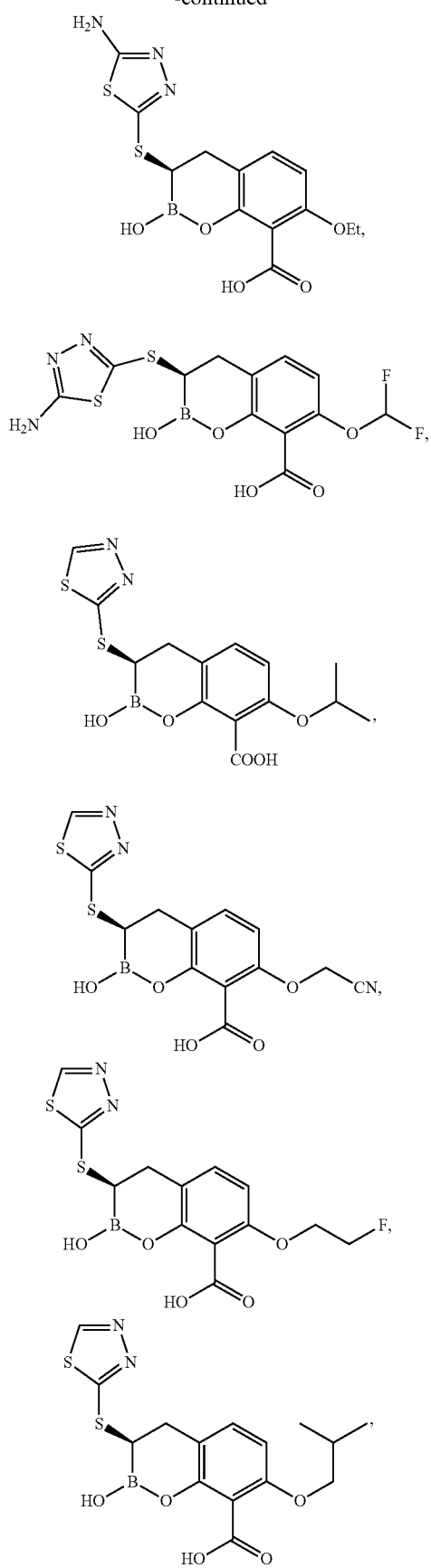
-continued
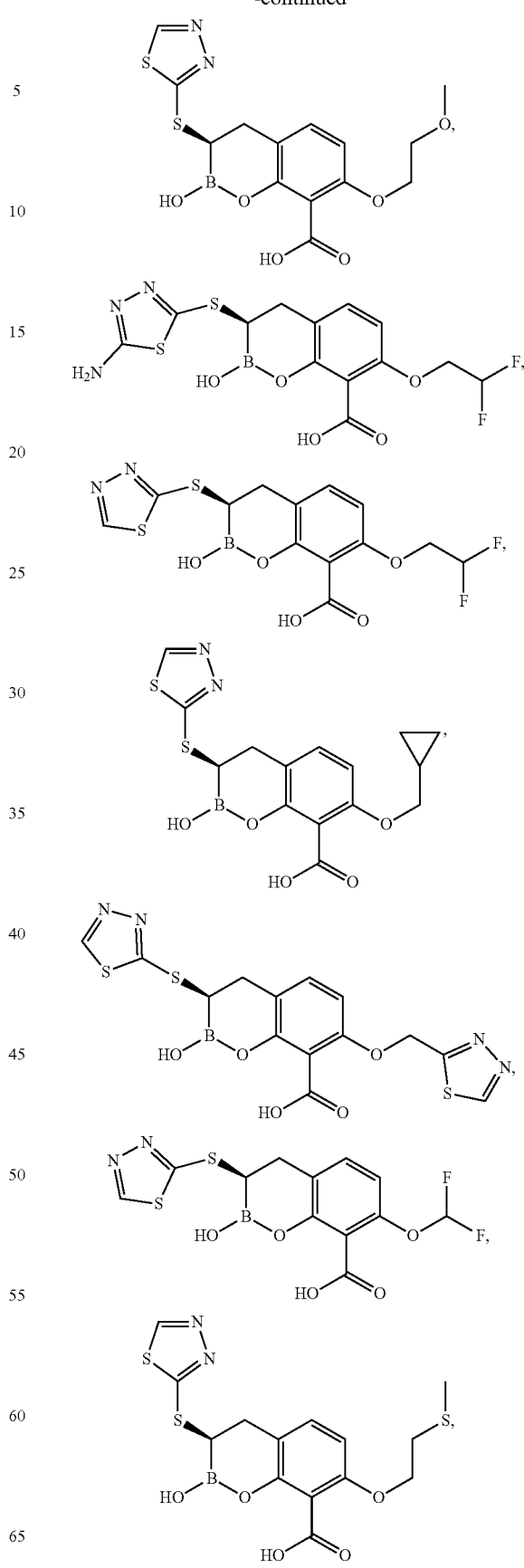

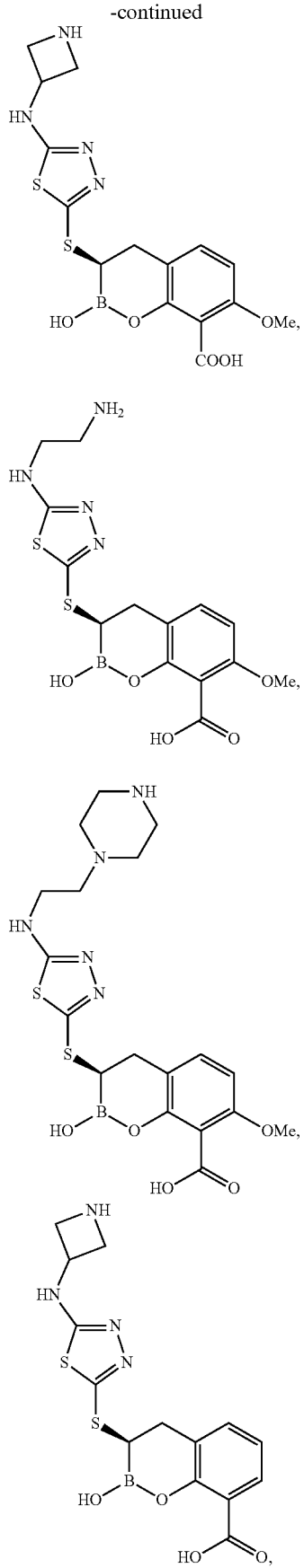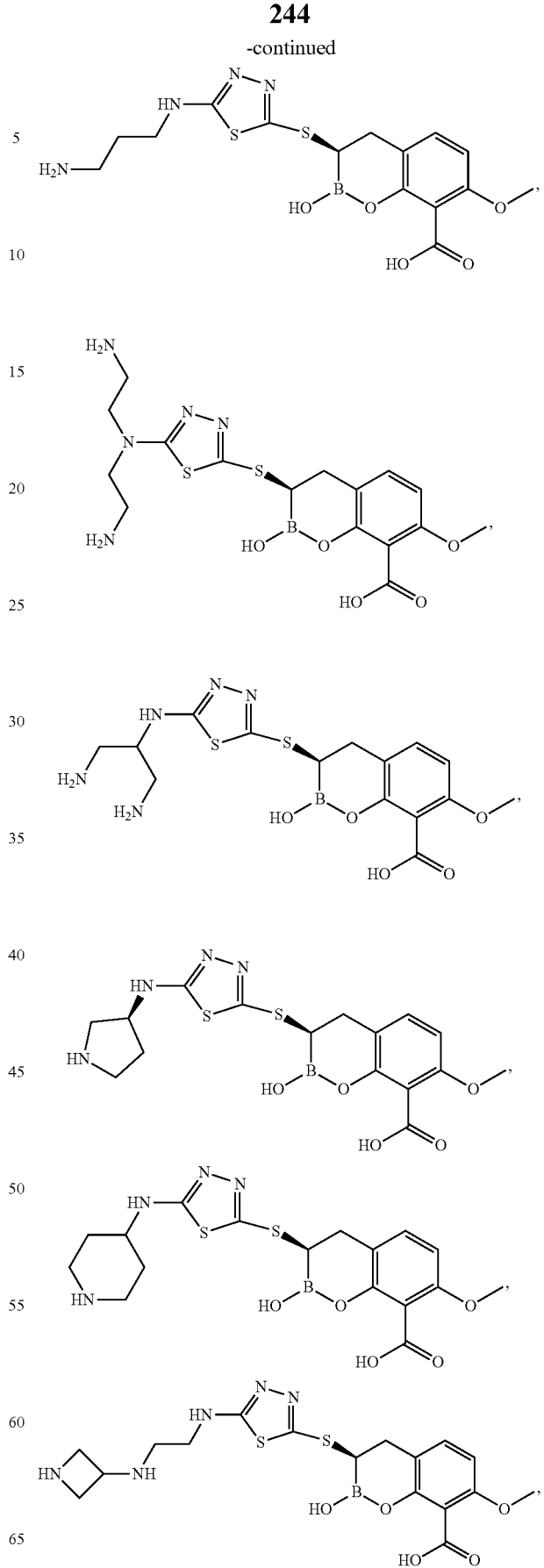

245
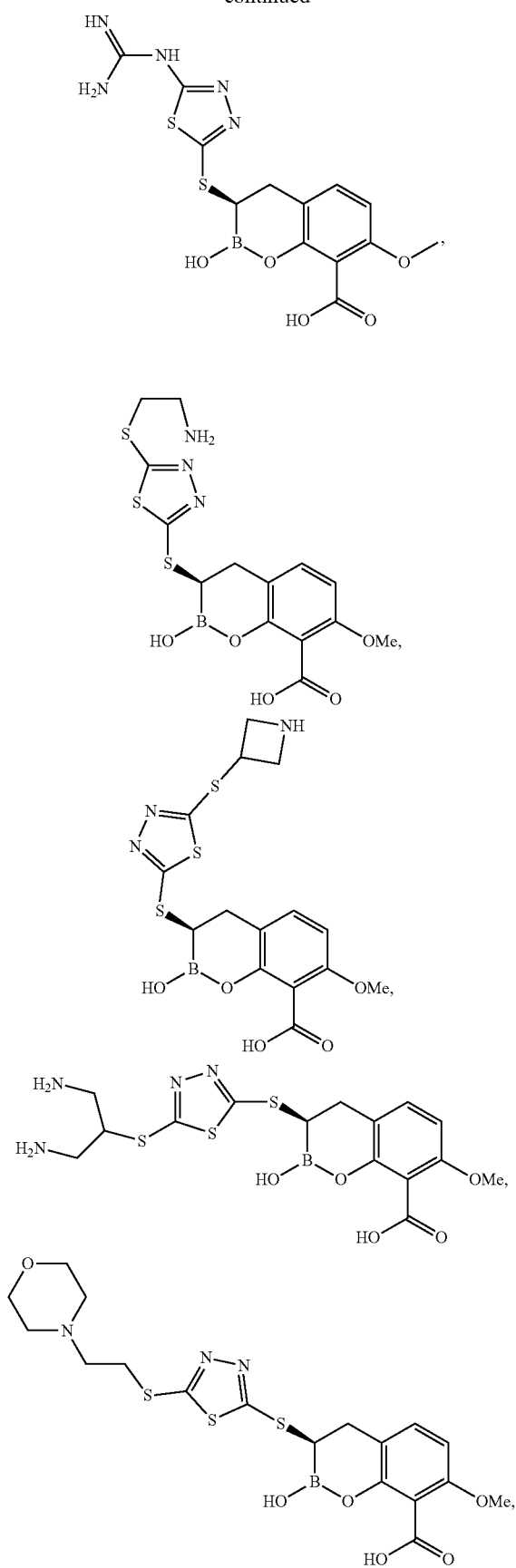
246
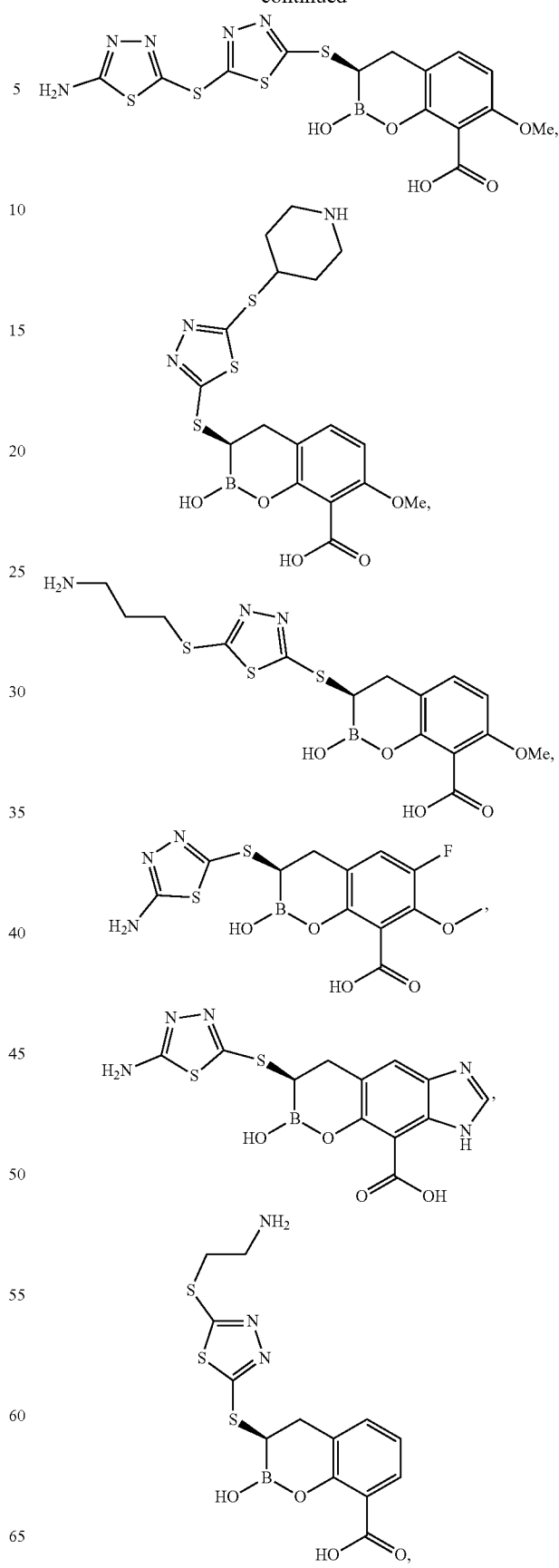

247
-continued

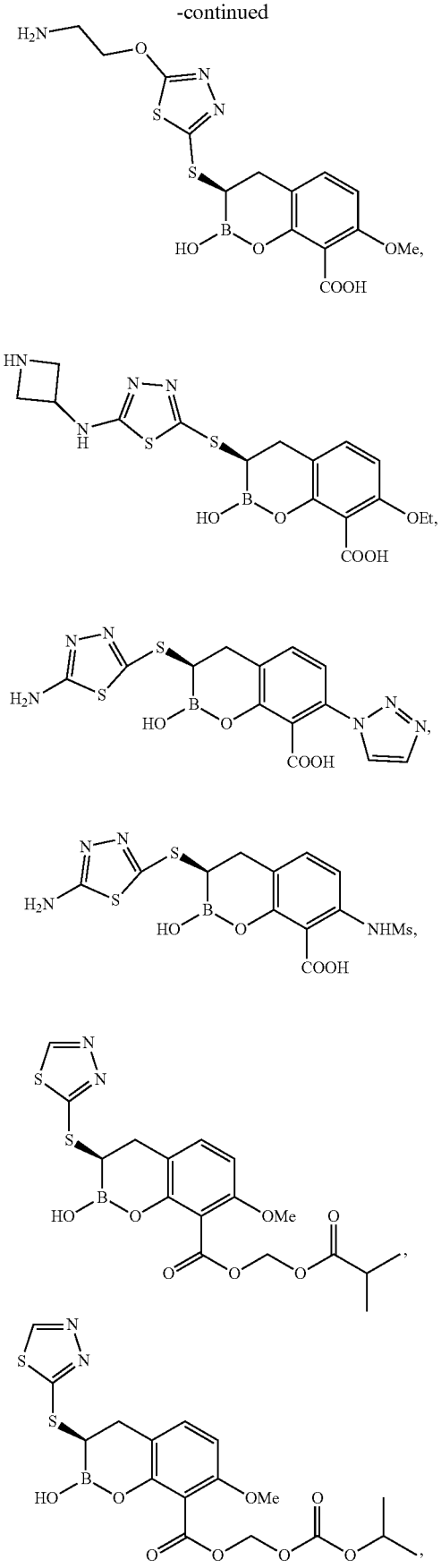

248
-continued

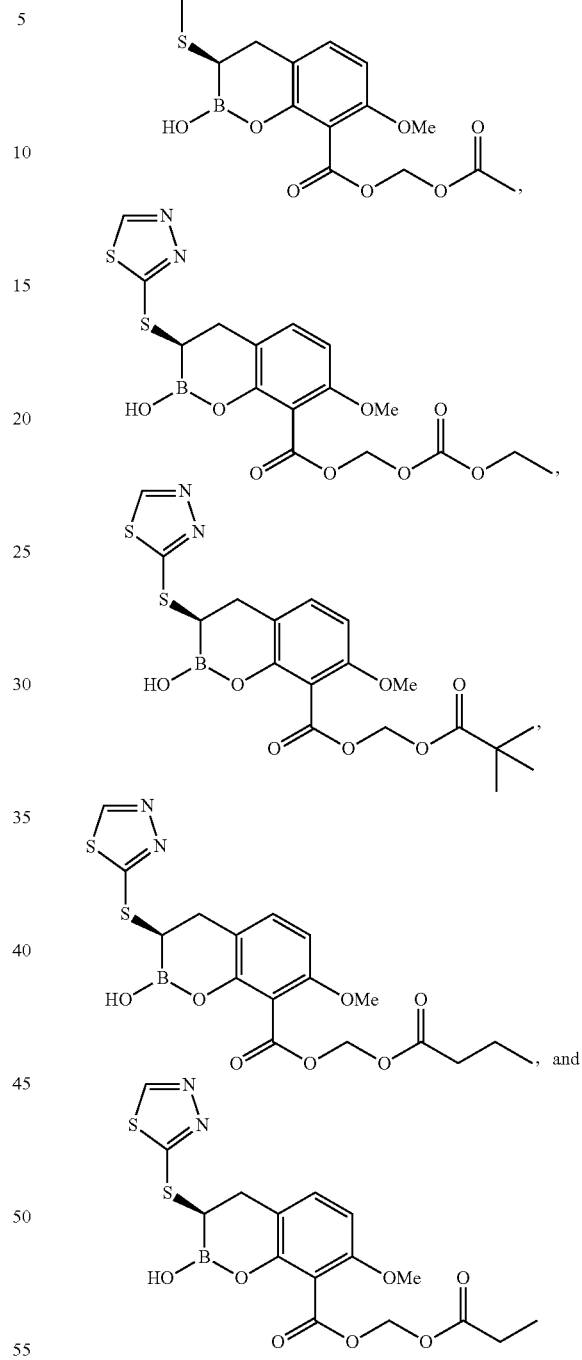

or pharmaceutically acceptable salts thereof.

38. A pharmaceutical composition comprising a therapeutically effective amount of a compound of claim 1 and a pharmaceutically acceptable excipient.

39. The pharmaceutical composition of claim 38, further comprising an additional medicament, wherein the additional medicament is selected from an antibacterial agent, an antifungal agent, an antiviral agent, an anti-inflammatory agent, or an anti-allergic agent.

40. The composition of claim 39, wherein the additional medicament is a β-lactam antibacterial agent selected from Ceftazidime, Biapenem, Doripenem, Ertapenem, Imipenem, Meropenem, Tebipenem, Apapenem, Panipenem, Aztreonam, Tigemonam, BAL30072, SYN 2416, or Carumonam.

41. A method of treating a bacterial infection, comprising administering to a subject in need thereof, a compound of claim 1.

42. The method of claim 41, further comprising administering to the subject an additional medicament, wherein the additional medicament is selected from an antibacterial agent, an antifungal agent, an antiviral agent, an anti-inflammatory agent, or an anti-allergic agent.

43. The method of claim 41, wherein the additional medicament is a β-lactam antibacterial agent selected from Ceftazidime, Biapenem, Doripenem, Ertapenem, Imipenem, Meropenem, Tebipenem, Apapenem, Panipenem, Aztreonam, Tigemonam BAL30072, SYN 2416; or Carumonam.

* * * * *